(12) United States Patent
Tempst et al.

(10) Patent No.: US 7,972,770 B2
(45) Date of Patent: Jul. 5, 2011

(54) METHODS OF DETECTION OF CANCER USING PEPTIDE PROFILES

(75) Inventors: Paul Tempst, New York, NY (US); Josep Villanueva, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 79 days.

(21) Appl. No.: 12/063,968

(22) PCT Filed: Aug. 16, 2006

(86) PCT No.: PCT/US2006/031957
§ 371 (c)(1),
(2), (4) Date: Oct. 20, 2008

(87) PCT Pub. No.: WO2007/022248
PCT Pub. Date: Feb. 22, 2007

(65) Prior Publication Data
US 2009/0208921 A1    Aug. 20, 2009

Related U.S. Application Data

(60) Provisional application No. 60/708,676, filed on Aug. 16, 2005.

(51) Int. Cl.
*C12Q 1/00* (2006.01)
(52) U.S. Cl. .......................................................... 435/4
(58) Field of Classification Search .................. None
See application file for complete search history.

(56) References Cited

U.S. PATENT DOCUMENTS

| 2005/0059013 A1 | 3/2005 | Chan et al. | |
|---|---|---|---|
| 2007/0054329 A1 | 3/2007 | Fung et al. | |
| 2008/0317771 A1* | 12/2008 | Spagnoli et al. | 424/185.1 |

FOREIGN PATENT DOCUMENTS

| WO | WO-2006/034032 | 3/2006 |
|---|---|---|
| WO | WO-2006/099126 | 9/2006 |
| WO | PCT/ISA/210 | 5/2008 |

OTHER PUBLICATIONS

Adam et al (Cancer Research, 2002, 62:3609-3614).*
Koomen et al (Rapid Communications in mass Spectrometry, 2004, 18:2537-2548).*
Marshall et al (J of Proteome Research, 2003, 2:361-371).*
Peccerella et al (Clinical Chemistry, 2010, 56:272-280).*
Tockman et al (Cancer Res., 1992, 52:2711s-2718s).*
Villanueva et al (J Cinical Investigation; 2006, 116:271-284, IDS).*
WO-Form PCT/ISA/237, May 22, 2008, Written Opinion.
Song et al. Quantification of fragments of human serum inter-alpha-trypsin inhibitor heavy chain 4 by a surface-enhanced laser desorption/ionization-based immunoassay. Clinical Chemistry. Jun. 2006. vol. 52. p. 1045-1053.
Fung et al. Classification of cancer types by measuring variants of host response proteins using SELDI serum assays. Int J Cancer. 2005. vol. 115. p. 783-789.
Villanueva et al. Differential exoprotease activities confer tumor-specific serum peptidome patterns. J of Clinical Investigation. Jan. 2006. vol. 116, p. 271-284.
Koomen et al. Direct tandem mass spectrometry reveals limitations in protein profiling experiments for plasma biomarker discover. J of Proteome Research. May/Jun. 2005. vol. 4. p. 972-981.
Caputo et al. Peptide profiling in epithelial tumor plasma by the emerging proteomic techniques. J. of Chromatography. May 2005. vol. 819, p. 59-66.

* cited by examiner

*Primary Examiner* — Laura B Goddard
(74) *Attorney, Agent, or Firm* — Edwards Angell Palmer & Dodge LLP; Peter C. Lauro, Esq.; Elbert Chiang

(57) ABSTRACT

The disclosed methods address the identification and monitoring of cancer in a subject using serum peptide profiles. Such profiles allow the detection of the differential presence of certain serum peptide markers in comparison with controls. The profiles can be determined employing mass spectrometry.

12 Claims, 111 Drawing Sheets

| | | PROSTATE | | |
|---|---|---|---|---|
| FPA | 1536.68 | ADSGEGDFLAEGGGVR | | |
| | 1465.65 | DSGEGDFLAEGGGVR | | |
| | 1350.64 | SGEGDFLAEGGGVR | | |
| | 1263.60 | GEGDFLAEGGGVR | | |
| | 1206.57 | EGDFLAEGGGVR | | |
| | 1077.53 | GDFLAEGGGVR | | |
| | 1020.47 | DFLAEGGGVR | | |
| | 905.50 | FLAEGGGVR | | |
| | 758.45 | LAEGGGVR | | |
| Fibrinogen-α | 3261.43 | (K) SSSYSKQFTSSTSYNRGDSTFESKSYKMA | | |
| | 3190.36 | (K) SSSYSKQFTSSTSYNRGDSTFESKSYKM | | |
| | 2931.20 | (K) SSSYSKQFTSSTSYNRGDSTFESKSY | | |
| | 2768.26 | (K) SSSYSKQFTSSTSYNRGDSTFESKS | | |
| | 2553.01 | (K) SSSYSKQFTSSTSYNRGDSTFES | | |
| | 2379.03 | .SSYSKQFTSSTSYNRGDSTFE | | |
| | 2816.25 | (R) GSESGIFTNTKESSSHHPGIAEFPSRG (K) | | |
| | 3239.22 | SYKMADEAGSEADHEGTHSTKRGHAKSRPV (R) | | |
| | 2659.03 | DEAGSEADHEGTHSTKRGHAKSRPV (R) | | |
| C3f | 2021.06 | SSKITHRIHWESASLLR | | |
| | 1864.95 | SSKITHRIHWESASLL. | | |
| | 1777.93 | SKITHRIHWESASLL. | | |
| | 1690.90 | KITHRIHWESASLL. | | |
| | 1562.84 | ITHRIHWESASLL. | | |
| | 1449.76 | THRIHWESASLL. | | |
| | 1348.70 | HRIHWESASLL. | | |
| | 1211.70 | RIHWESASLL. | | |
| | 1055.60 | IHWESASLL. | | |
| | 942.43 | HWESASLL. | | |
| | 1751.88 | SSKITHRIHWESASL.. | | |
| C4-α | 1895.99 | RNGFKSHALQLNNRQI (R) | | |
| | 1739.93 | NGFKSHALQLNNRQI (R) | | |
| | 1626.85 | NGFKSHALQLNNRQ. | | |
| | 1498.91 | NGFKSHALQLNNR.. | | |
| | 3200.52 | (R) GLEEELQFSLGSKINVKVGGNSKGTLKVLR | | |
| | 2704.13 | (R) GLEEELQFSLGSKINVKVGGNSKGTL | | |
| | 2305.20 | (R) GLEEELQFSLGSKINVKVGGNS | | |
| | 1762.87 | (R) GLEEELQFSLGSKINV | | |
| ITIH4 | 998.45 | HAAYHPFR | | |
| | 2183.91 | QLGLPGPPDVPDHAAYHPFR | | |
| | 3970.97 | (R) QAGAAGSRMNFRPGVLSSRQLGLPGPPDVPDHAAYHPF. | | |
| | 3272.50 | MNFRPGVLSSRQLGLPGPPDVPDHAAYHPF. | | |
| | 2724.48 | PGVLSSRQLGLPGPPDVPDHAAYHPF. | | |
| | 2627.48 | GVLSSRQLGLPGPPDVPDHAAYHPF. | | |
| | 2358.09 | SSRQLGLPGPPDVPDHAAYHPF. | | |
| | 2271.14 | SRQLGLPGPPDVPDHAAYHPF. | | |
| | 2028.00 | QLGLPGPPDVPDHAAYHPF. | | |
| | 1786.86 | GLPGPPDVPDHAAYHPF. | | |
| | 842.40 | HAAYHPF. | | |
| | 3156.52 | (R) NVHSGSTFFKYYLQGAKIPKPEASFSPR | | |
| | 2115.00 | (R) NVHSAGAAGSRMNFRPGVLSS (R) | | |
| APO A-I | 3377.45 | (R) AELQEGARQKLHELQEKLSPLGEEM$_{ox}$RDRA (R) | | |
| | 1807.78 | ELQEGARQKLHELQE | | |
| | 3182.46 | (R) QGLLPVLESFKVSFLSALEEYTKKLNTQ | | |
| | 1971.16 | VSFLSALEEYTKKLNTQ | | |
| | 2052.89 | (K) ATEHLSTLSEKAKPALEDL (R) | | |
| APO A-IV | 2508.16 | ISASAEELRQRLAPLAEDVRGNL (K) | | |
| | 2755.20 | (K) GNTEGLQKSLAELGGHLDQQVEEFR | | |
| | 1927.94 | SLAELGGHLDQQVEEFR | | |
| | 1771.81 | SLAELGGHLDQQVEEF. | | |
| APO E | 2565.45 | (R) AATVGSLAGQPLQERAQAWGERLR | | |
| | 2409.13 | (R) AATVGSLAGQPLQERAQAWGERL. | | |
| Clusterin | 1277.71 | HFFFPKSRIV (R) | | |
| | 822.41 | HFFFPK | | |
| Bradykinin | 1060.57 | RPPGFSPFR | | |
| | 904.48 | RPPGFSPF. | | |
| Kininogen HMW | 2209.08 | (R) KHNLGHGHKHERDQGHGHQ (R) | | |
| | 1943.88 | NLGHGHKHERDQGHGHQ (R) | | |
| | 2126.94 | (R) GHGLGHGHEQQHGLGHGHKF(K) | | |
| Factor XIII | 2602.15 | (R) AVPPNNSNAAEDDLPTVELQGVVPR | | |
| Transthyretin | 2451.11 | (K) ALGISPFHEHAEVVFTANDSGPR | | |

FIG. 5A

| Peptide (m/z) | Norm. Intensity Controls (Median) | Ratio of medians (cases/controls) | | | p-value Mann-Whitney | | | p-value Kluskal-Wallis Multiclass | |
|---|---|---|---|---|---|---|---|---|---|
| | | Prostate | Bladder | Breast | | | | | |
| 1536.68 | 979 | 0.58 | 0 | 0.54 | | | | 5.10E-12 | FPA |
| 1463.65 | 5134 | 0.66 | 0.35 | 0.8 | | | 0.128 | 1.88E-07 | |
| 1350.64 | 4497 | 0.47 | 0.46 | 0.35 | | | | 1.38E-14 | |
| 1263.6 | 3272 | 0.2 | 0.24 | 0.23 | | | | 2.74E-16 | |
| 1206.57 | 4517 | 0.5 | 0.44 | 0.69 | | | 0.0654 | 1.31E-09 | |
| 1077.53 | 3702 | 0.54 | 0.5 | 0.95 | | | 0.683 | 1.97E-14 | |
| 1020.47 | 4019 | 0.28 | 0.28 | 0.47 | | | 0.0323 | 1.67E-13 | |
| 905.5 | 3982 | 0.97 | 0.73 | 1.48 | 0.578 | | | 4.11E-08 | |
| 758.45 | 426 | 0.66 | 0.95 | 0.65 | | | 0.443 | 1.25E-08 | |
| 3261.43 | 4053 | 0.33 | 0.08 | 0.74 | | | 0.875 | 6.77E-21 | Fbrgn-α |
| 3190.36 | 2189 | 0.52 | 0 | 0.94 | | | 0.499 | 3.76E-17 | |
| 2931.2 | 2537 | 1.24 | 0.13 | 0.97 | 0.416 | | 0.937 | 5.39E-09 | |
| 2758.26 | 1871 | 0.77 | 0.03 | 0.98 | 0.0514 | | 0.695 | 8.37E-11 | |
| 2553.01 | 1333 | 1.35 | 1.31 | 1.5 | 0.163 | 0.101 | 0.0837 | 0.128 | |
| 2379.03 | 351 | 1.57 | 0.22 | 1.71 | 2.37E-04 | | | 1.54E-16 | |
| 2816.25 | 1 | 68 | 223 | 1 | 5.35E-03 | | 0.627 | 2.18E-15 | |
| 3239.22 | 1 | 1 | 1 | 1 | 0.316 | 0.82 | 0.906 | 0.575 | |
| 2659.03 | 144 | 1.37 | 1.18 | 2.45 | 0.0205 | 0.254 | | 3.78E-08 | |
| 2021.06 | 4773 | 1.05 | 0.86 | 0.93 | 0.193 | 0.147 | 1 | 0.041 | C3f |
| 1864.95 | 1219 | 2.18 | 3.33 | 0.3 | | | | 2.17E-19 | |
| 1777.93 | 232 | 4.37 | 7.7 | 0.96 | | | 0.522 | 1.85E-15 | |
| 1690.9 | 196 | 4.05 | 6.85 | 1.01 | | | 0.4 | 4.77E-13 | |
| 1562.84 | 789 | 0.79 | 1.13 | 0.54 | 0.46 | 0.0904 | | 3.64E-08 | |
| 1449.76 | 1 | 1885 | 2646 | 437 | | | 0.852 | 1.98E-14 | |
| 1211.7 | 177 | 7.86 | 10.6 | 0.01 | 8.63E-04 | | 0.251 | 6.69E-11 | |
| 1055.6 | 1 | 227 | 1051 | 1 | | | 8.13E-03 | 1.22E-13 | |
| 942.43 | 542 | 1.74 | 3.18 | 0.58 | 1.01E-03 | | | 6.77E-21 | |
| 1751.88 | 110 | 1.82 | 5.7 | 1.36 | 0.0103 | | 0.389 | 9.48E-13 | |
| 1895.99 | 819 | 1.27 | 3.33 | 2.95 | 0.0153 | | | 9.14E-17 | C4α |
| 1739.93 | 1020 | 0.75 | 0.65 | 2.76 | 0.0758 | 0.12 | | 2.84E-08 | |
| 1626.85 | 274 | 1.09 | 0.88 | 2.78 | 0.268 | 1 | | 4.28E-10 | |
| 1498.91 | 1 | 1 | 809 | 1 | 0.0525 | | 0.429 | 5.31E-15 | |
| 3200.52 | 1 | 1 | 1 | 1 | 0.46 | 0.0181 | 0.389 | 0.0349 | |
| 2704.13 | 1 | 61 | 49 | 133 | 0.0338 | 0.0243 | | 2.17E-06 | |
| 2305.2 | 54 | 3.75 | 2.36 | 3.49 | | | | 7.90E-10 | |
| 1762.87 | 95 | 1.62 | 0.01 | 3.16 | 0.268 | | | 2.32E-13 | |
| 998.45 | 1 | 121 | 256 | 147 | | | | 7.92E-09 | ITIH4 |
| 2183.91 | 233 | 1.71 | 1.79 | 2.83 | | 2.21E-04 | | 9.87E-11 | |
| 3970.97 | 1 | 1 | 957 | 1 | 1.00 | | 0.29 | 2.68E-09 | |
| 3272.5 | 1 | 1 | 1277 | 1 | 0.0122 | | 0.887 | 2.82E-14 | |
| 2724.48 | 93 | 1.75 | 6.17 | 1.64 | | | 4.31E-04 | 9.52E-13 | |
| 2627.48 | 88 | 2.24 | 0.26 | 1.07 | | 0.0235 | 0.887 | 8.19E-06 | |
| 2358.09 | 1 | 100 | 73 | 531 | 3.68E-04 | 4.39E-03 | | 8.65E-13 | |
| 2271.14 | 177 | 4.58 | 2.64 | 1.46 | | | 0.0981 | 3.08E-13 | |
| 2028.01 | 1 | 1 | 265 | 1 | 1 | 0.0181 | 0.8 | 0.0314 | |
| 1786.86 | 97 | 2.39 | 2.88 | 2.3 | 0.0165 | 0.00333 | | 2.59E-03 | |
| 842.4 | 96 | 1.49 | 0.01 | 1.04 | | | 0.245 | 2.73E-12 | |
| 2156.52 | 134 | 3.43 | 10.68 | 1.33 | | | 0.198 | 1.74E-19 | |
| 2115.01 | 95 | 3.22 | 12.23 | 10.61 | | | | 5.82E-18 | |
| 3377.45 | 1 | 1 | 1 | 1 | 1 | 0.887 | 0.625 | 0.879 | APO A-I |
| 1807.78 | 1 | 1 | 1 | 1 | 1 | 0.0484 | 0.329 | 0.158 | |
| 3182.46 | 130 | 0.74 | 6.36 | 1 | 0.0228 | | 0.923 | 1.38E-09 | |
| 1971.16 | 1 | 1 | 641 | 1 | 0.989 | | 0.424 | 1.89E-10 | |
| 2052.89 | 1 | 105 | 306 | 1 | 4.91E-04 | | 0.127 | 5.75E-12 | |
| 2508.16 | 117 | 1.38 | 1.2 | 7.96 | 0.0101 | 0.0929 | | 5.60E-14 | APO A-IV |
| 2755.2 | 89 | 1.11 | 12.35 | 1.22 | 0.605 | | 0.533 | 3.06E-07 | |
| 1927.94 | 1 | 79 | 671 | 1 | 0.0241 | | 0.12 | 1.47E-16 | |
| 1771.81 | 1 | 143 | 220 | 1 | 0.0418 | | 0.443 | 3.05E-06 | |

FIG. 5B

| | | | | | | | | | |
|---|---|---|---|---|---|---|---|---|---|
| 2565.43 | 1 | 1 | 902 | 1 | 0.532 | | 0.105 | 4.26E-13 | APO E |
| 2409.13 | 1 | 97 | 2124 | 109 | 8.82E-04 | | 6.77E-03 | 7.39E-13 | |
| 1277.71 | 1 | 251 | 1406 | 1 | | | 0.434 | 5.74E-20 | Clusterin-β |
| 822.41 | 178 | 1.15 | 4.66 | 0.76 | 0.11 | | 7.42E-03 | 3.24E-15 | |
| 1060.57 | 3972 | 0.77 | 0.43 | 1.9 | 4.89E-04 | | | 9.04E-24 | Bradykinin |
| 904.48 | 4265 | 1.06 | 0.79 | 1.62 | 0.593 | | | 3.65E-14 | |
| 2209.08 | 100 | 1.72 | 2.07 | 1.36 | 0.00215 | | 0.625 | 1.37E-04 | HMW Kinino |
| 1943.88 | 1 | 158 | 141 | 1 | | | 0.779 | 1.19E-09 | |
| 2126.94 | 1 | 1 | 1 | 71 | 0.453 | 0.639 | 4.66E-03 | 0.0286 | |
| 2502.15 | 163 | 2.84 | 2.3 | 4.73 | | 0.0317 | | 6.60E-10 | Factor XIIIa |
| 2451.11 | 58 | 0.02 | 1.17 | 3.07 | 0.64 | 0.396 | | 4.49E-06 | Transthyretr |

FIG. 5B (CONT'D)

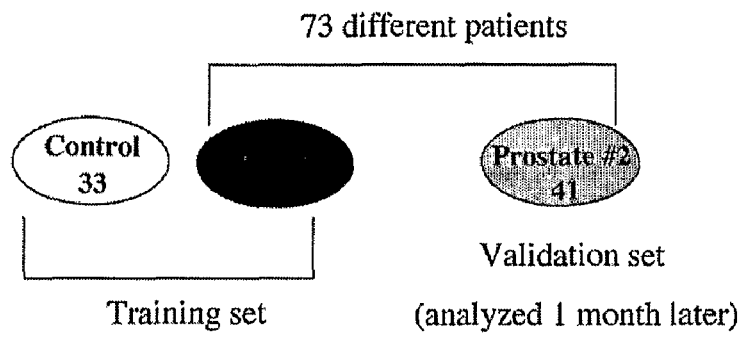
FIG. 8A
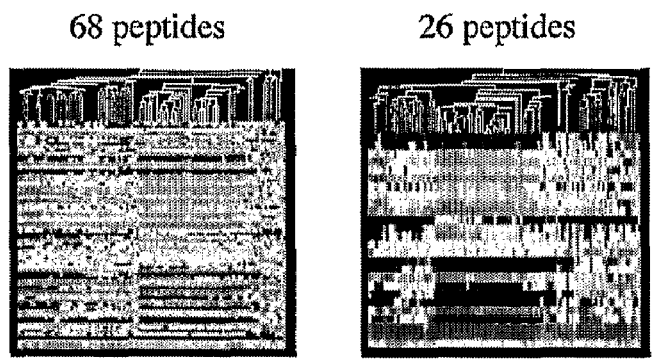
FIG. 8B
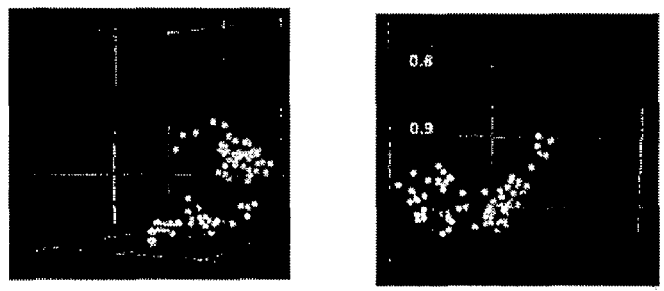
FIG. 8C
| # m/z-bins | Binary | Multiclass |
|---|---|---|
| 651 | 100% (41/41) | 97.5% (40/41) |
| 68 | 100% (41/41) | 97.5% (40/41) |
| 26 | 100% (41/41) | 97.5% (40/41) |
FIG. 8D

A

B

A

Binary Comparisons Mean ± STD (Median)

| M/Z-value | Prostate (14) | Breast (14) | Bladder (58) | Controls |
|---|---|---|---|---|
| 823 | 252.99 ± 173.92, (204.02) | 160.11 ± 69.57, (135.22) | 1064.54 ± 726.55, (829.12) | 105.36 ± 59.09, (177.91) |
| 830 | 254.8 ± 166.72, (233.97) | 143.99 ± 43.67, (142.23) | 1156.92 ± 703.1, (1243.67) | 176.1 ± 127.5, (149.42) |
| 890 | 504.67 ± 338.63, (543.63) | 309.71 ± 123.02, (280.38) | 778.16 ± 225.79, (752.41) | 404.31 ± 117.45, (371.2) |
| 936 | 4561.2 ± 1727.3, (4511.86) | 7338.56 ± 2182.97, (6918.05) | 3272.39 ± 767.81, (3381.28) | 4369.04 ± 530.06, (4265.11) |
| 944 | 1161.16 ± 752.6, (943.64) | 332.25 ± 102.72, (313.79) | 2817.62 ± 707.49, (2808.31) | 643.38 ± 420.86, (542) |
| 1023 | 1581.47 ± 1259.27, (1121.19) | 2769.8 ± 1505.14, (1894) | 1207.52 ± 762.91, (1116.83) | 4016.7 ± 464.05, (4018.76) |
| 1046 | 644.12 ± 245.1, (371.29) | 763.89 ± 221.41, (743.79) | 155.23 ± 151.58, (160.86) | 1002.57 ± 279.35, (894.87) |
| 1057 | 274.25 ± 299.72, (226.73) | 181.78 ± 247.01, (1) | 939.21 ± 493.65, (1050.72) | 25.32 ± 61.91, (1) |
| 1062 | 2911.33 ± 1457.22, (3074.48) | 8192.98 ± 2705.77, (7566.57) | 1746.85 ± 958.92, (1694.1) | 4216.94 ± 790.82, (3972.91) |
| 1079 | 1880.88 ± 1044.4, (2014.18) | 3068.8 ± 1709.02, (3515.63) | 1999.45 ± 528.38, (1833.42) | 3664.76 ± 401.86, (3702.34) |
| 1100 | 438.06 ± 226.06, (392.24) | 186.9 ± 59.59, (204.22) | 608.4 ± 262.61, (581) | 254.91 ± 72.11, (253.33) |
| 1125 | 252.64 ± 146.67, (214.62) | 477.82 ± 165.46, (445.61) | 115.07 ± 77.82, (128.27) | 521.36 ± 195.04, (515.14) |
| 1209 | 2259.24 ± 1661.17, (2267.99) | 3457.89 ± 2204.84, (3107.73) | 2171.06 ± 864.61, (1970.59) | 4558.92 ± 641.12, (4517.21) |
| 1214 | 1460.59 ± 1200.01, (1301.49) | 305.12 ± 398.04, (1) | 2038.25 ± 989.02, (1912.04) | 483.85 ± 741.63, (177.1) |
| 1231 | 142.29 ± 127.3, (162.25) | 177.67 ± 111.17, (222.86) | 867.3 ± 495, (1015.21) | 173.62 ± 133.9, (179.55) |
| 1266 | 908.3 ± 670.36, (628.46) | 1200.4 ± 1082.93, (755.41) | 988.66 ± 727.44, (785.8) | 3187.00 ± 640.76, (3271.91) |
| 1280 | 315.68 ± 237.5, (251.92) | 84.09 ± 166.11, (1) | 1446.41 ± 708.12, (1406.33) | 73.44 ± 278.74, (1) |
| 1313 | 106.62 ± 251.67, (1) | 36.1 ± 77.38, (1) | 715.63 ± 501.13, (634.96) | 38.84 ± 129.6, (1) |
| 1353 | 2080.43 ± 1235.52, (2102.44) | 2153.51 ± 1688.56, (1571.81) | 2107.42 ± 835.37, (2086.29) | 4545.13 ± 463.86, (4496.6) |
| 1383 | 145.8 ± 87.14, (164.77) | 783.38 ± 358.17, (795.73) | 192.51 ± 178.45, (151.76) | 173.54 ± 76.32, (183.51) |
| 1426 | 193.04 ± 195.89, (174.45) | 277.17 ± 80.82, (286.87) | 1103.34 ± 806.59, (840.46) | 320.38 ± 250.78, (261.41) |
| 1453 | 2159.29 ± 1380.63, (1865.15) | 390.67 ± 177.43, (437.78) | 2751.63 ± 1140.1, (2646.56) | 565.13 ± 755.93, (1) |
| 1468 | 3240.85 ± 1805.38, (3378.1) | 3949.53 ± 2241.27, (4081.59) | 2915.25 ± 948.24, (2834.33) | 5117.08 ± 720.94, (5133.73) |
| 1502 | 100.31 ± 147.84, (1) | 67.74 ± 113.81, (1) | 831.64 ± 535, (809.48) | 29.71 ± 81.34, (1) |
| 1522 | 688.1 ± 334.43, (596.26) | 1047.44 ± 452.72, (811.47) | 269.71 ± 299.37, (242.68) | 1465.61 ± 330.44, (1583.23) |
| 1534 | 588.53 ± 540.08, (758.39) | 944.03 ± 726.19, (746) | 1915.21 ± 742.33, (2058.15) | 866.59 ± 402.35, (788.51) |
| 1540 | 511.92 ± 415.35, (568.44) | 548.63 ± 337.55, (526.19) | 63.06 ± 247.7, (1) | 904.68 ± 283.76, (979.16) |
| 1566 | 866.76 ± 701.1, (620.6) | 448.06 ± 107.93, (424.39) | 1121.01 ± 631.63, (892.96) | 769.93 ± 167, (788.67) |
| 1619 | 494.63 ± 434.51, (345.33) | 411.56 ± 270.5, (308.13) | 183.73 ± 118.29, (179.97) | 565.78 ± 195.42, (533.41) |
| 1630 | 284.69 ± 140.7, (298.72) | 810.04 ± 377.15, (764.04) | 318.86 ± 183.28, (240.99) | 249.83 ± 113.53, (274.41) |
| 1694 | 1190.9 ± 1175.42, (795.86) | 158.28 ± 125, (197.94) | 1801.44 ± 1248.81, (1346.59) | 264.99 ± 280.67, (196.44) |
| 1743 | 868.29 ± 507.68, (794.05) | 2525.75 ± 1182.77, (2817.04) | 904.21 ± 659.21, (669.96) | 985.98 ± 272.35, (1020.07) |
| 1757 | 175.76 ± 150.02, (199.37) | 139.54 ± 140.04, (149.67) | 660.76 ± 269.38, (625.98) | 90.96 ± 75.34, (109.77) |
| 1782 | 1755.46 ± 1517.47, (1015.47) | 206.3 ± 110.37, (222.49) | 2209.42 ± 1326.83, (1789.4) | 348.30 ± 261.82, (232.33) |
| 1868 | 3335.23 ± 1759.63, (2068.63) | 444.93 ± 164.29, (369.94) | 3975.98 ± 807.39, (4057.03) | 1387.84 ± 932.62, (1219.19) |
| 1890 | 1159.19 ± 551.08, (1042.22) | 2540.46 ± 1183.38, (2415.05) | 2569.25 ± 761.88, (2732.08) | 617.45 ± 243.86, (819.5) |
| 1931 | 182.49 ± 219.7, (78.66) | 6.36 ± 29.14, (1) | 694.31 ± 78.06, (671.27) | 40.47 ± 65.75, (1) |
| 1975 | 45.77 ± 110.64, (1) | 56.5 ± 85.43, (1) | 740.54 ± 588.68, (640.68) | 31.52 ± 79, (1) |
| 1981 | 465.51 ± 303.8, (401.9) | 253.16 ± 94.16, (252.61) | 500.78 ± 192.1, (503.42) | 280.44 ± 83.01, (281.52) |
| 2119 | 423.08 ± 416.02, (307.12) | 938.9 ± 524.4, (1011.77) | 1196.66 ± 694.48, (1166) | 104.39 ± 139.48, (95.37) |
| 2145 | 147.6 ± 116.77, (147.98) | 175.22 ± 110.49, (164.93) | 566.47 ± 246.56, (587.13) | 88.45 ± 42.79, (85.25) |
| 2189 | 484.05 ± 193.51, (399.04) | 700.19 ± 340.28, (659.4) | 442.72 ± 223.55, (416.33) | 248.71 ± 72.2, (233.35) |
| 2273 | 1179.54 ± 966.82, (610.1) | 396.35 ± 448.85, (258.68) | 578.64 ± 448.48, (467.27) | 198.08 ± 126.21, (176.84) |
| 2341 | 225.26 ± 140.74, (197.02) | 235.01 ± 143.67, (236.19) | 771.06 ± 852.04, (548.12) | 118.8 ± 55.8, (112.58) |
| 2358 | 176.83 ± 285.35, (99.81) | 534.86 ± 312.47, (531.1) | 75.2 ± 76.55, (72.58) | 26.81 ± 49.77, (1) |
| 2383 | 202.55 ± 380.24, (549.5) | 628.11 ± 218.93, (680.55) | 198.26 ± 76.55, (76.29) | 329.12 ± 105.17, (350.32) |
| 2414 | 207.25 ± 204.92, (95.71) | 97.34 ± 70.28, (108.24) | 1818.24 ± 1301.3, (2124.24) | 84.07 ± 251.49, (1) |
| 2513 | 215.6 ± 379.84, (169.91) | 854.57 ± 405.59, (928.01) | 151.76 ± 74.32, (148.08) | 102.04 ± 60.83, (116.58) |
| 2570 | 63.36 ± 257.03, (1) | 0 ± 0, (1) | 960.6 ± 215.63, (901.87) | 54.15 ± 250.92, (1) |
| 2615 | 565.34 ± 322.05, (476.37) | 686.64 ± 335.04, (792.37) | 359.77 ± 315.07, (385.25) | 182.04 ± 73.01, (167.56) |
| 2729 | 310.64 ± 437.03, (192.51) | 152.86 ± 60.24, (152.26) | 530.65 ± 268.79, (573.43) | 109.58 ± 77.01, (92.98) |
| 2760 | 162.39 ± 302.21, (65.65) | 83.07 ± 70.13, (103.19) | 1333.1 ± 1073.2, (1104.71) | 107.06 ± 178.88, (89.45) |
| 2773 | 1374.94 ± 769.55, (1402.29) | 1729.28 ± 615.47, (1767.74) | 238.77 ± 450.16, (57.11) | 1844.65 ± 626.78, (1810.76) |
| 2937 | 2849.34 ± 1600.28, (3138.65) | 2460.84 ± 1085.04, (2461.74) | 449 ± 556.03, (327.65) | 2535.87 ± 532.94, (2536.62) |
| 3102 | 490.75 ± 219.94, (460.98) | 218.04 ± 232.1, (178.22) | 1378.69 ± 774.81, (1435.63) | 146.55 ± 76.97, (134.48) |
| 3188 | 185.07 ± 351.68, (69.45) | 116.96 ± 71.53, (130.31) | 994.5 ± 724.4, (814.41) | 146.72 ± 110.92, (130.05) |
| 3195 | 1230.27 ± 914.13, (1140.8) | 1968.93 ± 862.4, (2042.71) | 163.96 ± 352.72, (1) | 2238.86 ± 540.43, (2188.87) |
| 3267 | 1694.49 ± 1337.71, (1340.86) | 3845.22 ± 1507.73, (3737.23) | 363.36 ± 435.27, (305.7) | 4053.35 ± 603.64, (4055.38) |
| 3278 | 241 ± 545.8, (1) | 169.86 ± 331.01, (1) | 1187.05 ± 600.05, (1277) | 35.69 ± 153.42, (1) |
| 3960 | 1089.65 ± 860.43, (985.2) | 693.07 ± 377.07, (590.35) | 1748.34 ± 956.75, (1677.38) | 694.26 ± 210.11, (682.01) |
| 3976 | 92.08 ± 242.92, (1) | 274.17 ± 624.47, (1) | 1142.42 ± 880.3, (957.31) | 81.4 ± 165.25, (1) |
| 4197 | 885.71 ± 594.73, (876.96) | 1599.54 ± 357.22, (1684.00) | 68.51 ± 256.55, (1) | 1384.26 ± 345.28, (1260.57) |
| 4270 | 815.44 ± 772.4, (661.24) | 463.83 ± 1014.05, (205.45) | 2619.7 ± 1488.91, (2851.85) | 268.04 ± 572.24, (1) |
| 4631 | 050.45 ± 378.46, (310.99) | 954.7 ± 271.21, (956.77) | 664.56 ± 335.09, (747.07) | 1193.67 ± 292.57, (1194.53) |
| 4990 | 188.71 ± 488.44, (1) | 0 ± 0, (1) | 828.21 ± 457.82, (739.13) | 41.29 ± 139.31, (1) |
| 5052 | 431.3 ± 291.5, (440.99) | 547.41 ± 189.65, (524.93) | 220.54 ± 409.22, (1) | 606.09 ± 264.85, (571.51) |
| 5589 | 1054.81 ± 627.53, (1017.01) | 2566.05 ± 1033.3, (2365.27) | 243.27 ± 400.35, (146.37) | 1850.13 ± 522.29, (1871.1) |
| 6265 | 580.23 ± 381.87, (736.72) | 1376.35 ± 358.29, (1379.52) | 613.52 ± 262.95, (612.02) | 1230.99 ± 312.11, (1224.81) |

Ratio: Group/Control

| M/Z | Prostate | Breast | Bladder | Prostate2 |
|---|---|---|---|---|
| 823 | 1.15 | 0.75 | 4.66 | 0.52 |
| 830 | 1.57 | 0.95 | 8.32 | 0.58 |
| 890 | 1.46 | 0.79 | 2.03 | 1.03 |
| 906 | 1.06 | 1.62 | 0.79 | 2.09 |
| 944 | 1.74 | 0.56 | 5.18 | 2.01 |
| 1022 | 0.38 | 0.47 | 0.29 | 0.15 |
| 1046 | 0.42 | 0.83 | 0.19 | 0.40 |
| 1057 | 226.73 | 1.00 | 1050.72 | 191.06 |
| 1062 | 0.77 | 1.90 | 0.43 | 1.16 |
| 1079 | 0.54 | 0.95 | 0.50 | 0.59 |
| 1100 | 1.43 | 0.81 | 2.29 | 0.99 |
| 1125 | 0.42 | 0.87 | 0.25 | 0.28 |
| 1209 | 0.50 | 0.69 | 0.44 | 0.19 |
| 1214 | 7.86 | 0.91 | 10.50 | 7.39 |
| 1231 | 0.90 | 1.24 | 5.66 | 0.33 |
| 1266 | 0.20 | 0.23 | 0.24 | 0.11 |
| 1280 | 251.62 | 1.00 | 1406.33 | 231.96 |
| 1313 | 1.00 | 1.00 | 634.96 | 21.25 |
| 1353 | 0.47 | 0.35 | 0.46 | 0.25 |
| 1383 | 0.90 | 4.34 | 0.83 | 0.42 |
| 1426 | 0.67 | 1.10 | 3.22 | 0.40 |
| 1453 | 1885.15 | 437.78 | 2646.51 | 2217.87 |
| 1468 | 0.66 | 0.80 | 0.55 | 0.33 |
| 1502 | 1.00 | 1.00 | 809.48 | 98.91 |
| 1522 | 0.38 | 0.58 | 0.15 | 0.33 |
| 1534 | 0.97 | 0.95 | 2.61 | 8.73 |
| 1540 | 0.58 | 0.54 | 0.00 | 0.31 |
| 1566 | 0.79 | 0.54 | 1.13 | 0.60 |
| 1619 | 0.65 | 0.55 | 0.34 | 0.55 |
| 1630 | 1.09 | 2.75 | 0.88 | 0.89 |
| 1694 | 4.05 | 1.01 | 6.85 | 4.92 |
| 1743 | 0.75 | 2.76 | 0.66 | 1.23 |
| 1757 | 1.82 | 1.36 | 5.78 | 1.34 |
| 1782 | 4.37 | 0.96 | 7.70 | 6.79 |
| 1868 | 2.18 | 0.30 | 3.33 | 3.89 |
| 1899 | 1.27 | 2.95 | 3.33 | 1.97 |
| 1931 | 78.66 | 1.00 | 671.27 | 158.45 |
| 1975 | 1.00 | 1.00 | 640.68 | 52.59 |
| 1981 | 1.38 | 0.87 | 1.73 | 1.52 |
| 2119 | 3.22 | 10.61 | 12.23 | 2.84 |
| 2145 | 1.74 | 1.63 | 6.89 | 1.28 |
| 2189 | 1.71 | 2.83 | 1.79 | 2.17 |
| 2273 | 4.53 | 1.46 | 2.99 | 6.30 |
| 2341 | 1.75 | 2.10 | 4.87 | 1.58 |
| 2358 | 96.81 | 531.10 | 72.58 | 112.76 |
| 2383 | 1.57 | 1.71 | 0.22 | 3.46 |
| 2414 | 96.71 | 109.24 | 2124.24 | 64.14 |
| 2513 | 1.38 | 7.96 | 1.20 | 1.69 |
| 2570 | 1.00 | 1.00 | 901.67 | 170.85 |
| 2615 | 2.84 | 4.73 | 2.30 | 5.86 |
| 2729 | 1.75 | 1.64 | 6.17 | 3.64 |
| 2760 | 1.11 | 1.22 | 12.35 | 5.42 |
| 2773 | 0.77 | 0.95 | 0.03 | 1.61 |
| 2937 | 1.24 | 0.97 | 0.13 | 2.32 |
| 3162 | 3.43 | 1.33 | 10.68 | 4.23 |
| 3188 | 0.74 | 1.00 | 0.26 | 0.01 |
| 3193 | 0.52 | 0.94 | 0.00 | 0.94 |
| 3207 | 0.33 | 0.62 | 0.08 | 0.74 |
| 3278 | 1.00 | 1.00 | 1277.00 | 399.45 |
| 3960 | 1.33 | 0.87 | 2.46 | 1.88 |
| 3976 | 1.00 | 1.00 | 957.31 | 302.46 |
| 4197 | 0.70 | 1.34 | 0.00 | 1.51 |
| 4270 | 661.24 | 205.45 | 2851.85 | 753.39 |
| 4631 | 0.69 | 0.83 | 0.63 | 1.45 |
| 4990 | 1.00 | 1.00 | 739.13 | 63.32 |
| 5052 | 0.77 | 0.62 | 0.00 | 0.84 |
| 5888 | 0.54 | 1.26 | 0.08 | 1.48 |
| 9265 | 0.60 | 1.13 | 0.50 | 1.72 |

FIG. 13B

C p-value

| M/Z | Prostate | Breast | Bladder | Prostate2 | Multiclass |
|---|---|---|---|---|---|
| 823 | 0.11 | 7.42E-03 | 1.30E-12 | 3.27E-05 | 3.24E-15 |
| 830 | 2.53E-05 | 0.558 | 1.05E-09 | 1.21E-04 | 1.85E-15 |
| 850 | 1.55E-04 | 9.54E-03 | 6.72E-10 | 0.805 | 1.64E-14 |
| 906 | 0.593 | 7.39E-10 | 3.12E-07 | 5.08E-07 | 3.65E-14 |
| 944 | 1.01E-03 | 3.56E-05 | 7.65E-13 | 9.07E-05 | 6.77E-21 |
| 1022 | 1.34E-11 | 0.0323 | 2.80E-13 | 6.20E-13 | 1.67E-13 |
| 1045 | 2.20E-11 | 1.22E-03 | 1.80E-13 | 8.34E-05 | 9.04E-24 |
| 1057 | 5.29E-07 | 8.13E-03 | 1.80E-13 | 2.35E-09 | 1.22E-13 |
| 1062 | 4.59E-04 | 1.03E-11 | 1.03E-12 | 0.272 | 9.04E-24 |
| 1079 | 2.94E-11 | 0.683 | 7.65E-13 | 9.09E-05 | 1.97E-14 |
| 1100 | 2.96E-05 | 0.0356 | 5.55E-08 | 0.665 | 7.10E-15 |
| 1125 | 6.84E-08 | 0.676 | 7.65E-13 | 3.28E-04 | 3.51E-18 |
| 1209 | 4.18E-08 | 0.0554 | 1.30E-12 | 1.91E-10 | 1.31E-09 |
| 1214 | 8.63E-04 | 0.251 | 9.43E-08 | 4.13E-07 | 8.09E-11 |
| 1231 | 0.523 | 0.857 | 1.10E-10 | 0.02 | 9.53E-11 |
| 1266 | 6.48E-17 | 2.75E-07 | 1.05E-10 | 4.47E-20 | 2.74E-16 |
| 1280 | 4.81E-09 | 0.433 | 1.95E-13 | 5.19E-13 | 5.74E-20 |
| 1313 | 0.193 | 0.834 | 2.04E-11 | 6.81E-05 | 2.40E-12 |
| 1353 | 1.01E-15 | 4.82E-05 | 4.50E-13 | 6.20E-17 | 1.38E-14 |
| 1383 | 0.245 | 5.56E-13 | 0.500 | 3.29E-07 | 6.74E-13 |
| 1425 | 5.66E-05 | 0.601 | 8.63E-06 | 6.90E-11 | 8.37E-11 |
| 1453 | 6.66E-07 | 0.652 | 6.37E-10 | 1.40E-12 | 1.98E-14 |
| 1468 | 1.44E-05 | 0.128 | 1.25E-11 | 4.92E-05 | 1.88E-07 |
| 1502 | 0.0525 | 0.429 | 2.03E-15 | 1.71E-10 | 5.31E-15 |
| 1522 | 2.20E-11 | 1.04E-03 | 2.16E-12 | 1.76E-18 | 1.18E-19 |
| 1534 | 0.977 | 0.854 | 9.76E-06 | 0.513 | 1.33E-05 |
| 1540 | 1.08E-04 | 1.38E-04 | 2.52E-10 | 1.26E-11 | 5.10E-12 |
| 1565 | 0.46 | 6.15E-10 | 0.0904 | 2.90E-10 | 3.04E-08 |
| 1619 | 0.023 | 0.0178 | 1.05E-10 | 2.33E-04 | 4.80E-09 |
| 1630 | 0.285 | 6.69E-12 | 1 | 0.821 | 4.28E-10 |
| 1654 | 1.09E-04 | 0.4 | 5.73E-11 | 1.22E-15 | 4.77E-13 |
| 1743 | 0.0758 | 3.92E-06 | 0.129 | 0.0835 | 2.84E-08 |
| 1757 | 0.0103 | 0.369 | 4.50E-13 | 8.46E-04 | 9.48E-13 |
| 1782 | 5.29E-07 | 0.522 | 1.05E-09 | 1.18E-18 | 1.85E-15 |
| 1868 | 1.50E-05 | 1.39E-05 | 3.34E-11 | 1.18E-18 | 2.17E-19 |
| 1899 | 0.0153 | 1.04E-08 | 4.50E-13 | 6.05E-07 | 9.14E-17 |
| 1931 | 0.0241 | 0.12 | 6.60E-14 | 6.03E-09 | 1.47E-16 |
| 1975 | 0.989 | 0.424 | 4.10E-09 | 4.41E-07 | 1.89E-10 |
| 1981 | 2.15E-03 | 0.683 | 7.70E-06 | 1.03E-07 | 1.15E-07 |
| 2119 | 2.36E-07 | 8.19E-10 | 2.75E-11 | 6.62E-09 | 5.82E-18 |
| 2145 | 0.0189 | 5.27E-05 | 7.65E-13 | 0.131 | 3.45E-14 |
| 2189 | 6.59E-07 | 1.46E-08 | 2.21E-04 | 1.65E-07 | 9.87E-11 |
| 2273 | 7.63E-12 | 0.0091 | 5.29E-06 | 1.67E-13 | 3.08E-13 |
| 2341 | 3.07E-04 | 2.40E-04 | 1.05E-10 | 1.91E-04 | 1.18E-11 |
| 2358 | 3.68E-04 | 4.07E-12 | 4.39E-03 | 5.38E-12 | 8.65E-13 |
| 2383 | 4.37E-04 | 1.26E-07 | 1.25E-10 | 8.74E-11 | 1.54E-16 |
| 2414 | 8.52E-04 | 6.77E-03 | 3.52E-12 | 9.07E-05 | 7.39E-13 |
| 2513 | 0.0101 | 5.56E-13 | 0.0029 | 1.74E-05 | 5.60E-14 |
| 2570 | 0.532 | 0.105 | 2.81E-07 | 9.19E-10 | 4.26E-13 |
| 2615 | 1.43E-08 | 2.08E-07 | 0.0317 | 6.55E-19 | 6.60E-10 |
| 2720 | 5.99E-05 | 4.31E-04 | 4.45E-09 | 3.58E-11 | 9.52E-13 |
| 2760 | 0.605 | 0.533 | 1.95E-07 | 4.07E-08 | 3.06E-07 |
| 2773 | 0.0514 | 0.695 | 8.42E-11 | 2.30E-03 | 8.37E-11 |
| 2937 | 0.416 | 0.937 | 4.19E-11 | 4.55E-05 | 5.39E-09 |
| 3162 | 2.04E-12 | 0.198 | 7.04E-10 | 2.48E-15 | 1.74E-19 |
| 3185 | 0.0228 | 0.923 | 7.64E-09 | 7.31E-08 | 1.38E-09 |
| 3165 | 7.74E-07 | 0.490 | 1.95E-13 | 0.429 | 3.76E-17 |
| 3267 | 7.63E-12 | 0.875 | 1.82E-13 | 0.0218 | 6.77E-21 |
| 3278 | 0.0122 | 0.857 | 2.44E-14 | 2.65E-11 | 2.82E-14 |
| 3960 | 0.0514 | 0.546 | 1.48E-06 | 4.32E-07 | 4.78E-06 |
| 3976 | 1 | 0.29 | 5.85E-09 | 7.70E-06 | 2.68E-09 |
| 4197 | 5.73E-04 | 0.105 | 1.95E-13 | 4.14E-04 | 3.80E-16 |
| 4270 | 2.63E-04 | 0.276 | 4.92E-09 | 5.54E-07 | 1.36E-09 |
| 4631 | 3.58E-03 | 0.0323 | 3.33E-03 | 2.48E-03 | 4.27E-07 |
| 4890 | 0.288 | 0.322 | 5.15E-04 | 2.63E-05 | 5.90E-18 |
| 5052 | 8.63E-04 | 0.424 | 5.52E-03 | 0.0798 | 1.35E-08 |
| 5888 | 5.28E-06 | 0.0186 | 1.25E-11 | 0.0449 | 1.90E-19 |
| 9265 | 4.16E-04 | 0.256 | 2.03E-09 | 1.30E-04 | 1.76E-11 |

FIG. 13C

Table S2: Serum Peptide Identifications (Villanueva et al.)

| m/z | MH+ | Δ(Da) | AA sequence |
|---|---|---|---|

1) Fibrinopeptide A (FPA); NCBI # 229185 — Fibrinogen alpha; NCBI # 4033511 (Res. 20-35)

| m/z | MH+ | Δ(Da) | AA sequence |
|---|---|---|---|
| 758.45 | 758.41 | (0.04) | LAEGGGVR |
| 905.50 | 905.48 | (0.02) | FLAEGGGVR |
| 1020.47 | 1020.51 | (0.04) | DFLAEGGGVR |
| 1077.53 | 1077.53 | (0.00) | GDFLAEGGGVR |
| 1206.57 | 1206.58 | (0.01) | EGDFLAEGGGVR |
| 1263.60 | 1263.59 | (0.01) | GEGDFLAEGGGVR |
| 1350.64 | 1350.63 | (0.01) | SGEGDFLAEGGGVR |
| 1465.65 | 1465.65 | (0.00) | DSGEGDFLAEGGGVR |
| 1536.68 | 1536.69 | (0.01) | ADSGEGDFLAEGGGVR = FPA |

Fibrinogen alpha; NCBI # 4033511 (Res. 548-574 and 576-604, separated by K575; 605-629)

| m/z | MH+ | Δ(Da) | AA sequence |
|---|---|---|---|
| 2816.25 | 2816.31 | (0.06) | (R) GSESGIFTNTKESSSHHPGIAEFPSRG (K) |
| 2553.01 | 2553.09 | (0.08) | | (K) SSSYSKQFTSSTSYNRGDSTFES |
| 2768.26 | 2768.22 | (0.04) | | (K) SSSYSKQFTSSTSYNRGDSTFESKS |
| 2931.20 | 2931.28 | (0.08) | | (K) SSSYSKQFTSSTSYNRGDSTFESKSY |
| 3190.36 | 3190.42 | (0.06) | | (K) SSSYSKQFTSSTSYNRGDSTFESKSYKM |
| 3261.43 | 3261.45 | (0.02) | | (K) SSSYSKQFTSSTSYNRGDSTFESKSYKMA |
| 2379.03 | 2379.03 | (0.00) | | (K) .SSYSKQFTSSTSYNRGDSTFE |
| 3206.34 | 3190.42 [Met_ox] = 3206.41 | | |
| 3277.39 | 3261.45 [Met_ox] = 3277.44 | | | gsesgiftntkessshhpgiaefpsrgksssyskqftsststsynrgdstfesksykma (548-604)

| | | | |
|---|---|---|---|
| 2659.03 | 2659.24 | (0.21) | .....DEAGSEADHEGTHSTKRGHAKSRPV (R) |
| 3239.22 | 3239.51 | (0.29) | SYKMADEAGSEADHEGTHSTKRGHAKSRPV (R) |

FIG. 14

2) Complement C3f (C3f); NCBI #226159 — COMPLEMENT C3; NCBI # 68766 (Res. 1304-1320)

| | | |
|---|---|---|
| 942.43 | 942.47 (0.04) | HWESASLL. |
| 1055.60 | 1055.55 (0.05) | IHWESASLL. |
| 1211.70 | 1211.65 (0.05) | RIHWESASLL. |
| 1348.70 | 1348.71 (0.01) | HRIHWESASLL. |
| 1449.76 | 1449.76 (0.00) | THRIHWESASLL. |
| 1562.84 | 1562.84 (0.00) | ITHRIHWESASLL. |
| 1690.90 | 1690.93 (0.03) | KITHRIHWESASLL. |
| 1777.93 | 1777.97 (0.04) | SKITHRIHWESASLL. |
| 1864.95 | 1864.99 (0.04) | SSKITHRIHWESASLL. |
| 2021.06 | 2021.10 (0.04) | SSKITHRIHWESASLLR  = C3f |
| 1751.88 | 1751.91 (0.03) | SSKITHRIHWESASL.. |

3) Complement C4 precursor; NCBI # 20141171 — all peptides map to C4-alpha
(Res. 1337-1351 and 1353-1382, separated by R1352)

| | | |
|---|---|---|
| 1498.91 | 1498.78 (0.13) | NGFKSHALQLNNR.. |
| 1626.85 | 1626.84 (0.01) | NGFKSHALQLNNRQ. |
| 1739.93 | 1739.92 (0.01) | NGFKSHALQLNNRQI (R) |
| 1895.99 | 1896.02 (0.03) | RNGFKSHALQLNNRQI (R) |
| 1762.87 | 1762.92 (0.05) | (R) GLEEELQFSLGSKINV |
| 2305.20 | 2305.19 (0.01) | (R) GLEEELQFSLGSKINVKVGGNS |
| 2704.13 | 2704.44 (0.31) | (R) GLEEELQFSLGSKINVKVGGNSKGTL |
| 3200.52 | 3200.79 (0.27) | (R) GLEEELQFSLGSKINVKVGGNSKGTLKVLR |

(Res. 957-979)

| | | |
|---|---|---|
| 2551.06 | 2551.16 (0.10) | (R) TIEIPGNSDPNMIPDGDENSYVR |

FIG. 14 (CONT'D)

4) Inter-alpha-trypsin inhibitor heavy chain H4 (ITIH4); NCBI # 13432192

(Res. 650-688)

| | | |
|---|---|---|
| 842.40 | 842.39 (0.01) | HAAYHPF. |
| 1786.86 | 1786.85 (0.01) | GLPGPPDVPDHAAYHPF. |
| 2028.01 | 2027.99 (0.02) | QLGLPGPPDVPDHAAYHPF. |
| 2271.14 | 2271.12 (0.02) | SRQLGLPGPPDVPDHAAYHPF. |
| 2358.09 | 2358.15 (0.06) | SSRQLGLPGPPDVPDHAAYHPF. |
| 2627.48 | 2627.34 (0.14) | GVLSSRQLGLPGPPDVPDHAAYHPF. |
| 2724.48 | 2724.38 (0.10) | PGVLSSRQLGLPGPPDVPDHAAYHPF. |
| 3272.50 | 3272.63 (0.13) | MNFRPGVLSSRQLGLPGPPDVPDHAAYHPF. |
| 3970.97 | 3970.97 (0.00) | (R) QAGAAGSRMNFRPGVLSSRQLGLPGPPDVPDHAAYHPF. = 'propeptide' (minus R) |
| 2183.91 | 2184.09 (0.18) | QLGLPGPPDVPDHAAYHPFR |
| 998.45 | 998.49 (0.04) | HAAYHPFR |

(Res. 617-644)

| | | |
|---|---|---|
| 3156.52 | 3156.61 (0.09) | (R) NVHSGSTFFKYYLQGAKIPKPEASFSPR |

ITIH4 splice variant: PRO1851; NCBI # 7770149 (Res. 347-367)

| | | |
|---|---|---|
| 2115.01 | 2115.04 (0.03) | (R) NVHSAGAAGSRMNFRPGVLSS (R) |

FIG.1H (CONT'D)

5) Apolipoprotein A-I; NCBI # 4557321 (Res. 220-238 and 240-267, separated by R239)

2052.89  2053.07 (0.18)    (K) ATEHLSTLSEKAKPALEDL (R)
3182.46  3182.72 (0.26)              (R) QGLLPVLESFKVSFLSALEEYTKKLNTQ|c-t
1971.16  1971.04 (0.12)                           VSFLSALEEYTKKLNTQ|c-t (Res. 148-176)

1807.78  1807.92 (0.14)          ELQEGARQKLHELQE
3377.45  3377.71 (0.26)    (R) AELQEGARQKLHELQEKLSPLGEEM$_{ox}$RDRA (R)

6) Apolipoprotein A-IV; NCBI # 114006 (Res. 256-278 and 280-304, separated by K279)

2508.16  2508.35 (0.19)    LSASAEELRQRLAPLAEDVRGNL (K)
1771.81  1771.84 (0.03)                              SLAELGGHLDQQVEEF.
2599.18  2599.25 (0.07)                (K) GNTEGLQKSLAELGGHLDQQVEEF.
2755.20  2755.35 (0.15)                (K) GNTEGLQKSLAELGGHLDQQVEEFR
1927.94  1927.94 (0.00)                              SLAELGGHLDQQVEEFR

7) Apolipoprotein C-I; NCBI # 114016

2778.15  2778.44 (0.29)    DVSSALDKLKEFGNTLEDKARELIS (R)

8) Apolipoprotein E; NCBI # 114039 (Res. 210-233)

2267.07  2267.18 (0.11)          TVGSLAGQPLQERAQAWGERL.
2409.13  2409.26 (0.13)    (R) AATVGSLAGQPLQERAQAWGERL.
2565.45  2565.36 (0.09)    (R) AATVGSLAGQPLQERAQAWGERLR

9) CLUSTERIN precursor; NCBI # 42716297 (Res. 269-278; C-t of beta-chain, minus R279)

822.41   822.43 (0.02)    HFFFPK
1277.71  1277.71 (0.00)    HFFFPKSRIV (R)

FIG.14 (CONT'D)

1) FIBRINOGEN ALPHA (NCBI # 4033511) -- FPA = 20-35

```
  1 mfsmrivclv lsvvgtawtA DSGEGDFLAE GGGVRgprvv erhqsackds dwpfcsdedw
 61 nykcpsgcrm kglidevnqd ftnrinklkn slfeyqknnk dshslttnim eilrgdfssa
121 nnrdntynrv sedlrsriev lkrkviekvq hiqllqknvr aqlvdmkrle vdidikirsc
181 rgscsralar evdlkdyedq qkqleqviak dllpsrdrqh lplikmkpvp dlvpgnfksq
241 lqkvppewka ltdmpqmrme lerpggneit rggstsygtg setesprnps sagswnsgss
301 gpgstgnrnp gssgtggtat wkpgssgpgs tgswnsgssg tgstgnqnpg sprpgstgtw
361 npgssergsa ghwtsessvs gstgqwhses gsfrpdspgs gnarpnnpdw gtfeevsgnv
421 spgtrreyht eklvtskgdk elrtgkekvt sgsttttrrs csktvtktvi gpdghkevtk
481 evvtsedgsd cpeamdlgtl sgigtldgfr hrhpdeaaff dtastgktfp gffspmlgef
541 vsetesrgse sgiftntkes sshhpgiaef psrgksssys kqftsstsyn rgdstfesks
601 vkmadeagse adhegthstk rghaksrpvr gihtsplgkp slsp
```

FIG. 15

2) COMPLEMENT C3 (NCBI # 68766) -- C3f = 1304-1320

```
   1 mgptsgpsll llllthlpla lgspmysiit pnilrlesee tmvleahdaq gdvpvtvtvh
  61 dfpgkklvls sektvltpat nhmgnvtfti panrefksek grnkfvtvga tfgtqvvekv
 121 vlvslqsgyl fiqtdktlyt pgstvlyrif tvnhkllpvg rtvmvnienp egipvkqdsl
 181 ssqnqlgvlp lswdipelvn mgqwkirayy enspqqvfst efevkeyvlp sfevivepte
 241 kfyyiynekg levtitarfl ygkkvegtaf vifgiqdgeq risipeslkr ipiedgsgev
 301 vlsrkvlldg vqnlraedlv gkslyvsatv ilhsgsdmvq aersgipivt spyqihftkt
 361 pkyfkpgmpf dlmvfvtnpd gspayrvpva vqggedtvqsl tqggdvakls inthpsqkpl
 421 siturtkkge lseaegatrt mqalpystvg nsnnylhlsv lrtelrpget lnvnfllrmd
 481 raheakiryy tylimnkgrl lkagrqvrep gqdlvvlpls ittdfipsfr lvayytliga
 541 sggrevvads vwvdvkdscv gslvvksgqs edrqpvpgqq mtlkiegdhg arvvlvavdk
 601 gvfvinkknk ltqskiwdvv ekadigctpg sgkdyagvfs daglftfsss gqqtaqrael
 661 qcpqpaarrr rsvqltekrm dkvgkypkel rkccedgmre npmrfscqrr trfislgeac
 721 kkvfldcccny itelrrqhar ashlglarsn ldediiaeen ivsrsefpes wlwnvedike
 781 ppkngistkl mniflkdsit tweilavsms dkkgicvadp fevtvmqdff idlrlpysvv
 841 rneqveirav lynyrqnqel kvrvellhnp afcslattkr rhqqtvtipp ksslsvpyvi
 901 vplktglqev evkaavyhhf isdgvrkslk vvpegirmmk tvavrtldpe rlgregvqke
 961 dippadlsdq vpdtesetri llggtpvaqm tedavdaerl khlivtpsgc geqnmigmtp
1021 tviavhylde teqwekfgle krggalelik kgytgqlafr qpssafaafv krapstwlta
1081 yvvkvfslav nliaidsqvl cgavkwlile kqkpdgvfqe dapvihqemi gglrnnnekd
1141 maltafvlis lqeakdicee qvnslpgsit kagdfleany eatsyallal iagyalaqmg
1201 rlkgpllnkf lttakdknrw edpgkqlynv elnldvslql lqlkdfdfvp pvvrwineqr
1261 ygggygstq atfmvfqala qyqkdapdhg tlsvvtmyha kakdqltcnk fdlkvtlkpa petekrpqda
1321 seetkenegf tvtaegkgqg sildismmtg fapdtddllkq langvdryis kyeldkafsd
1381 kntmileict ryrgdqdatm fkvhqyfnve liqpgavkvy ayynleessct rfyhpekedg
1441 rntliyldk vshseddcla qksddkvtle erldkacepg vdyvyktrlv kvqlsndfde
1501 klnklcrdel crcaeencfi qrtfispikc realkleekk hylmwglssd fwgekpnlsy
1561 yimaieqtik sgsdevqvgq engkgcqdlg aftesmvvfg cpn
1621 iigkdtwveh wpeedecqde
```

FIG. 15 (CONT' D)

3) COMPLEMENT C4 PRECURSOR (NCBI # 201411771) -- C4-alpha = 680-1446

```
   1 mrllwgliwa ssfftlslgk prlllfspsv vhlgvplsvg vglqdvprgq vvkgsvflrn
  61 psrnnvpcsp kvdftlsser dfallslqvp lkdakscglh qlirgpevql vahspwlkds
 121 lsrttniqgi nlfssrrgh lflqtdqpiy npgqrvryrv faldqkmrps tdtitvmven
 181 shglrvrkke vympssifqd dfvipdisep gtwkisarfs dglesnsstq fevkkyvlpn
 241 fevkitpgkp yiltvpghld emqldiqary iyqkpvqgva yvrfgllded gkktffrgle
 301 sqtklvnggs hislskaefg daleklnmgi tdlqglrlyv aaailespgg emeeaeltsw
 361 yfvsspfsld lsktkrhlvp gapfllqalv remsgspasg ipvkvsatvs spgsvpevqd
 421 iqqntdgsgq vsipiiipqt iselqlsvsa gsphpaiarl tvaappsggp gflsierpds
 481 rpprvgdtln lnlravgsga tfshyyymil srgqivfmnr epkrtitsvs vfvdhhlaps
 541 fyfvafyyhg dhpvanslrv dvqagacegk lelsvdgakq yngesvklh letdslalva
 601 lgaldtalya agskshkpln mgkvfeamns ydlgcgpggg dsalqvfgaa glafsdgdqw
 661 tlsrkrlscp kekttrkkrN VNFQKAINEK LGQYASPTAK RCCQDGVTRL PMMRSCEQRA
 721 ARVQQPDCRE PFLSCCQFAE SLRKKSRDKG QAGLQRALEI LQEEDLIDED DIPVRSFFPE
 781 NWLWRVETVD RFQILTLWLP DSLTTWEIHG LSLSKTKGLC VATPVQLRVF REFHLHLRLP
 841 MSVRRFEQLE LRPVLYNYLD KNLTVSVHVS PVEGLCLAGG GGLAQVLVP AGSARPVAFS
 901 VVPTAAAAVS LKVVARGSFE FPVGDAVSKV LQIEKEGAIH REELVYELNP LDHRGRTLEI
 961 PGNSDPNMIP DGDFNSYVRV TASDPLDTLG SEGALSPGGV ASLLRLPRGC GEQTMIYLAP
1021 TLAASRYLDK TEQWSTLPPE TKDHAVDLIQ KGYMRIQQFR KADGSYAAWL SRDSSTWLTA
1081 FVLKVLSLAQ EQVGGSPEKL QETSNWLLSQ QOADGSFQDP CPVLDRSMQG GLVGNDETVA
1141 LTAFVTIALH HGLAVFQDEG AEPLKQRVEA SISKANSFLG EKASAGLLGA HAAATTAYAL
1201 SLTKAPVDLL GVAHNNLMAM AQETGDNLYW GSVTGSQSNA VSPTPAPRNP SDPMPQAPAL
1261 WIETTAYALL HLLLHEGKAE MADQASAFLT ROGSFQGGFR STQDTVIALD ALSAYWIASH
1321 TTEERGLNVT LSSTGRNGFK SHALQLNNRQ IRGLEEELQF SLGSKINVKV GGNSKGTLKV
1381 LRTYNVLDMK NTTCQDLQIE VTVKGHVEYT MEANEDYEDY EYDELPAKDD PDAPLQPVTP
1441 LQLFEGrnr rreapkvve eqesrvhytv ciwrngkvgl sgmaiadvtl lsgfhalrad
1501 lekltslsdr yvshfetegp hvllyfdsvp tsrecvgfea vgevpvglvq pasatlydyy
1561 nperrcsvfy gapsksrlla tlcsaevcqc aegkcprqrr alerglqded gyrmkfacyy
1621 prveygfqvk vlredsraaf rlfetkitqv lhftkdvkaa anqmrnflvr ascrlrlepg
1681 keylimgldg atydleghpq ylldsnswie empserlcrs trgraaacagl ndflqeygtq
1741 gcqv
```

FIG. 15 (CONT'D)

4) ITIH4 (NCBI # 13432192) – PROPEPTIDE = 662-688

```
  1 mkpprpvrtc skvlvllsll aihqttaek ngidiyslty dsrvssrfah tvvtsrvnr
 61 antvqeatfq melpkkafit nfsmnidgmt ypgiikekae aqaqysaava kgksaglvka
121 tgrnmeqfqv svsvapnaki tfelvyeell krrlgvyell lkvrpqqlvk hlqmdihife
181 pqgisflete stfmntnqlvd alttwqnktk ahirfkptls qqqkspeqqe tvldgnliir
241 ydvdraisgg siqiengyfv hyfapegltt mpknvvfvid ksgsmsgrki qqtrealiki
301 lddisprdqf nlivfsteat qwrpslvpas aenvnkarsf aagigalggt nindamlmav
361 qlldssnqee rlpegsvsli illtdgdptv getnprsiqn nvreavsgry slfclgfgfd
421 vsyaflekla ldngglarri hedsdsalql qdfyqevanp lltavtfeyp snaveevtqn
481 nfrllfkgse mvvagklqdr gpdvitatvs gklptqnitf qtessvaeqe aefqspkyif
541 hnfmerlway ltiqqlleqt vsasdadqqa lrnqalnlsl aysfvtplts mvvtkpddqe
601 qsqvaekpme gesrnrnvhs gstffkyylq gakipkpeas fsprrgwnrg agaagsrmmf
661 rPGVLSSRQL GLPGPPDVPD HAAYHPFRrl ailpasappa tsnpdpavsr vmnmkieett
721 mttqtpapiq apsailplpg qsvericvdp rhrqgpvnll sdpeqgvevt gqyerekagf
781 swievtfknp lvwvhaspeh vvvtrnrrss aykwketlfs vmpglkmtmd ktglllisdp
841 dkvtigllfw dgrgeglrli lrdtdrfssh vggtlgqfyq evlwgspaas ddgrrtlrvq
901 gndhsatrer rldyqegppg veiscwsvel
```

FIG.15 (CONT'D)

5) PRO1851 (NCBI # 7770149) - ITIH4 alternative spliced form

```
  1 mpknvvfvid ksgsmsgrki gqtrealiki lddlsprdgf nlivfsteat qwrpslvpas
 61 aenvnkarsf aagigalggt nindamlmav qlldssngee rlpegsvsli illtdgdptv
121 getnprsiqn nvreavsgry slfclgfgfd vsyaflekla ldngglarri hedsdsalql
181 qdfygevanp lltavtfeyp snaveevtqn nfrrllfkgse mvvagklqdr gpdvltatvs
241 gklptqnitf qtessvaege aefqspkyif hnfmerlway ltiqqlleqt vsasdadqqa
301 lrngainlsl aysfvtplts mvvtkpddqe qsqvaekpme gesrnrnvhs agaagsrmnf
361 rpgvlssrql glpgppdvpd haayhpfrrl ailpasappa tsnpdpavsr vmnmkieett
421 mttqtpacps csrsrapavp apigapsail plpggsverl cvdprhrggp vnllsdpeqg
481 vevtgqyere kagfswievt fknplvwvha spehvvvtrn rrssaykwke tlfsvmpglk
541 mtmdktglll lsdpdkvtig llfwdgrgeg lrlllrdtdr fsshvggtlg qfyqevlwgs
601 paasddgrrt lrvqgndhsa trerrldyqe gppgveiscw svel
```

FIG.15 (CONT'D)

6) APOLIPOPROTEIN A-I (NCBI # 4557321)

```
  1 mkaavltlav lfltgsqarh fwqgdeppqs pwdrvkdlat vyvdvlkdsg rdyvsqfegs
 61 algkqlnlkl ldnwdsvtst fsklreqlgp vtqefwdnle keteglrqem skdleevkak
121 vqpylddfqk kwqeemelyr qkveplrael qegarqklhe lqeklsplqe emrdrarahv
181 dalrthlapy sdelrqrlaa rlealkengg arlaeyhaka tehlstlsek akpaledlrg
241 glpvlesfk vsflsaleey tkklntq
```

7) APOLIPOPROTEIN A-IV (NCBI # 114006)

```
  1 mflkavvltl alvavagara evsadgvatv mwdyfsqlsn nakeavehlq kseltqqina
 61 lfqdklgevn tyagdlqkkl vpfatelher lakdseklke eigkeleelr arllphanev
121 sqkigdnlre lqqrlepyad qlrtqvntqa eqlrrqltpy aqrmervlre nadslqaslr
181 phadelkaki dqnveelkgr ltpyadefkv kidgtveelr rslapyaqdt qeklnhqleg
241 ltfqmkknae elkarisasa eelrqrlapl aedvrqnlkg nteglqksla elgghldqqv
301 eefrrvepy genfnkalvq qmeqlrqklg phagdveghl sflekdlrdk vnsffstfke
361 kesqdktlsl peleqqgeqq geqqeqvqm lapeis
```

FIG. 15 (CONT'D)

8) APOLIPOPROTEIN E (NCBI # 114039)

```
  1 mkvlwaallv tflagcqakv egavetepep elrqqtewqs gqrwelalgr fwdylrwvqt
 61 lseqvqeell ssqvtqelra lmdetmkelk aykseleeql tpvaeetrar lskelqaaqa
121 rlgadmedvc grlvqyrgev qamlggstee lrvrlashlr klrkrllrda ddlqkrlavy
181 qagaregaer glsairerlg plveggrvra atvgslagqp lqeraqawge rlrarmeemg
241 srtrdrldev keqvaevrak leeqaqqirl qaeafqarlk swfeplvedm qrqwaglvek
301 vqaavgtsaa pvpsdnh
```

FIG. 15 (CONT'D)

| Mass | Prostate | Breast | Bladder | Control | Prostate2 |
|---|---|---|---|---|---|
| 702 | 15.7 ± 34.56, (1) | 0 ± 0, (1) | 59.34 ± 56.24, (65.86) | 16.38 ± 29.66, (1) | 19.21 ± 17.71, (13.64) |
| 707 | 8.9 ± 28.67, (1) | 0 ± 0, (1) | 100.12 ± 358.56, (1) | 6.77 ± 28.03, (1) | 17.82 ± 23.22, (4.46) |
| 711 | 434.68 ± 199.82, (413.71) | 288.19 ± 178.73, (230) | 364.17 ± 251.35, (300.4) | 360.8 ± 145.38, (342.77) | 368.01 ± 231.73, (361.54) |
| 715 | 107.31 ± 102.83, (103.54) | 99.08 ± 56.97, (101.04) | 38.49 ± 56.19, (1) | 63.18 ± 50.98, (80.33) | 63.9 ± 51.9, (59.67) |
| 719 | 75.02 ± 65.32, (83.56) | 25.68 ± 38.85, (1) | 257.65 ± 194.25, (189.58) | 50.29 ± 40.91, (66.28) | 33.57 ± 64.69, (3.53) |
| 725 | 175.63 ± 74.46, (184.62) | 93.64 ± 47.5, (78.8) | 93.24 ± 44.26, (91.15) | 111.23 ± 41.1, (97.17) | 260.61 ± 269.97, (170.65) |
| 731 | 157.69 ± 208.4, (123.28) | 80.77 ± 49.69, (76.13) | 78 ± 37.89, (90.05) | 92.15 ± 23.53, (94.42) | 26.41 ± 20.5, (29.28) |
| 735 | 133.82 ± 63.31, (130.05) | 101.36 ± 61.2, (80.9) | 58.18 ± 44.5, (65.74) | 92.45 ± 48.92, (92.37) | 75.73 ± 61.47, (66.8) |
| 743 | 223.48 ± 60.97, (228.64) | 162.2 ± 37.33, (153.72) | 518.01 ± 401.46, (303.19) | 182.39 ± 47.05, (180.24) | 215.28 ± 115.21, (184.97) |
| 749 | 167.31 ± 49.71, (173.06) | 102.56 ± 38.93, (106.7) | 223.16 ± 116.39, (198.43) | 114.01 ± 25.07, (110.89) | 116.71 ± 84.25, (83.2) |
| 755 | 77.91 ± 75.25, (80.1) | 47.08 ± 47.76, (60.18) | 43.42 ± 66.9, (1) | 30.79 ± 43.2, (1) | 11.85 ± 17.56, (3.26) |
| 759 | 319.1 ± 143.14, (283.07) | 287.91 ± 96.3, (276.8) | 508.49 ± 363.13, (403.56) | 427.42 ± 86.93, (425.79) | 282.34 ± 210.42, (223.84) |
| 763 | 40.79 ± 72.37, (1) | 24.64 ± 47.52, (1) | 45.38 ± 79.46, (1) | 0 ± 0, (1) | 13.3 ± 57.94, (1) |
| 766 | 160.28 ± 51.14, (167.69) | 138.39 ± 71.65, (115.14) | 241.46 ± 272.24, (124.55) | 102.96 ± 56.71, (110.12) | 66.39 ± 76.02, (45.32) |
| 771 | 175.72 ± 67.14, (164.55) | 117.65 ± 34.92, (109.64) | 94.27 ± 63.52, (104.66) | 150.04 ± 26.25, (150.29) | 60.67 ± 44.67, (46.95) |
| 777 | 175.6 ± 133.01, (161.91) | 118.74 ± 77.74, (120.53) | 143.86 ± 80.68, (149.92) | 142.25 ± 61.89, (164.24) | 49.72 ± 33.61, (43.13) |
| 783 | 182.75 ± 100.2, (166.01) | 127.82 ± 44.1, (126.68) | 409.01 ± 223.51, (324.93) | 184.15 ± 150.94, (133.35) | 97.67 ± 58.7, (83.91) |
| 787 | 126.51 ± 101.33, (130.6) | 70.12 ± 52.8, (97.69) | 83.55 ± 99.84, (36.03) | 75.79 ± 45.62, (94.56) | 132.99 ± 154.09, (70.39) |
| 793 | 70.51 ± 66.23, (87.38) | 83.6 ± 52.25, (96.65) | 19.44 ± 40.43, (1) | 34.34 ± 43.84, (1) | 20.66 ± 19.96, (15.99) |
| 798 | 189.47 ± 87.28, (180.24) | 110.21 ± 49.23, (104.89) | 122.05 ± 126.01, (107.24) | 117.44 ± 32.74, (122.34) | 62.75 ± 27.4, (59.33) |
| 804 | 169.43 ± 144.11, (125.5) | 98.69 ± 58.97, (107.67) | 235.44 ± 88.18, (191.12) | 53.48 ± 52.54, (76.97) | 37.91 ± 39.41, (27.99) |
| 812 | 224.77 ± 64.57, (228.36) | 158.46 ± 52.56, (161.26) | 244.29 ± 67.29, (232.98) | 175.1 ± 27.64, (176.96) | 127.78 ± 64.83, (109.21) |
| 824 | 252.99 ± 173.92, (204.02) | 160.11 ± 69.57, (135.22) | 1064.54 ± 726.55, (829.12) | 195.36 ± 80.69, (177.91) | 224.07 ± 418.06, (92.8) |
| 830 | 254.8 ± 166.72, (233.97) | 143.99 ± 43.67, (142.23) | 1156.92 ± 703.1, (1243.67) | 176.1 ± 127.5, (149.42) | 152.68 ± 218.34, (87.28) |
| 836 | 79.66 ± 65.73, (106.33) | 116.24 ± 43.02, (122.5) | 99.5 ± 85.5, (95.8) | 59.77 ± 46.84, (86.27) | 41.55 ± 32.47, (30.91) |
| 841 | 139.64 ± 55.63, (143.77) | 100.08 ± 41.25, (99.98) | 14.99 ± 36.66, (1) | 77.79 ± 46.96, (96.22) | 36.99 ± 26.25, (31.42) |
| 848 | 255.1 ± 61.95, (264.37) | 144.8 ± 62.78, (154.85) | 332.49 ± 184.64, (284.06) | 167.86 ± 29.4, (162.73) | 135.86 ± 119.16, (102.08) |
| 851 | 244.17 ± 140.56, (229.89) | 127.93 ± 106.52, (146.07) | 114.07 ± 130.57, (130.68) | 131.02 ± 63.97, (140.86) | 146.57 ± 138.6, (150.54) |
| 856 | 228.22 ± 112.83, (230.92) | 198.29 ± 66.48, (206) | 208.08 ± 98.93, (195.67) | 137.27 ± 59.61, (154.37) | 89.78 ± 99.33, (71.15) |
| 862 | 149.5 ± 77.73, (154.9) | 162.61 ± 68.51, (171.72) | 227.88 ± 120.11, (181.91) | 167.47 ± 32.87, (161.43) | 44.69 ± 35.14, (37.09) |

FIG. 16A

| Mass | Prostate | Breast | Bladder | Control | Prostate2 |
|---|---|---|---|---|---|
| 866 | 7.17 ± 28.37, (1) | 21.53 ± 55.78, (1) | 6.66 ± 29.79, (1) | 13.34 ± 36.65, (1) | 4.15 ± 9.2, (1) |
| 872 | 404.06 ± 150.18, (401.64) | 255.84 ± 54.97, (259.33) | 276.56 ± 102.56, (259.94) | 312.74 ± 64.06, (318.59) | 275.58 ± 139.1, (252.65) |
| 881 | 116.38 ± 105.55, (127.22) | 159.87 ± 63.04, (170.42) | 95.92 ± 89.05, (114.7) | 60 ± 61.3, (86.35) | 56.52 ± 36.09, (52.38) |
| 886 | 49.45 ± 85.48, (1) | 81.84 ± 122.23, (1) | 29.96 ± 64.91, (1) | 25.4 ± 60.92, (1) | 9.46 ± 19.41, (1) |
| 891 | 594.67 ± 338.63, (543.63) | 309.71 ± 123.02, (280.38) | 778.16 ± 225.79, (752.41) | 404.31 ± 117.45, (371.2) | 441.15 ± 247.2, (383.95) |
| 896 | 76.47 ± 113.11, (1) | 44 ± 77.84, (1) | 31.61 ± 89.63, (1) | 10.6 ± 34.53, (1) | 24.72 ± 41.03, (4.68) |
| 904 | 353.31 ± 227.45, (347.31) | 380.81 ± 262.83, (434.09) | 146.37 ± 133.1, (144.31) | 70.75 ± 97.88, (1) | 214.67 ± 215.03, (172.32) |
| 907 | 4561.2 ± 1727.3, (4511.86) | 7338.56 ± 2182.97, (6910.05) | 3272.39 ± 767.81, (3381.28) | 4369.04 ± 539.06, (4265.11) | 8771.13 ± 3866.19, (8924.59) |
| 912 | 124.61 ± 220.27, (1) | 180.84 ± 324.62, (1) | 693.34 ± 740.76, (471.31) | 165.49 ± 358.41, (1) | 253.51 ± 388.21, (37.21) |
| 916 | 19.02 ± 51.95, (1) | 23.01 ± 58.11, (1) | 0 ± 0, (1) | 2.85 ± 16.35, (1) | 41.29 ± 42.9, (31.5) |
| 922 | 2437.38 ± 1346.6, (2035.51) | 2878.38 ± 1682.73, (2718.47) | 2280.99 ± 800.29, (2568.07) | 1633.3 ± 626.86, (1634.52) | 3225.99 ± 2175.09, (2953.29) |
| 929 | 136.34 ± 120.2, (158.84) | 226.83 ± 116.74, (250.39) | 114.06 ± 201.25, (1) | 163.46 ± 110.3, (166.42) | 300.91 ± 209.4, (247.06) |
| 935 | 95.06 ± 109.93, (1) | 53.35 ± 90.61, (1) | 124.29 ± 173.7, (59.52) | 24.42 ± 54.23, (1) | 48.22 ± 61.51, (30.62) |
| 940 | 8.99 ± 35.86, (1) | 0 ± 0, (1) | 7.88 ± 35.22, (1) | 0 ± 0, (1) | 5.99 ± 13.41, (1) |
| 944 | 1161.36 ± 752.6, (943.64) | 332.25 ± 102.72, (313.79) | 2817.62 ± 707.49, (2808.31) | 643.38 ± 420.99, (542) | 1240.77 ± 686.78, (1087.98) |
| 949 | 131.64 ± 347.08, (1) | 99.83 ± 104.06, (114.34) | 79.26 ± 185.87, (1) | 22.86 ± 49.78, (1) | 57.51 ± 57.03, (45.01) |
| 956 | 123.61 ± 106.55, (151.14) | 149.19 ± 82.87, (166.27) | 250.43 ± 205.47, (190.31) | 73.28 ± 70.33, (105.93) | 30.18 ± 24.88, (25.25) |
| 960 | 253.63 ± 67.96, (259.04) | 246.81 ± 56.59, (233.44) | 403.76 ± 201.13, (352.98) | 237 ± 77.53, (247.14) | 153.34 ± 82.18, (141.64) |
| 970 | 296.78 ± 121.9, (255.22) | 262.67 ± 108.26, (248.04) | 364.46 ± 201.98, (288.2) | 327 ± 179.93, (288.08) | 229.05 ± 138.64, (201.98) |
| 976 | 178.33 ± 91.89, (196.72) | 161.53 ± 72.18, (177.38) | 196.87 ± 114.44, (185.98) | 177.68 ± 46.53, (182.18) | 47.07 ± 40.35, (36.22) |
| 980 | 67.56 ± 114.58, (1) | 20.17 ± 50.8, (1) | 115.29 ± 203.66, (1) | 10.83 ± 34.88, (1) | 24.33 ± 34.17, (13.94) |
| 984 | 56.27 ± 82.27, (1) | 57.71 ± 85.82, (1) | 42.4 ± 67.84, (1) | 29.36 ± 53.32, (1) | 25.91 ± 40.76, (1) |
| 992 | 383.92 ± 185.43, (346.21) | 316.88 ± 150.31, (273.67) | 165.58 ± 95.59, (168.41) | 193.23 ± 70.71, (178.17) | 575.94 ± 760.18, (392.14) |
| 995 | 201.14 ± 162.77, (167.57) | 184.01 ± 214.2, (186.65) | 577.59 ± 434.07, (409.88) | 30.1 ± 69.09, (1) | 156.07 ± 418, (1) |
| 1000 | 115.85 ± 113.29, (121.34) | 110.78 ± 92.99, (147) | 243.37 ± 175.88, (256.16) | 11.03 ± 35.55, (1) | 31.27 ± 29.77, (27.41) |
| 1007 | 134.77 ± 104.68, (139.5) | 153.34 ± 97.28, (181.68) | 343.98 ± 153.5, (324.81) | 216.92 ± 39.86, (216.28) | 89.84 ± 62.51, (68.69) |
| 1013 | 331.69 ± 195.86, (354.69) | 226.39 ± 171.71, (202.11) | 232.67 ± 140.27, (202.64) | 57.31 ± 148.22, (1) | 397.63 ± 266.44, (335.19) |
| 1018 | 398.26 ± 316.39, (404.38) | 448.33 ± 337.77, (404.96) | 99.94 ± 119.61, (56.61) | 255.42 ± 200.61, (238.4) | 588.12 ± 589.58, (484.28) |
| 1023 | 1581.47 ± 1259.27, (1121.19) | 2769.8 ± 1905.14, (1894) | 1207.52 ± 762.91, (1116.83) | 4016.7 ± 464.05, (4018.76) | 1086.95 ± 1494.74, (593.22) |
| 1031 | 69.31 ± 108.35, (1) | 89.54 ± 125.7, (1) | 156.26 ± 158.92, (141.03) | 91.47 ± 88.06, (124.16) | 42.38 ± 46.36, (28.94) |

FIG. 16A (CONT'D)

| Mass | Prostate | Breast | Bladder | Control | Prostate2 |
|---|---|---|---|---|---|
| 1035 | 248.87 ± 122.86, (230.86) | 250.17 ± 124.7, (271.17) | 286.84 ± 100.44, (286.72) | 83.92 ± 86.41, (122.23) | 245.85 ± 96.35, (230.38) |
| 1042 | 155.45 ± 117.15, (178.8) | 95.33 ± 143.29, (1) | 88.84 ± 69.39, (117.78) | 18.81 ± 78.55, (1) | 61.89 ± 127.33, (11.05) |
| 1048 | 444.12 ± 245.1, (371.99) | 763.89 ± 221.41, (743.79) | 155.23 ± 151.88, (160.86) | 1002.57 ± 279.33, (894.87) | 793.52 ± 1477.99, (357.23) |
| 1058 | 274.25 ± 299.72, (226.73) | 181.78 ± 247.01, (1) | 939.21 ± 493.65, (1050.72) | 25.32 ± 61.91, (1) | 249.76 ± 244.24, (191.06) |
| 1063 | 2911.33 ± 1457.22, (3074.48) | 8192.98 ± 2705.77, (7566.57) | 1746.85 ± 958.92, (1694.1) | 4216.94 ± 790.82, (3972.51) | 6077.96 ± 4513.21, (4616.19) |
| 1066 | 110.15 ± 175.79, (1) | 224.48 ± 191.08, (239.92) | 46.04 ± 85.01, (1) | 475.81 ± 170.73, (439.06) | 3.35 ± 9.63, (1) |
| 1069 | 5.53 ± 31.27, (1) | 102.92 ± 179.21, (1) | 21.78 ± 53.41, (1) | 0 ± 0, (1) | 87.91 ± 154.55, (25.74) |
| 1072 | 30.58 ± 74.3, (1) | 15.57 ± 71.33, (1) | 7.19 ± 32.17, (1) | 0 ± 0, (1) | 22.35 ± 52.93, (1) |
| 1079 | 1880.88 ± 1044.4, (2014.18) | 3688.8 ± 1709.02, (3515.63) | 1909.45 ± 528.38, (1833.42) | 3664.76 ± 401.86, (3702.34) | 2858.73 ± 2383.07, (2176.95) |
| 1085 | 69.62 ± 99.78, (1) | 55.09 ± 127.13, (1) | 7.69 ± 34.41, (1) | 141.89 ± 288.99, (1) | 112.5 ± 124.68, (59.32) |
| 1090 | 28.6 ± 69.01, (1) | 25.4 ± 80.51, (1) | 22.13 ± 45.6, (1) | 0 ± 0, (1) | 17.5 ± 25.23, (6.86) |
| 1094 | 67.42 ± 95.88, (1) | 85.28 ± 114.52, (1) | 121.87 ± 89.27, (142.67) | 0 ± 0, (1) | 57.46 ± 54.42, (42.78) |
| 1101 | 438.06 ± 226.06, (362.24) | 186.9 ± 89.59, (204.22) | 600.4 ± 292.61, (581) | 254.91 ± 72.11, (253.33) | 350.68 ± 330.27, (251.78) |
| 1106 | 106.69 ± 108.6, (139.55) | 104.63 ± 104.12, (160.37) | 17.78 ± 43.53, (1) | 67.78 ± 77.15, (1) | 48.77 ± 60.3, (33.97) |
| 1111 | 50.57 ± 78.2, (1) | 116.13 ± 107.07, (161.06) | 133.03 ± 78.57, (142.89) | 7.78 ± 31.5, (1) | 35.34 ± 67.41, (22.73) |
| 1116 | 197.81 ± 79.41, (200.22) | 142.72 ± 119, (198.22) | 289.51 ± 101.54, (283.24) | 120.11 ± 108.24, (135.24) | 91.22 ± 65.75, (79.39) |
| 1119 | 116.56 ± 117.09, (146.8) | 199.9 ± 127.41, (234.56) | 123.58 ± 100, (152.31) | 78.38 ± 115.34, (1) | 76.8 ± 96.51, (44.87) |
| 1126 | 252.64 ± 146.67, (214.62) | 477.82 ± 166.46, (445.61) | 115.07 ± 77.82, (128.22) | 521.36 ± 195.04, (515.14) | 313.51 ± 325.69, (144.04) |
| 1131 | 66.53 ± 108.73, (1) | 20.23 ± 67.23, (1) | 12.22 ± 37.67, (1) | 14.08 ± 46.1, (1) | 42.61 ± 41.64, (40.34) |
| 1135 | 133.65 ± 90.96, (162.93) | 65.95 ± 98.46, (1) | 94.7 ± 84.6, (111.4) | 161.87 ± 110.4, (197) | 43.91 ± 40.67, (44.13) |
| 1139 | 197.1 ± 80.04, (210.75) | 206.72 ± 182.11, (212.91) | 123.88 ± 217.78, (1) | 216.54 ± 110.18, (236.25) | 134.87 ± 118.72, (94.65) |
| 1144 | 224.72 ± 109.79, (244.43) | 162 ± 160.7, (194.91) | 639.83 ± 439.99, (549.49) | 220.74 ± 235.54, (203.21) | 114.62 ± 159.11, (75.31) |
| 1150 | 43.59 ± 72.29, (1) | 136.9 ± 118.12, (169.49) | 11.17 ± 34.4, (1) | 55.08 ± 66.48, (1) | 39.93 ± 38.68, (30.19) |
| 1153 | 39.05 ± 75.88, (1) | 48.74 ± 103.07, (1) | 12.86 ± 39.59, (1) | 0 ± 0, (1) | 19.34 ± 25.24, (9.88) |
| 1156 | 109.82 ± 298.72, (1) | 50.16 ± 93.57, (1) | 227.26 ± 183.07, (213.15) | 14.03 ± 45.57, (1) | 47.57 ± 95.99, (21.39) |
| 1159 | 185.58 ± 103.81, (199.59) | 18.36 ± 59.05, (1) | 298.57 ± 122.63, (263.54) | 32.34 ± 70.73, (1) | 66.66 ± 74.54, (56.23) |
| 1162 | 54.07 ± 133.35, (1) | 12.36 ± 56.62, (1) | 8.11 ± 36.26, (1) | 81.62 ± 79.11, (119.43) | 23.69 ± 44.75, (1) |
| 1166 | 153 ± 133.35, (186.23) | 230.61 ± 95.15, (237.33) | 67.52 ± 87.82, (1) | 357.8 ± 65.09, (348) | 77.14 ± 56.45, (70.52) |
| 1170 | 120.77 ± 95.13, (151.01) | 103.61 ± 116.05, (1) | 82.77 ± 101.45, (50.22) | 35.08 ± 63.79, (1) | 33.67 ± 30.27, (27.34) |
| 1174 | 182.92 ± 128.59, (199.74) | 112.55 ± 113.86, (149.64) | 44.9 ± 75.47, (1) | 3.81 ± 21.89, (1) | 168.1 ± 368.24, (79.51) |
| 1177 | 89.29 ± 101.87, (1) | 73.17 ± 98.02, (1) | 41.14 ± 65.72, (1) | 43.78 ± 63.68, (1) | 43.93 ± 49.91, (34.83) |

FIG. 16A (CONT'D)

| Mass | Prostate | Breast | Bladder | Control | Prostate2 |
|---|---|---|---|---|---|
| 1183 | 73.01 ± 92.45, (1) | 84.6 ± 113.12, (1) | 189.11 ± 88.64, (182.75) | 7.01 ± 28.17, (1) | 47.96 ± 52.14, (40.58) |
| 1188 | 44.07 ± 88.54, (1) | 42.23 ± 91.6, (1) | 8.41 ± 37.62, (1) | 0 ± 0, (1) | 33 ± 44.57, (15.59) |
| 1191 | 119.76 ± 104.3, (143.53) | 169.78 ± 143.57, (204.78) | 35.47 ± 79.14, (1) | 303.69 ± 92.24, (298.67) | 82.54 ± 50.33, (81.41) |
| 1197 | 130.82 ± 88.4, (159.26) | 305.84 ± 132.93, (278.24) | 63.9 ± 90.75, (1) | 75.34 ± 107.19, (1) | 79.37 ± 53.66, (64.44) |
| 1201 | 29.61 ± 69.99, (1) | 81.97 ± 134.15, (1) | 29.07 ± 61.01, (1) | 59.47 ± 113.22, (1) | 12.82 ± 30.22, (1) |
| 1206 | 132.7 ± 198.03, (1) | 303.43 ± 312.11, (290.73) | 185.24 ± 172.39, (178.45) | 26.34 ± 57.93, (1) | 113.53 ± 129.79, (77.22) |
| 1209 | 2259.24 ± 1661.17, (2267.99) | 3437.89 ± 2294.84, (3107.73) | 2171.06 ± 864.61, (1970.59) | 4558.92 ± 641.12, (4517.21) | 1610.74 ± 1827.13, (844.39) |
| 1214 | 1460.59 ± 1300.61, (1391.49) | 205.32 ± 398.04, (1) | 2038.25 ± 989.02, (1912.04) | 483.85 ± 741.93, (177.1) | 1408.07 ± 755.48, (1308.28) |
| 1217 | 66.24 ± 182.41, (1) | 43.27 ± 91.89, (1) | 61.16 ± 167.08, (1) | 23.56 ± 83.9, (1) | 0 ± 0, (1) |
| 1221 | 109.73 ± 198.98, (1) | 70.95 ± 115.29, (1) | 7.36 ± 32.92, (1) | 0 ± 0, (1) | 332.19 ± 310, (247.69) |
| 1226 | 27.23 ± 76.57, (1) | 22.32 ± 70.71, (1) | 0 ± 0, (1) | 0 ± 0, (1) | 39.92 ± 51.32, (16.58) |
| 1231 | 142.29 ± 127.3, (162.25) | 177.67 ± 111.17, (222.86) | 967.3 ± 495, (1016.21) | 173.62 ± 133.9, (179.55) | 86.15 ± 87.94, (59.33) |
| 1234 | 73.7 ± 99.31, (1) | 151.55 ± 131.86, (181.38) | 36.8 ± 79.08, (1) | 118.83 ± 111.4, (137.95) | 59.68 ± 66.86, (35.76) |
| 1237 | 93.08 ± 100.98, (57.89) | 61.24 ± 103.35, (1) | 24.14 ± 75.64, (1) | 3.15 ± 18.08, (1) | 53.34 ± 55.18, (36.38) |
| 1240 | 38.28 ± 83.34, (1) | 98.08 ± 118.86, (1) | 0 ± 0, (1) | 0 ± 0, (1) | 39.51 ± 34.34, (38.07) |
| 1244 | 61.75 ± 92.47, (1) | 62.81 ± 103.06, (1) | 30.98 ± 64.44, (1) | 90.42 ± 114.12, (1) | 37.8 ± 35.61, (33.4) |
| 1254 | 143.45 ± 102.04, (164.89) | 271 ± 67.97, (262.97) | 61.37 ± 103.19, (1) | 143.41 ± 66.92, (159.05) | 92.37 ± 47.88, (85.59) |
| 1262 | 79.02 ± 103.85, (1) | 57.01 ± 106.75, (1) | 64.39 ± 142.59, (1) | 22.21 ± 67.18, (1) | 89.06 ± 93.9, (69.02) |
| 1267 | 908.3 ± 670.36, (638.46) | 1200.4 ± 1082.93, (755.41) | 988.66 ± 727.44, (785.8) | 3187.09 ± 640.76, (3271.91) | 497.93 ± 496.36, (358.12) |
| 1275 | 187.79 ± 271.43, (145.83) | 119.77 ± 178.74, (1) | 92.66 ± 285.94, (1) | 19.33 ± 54.58, (1) | 99.06 ± 104.04, (69.48) |
| 1280 | 315.68 ± 237.5, (251.92) | 84.09 ± 166.11, (1) | 1446.41 ± 708.12, (1406.33) | 73.44 ± 278.74, (1) | 551.79 ± 983.17, (231.96) |
| 1292 | 124.41 ± 84.32, (153.53) | 210.12 ± 87.92, (231.12) | 215.95 ± 133.03, (204.47) | 172.97 ± 48.26, (167.54) | 85.99 ± 49.05, (72.92) |
| 1300 | 155.18 ± 88.77, (164.59) | 248.6 ± 101.09, (265.47) | 196.88 ± 177.37, (168.89) | 54.92 ± 66.04, (1) | 339.73 ± 1302.63, (114.01) |
| 1308 | 157.48 ± 80.96, (168.19) | 149.93 ± 103.15, (181.38) | 116.12 ± 192.4, (1) | 161.1 ± 56.61, (174.84) | 75.82 ± 59.55, (64.14) |
| 1314 | 106.62 ± 251.67, (1) | 36.1 ± 77.88, (1) | 715.63 ± 501.13, (634.96) | 38.84 ± 129.6, (1) | 76.42 ± 260.38, (21.25) |
| 1318 | 110.15 ± 99.05, (132.47) | 136.37 ± 104.62, (162.31) | 75.44 ± 78.32, (61.03) | 131.32 ± 81.93, (149.21) | 81.89 ± 43.22, (85.59) |
| 1323 | 72.82 ± 86.8, (1) | 59.99 ± 98.36, (1) | 32.86 ± 84.63, (1) | 34.75 ± 63.39, (1) | 59.56 ± 68.13, (44.9) |
| 1327 | 63.57 ± 85.02, (1) | 6.66 ± 30.5, (1) | 24.17 ± 50.16, (1) | 24.96 ± 84.39, (1) | 42.57 ± 79.03, (28.21) |
| 1332 | 120.44 ± 179.15, (1) | 143.26 ± 107.32, (186.86) | 102.51 ± 173.74, (1) | 12.02 ± 38.67, (1) | 75.04 ± 81.68, (67.26) |
| 1337 | 155.51 ± 172.66, (157.81) | 161.51 ± 163.35, (186.54) | 264.07 ± 222.02, (211.6) | 151.35 ± 71.93, (165.8) | 56.37 ± 38.43, (52.71) |
| 1345 | 25 ± 59.96, (1) | 127.25 ± 128.86, (177.17) | 208.91 ± 367.88, (64.05) | 24.27 ± 59.01, (1) | 69.86 ± 90.28, (45.37) |

FIG. 16A (CONT'D)

| Mass | Prostate | Breast | Bladder | Control | Prostate2 |
|---|---|---|---|---|---|
| 1354 | 2080.48 ± 1235.52, (2102.44) | 2153.51 ± 1680.56, (1571.81) | 2107.42 ± 835.37, (2086.29) | 4545.13 ± 463.86, (4496.6) | 1487.21 ± 1123.56, (1111.37) |
| 1362 | 44.06 ± 86.09, (1) | 89.65 ± 130.65, (1) | 13.22 ± 40.99, (1) | 5.25 ± 30.15, (1) | 57.51 ± 78.63, (43.57) |
| 1366 | 61.22 ± 106.98, (1) | 42.89 ± 92.55, (1) | 49.61 ± 83.37, (1) | 6.9 ± 39.64, (1) | 109 ± 124.62, (78.23) |
| 1370 | 250.91 ± 238.9, (240.69) | 113.29 ± 140.62, (1) | 54.23 ± 82.72, (1) | 46.37 ± 69.21, (1) | 108.17 ± 129.96, (94.02) |
| 1375 | 86.55 ± 156.3, (1) | 25.17 ± 63.8, (1) | 88.55 ± 77.06, (123.34) | 29.56 ± 58.75, (1) | 32.35 ± 34.28, (23.67) |
| 1383 | 145.8 ± 87.14, (164.77) | 781.38 ± 358.17, (795.73) | 192.51 ± 178.45, (151.76) | 173.54 ± 76.32, (183.51) | 79.27 ± 55.76, (76.95) |
| 1393 | 316.36 ± 84.46, (326.4) | 356.89 ± 269.94, (329.4) | 379.59 ± 109.99, (369.98) | 411.49 ± 70.16, (402.55) | 251.06 ± 87.55, (261.53) |
| 1399 | 81.41 ± 179.16, (1) | 12.77 ± 58.5, (1) | 47.28 ± 77.66, (1) | 0 ± 0, (1) | 204.19 ± 844.16, (6.97) |
| 1406 | 299.89 ± 221.75, (237.35) | 177.12 ± 119.82, (226.54) | 141.6 ± 119.52, (169.06) | 178.01 ± 133.66, (202.96) | 166 ± 109.88, (136.51) |
| 1415 | 147.55 ± 162.03, (144.35) | 206.03 ± 100.44, (231.82) | 173.85 ± 116.38, (199.41) | 214.2 ± 174.5, (209.03) | 120.81 ± 252.81, (61.75) |
| 1421 | 105.82 ± 110.18, (143.06) | 79.81 ± 106.36, (1) | 131.37 ± 140.95, (82.76) | 157.01 ± 127.11, (180.06) | 125.56 ± 118.32, (117.84) |
| 1427 | 193.04 ± 195.89, (174.45) | 277.17 ± 80.82, (286.87) | 1103.34 ± 806.59, (840.46) | 320.38 ± 250.78, (261.41) | 165.85 ± 424.29, (103.34) |
| 1434 | 58.02 ± 117.18, (1) | 117.37 ± 129.33, (1) | 70.69 ± 92.94, (1) | 9.15 ± 37.65, (1) | 100.97 ± 47.83, (89.56) |
| 1441 | 44.46 ± 119.6, (1) | 0 ± 0, (1) | 11.87 ± 53.09, (1) | 21.97 ± 48.2, (1) | 27.61 ± 30.67, (15.06) |
| 1447 | 38.45 ± 139.16, (1) | 0 ± 0, (1) | 11.79 ± 52.74, (1) | 0 ± 0, (1) | 39.24 ± 54.44, (1) |
| 1453 | 2159.29 ± 1380.63, (1885.15) | 390.67 ± 177.43, (437.78) | 2751.62 ± 1140.1, (2646.51) | 565.13 ± 755.93, (1) | 2536.49 ± 1312.72, (2217.87) |
| 1458 | 15.22 ± 60.18, (1) | 45.92 ± 97.1, (1) | 0 ± 0, (1) | 0 ± 0, (1) | 5.71 ± 23.77, (1) |
| 1463 | 189.2 ± 334.15, (1) | 433.33 ± 274.4, (381.49) | 233.83 ± 398.47, (1) | 605.36 ± 414.09, (687.72) | 52.57 ± 106.49, (1) |
| 1469 | 3240.85 ± 1805.38, (3378.1) | 3949.53 ± 2241.27, (4081.59) | 2915.25 ± 948.24, (2834.33) | 5117.08 ± 720.94, (5133.73) | 2514.51 ± 2263.22, (1708.9) |
| 1476 | 46.8 ± 125.78, (1) | 153.2 ± 550.9, (1) | 123.78 ± 553.54, (1) | 512.86 ± 1015.21, (1) | 64.79 ± 90.57, (36.2) |
| 1488 | 97.94 ± 126.38, (1) | 182.65 ± 117.08, (227.38) | 470.08 ± 366.67, (467.82) | 152.78 ± 136.31, (135.85) | 123.47 ± 230.59, (86.28) |
| 1494 | 29.39 ± 118.67, (1) | 0 ± 0, (1) | 0 ± 0, (1) | 0 ± 0, (1) | 25.68 ± 32.74, (16.93) |
| 1502 | 100.31 ± 147.84, (1) | 67.74 ± 113.81, (1) | 831.64 ± 535, (809.48) | 29.71 ± 81.34, (1) | 128.57 ± 104.83, (98.91) |
| 1507 | 156.83 ± 101.11, (167.5) | 110.38 ± 127.88, (1) | 31.57 ± 68.81, (1) | 129.59 ± 110.22, (115.82) | 107.63 ± 53.71, (107.2) |
| 1516 | 86.2 ± 147.75, (1) | 58.43 ± 109.24, (1) | 254.36 ± 192.8, (206.28) | 0 ± 0, (1) | 143.04 ± 136.48, (111.62) |
| 1523 | 688.1 ± 334.43, (598.26) | 1047.44 ± 452.72, (911.47) | 269.71 ± 299.37, (242.68) | 1465.61 ± 330.44, (1583.23) | 532.58 ± 265.29, (521.02) |
| 1534 | 888.53 ± 546.08, (768.39) | 944.93 ± 726.19, (746) | 1915.21 ± 742.33, (2058.15) | 866.59 ± 492.35, (788.51) | 1079.75 ± 1146.31, (574.55) |
| 1540 | 511.92 ± 415.35, (568.44) | 548.63 ± 337.96, (526.19) | 63.06 ± 247.7, (1) | 904.68 ± 283.76, (979.16) | 347.9 ± 278.05, (301.25) |
| 1548 | 93.37 ± 125.03, (1) | 393.53 ± 176.03, (310.95) | 20.5 ± 42.12, (1) | 114.56 ± 142.04, (1) | 173.01 ± 116.8, (162.04) |
| 1555 | 156.66 ± 205.91, (126.61) | 0 ± 0, (1) | 223.58 ± 226.75, (196.45) | 29.09 ± 52.59, (1) | 119.19 ± 155.99, (80.36) |
| 1561 | 25.49 ± 144.17, (1) | 0 ± 0, (1) | 0 ± 0, (1) | 0 ± 0, (1) | 2.63 ± 12.89, (1) |

FIG. 16A (CONT'D)

| Mass | Prostate | Breast | Bladder | Control | Prostate2 |
|---|---|---|---|---|---|
| 1567 | 866.76 ± 701.1, (620.9) | 448.06 ± 107.93, (424.35) | 1121.01 ± 631.83, (892.96) | 769.93 ± 167, (788.67) | 480.33 ± 192.65, (469.61) |
| 1573 | 75.01 ± 146.21, (1) | 117.35 ± 129.24, (1) | 12.31 ± 38, (1) | 5.89 ± 23.68, (1) | 61.85 ± 49.32, (48.71) |
| 1579 | 47.07 ± 101.92, (1) | 47.26 ± 90.75, (1) | 86.2 ± 84.6, (113.26) | 30.7 ± 48.02, (1) | 33.33 ± 29.02, (26.57) |
| 1586 | 50.76 ± 72.76, (1) | 193.05 ± 150.98, (256.7) | 13.64 ± 33.4, (1) | 14.55 ± 40.21, (1) | 33.47 ± 46.07, (21.65) |
| 1590 | 70.42 ± 113.64, (1) | 26.33 ± 66.22, (1) | 248.64 ± 250.65, (182.2) | 20.77 ± 52.5, (1) | 86.59 ± 137.86, (64.09) |
| 1595 | 153.1 ± 107.7, (163.23) | 77.26 ± 104.42, (1) | 141.15 ± 96.22, (150.46) | 91.61 ± 70.87, (114.47) | 86.17 ± 69.15, (92.8) |
| 1602 | 68.81 ± 87.33, (1) | 175.59 ± 136.34, (186.98) | 27.59 ± 49.24, (1) | 114.25 ± 76.58, (139.24) | 86.74 ± 61.65, (82.17) |
| 1610 | 208.14 ± 262.1, (149.88) | 97.6 ± 119.46, (1) | 192.02 ± 125.51, (182.33) | 75.59 ± 75.07, (97.65) | 116.97 ± 214.53, (76.52) |
| 1618 | 494.63 ± 434.51, (345.33) | 411.56 ± 270.5, (308.13) | 183.73 ± 118.29, (179.97) | 565.78 ± 195.43, (533.41) | 450.61 ± 429.73, (291.93) |
| 1625 | 77.69 ± 107.6, (1) | 12.45 ± 57.04, (1) | 32.13 ± 66.58, (1) | 28.83 ± 66.29, (1) | 16.05 ± 29.92, (1) |
| 1630 | 284.69 ± 140.7, (298.72) | 810.04 ± 377.15, (764.04) | 318.86 ± 183.28, (240.99) | 249.83 ± 113.53, (274.41) | 354.15 ± 305.72, (243.35) |
| 1635 | 169.02 ± 139.82, (211.73) | 107.7 ± 150.57, (1) | 13.97 ± 44.66, (1) | 250.78 ± 85.77, (262.1) | 121.63 ± 111.8, (109.57) |
| 1642 | 186.76 ± 100.67, (184.44) | 261.41 ± 106.04, (250.51) | 289.49 ± 80.3, (270.99) | 214.64 ± 66.32, (218.47) | 144.93 ± 156.88, (99.73) |
| 1655 | 91.84 ± 220.3, (1) | 118.69 ± 103.67, (141.92) | 26.54 ± 69.81, (1) | 48.14 ± 51.2, (1) | 54.97 ± 47.01, (44.62) |
| 1659 | 107.81 ± 168.52, (1) | 80.74 ± 122.09, (1) | 53.54 ± 81.54, (1) | 34.16 ± 46.82, (1) | 123.92 ± 262.35, (58.87) |
| 1668 | 103.61 ± 326.28, (1) | 199.89 ± 121.51, (210.79) | 45.5 ± 94.43, (1) | 48.85 ± 45.88, (76.35) | 38.41 ± 28.81, (35.09) |
| 1672 | 68.97 ± 81.96, (1) | 294.52 ± 172.71, (331.42) | 45.58 ± 75.27, (1) | 44.66 ± 50.71, (1) | 39.77 ± 53.37, (24.05) |
| 1679 | 72.23 ± 83.74, (1) | 154.2 ± 144.85, (169.63) | 135.67 ± 95.67, (140.83) | 28.71 ± 49, (1) | 66.85 ± 43.37, (56.69) |
| 1683 | 70.54 ± 148.4, (1) | 30.69 ± 57.35, (1) | 69.16 ± 74.38, (44.53) | 48.37 ± 51.37, (1) | 53.38 ± 121.03, (28.32) |
| 1691 | 193.05 ± 184.66, (147.13) | 164.84 ± 129.27, (200.74) | 188.38 ± 59.57, (179.91) | 52.77 ± 54.88, (76.7) | 64.77 ± 60.46, (64.29) |
| 1696 | 1190.9 ± 1175.42, (795.86) | 158.28 ± 125, (197.94) | 1801.44 ± 1248.81, (1346.59) | 264.99 ± 200.67, (196.44) | 1231.21 ± 838.78, (966.34) |
| 1706 | 899.28 ± 947.71, (540.11) | 267.99 ± 170.59, (245.55) | 350.36 ± 325.32, (290.82) | 101.36 ± 110.28, (105.99) | 755.16 ± 724.95, (503) |
| 1710 | 95.79 ± 133.32, (1) | 335.69 ± 203.4, (322.88) | 11.55 ± 35.63, (1) | 56.86 ± 54.28, (80.42) | 49.24 ± 189.68, (1) |
| 1715 | 16.97 ± 54.52, (1) | 17.4 ± 54.96, (1) | 86.3 ± 102.6, (39.06) | 10.36 ± 28.65, (1) | 32.56 ± 38.41, (22.29) |
| 1724 | 181.19 ± 112.61, (188.3) | 355.36 ± 282.81, (335.15) | 125.17 ± 73.19, (147.24) | 248.39 ± 74.81, (231.19) | 174.36 ± 130.34, (141.39) |
| 1729 | 142.01 ± 167.97, (113.2) | 83.53 ± 327.2, (1) | 39.12 ± 63.26, (1) | 15.81 ± 38.23, (1) | 159.64 ± 274.56, (87.93) |
| 1738 | 45.15 ± 178.58, (1) | 46.39 ± 99.63, (1) | 0 ± 0, (1) | 2.82 ± 16.22, (1) | 37.06 ± 54.92, (22.46) |
| 1744 | 868.29 ± 507.68, (764.05) | 2528.75 ± 1182.77, (2817.04) | 904.21 ± 659.21, (669.96) | 985.98 ± 272.35, (1020.07) | 1717.87 ± 1583.74, (1250.31) |
| 1750 | 6.61 ± 37.38, (1) | 0 ± 0, (1) | 0 ± 0, (1) | 0 ± 0, (1) | 7.38 ± 17.47, (1) |
| 1757 | 175.76 ± 150.02, (199.37) | 139.54 ± 140.04, (149.67) | 660.76 ± 269.38, (625.98) | 90.96 ± 76.14, (109.77) | 193.16 ± 143.93, (147.16) |
| 1767 | 212.75 ± 365.36, (154.36) | 298.46 ± 112.16, (300.51) | 9.4 ± 42.05, (1) | 86.21 ± 55.43, (95.14) | 159.92 ± 142.92, (112.37) |

FIG. 16A (CONT'D)

| Mass | Prostate | Breast | Bladder | Control | Prostate2 |
|---|---|---|---|---|---|
| 1776 | 323.96 ± 611.92, (147.62) | 47.06 ± 105.79, (1) | 241.68 ± 178.26, (219.86) | 43.19 ± 53.05, (1) | 193.33 ± 506.69, (40.57) |
| 1782 | 1755.48 ± 1517.47, (1015.47) | 206.3 ± 110.37, (222.49) | 2209.42 ± 1326.83, (1789.4) | 348.39 ± 261.82, (232.33) | 2003.61 ± 1298.7, (1577.44) |
| 1791 | 473.77 ± 560.28, (231.53) | 186.57 ± 113.18, (223.32) | 402.93 ± 393.52, (279.31) | 70.8 ± 59.78, (96.93) | 989.64 ± 1334.3, (530.17) |
| 1797 | 129.16 ± 313.88, (1) | 103.85 ± 138.9, (1) | 17.05 ± 53.6, (1) | 25.44 ± 42.8, (1) | 103.85 ± 125.77, (67.13) |
| 1807 | 80.81 ± 161.83, (1) | 148.47 ± 94.7, (171.84) | 278.82 ± 191.66, (252.34) | 42.24 ± 55.26, (1) | 114.71 ± 111.05, (79.02) |
| 1813 | 76.61 ± 255.43, (1) | 18.84 ± 50.97, (1) | 4.97 ± 22.21, (1) | 31.35 ± 45.42, (1) | 48.24 ± 38.23, (46.65) |
| 1820 | 187.63 ± 245.88, (155.14) | 298.35 ± 105.17, (268.4) | 254.28 ± 177.3, (232.41) | 77.45 ± 50.54, (97.86) | 184.01 ± 294.63, (109.75) |
| 1827 | 107.52 ± 201.5, (1) | 122.57 ± 172.72, (1) | 0 ± 0, (1) | 58.56 ± 60.27, (80.57) | 58.5 ± 59.04, (52.86) |
| 1832 | 50.83 ± 74.09, (1) | 197.33 ± 128.78, (205.88) | 20.93 ± 52.17, (1) | 77.55 ± 47.09, (90.33) | 83.77 ± 124.88, (47.6) |
| 1838 | 60.72 ± 92.46, (1) | 53.7 ± 92.68, (1) | 68.02 ± 111.13, (1) | 15.48 ± 33.86, (1) | 33.95 ± 52.23, (26.22) |
| 1845 | 83.36 ± 133, (1) | 58.78 ± 87.71, (1) | 175.95 ± 131.23, (170.72) | 24.01 ± 44.91, (1) | 90.67 ± 88.81, (62.97) |
| 1853 | 113.15 ± 135.12, (104.62) | 229.21 ± 106.63, (227.08) | 102.45 ± 107.14, (99.62) | 73.92 ± 54.56, (87.76) | 157.43 ± 203.25, (83.54) |
| 1861 | 131.04 ± 205.08, (1) | 11.64 ± 53.32, (1) | 181.25 ± 228.03, (155.44) | 13.96 ± 38.36, (1) | 13.72 ± 45.27, (1) |
| 1870 | 3335.21 ± 1759.63, (2660.63) | 444.93 ± 164.29, (369.54) | 3975.98 ± 897.39, (4057.03) | 1387.84 ± 932.62, (1219.19) | 5515.72 ± 2679.45, (4744.82) |
| 1876 | 195.67 ± 467.37, (1) | 0 ± 0, (1) | 351.27 ± 511.99, (304.82) | 8.59 ± 34.68, (1) | 4.95 ± 21.92, (1) |
| 1884 | 130.22 ± 345.12, (1) | 232.33 ± 123.25, (227.61) | 114.81 ± 170.95, (1) | 29.76 ± 50.14, (1) | 96.08 ± 150.11, (55.19) |
| 1890 | 136.11 ± 325.23, (1) | 121.71 ± 138.29, (1) | 22.89 ± 58, (1) | 62.06 ± 75.69, (1) | 288.16 ± 262.31, (191.1) |
| 1900 | 1159.19 ± 551.08, (1042.22) | 2549.48 ± 1183.38, (2415.09) | 2569.25 ± 761.88, (2732.08) | 817.45 ± 243.86, (819.5) | 1764.02 ± 1003.2, (1615.56) |
| 1906 | 5.47 ± 30.96, (1) | 22.55 ± 56.75, (1) | 0 ± 0, (1) | 0 ± 0, (1) | 21.75 ± 20.83, (19.25) |
| 1912 | 0 ± 0, (1) | 23.71 ± 77.03, (1) | 0 ± 0, (1) | 2.39 ± 13.76, (1) | 2.12 ± 9.18, (1) |
| 1918 | 44.26 ± 68.34, (1) | 169.82 ± 87.62, (182.34) | 192.85 ± 240.86, (154.41) | 69.74 ± 49.2, (85.36) | 89.55 ± 63.72, (71.76) |
| 1926 | 105.01 ± 105.81, (120.52) | 190.03 ± 109.27, (207.96) | 100.53 ± 124.05, (58.2) | 21.32 ± 38.48, (1) | 96.75 ± 95.48, (75.75) |
| 1931 | 182.49 ± 219.7, (78.66) | 6.36 ± 29.14, (1) | 694.31 ± 390.38, (671.27) | 40.47 ± 95.75, (1) | 267.37 ± 341.17, (158.45) |
| 1939 | 102.37 ± 138, (1) | 203.97 ± 116.43, (226.08) | 32.65 ± 100.9, (1) | 37.17 ± 51.67, (1) | 143.07 ± 465.99, (51.41) |
| 1945 | 225.89 ± 379.03, (157.72) | 5.63 ± 25.81, (1) | 127.2 ± 107.92, (140.58) | 15.07 ± 58.57, (1) | 327.59 ± 516.72, (146.86) |
| 1956 | 202.07 ± 211.51, (174.88) | 315.65 ± 148.53, (305.53) | 143.58 ± 83.29, (135.54) | 24.87 ± 41.75, (1) | 184.02 ± 135.22, (162.96) |
| 1961 | 26.48 ± 127.65, (1) | 64.65 ± 119.14, (1) | 7.92 ± 35.42, (1) | 39.37 ± 51.72, (1) | 46.12 ± 46.3, (36.51) |
| 1975 | 45.77 ± 110.64, (1) | 56.5 ± 85.43, (1) | 749.54 ± 588.68, (640.68) | 31.52 ± 79, (1) | 93.08 ± 124.5, (52.59) |
| 1982 | 465.51 ± 303.8, (401.9) | 253.16 ± 94.16, (252.61) | 509.78 ± 192.1, (503.42) | 280.44 ± 83.61, (291.52) | 525.66 ± 239.21, (442.88) |
| 1990 | 15.52 ± 73.18, (1) | 122.96 ± 149.32, (127.61) | 151.34 ± 188.52, (1) | 22.3 ± 45.73, (1) | 55.75 ± 122.43, (1) |
| 1995 | 27.38 ± 53.92, (1) | 27.84 ± 60.2, (1) | 14.47 ± 36.54, (1) | 25.37 ± 51.83, (1) | 48.56 ± 66.94, (38.43) |

FIG. 16A (CONT'D)

| Mass | Prostate | Breast | Bladder | Control | Prostate2 |
|---|---|---|---|---|---|
| 2001 | 37.57 ± 59.3, (1) | 141.07 ± 115.56, (160.91) | 36.6 ± 63.28, (1) | 34.66 ± 52.35, (1) | 43.61 ± 112.95, (1) |
| 2009 | 497.96 ± 299.9, (482.05) | 235.79 ± 160.84, (239.32) | 380.47 ± 344.5, (329.08) | 178.3 ± 240.96, (1) | 758.11 ± 611.2, (617.58) |
| 2016 | 929.78 ± 1325.16, (1) | 67.12 ± 178.78, (1) | 279.12 ± 367.28, (1) | 59.01 ± 339, (1) | 1611.62 ± 1273.27, (1320.49) |
| 2025 | 5025.6 ± 1531.65, (5028.59) | 4961.75 ± 2368.81, (4450.01) | 4036.91 ± 828.52, (4100.91) | 4410.54 ± 1358.12, (4775.38) | 8896.57 ± 3784.16, (8595.76) |
| 2031 | 396.9 ± 1005.96, (1) | 67.06 ± 142.36, (1) | 746.16 ± 812.32, (264.99) | 97.93 ± 286.56, (1) | 467.68 ± 1192.91, (1) |
| 2038 | 47.88 ± 230.32, (1) | 185.61 ± 335.26, (1) | 21.52 ± 74.1, (1) | 10.85 ± 35.14, (1) | 72.7 ± 91.65, (44.45) |
| 2048 | 86.72 ± 164.95, (1) | 140.97 ± 166.71, (120.15) | 29.77 ± 56.09, (1) | 37.33 ± 52.81, (1) | 129.81 ± 133.57, (103.96) |
| 2058 | 128.7 ± 235.87, (105.06) | 76.67 ± 100.33, (1) | 311.93 ± 153.04, (306) | 23.29 ± 43.42, (1) | 160.27 ± 87.94, (137.69) |
| 2065 | 78.68 ± 445.1, (1) | 20.74 ± 52.29, (1) | 0 ± 0, (1) | 0 ± 0, (1) | 18.11 ± 22.35, (9.12) |
| 2072 | 21.58 ± 72.94, (1) | 94.9 ± 86.46, (131.95) | 16.22 ± 28.93, (1) | 26.54 ± 38.93, (1) | 98.67 ± 144.14, (61.28) |
| 2078 | 149.26 ± 187.54, (125.13) | 27.46 ± 51.53, (1) | 10.42 ± 46.6, (1) | 65.82 ± 88.26, (69.12) | 255.65 ± 162.85, (218.31) |
| 2087 | 407.48 ± 212.64, (408.84) | 332.82 ± 168.41, (252.48) | 299.64 ± 190.5, (256.2) | 324.96 ± 192.26, (277.81) | 620.65 ± 422.49, (500.47) |
| 2095 | 69.4 ± 171.19, (1) | 132.75 ± 145.78, (145.21) | 6.96 ± 31.14, (1) | 32.73 ± 57.21, (1) | 111.95 ± 199.2, (68.99) |
| 2113 | 277.22 ± 136.86, (281.87) | 147.5 ± 154.94, (179.25) | 177.21 ± 130.48, (151.39) | 246.34 ± 71.99, (247.92) | 305.83 ± 127.39, (301.6) |
| 2119 | 423.08 ± 416.02, (307.12) | 938.9 ± 524.4, (1011.77) | 1196.66 ± 694.48, (1166) | 104.39 ± 139.48, (95.37) | 528.79 ± 557.77, (270.87) |
| 2127 | 66.76 ± 99.54, (1) | 33.35 ± 73.21, (1) | 18.62 ± 62.64, (1) | 51.58 ± 52.37, (65.26) | 201.12 ± 455.03, (87.17) |
| 2132 | 42.92 ± 81.95, (1) | 77.89 ± 81.56, (70.98) | 31.62 ± 62.62, (1) | 14.2 ± 30.69, (1) | 88.29 ± 267.63, (49.46) |
| 2147 | 147.6 ± 116.77, (147.98) | 175.22 ± 110.49, (164.93) | 566.47 ± 246.56, (587.13) | 88.45 ± 42.79, (85.25) | 185.68 ± 199.78, (108.99) |
| 2153 | 194.66 ± 140.92, (164.63) | 144.26 ± 112.51, (180.51) | 308.25 ± 191.65, (259.23) | 86.52 ± 59.24, (105.34) | 201.1 ± 219.62, (144.66) |
| 2164 | 139.5 ± 194.49, (90.98) | 202.42 ± 80.9, (189.47) | 52.63 ± 82.19, (1) | 118.76 ± 35.29, (118.56) | 84.12 ± 234.32, (16.26) |
| 2174 | 158.83 ± 85.59, (162.45) | 220.81 ± 130.48, (242.5) | 165.33 ± 100.95, (147.15) | 69.66 ± 53.39, (86.16) | 259.67 ± 333.81, (174.88) |
| 2179 | 3.73 ± 21.1, (1) | 63.79 ± 107.31, (1) | 3.85 ± 17.23, (1) | 19.16 ± 37.96, (1) | 37.72 ± 43.77, (20.92) |
| 2189 | 444.65 ± 193.51, (399.04) | 700.19 ± 340.28, (659.4) | 442.72 ± 223.55, (418.33) | 248.71 ± 72.2, (233.35) | 573.94 ± 356.56, (507.52) |
| 2196 | 61.52 ± 110.78, (1) | 14.16 ± 38.25, (1) | 14.93 ± 37.15, (1) | 49.15 ± 76.78, (1) | 106.14 ± 172.2, (1) |
| 2214 | 193.71 ± 122.9, (172.3) | 126.92 ± 96.58, (155.67) | 204.19 ± 67.36, (207.13) | 114.89 ± 58.22, (99.95) | 251.57 ± 221.36, (198.49) |
| 2226 | 101.52 ± 80.22, (109.11) | 241.59 ± 103.17, (261.22) | 53.25 ± 55.9, (56.11) | 76.34 ± 36.88, (78.33) | 90.8 ± 63.68, (67.18) |
| 2235 | 41.46 ± 52.54, (1) | 100.81 ± 79.33, (132.3) | 55.76 ± 50.02, (63.97) | 52.25 ± 31.51, (60.29) | 67.04 ± 50.73, (59.29) |
| 2242 | 33.97 ± 118.02, (1) | 0 ± 0, (1) | 2.78 ± 12.42, (1) | 4.73 ± 19.66, (1) | 49.34 ± 108.25, (23.86) |
| 2250 | 67.38 ± 92.9, (31.87) | 184.92 ± 74.73, (188.62) | 54.14 ± 76.61, (1) | 67.17 ± 32.75, (72.97) | 62.79 ± 70.86, (58.79) |
| 2256 | 177.99 ± 332.64, (87.53) | 105.95 ± 93.09, (117.25) | 300.26 ± 254.34, (211) | 54.7 ± 53.85, (65.13) | 157.9 ± 342.42, (58.07) |
| 2262 | 70.07 ± 316.98, (1) | 135.74 ± 83.39, (175.95) | 0 ± 0, (1) | 3.68 ± 14.73, (1) | 11.22 ± 22.05, (1) |

FIG. 16A (CONT'D)

| Mass | Prostate | Breast | Bladder | Control | Prostate2 |
|---|---|---|---|---|---|
| 2273 | 1179.54 ± 966.02, (810.1) | 396.38 ± 501.88, (258.68) | 578.94 ± 448.48, (467.27) | 198.98 ± 126.21, (176.84) | 1353.28 ± 1065.85, (1114.48) |
| 2280 | 178.99 ± 578.39, (83.29) | 145.58 ± 93.66, (174.19) | 14.28 ± 34.89, (1) | 127.15 ± 74.84, (139.62) | 43.42 ± 140.96, (1) |
| 2292 | 149.5 ± 285.97, (96) | 216.14 ± 85.51, (218.55) | 72.45 ± 59.24, (72.13) | 80.27 ± 50.02, (92.89) | 138.79 ± 111.1, (121.11) |
| 2303 | 24.45 ± 81.36, (1) | 37.23 ± 68.81, (1) | 87.96 ± 104.84, (73.06) | 29.54 ± 38, (1) | 27.59 ± 84.86, (1) |
| 2310 | 249.31 ± 268.18, (201.23) | 170.99 ± 82.6, (186.87) | 124.57 ± 65.56, (137.44) | 42.8 ± 52.52, (53.6) | 212.82 ± 168.07, (151.35) |
| 2318 | 51.46 ± 182.08, (1) | 91.28 ± 83.52, (127.69) | 0 ± 0, (1) | 18.29 ± 30.93, (1) | 27.89 ± 46.53, (1) |
| 2334 | 88.96 ± 63.26, (108.78) | 60.91 ± 70.15, (1) | 45.49 ± 38.98, (55.85) | 25.16 ± 34.6, (1) | 91.4 ± 50.26, (90.33) |
| 2342 | 225.26 ± 140.74, (197.02) | 235.01 ± 143.67, (236.19) | 771.06 ± 852.04, (548.12) | 118.8 ± 96.8, (112.58) | 214 ± 145.52, (177.81) |
| 2351 | 71.89 ± 83.6, (1) | 367.83 ± 164.56, (395.58) | 7.21 ± 22.59, (1) | 148.13 ± 59.67, (163.65) | 164.35 ± 245.83, (118.78) |
| 2363 | 179.83 ± 285.35, (99.81) | 534.86 ± 312.47, (531.1) | 75.2 ± 76.55, (72.58) | 26.81 ± 49.77, (1) | 180.94 ± 226.09, (112.76) |
| 2369 | 15.27 ± 56.73, (1) | 14.76 ± 67.64, (1) | 16.26 ± 28.95, (1) | 0 ± 0, (1) | 9.59 ± 23.22, (1) |
| 2376 | 42.2 ± 238.72, (1) | 0 ± 0, (1) | 0 ± 0, (1) | 0 ± 0, (1) | 1.07 ± 6.85, (1) |
| 2383 | 602.55 ± 380.24, (549.5) | 628.11 ± 218.93, (600.55) | 98.26 ± 72.59, (76.29) | 329.12 ± 105.17, (350.32) | 1158.1 ± 571.89, (1213.58) |
| 2398 | 26.55 ± 70.34, (1) | 17.19 ± 44.3, (1) | 65.89 ± 136.67, (1) | 5.24 ± 16.94, (1) | 95.21 ± 191.23, (36.37) |
| 2414 | 207.25 ± 264.92, (96.71) | 97.34 ± 70.28, (109.24) | 1818.24 ± 1301.3, (2124.24) | 84.07 ± 281.49, (1) | 292.95 ± 634.15, (64.14) |
| 2423 | 274.94 ± 150.2, (269.64) | 350.21 ± 152.05, (346.07) | 177.31 ± 214.58, (104.68) | 214.04 ± 90.95, (205.57) | 276.91 ± 206.36, (226.25) |
| 2434 | 138.13 ± 298.32, (77.39) | 79.95 ± 164.68, (1) | 25.6 ± 29.8, (1) | 53.61 ± 52.63, (55.22) | 50.42 ± 76.37, (30.36) |
| 2448 | 73.26 ± 264.88, (1) | 28.14 ± 46.08, (1) | 44.86 ± 41.85, (54.96) | 11.66 ± 22.94, (1) | 32.44 ± 28.62, (29.32) |
| 2456 | 144.81 ± 390.91, (1) | 154.77 ± 69.02, (177.89) | 151.55 ± 405.32, (67.63) | 48.73 ± 29.22, (57.95) | 330.77 ± 841.48, (45.13) |
| 2471 | 301.38 ± 186.82, (236.25) | 253.59 ± 80.86, (247.36) | 88.78 ± 55.17, (83.38) | 143.32 ± 40.8, (133.74) | 524.74 ± 391.65, (457.95) |
| 2477 | 55.94 ± 72.01, (1) | 226.85 ± 152.35, (234.02) | 90.17 ± 62.32, (96.22) | 30.64 ± 37.24, (1) | 26.39 ± 30.73, (20.64) |
| 2483 | 30.37 ± 58.13, (1) | 8.84 ± 40.52, (1) | 2.61 ± 11.68, (1) | 2.65 ± 15.23, (1) | 34.23 ± 35.35, (22.8) |
| 2498 | 169.01 ± 155.56, (140.09) | 365.29 ± 181.5, (313.07) | 48 ± 48.99, (51.59) | 290.89 ± 96.69, (303.46) | 168.33 ± 100.77, (133.18) |
| 2512 | 215.6 ± 379.84, (160.91) | 854.57 ± 405.59, (928.01) | 151.76 ± 74.32, (140.08) | 102.04 ± 60.83, (116.58) | 224.17 ± 164.33, (196.53) |
| 2519 | 86.58 ± 489.77, (1) | 5.59 ± 25.6, (1) | 3.45 ± 15.42, (1) | 2.24 ± 12.89, (1) | 12.95 ± 18.16, (1) |
| 2529 | 47.87 ± 177.93, (1) | 45.69 ± 88.4, (1) | 37.91 ± 49.6, (19.19) | 8.83 ± 21.33, (1) | 27 ± 25.75, (21.25) |
| 2536 | 161.21 ± 186.56, (133.88) | 106.04 ± 85.31, (125.64) | 41.21 ± 61.38, (1) | 38.03 ± 53.24, (1) | 235.42 ± 115.94, (241.36) |
| 2543 | 20.3 ± 64.3, (1) | 34.88 ± 71.46, (1) | 0 ± 0, (1) | 0 ± 0, (1) | 21.66 ± 52.11, (1) |
| 2551 | 33 ± 93.36, (1) | 0 ± 0, (1) | 48.64 ± 86.43, (1) | 6.53 ± 26.73, (1) | 55.09 ± 182.27, (1) |
| 2558 | 1887.33 ± 1049.03, (1803.51) | 1942.58 ± 1013.52, (2005.09) | 1790.33 ± 875.77, (1741.67) | 1435.1 ± 368.04, (1333.37) | 3528.74 ± 1599.46, (3586.94) |
| 2570 | 63.36 ± 287.03, (1) | 0 ± 0, (1) | 960.6 ± 826.63, (901.87) | 54.15 ± 259.92, (1) | 292.63 ± 413.08, (170.85) |

FIG. 16A (CONT'D)

| Mass | Prostate | Breast | Bladder | Control | Prostate2 |
|---|---|---|---|---|---|
| 2578 | 9.3 ± 52.6, (1) | 0 ± 0, (1) | 0 ± 0, (1) | 0 ± 0, (1) | 1.19 ± 4.09, (1) |
| 2587 | 127.94 ± 193.55, (88.45) | 24.24 ± 52.46, (1) | 63.96 ± 69.49, (75.44) | 24.41 ± 35.07, (1) | 124.47 ± 178.05, (73.94) |
| 2595 | 5.61 ± 31.72, (1) | 0 ± 0, (1) | 0 ± 0, (1) | 0 ± 0, (1) | 1.55 ± 6.92, (1) |
| 2601 | 0 ± 0, (1) | 26.6 ± 49.13, (1) | 8.14 ± 36.4, (1) | 0 ± 0, (1) | 34.24 ± 44.6, (1) |
| 2607 | 565.34 ± 322.95, (476.37) | 686.64 ± 335.04, (792.37) | 389.77 ± 315.07, (385.25) | 182.64 ± 73.01, (167.56) | 1050.89 ± 708.15, (981.87) |
| 2617 | 85.24 ± 163.03, (1) | 231.48 ± 111.76, (218.19) | 19.79 ± 38.46, (1) | 29.85 ± 48.93, (1) | 272.97 ± 530.07, (94.95) |
| 2632 | 287.45 ± 355.26, (196.28) | 99.24 ± 103.36, (94.1) | 32.07 ± 38.57, (22.86) | 86 ± 29.56, (87.68) | 269.6 ± 238.06, (175.91) |
| 2651 | 260.04 ± 1111.31, (1) | 32.23 ± 54.19, (1) | 251.75 ± 440.33, (136.37) | 20.57 ± 30.17, (1) | 359.13 ± 839.86, (61.22) |
| 2658 | 21.91 ± 87.28, (1) | 0 ± 0, (1) | 1.88 ± 8.43, (1) | 0 ± 0, (1) | 2.16 ± 7.47, (1) |
| 2664 | 226.6 ± 167.81, (197.43) | 370.88 ± 127.75, (351.73) | 197.42 ± 132.86, (170.07) | 142.27 ± 55.9, (143.84) | 602.83 ± 454.03, (468.39) |
| 2675 | 223.68 ± 141.35, (223.95) | 176.82 ± 110.1, (192.83) | 15.92 ± 25.99, (1) | 85.94 ± 43.19, (100.61) | 224.03 ± 178.72, (270.7) |
| 2686 | 206.15 ± 122.59, (223.65) | 295.74 ± 108.31, (289.64) | 26.1 ± 36.22, (1) | 101.9 ± 40.57, (105.76) | 281.23 ± 163.54, (284.66) |
| 2694 | 13.34 ± 53.26, (1) | 0 ± 0, (1) | 2.68 ± 12.01, (1) | 0 ± 0, (1) | 4.03 ± 19.2, (1) |
| 2700 | 0 ± 0, (1) | 16.73 ± 43.47, (1) | 3.94 ± 12.15, (1) | 0 ± 0, (1) | 26.05 ± 17.7, (25.21) |
| 2714 | 94.33 ± 146.04, (60.51) | 119.33 ± 63.99, (133.14) | 43.12 ± 28.17, (49.16) | 20.89 ± 26.84, (1) | 204.85 ± 445.14, (66.16) |
| 2720 | 22.58 ± 87.15, (1) | 53.14 ± 70.4, (1) | 2.6 ± 11.63, (1) | 8.49 ± 20.76, (1) | 11.85 ± 18.01, (1) |
| 2730 | 310.64 ± 437.03, (162.51) | 152.86 ± 60.24, (152.26) | 530.95 ± 268.79, (573.43) | 109.58 ± 77.01, (92.98) | 547.54 ± 871.12, (338.64) |
| 2739 | 3.89 ± 21.99, (1) | 11.13 ± 35.19, (1) | 0 ± 0, (1) | 0 ± 0, (1) | 0 ± 0, (1) |
| 2745 | 133.91 ± 117.14, (143.01) | 230.13 ± 64.22, (242.01) | 26.44 ± 51.56, (1) | 81.68 ± 40.25, (86.87) | 183.75 ± 184.01, (151.15) |
| 2761 | 162.39 ± 302.21, (98.96) | 83.07 ± 70.13, (109.19) | 1333.1 ± 1073.2, (1104.71) | 107.96 ± 178.88, (89.45) | 538.48 ± 386.44, (485.2) |
| 2773 | 1374.94 ± 769.55, (1402.29) | 1729.28 ± 915.47, (1767.74) | 230.77 ± 460.16, (57.11) | 1844.05 ± 626.78, (1810.76) | 3031.52 ± 1958.73, (2923.05) |
| 2784 | 31.61 ± 133.01, (1) | 13.54 ± 34.55, (1) | 3.96 ± 12.18, (1) | 0 ± 0, (1) | 8.2 ± 23.08, (1) |
| 2792 | 102.43 ± 200.54, (70.34) | 33.81 ± 56.69, (1) | 22.54 ± 24, (16.25) | 3.01 ± 17.29, (1) | 123.21 ± 125.73, (77.12) |
| 2799 | 3.27 ± 18.48, (1) | 6.61 ± 30.31, (1) | 1.69 ± 7.54, (1) | 0 ± 0, (1) | 4.89 ± 23.61, (1) |
| 2806 | 3.47 ± 19.61, (1) | 0 ± 0, (1) | 1.86 ± 8.31, (1) | 0 ± 0, (1) | 25.09 ± 16.19, (22.05) |
| 2822 | 75.88 ± 98.87, (68.2) | 9.9 ± 25.8, (1) | 235.19 ± 135.75, (222.55) | 14.74 ± 27.55, (1) | 114.63 ± 109.51, (86.93) |
| 2832 | 11.36 ± 32.57, (1) | 156.88 ± 73.56, (166.86) | 5.92 ± 18.23, (1) | 22.29 ± 29, (1) | 36.09 ± 27.05, (30.22) |
| 2841 | 12.83 ± 41.49, (1) | 15.84 ± 39.85, (1) | 18.09 ± 32.63, (1) | 2.45 ± 14.1, (1) | 31.17 ± 80.88, (3.07) |
| 2849 | 201.66 ± 152.1, (152.7) | 136.77 ± 50.03, (142.74) | 4.52 ± 13.95, (1) | 60.4 ± 25.56, (63.14) | 349.04 ± 399.1, (225.96) |
| 2858 | 0 ± 0, (1) | 0 ± 0, (1) | 0 ± 0, (1) | 0 ± 0, (1) | 10.47 ± 14.61, (3.51) |
| 2866 | 58.29 ± 67.58, (31.17) | 81.45 ± 81.45, (82.44) | 0 ± 0, (1) | 5.59 ± 18.59, (1) | 135.24 ± 143.73, (72.32) |

FIG. 16A (CONT'D)

| Mass | Prostate | Breast | Bladder | Control | Prostate2 |
|---|---|---|---|---|---|
| 2874 | 52.42 ± 74.4, (1) | 356.35 ± 173.52, (357.82) | 45.58 ± 34.08, (52.61) | 29.57 ± 29.71, (46.4) | 45.73 ± 45.29, (33.48) |
| 2888 | 155.3 ± 34.62, (156.5) | 121.21 ± 92.43, (140.8) | 104.93 ± 41.31, (94.61) | 95.14 ± 19.65, (93.11) | 248.9 ± 232.55, (181.35) |
| 2904 | 76.52 ± 74.67, (79.23) | 32.79 ± 56.01, (1) | 18.46 ± 29.81, (1) | 39.55 ± 42.57, (1) | 94.65 ± 73.31, (77.5) |
| 2917 | 42.31 ± 61.07, (1) | 36.46 ± 57.41, (1) | 162.92 ± 96.92, (153.77) | 45.8 ± 41.88, (60.31) | 144 ± 209.86, (91.81) |
| 2937 | 2849.34 ± 1600.28, (3138.65) | 2460.84 ± 1085.04, (2461.74) | 449 ± 566.03, (327.68) | 2535.87 ± 532.94, (2536.62) | 5675.32 ± 2738.97, (5895.93) |
| 2948 | 13.64 ± 61.79, (1) | 13.01 ± 59.63, (1) | 0 ± 0, (1) | 30.27 ± 98.49, (1) | 41.22 ± 77.33, (1) |
| 2957 | 187.86 ± 210.06, (78.77) | 413.78 ± 153.44, (369.51) | 17.97 ± 26.24, (1) | 264.18 ± 160.11, (266.62) | 465.84 ± 274.37, (436.44) |
| 2966 | 21.05 ± 83.37, (1) | 2.64 ± 12.09, (1) | 2.19 ± 9.82, (1) | 0 ± 0, (1) | 9.16 ± 13.43, (1) |
| 2981 | 205.59 ± 892.84, (1) | 116.22 ± 53.53, (121.1) | 226.74 ± 195.86, (168.41) | 14.26 ± 38.03, (1) | 74.95 ± 118.46, (33.24) |
| 2989 | 22.54 ± 115.77, (1) | 0 ± 0, (1) | 0 ± 0, (1) | 0 ± 0, (1) | 2.72 ± 8.08, (1) |
| 2997 | 230.46 ± 817.12, (83.4) | 161.11 ± 100.87, (155.43) | 11.26 ± 20.37, (1) | 42.1 ± 36.04, (49.4) | 124.32 ± 84.52, (113.63) |
| 3005 | 20.4 ± 34.17, (1) | 82.44 ± 74.61, (82.27) | 6.73 ± 16.77, (1) | 32.97 ± 31.43, (43.36) | 31.64 ± 24.43, (33.25) |
| 3021 | 30.37 ± 46.89, (1) | 79.97 ± 54.7, (85.34) | 14.35 ± 24.37, (1) | 8.63 ± 18.73, (1) | 78.08 ± 81.28, (57.92) |
| 3034 | 158.48 ± 106.28, (149.42) | 160.43 ± 72.75, (168.72) | 50.07 ± 26.07, (54.45) | 9.81 ± 21.47, (1) | 136.45 ± 111.91, (119.18) |
| 3043 | 15.7 ± 48.04, (1) | 65.55 ± 56.49, (83.76) | 14.21 ± 25.73, (1) | 5.45 ± 17.6, (1) | 5.35 ± 15.5, (1) |
| 3051 | 100.32 ± 133.33, (72.1) | 38.97 ± 57.77, (1) | 30.6 ± 34.16, (17.05) | 22.77 ± 25.62, (1) | 74.33 ± 44.46, (73.01) |
| 3059 | 73.61 ± 118.21, (65.29) | 45.83 ± 61.21, (1) | 93.21 ± 55.12, (81.48) | 11.69 ± 24.74, (1) | 59.6 ± 36.11, (48.9) |
| 3071 | 6.8 ± 21.92, (1) | 8.8 ± 40.34, (1) | 4.56 ± 14.24, (1) | 0 ± 0, (1) | 19.93 ± 50.5, (1) |
| 3080 | 5.23 ± 16.87, (1) | 12.35 ± 27.04, (1) | 0 ± 0, (1) | 3.4 ± 14.02, (1) | 47.52 ± 31.3, (38.98) |
| 3092 | 18.89 ± 43.29, (1) | 95.92 ± 66.2, (109.8) | 0 ± 0, (1) | 29.23 ± 28.08, (41.3) | 49.5 ± 34.71, (41.55) |
| 3101 | 50.59 ± 50.43, (58.82) | 32.56 ± 45.44, (1) | 9.55 ± 19.67, (1) | 56.22 ± 24.78, (58.98) | 76.17 ± 40.94, (75.21) |
| 3108 | 31.65 ± 39.85, (1) | 73.08 ± 51.72, (95.13) | 9.16 ± 18.83, (1) | 17.48 ± 23.79, (1) | 57.16 ± 38.26, (53.18) |
| 3116 | 37.99 ± 51.87, (1) | 41.08 ± 41.71, (54.67) | 3.39 ± 15.18, (1) | 14.39 ± 24.18, (1) | 95.38 ± 97.04, (62.94) |
| 3132 | 34.38 ± 51.6, (1) | 3.18 ± 14.56, (1) | 32.06 ± 34.71, (21.72) | 6.32 ± 17.42, (1) | 64.1 ± 104.22, (25.52) |
| 3143 | 78.31 ± 194.01, (1) | 47.04 ± 47.76, (65.41) | 150.96 ± 74.46, (154.41) | 19.15 ± 33.2, (1) | 171.01 ± 159.51, (143.51) |
| 3157 | 131.56 ± 96.7, (115.74) | 46.84 ± 62.52, (1) | 1378.69 ± 774.81, (1435.63) | 52.33 ± 30.61, (63.11) | 8.02 ± 25.78, (1) |
| 3165 | 490.75 ± 219.94, (460.99) | 218.04 ± 232.1, (178.22) | 0 ± 0, (1) | 146.55 ± 76.97, (134.48) | 792.68 ± 639.09, (568.73) |
| 3173 | 38.22 ± 151.03, (1) | 0 ± 0, (1) | 0 ± 0, (1) | 0 ± 0, (1) | 2.82 ± 13.12, (1) |
| 3181 | 44.78 ± 253.29, (1) | 26.47 ± 56.7, (1) | 994.5 ± 724.4, (814.41) | 4.17 ± 16.71, (1) | 57.92 ± 61.88, (42.27) |
| 3188 | 185.07 ± 351.68, (96.45) | 116.96 ± 71.53, (130.31) | 163.96 ± 352.72, (1) | 146.72 ± 110.92, (130.05) | 41.03 ± 91.03, (1) |
| 3196 | 1230.27 ± 914.13, (1140.9) | 1968.93 ± 882.4, (2048.72) | | 2238.86 ± 540.43, (2188.87) | 2111.66 ± 1363.53, (2053.78) |

FIG. 16A (CONT'D)

| Mass | Prostate | Breast | Bladder | Control | Prostate2 |
|---|---|---|---|---|---|
| 3207 | 6.85 ± 38.73, (1) | 19.14 ± 87.71, (1) | 8.84 ± 19.05, (1) | 0 ± 0, (1) | 82.81 ± 114.89, (44.46) |
| 3221 | 359.63 ± 291.77, (323.94) | 434.02 ± 269.41, (347.58) | 164.34 ± 137.7, (128.77) | 322.25 ± 174.73, (259.59) | 406.93 ± 267.14, (327.64) |
| 3229 | 67.41 ± 136.86, (1) | 11.25 ± 36.44, (1) | 133.58 ± 120.55, (116.01) | 0 ± 0, (1) | 43.24 ± 75.63, (18.47) |
| 3239 | 12.68 ± 44.81, (1) | 35.08 ± 56.92, (1) | 2.65 ± 11.86, (1) | 14.22 ± 30.82, (1) | 2.36 ± 10.89, (1) |
| 3246 | 60.4 ± 100.04, (1) | 45.8 ± 85.53, (1) | 11.86 ± 21.28, (1) | 22.49 ± 48.58, (1) | 233.22 ± 217.61, (194.98) |
| 3259 | 123.98 ± 90.66, (119.58) | 245.5 ± 140.53, (257.78) | 33.95 ± 45.44, (1) | 183.96 ± 133.11, (170.53) | 21.15 ± 76.23, (1) |
| 3267 | 1694.49 ± 1337.71, (1340.86) | 3845.22 ± 1607.33, (3737.23) | 363.36 ± 435.27, (308.7) | 4053.35 ± 608.94, (4055.38) | 3076.52 ± 2224.74, (3018.83) |
| 3278 | 241 ± 545.8, (1) | 109.86 ± 331.01, (1) | 1187.65 ± 600.05, (1277) | 35.09 ± 153.42, (1) | 555.7 ± 599.36, (399.45) |
| 3295 | 93.57 ± 209.46, (1) | 24.72 ± 59.09, (1) | 140.69 ± 231.81, (1) | 18.51 ± 28.23, (1) | 109.31 ± 110.44, (78.19) |
| 3307 | 37.44 ± 108.39, (1) | 4.05 ± 18.55, (1) | 3.67 ± 11.72, (1) | 8.17 ± 31.02, (1) | 115.62 ± 134.81, (84.75) |
| 3320 | 1303.08 ± 777.44, (1102.16) | 1010.24 ± 768.1, (716.5) | 739.8 ± 431, (624.43) | 874.58 ± 605.62, (685.39) | 2049.13 ± 1322.99, (1806.91) |
| 3328 | 238.64 ± 390.54, (1) | 10.26 ± 26.65, (1) | 236.78 ± 263.01, (126.49) | 9.66 ± 47.61, (1) | 132.55 ± 286.31, (1) |
| 3336 | 22.81 ± 129.01, (1) | 13.11 ± 47.34, (1) | 0 ± 0, (1) | 0 ± 0, (1) | 0.83 ± 3, (1) |
| 3345 | 64.89 ± 118.39, (1) | 0 ± 0, (1) | 3.46 ± 10.88, (1) | 4.01 ± 12.97, (1) | 29.27 ± 53.22, (10.15) |
| 3357 | 147.28 ± 123.05, (135.88) | 85.31 ± 68.49, (93.62) | 30.66 ± 29, (35.41) | 56.56 ± 36.53, (49.73) | 204.75 ± 117.77, (169.79) |
| 3367 | 176.42 ± 431.3, (78.34) | 116.32 ± 51.11, (101.25) | 88.12 ± 46.19, (91.52) | 72.59 ± 48.26, (66.67) | 166.13 ± 218.61, (109.82) |
| 3376 | 44.69 ± 149.9, (1) | 49.36 ± 44.74, (50.37) | 16.63 ± 31.6, (1) | 30.25 ± 28.16, (38.51) | 48.97 ± 52.97, (36.5) |
| 3385 | 60.77 ± 343.74, (1) | 0 ± 0, (1) | 1.63 ± 7.28, (1) | 1.59 ± 9.11, (1) | 2.34 ± 11.24, (1) |
| 3393 | 88.92 ± 502.98, (1) | 9.91 ± 31.41, (1) | 3.08 ± 9.55, (1) | 1.12 ± 6.43, (1) | 21.93 ± 11.64, (21.41) |
| 3409 | 22.15 ± 35.03, (1) | 74.08 ± 44.23, (88.41) | 0 ± 0, (1) | 40.48 ± 16.83, (41.95) | 40.54 ± 27.8, (35.05) |
| 3434 | 77.78 ± 34.93, (73.37) | 104.53 ± 64.13, (105.06) | 64.49 ± 47.12, (52.23) | 61.92 ± 19.75, (63.71) | 73.66 ± 45.97, (60.51) |
| 3443 | 3.44 ± 13.78, (1) | 21.18 ± 45.43, (1) | 4.15 ± 12.79, (1) | 0 ± 0, (1) | 1.26 ± 4.5, (1) |
| 3452 | 79.05 ± 41, (83.42) | 176.87 ± 52.85, (158.48) | 55.21 ± 37.7, (52.59) | 91.87 ± 24.31, (88.35) | 71.87 ± 55.78, (57.51) |
| 3476 | 52.22 ± 256.29, (1) | 3.63 ± 16.63, (1) | 60.46 ± 50.78, (52.54) | 0.9 ± 5.19, (1) | 130.48 ± 383.45, (22.44) |
| 3491 | 2.67 ± 10.75, (1) | 18.17 ± 40.13, (1) | 3.11 ± 9.61, (1) | 3.68 ± 8.99, (1) | 24.21 ± 20.6, (18.99) |
| 3504 | 2.54 ± 14.37, (1) | 4.44 ± 20.35, (1) | 0 ± 0, (1) | 0.96 ± 5.51, (1) | 2.16 ± 6.73, (1) |
| 3512 | 104.91 ± 121.75, (89.08) | 91.3 ± 45.93, (78.82) | 12.29 ± 25.87, (1) | 24.85 ± 16.13, (28.95) | 90.07 ± 90.83, (53.54) |
| 3523 | 120.46 ± 109.03, (93.32) | 50.99 ± 43.58, (58.03) | 133.57 ± 80.05, (116.73) | 21.62 ± 17.34, (24.48) | 155.27 ± 163.1, (99.44) |
| 3532 | 40.53 ± 66.57, (36.21) | 6.71 ± 21.18, (1) | 31.84 ± 17.52, (35.7) | 11.14 ± 15.45, (1) | 13.7 ± 54.79, (1) |
| 3547 | 9.47 ± 18.77, (1) | 24.23 ± 31.43, (1) | 5.42 ± 11.35, (1) | 11.47 ± 13.23, (1) | 23.4 ± 16.89, (18.61) |
| 3558 | 0 ± 0, (1) | 4.11 ± 13.29, (1) | 0 ± 0, (1) | 1.21 ± 4.85, (1) | 1.27 ± 5.57, (1) |

FIG. 16A (CONT'D)

| Mass | Prostate | Breast | Bladder | Control | Prostate2 |
|---|---|---|---|---|---|
| 3568 | 9.68 ± 19.37, (1) | 39.6 ± 31.17, (46.82) | 3.32 ± 8.14, (1) | 12.38 ± 14.02, (1) | 15.3 ± 10.21, (14.3) |
| 3579 | 0 ± 0, (1) | 13.84 ± 23.73, (1) | 4.92 ± 12.21, (1) | 7.28 ± 12.1, (1) | 12.44 ± 9.52, (12.55) |
| 3590 | 25.43 ± 25.62, (31.95) | 44.06 ± 25.03, (52.32) | 35.44 ± 22.99, (32.23) | 11.59 ± 12.32, (1) | 25.34 ± 15.67, (21.53) |
| 3598 | 6.96 ± 17.43, (1) | 7.2 ± 18.28, (1) | 30.84 ± 28.48, (28.3) | 5.67 ± 11.57, (1) | 9.38 ± 13.1, (4.41) |
| 3610 | 5.74 ± 14.68, (1) | 38.91 ± 35.62, (34.55) | 2.44 ± 7.54, (1) | 8.97 ± 13.74, (1) | 15.8 ± 17.86, (11.17) |
| 3618 | 5.06 ± 12.09, (1) | 23.27 ± 41.66, (1) | 11.19 ± 14.71, (1) | 6.61 ± 11.14, (1) | 15.03 ± 16.14, (12.96) |
| 3626 | 4.13 ± 17.77, (1) | 8.21 ± 18.06, (1) | 4.55 ± 11.34, (1) | 1.47 ± 5.87, (1) | 2.38 ± 5.8, (1) |
| 3635 | 67.74 ± 88.53, (51.61) | 52.84 ± 22.12, (56.44) | 23.95 ± 30.66, (22.55) | 31.58 ± 9.73, (30.83) | 91.55 ± 348.69, (34.67) |
| 3646 | 39.02 ± 26.96, (42.77) | 21.97 ± 25.09, (1) | 8.93 ± 14.74, (1) | 8.04 ± 13.19, (1) | 22.64 ± 32.08, (14.72) |
| 3656 | 9.88 ± 20.28, (1) | 13.47 ± 28.6, (1) | 5.11 ± 12.56, (1) | 3.38 ± 8.19, (1) | 18.19 ± 23.13, (14.82) |
| 3671 | 23.26 ± 25.3, (12.97) | 24.16 ± 30.45, (1) | 9.69 ± 20.57, (1) | 7.66 ± 13.37, (1) | 21.32 ± 21.54, (16.51) |
| 3689 | 76.36 ± 53.69, (57.66) | 42.43 ± 35.38, (51.75) | 119.03 ± 73.55, (108.56) | 17.74 ± 16.15, (19.98) | 73.85 ± 77.04, (52.02) |
| 3698 | 2.06 ± 8.2, (1) | 2.52 ± 11.55, (1) | 0 ± 0, (1) | 3.85 ± 9.3, (1) | 8.8 ± 6.55, (9.45) |
| 3709 | 3 ± 11.86, (1) | 4.18 ± 13.39, (1) | 7.38 ± 13.43, (1) | 1.41 ± 5.71, (1) | 8.76 ± 12.12, (3.03) |
| 3718 | 11.83 ± 21.53, (1) | 37.45 ± 30.61, (45.59) | 2.95 ± 9.19, (1) | 4.37 ± 9.55, (1) | 17.8 ± 10.76, (16.06) |
| 3735 | 7.2 ± 15.8, (1) | 13.68 ± 25.25, (1) | 0 ± 0, (1) | 3.87 ± 9.34, (1) | 15.17 ± 10, (14.61) |
| 3743 | 19.75 ± 25.37, (1) | 43.74 ± 29.57, (46.37) | 6.91 ± 12.53, (1) | 9.67 ± 13.43, (1) | 16.61 ± 13.23, (15.19) |
| 3758 | 27.51 ± 42.87, (1) | 32.29 ± 31.74, (35.75) | 5.56 ± 11.72, (1) | 7.48 ± 12.96, (1) | 25.47 ± 24.16, (19.52) |
| 3768 | 12.67 ± 25.34, (1) | 4.88 ± 15.43, (1) | 0 ± 0, (1) | 4.67 ± 11.65, (1) | 9.05 ± 29.05, (1) |
| 3778 | 109.47 ± 62.87, (111.01) | 53.83 ± 39.31, (56.7) | 189.11 ± 118.37, (175.16) | 24.73 ± 16.56, (24.98) | 125.2 ± 116.02, (77.9) |
| 3787 | 16.37 ± 85.17, (1) | 0 ± 0, (1) | 0 ± 0, (1) | 2.05 ± 8.48, (1) | 2.76 ± 5.23, (1) |
| 3798 | 12.4 ± 41.56, (1) | 6.73 ± 17.06, (1) | 0 ± 0, (1) | 4.99 ± 10.88, (1) | 17.33 ± 19.41, (13.26) |
| 3818 | 83.68 ± 58.63, (68.44) | 42.81 ± 29.91, (44.15) | 89.52 ± 52.31, (80.24) | 17.44 ± 14.1, (21.81) | 82.26 ± 65.52, (64.13) |
| 3828 | 27.67 ± 104.26, (1) | 3.35 ± 10.77, (1) | 1.06 ± 4.74, (1) | 1.82 ± 7.43, (1) | 9.42 ± 11.12, (5.99) |
| 3841 | 0.84 ± 4.77, (1) | 2.29 ± 10.51, (1) | 1.19 ± 5.31, (1) | 0 ± 0, (1) | 4.03 ± 6.15, (1) |
| 3852 | 0 ± 0, (1) | 9.87 ± 19.31, (1) | 0 ± 0, (1) | 0 ± 0, (1) | 15.06 ± 7.24, (13.25) |
| 3863 | 2.66 ± 10.5, (1) | 0 ± 0, (1) | 0 ± 0, (1) | 0.52 ± 3, (1) | 12.82 ± 9.35, (12.13) |
| 3888 | 91.97 ± 41.34, (87.89) | 123.67 ± 37.24, (124.79) | 34.34 ± 22.19, (37.52) | 75.2 ± 23.27, (78.01) | 143.94 ± 58.77, (143.21) |
| 3897 | 3.52 ± 12.02, (1) | 3.19 ± 14.61, (1) | 0 ± 0, (1) | 0.63 ± 3.63, (1) | 6.69 ± 13.46, (1) |
| 3908 | 0 ± 0, (1) | 11.54 ± 29.5, (1) | 7 ± 15.8, (1) | 1.93 ± 7.86, (1) | 1.99 ± 5.73, (1) |
| 3920 | 11.79 ± 30.73, (1) | 19.15 ± 32.52, (1) | | 18.76 ± 24.73, (1) | 30.16 ± 24.64, (25.61) |

FIG. 16A (CONT'D)

| Mass | Prostate | Breast | Bladder | Control | Prostate2 |
|---|---|---|---|---|---|
| 3931 | 50.87 ± 48.64, (51.33) | 59.79 ± 49.3, (70.29) | 61.81 ± 51.81, (51.17) | 41.71 ± 33.11, (46.43) | 19.29 ± 30.57, (1) |
| 3940 | 0 ± 0, (1) | 0 ± 0, (1) | 2.02 ± 9.02, (1) | 0 ± 0, (1) | 244.31 ± 522.62, (147.49) |
| 3960 | 1089.65 ± 699.43, (905.2) | 693.97 ± 377.07, (590.35) | 1740.34 ± 956.75, (1677.38) | 694.26 ± 210.11, (682.01) | 1581.36 ± 1092.46, (1282.84) |
| 3977 | 92.08 ± 242.92, (1) | 274.17 ± 624.47, (1) | 1142.42 ± 880.3, (957.31) | 81.4 ± 165.25, (1) | 562.91 ± 724.07, (302.46) |
| 3989 | 17.73 ± 29.68, (1) | 11.5 ± 44.64, (1) | 68.91 ± 82.73, (32.35) | 1.93 ± 7.75, (1) | 28.09 ± 33.35, (17.57) |
| 3999 | 0 ± 0, (1) | 0 ± 0, (1) | 5.37 ± 24.02, (1) | 0 ± 0, (1) | 0 ± 0, (1) |
| 4008 | 1.03 ± 5.83, (1) | 0 ± 0, (1) | 0 ± 0, (1) | 0 ± 0, (1) | 3.24 ± 12.15, (1) |
| 4029 | 8.53 ± 33.67, (1) | 15.56 ± 71.28, (1) | 0 ± 0, (1) | 0 ± 0, (1) | 14.81 ± 33.36, (1) |
| 4048 | 373.68 ± 174.82, (344.77) | 238.73 ± 175.22, (239.04) | 242.37 ± 144.74, (260.92) | 111.84 ± 109.46, (149.81) | 462.68 ± 271.02, (440.59) |
| 4064 | 3.71 ± 20.98, (1) | 29.71 ± 80.08, (1) | 0 ± 0, (1) | 28.07 ± 69.7, (1) | 1.36 ± 8.69, (1) |
| 4080 | 176.73 ± 164.48, (180.49) | 239.5 ± 120.05, (270.92) | 20.34 ± 66.13, (1) | 337.87 ± 143.66, (350.89) | 134.19 ± 151.38, (120.81) |
| 4090 | 24.38 ± 102.09, (1) | 18.68 ± 85.59, (1) | 5.88 ± 26.29, (1) | 8.85 ± 50.83, (1) | 4.64 ± 18.23, (1) |
| 4104 | 5.86 ± 33.14, (1) | 0 ± 0, (1) | 0 ± 0, (1) | 0 ± 0, (1) | 0 ± 0, (1) |
| 4114 | 63.55 ± 111.66, (1) | 83.33 ± 187.29, (1) | 72.08 ± 133.59, (1) | 45.06 ± 92.58, (1) | 29.51 ± 75.36, (1) |
| 4130 | 66.67 ± 155.61, (1) | 7.46 ± 34.17, (1) | 5.49 ± 24.55, (1) | 43.67 ± 95.68, (1) | 30.56 ± 140.05, (1) |
| 4140 | 52.34 ± 115.03, (1) | 0 ± 0, (1) | 76.26 ± 96.77, (1) | 26.08 ± 104.84, (1) | 127.67 ± 132.18, (99.82) |
| 4152 | 34.49 ± 114.69, (1) | 27.94 ± 89.25, (1) | 0 ± 0, (1) | 5.23 ± 30.07, (1) | 9.72 ± 33.16, (1) |
| 4161 | 17.11 ± 96.77, (1) | 0 ± 0, (1) | 0 ± 0, (1) | 0 ± 0, (1) | 0 ± 0, (1) |
| 4172 | 14.48 ± 81.9, (1) | 0 ± 0, (1) | 5.2 ± 23.26, (1) | 0 ± 0, (1) | 4.33 ± 27.73, (1) |
| 4182 | 220.6 ± 165.66, (213.45) | 255.77 ± 172.1, (280.03) | 27.74 ± 80.49, (1) | 343.63 ± 124.03, (332.11) | 39.85 ± 95.71, (1) |
| 4192 | 885.71 ± 594.73, (876.96) | 1599.54 ± 367.22, (1684.09) | 68.51 ± 256.55, (1) | 1384.26 ± 345.28, (1260.57) | 2029.71 ± 1016.84, (1899.29) |
| 4202 | 71.24 ± 300.73, (1) | 31.01 ± 142.11, (1) | 0 ± 0, (1) | 0 ± 0, (1) | 0 ± 0, (1) |
| 4215 | 82.66 ± 183.01, (1) | 225.52 ± 189.93, (216.91) | 16.63 ± 74.39, (1) | 300.99 ± 183.35, (328.21) | 8.54 ± 50.37, (1) |
| 4237 | 13.44 ± 76.01, (1) | 0 ± 0, (1) | 16.63 ± 74.39, (1) | 0 ± 0, (1) | 0.99 ± 6.34, (1) |
| 4251 | 24.98 ± 115.11, (1) | 0 ± 0, (1) | 54.82 ± 127.33, (1) | 0 ± 0, (1) | 0 ± 0, (1) |
| 4262 | 9.41 ± 53.24, (1) | 0 ± 0, (1) | 589.76 ± 1433.53, (1) | 19.51 ± 112.05, (1) | 130.9 ± 554.95, (1) |
| 4272 | 815.44 ± 772.4, (661.24) | 461.83 ± 1014.05, (205.45) | 2619.7 ± 1488.91, (2851.85) | 268.04 ± 572.24, (1) | 1726.88 ± 2553.58, (753.39) |
| 4284 | 48.67 ± 187.27, (1) | 53.96 ± 111.42, (1) | 114.71 ± 189.56, (1) | 78.1 ± 142.11, (1) | 47.63 ± 209.69, (1) |
| 4295 | 12.48 ± 52.05, (1) | 20.59 ± 65.05, (1) | 82.7 ± 238.18, (1) | 13.22 ± 54.56, (1) | 5.21 ± 21.52, (1) |
| 4328 | 0 ± 0, (1) | 0 ± 0, (1) | 0 ± 0, (1) | 0 ± 0, (1) | 38.91 ± 63.19, (1) |
| 4345 | 10.2 ± 57.69, (1) | 0 ± 0, (1) | 12.35 ± 38.04, (1) | 0 ± 0, (1) | 14.37 ± 26.43, (1) |

FIG. 16A (CONT'D)

| Mass | Prostate | Breast | Bladder | Control | Prostate2 |
|---|---|---|---|---|---|
| 4362 | 0 ± 0, (1) | 0 ± 0, (1) | 6.41 ± 28.66, (1) | 0 ± 0, (1) | 25.04 ± 45.19, (1) |
| 4373 | 5.43 ± 30.71, (1) | 0 ± 0, (1) | 0 ± 0, (1) | 21.94 ± 60.75, (1) | 81.26 ± 59.39, (91.75) |
| 4390 | 0 ± 0, (1) | 0 ± 0, (1) | 0 ± 0, (1) | 0 ± 0, (1) | 9.43 ± 22.01, (1) |
| 4409 | 43.04 ± 63.73, (1) | 60.7 ± 82.76, (1) | 5.99 ± 26.8, (1) | 108.46 ± 75.56, (137.83) | 4.56 ± 17.82, (1) |
| 4429 | 347.03 ± 296.43, (346.6) | 474.45 ± 432.01, (429.48) | 617.34 ± 468.2, (526.95) | 425.04 ± 190.26, (472.1) | 415.92 ± 494.6, (206.28) |
| 4444 | 195.13 ± 220.25, (136.65) | 222.24 ± 261.77, (164.97) | 212.89 ± 289.67, (1) | 112.73 ± 196.26, (1) | 120.61 ± 251.07, (1) |
| 4455 | 31.36 ± 102.64, (1) | 24.18 ± 63.18, (1) | 59.14 ± 98.09, (1) | 8.7 ± 34.8, (1) | 9.11 ± 26.72, (1) |
| 4468 | 0 ± 0, (1) | 19.95 ± 63.12, (1) | 0 ± 0, (1) | 0 ± 0, (1) | 4.59 ± 16.59, (1) |
| 4480 | 0 ± 0, (1) | 0 ± 0, (1) | 0 ± 0, (1) | 0 ± 0, (1) | 20.39 ± 41.18, (1) |
| 4490 | 5.03 ± 28.46, (1) | 12.75 ± 58.44, (1) | 0 ± 0, (1) | 0 ± 0, (1) | 3.84 ± 14.09, (1) |
| 4511 | 0 ± 0, (1) | 24.45 ± 78.9, (1) | 5.61 ± 25.09, (1) | 0 ± 0, (1) | 30.66 ± 40.76, (1) |
| 4531 | 30.78 ± 73.65, (1) | 57.99 ± 95.97, (1) | 11.44 ± 51.17, (1) | 30.64 ± 84.12, (1) | 24.76 ± 38.88, (1) |
| 4556 | 120.4 ± 212.57, (1) | 59.45 ± 110.73, (1) | 87.24 ± 161.43, (1) | 77.88 ± 174.27, (1) | 213.5 ± 142.8, (192.51) |
| 4566 | 77.49 ± 185.74, (1) | 0 ± 0, (1) | 32.17 ± 101.01, (1) | 11.6 ± 66.65, (1) | 14.99 ± 38.62, (1) |
| 4583 | 7.69 ± 43.48, (1) | 0 ± 0, (1) | 0 ± 0, (1) | 0 ± 0, (1) | 8.69 ± 21.94, (1) |
| 4614 | 182.7 ± 204.12, (61.21) | 210.55 ± 110.12, (252.86) | 88.02 ± 118.23, (1) | 324.54 ± 136.04, (366.35) | 3.18 ± 14.23, (1) |
| 4631 | 950.45 ± 378.46, (819.99) | 994.7 ± 271.21, (986.77) | 664.56 ± 335.09, (747.07) | 1191.67 ± 292.57, (1194.98) | 1787.91 ± 853.31, (1732.22) |
| 4641 | 14.27 ± 80.75, (1) | 0 ± 0, (1) | 49.75 ± 155.5, (1) | 0 ± 0, (1) | 1.57 ± 10.06, (1) |
| 4655 | 194.42 ± 215.28, (62.13) | 291.85 ± 137.22, (333.2) | 152.5 ± 128.48, (191.31) | 305.08 ± 156.47, (343.17) | 8.95 ± 26.89, (1) |
| 4686 | 43.81 ± 139.29, (1) | 0 ± 0, (1) | 0 ± 0, (1) | 0 ± 0, (1) | 13.5 ± 31.88, (1) |
| 4696 | 147.11 ± 212.84, (1) | 55.4 ± 139.52, (1) | 93.16 ± 148.83, (1) | 46.84 ± 133.02, (1) | 292.98 ± 176.63, (272.25) |
| 4721 | 7.86 ± 31.22, (1) | 26.75 ± 67.34, (1) | 19.06 ± 47.61, (1) | 10.87 ± 37.11, (1) | 25.07 ± 33.71, (1) |
| 4776 | 141.17 ± 133.85, (149.39) | 71.3 ± 95.13, (1) | 13.56 ± 60.62, (1) | 18 ± 50.14, (1) | 257.82 ± 225.16, (205.8) |
| 4804 | 56.89 ± 125.59, (1) | 32.99 ± 71.14, (1) | 0 ± 0, (1) | 28.12 ± 51.2, (1) | 27.08 ± 38.02, (1) |
| 4836 | 0 ± 0, (1) | 0 ± 0, (1) | 5.67 ± 25.34, (1) | 0 ± 0, (1) | 66.69 ± 34.26, (61.66) |
| 4864 | 0 ± 0, (1) | 0 ± 0, (1) | 0 ± 0, (1) | 0 ± 0, (1) | 31.39 ± 37.8, (1) |
| 4889 | 3.99 ± 22.55, (1) | 0 ± 0, (1) | 0 ± 0, (1) | 0 ± 0, (1) | 34.31 ± 41.83, (1) |
| 4917 | 0 ± 0, (1) | 7.95 ± 36.43, (1) | 0 ± 0, (1) | 0 ± 0, (1) | 30.58 ± 32.24, (32.03) |
| 4950 | 50.63 ± 73.81, (1) | 249.7 ± 163.99, (301.26) | 0 ± 0, (1) | 44.49 ± 68.37, (1) | 77.73 ± 47.75, (75.25) |
| 4983 | 176.31 ± 692.3, (1) | 0 ± 0, (1) | 10.78 ± 33.67, (1) | 8.7 ± 34.84, (1) | 78.23 ± 393.57, (1) |
| 5013 | 188.71 ± 488.44, (1) | 0 ± 0, (1) | 828.21 ± 487.82, (739.13) | 41.29 ± 139.31, (1) | 668.48 ± 2025.22, (63.32) |

FIG. 16A (CONT'D)

| Mass | Prostate | Breast | Bladder | Control | Prostate2 |
|---|---|---|---|---|---|
| 5040 | 132.83 ± 273.92, (122.57) | 58.17 ± 95.57, (1) | 8.45 ± 37.79, (1) | 111.52 ± 88.13, (128.74) | 11.65 ± 32.74, (1) |
| 5068 | 431.3 ± 291.5, (440.99) | 547.41 ± 189.68, (524.93) | 229.54 ± 409.22, (1) | 606.09 ± 264.85, (571.51) | 707.3 ± 1025.13, (481.38) |
| 5108 | 0 ± 0, (1) | 0 ± 0, (1) | 0 ± 0, (1) | 0 ± 0, (1) | 9.38 ± 28.7, (1) |
| 5145 | 279.64 ± 197.51, (268.86) | 270.65 ± 187.76, (300.64) | 852.96 ± 564.1, (753.51) | 477.1 ± 253.88, (516.89) | 457.47 ± 533.68, (292.14) |
| 5175 | 0 ± 0, (1) | 6.05 ± 27.73, (1) | 7.29 ± 32.58, (1) | 0 ± 0, (1) | 15.06 ± 33.91, (1) |
| 5204 | 0 ± 0, (1) | 0 ± 0, (1) | 0 ± 0, (1) | 0 ± 0, (1) | 17.06 ± 28.75, (1) |
| 5238 | 33.44 ± 138.64, (1) | 10.95 ± 50.17, (1) | 0 ± 0, (1) | 0 ± 0, (1) | 57.22 ± 37.44, (53.59) |
| 5267 | 2.68 ± 15.18, (1) | 0 ± 0, (1) | 0 ± 0, (1) | 0 ± 0, (1) | 12.97 ± 25.73, (1) |
| 5294 | 0 ± 0, (1) | 0 ± 0, (1) | 0 ± 0, (1) | 0 ± 0, (1) | 3.67 ± 16.57, (1) |
| 5322 | 502.57 ± 340.08, (498.8) | 511.42 ± 183.73, (480.44) | 127.16 ± 147.33, (121.6) | 420.39 ± 141.26, (407.39) | 1237.65 ± 800.81, (1154.61) |
| 5351 | 121.56 ± 389.47, (1) | 7.62 ± 34.92, (1) | 198.65 ± 108.62, (199.61) | 12.26 ± 51.63, (1) | 22.24 ± 39.14, (1) |
| 5383 | 22.5 ± 73.14, (1) | 0 ± 0, (1) | 28.86 ± 75.04, (1) | 0 ± 0, (1) | 32.26 ± 34.01, (30.16) |
| 5413 | 4.97 ± 28.12, (1) | 0 ± 0, (1) | 148.98 ± 134.87, (195.84) | 3.29 ± 18.92, (1) | 15.74 ± 40.22, (1) |
| 5441 | 15.13 ± 61.46, (1) | 0 ± 0, (1) | 11.68 ± 28.53, (1) | 0 ± 0, (1) | 28.04 ± 24.58, (32.62) |
| 5477 | 0 ± 0, (1) | 11.05 ± 34.92, (1) | 0 ± 0, (1) | 5.4 ± 21.59, (1) | 31.35 ± 27, (36.23) |
| 5509 | 0 ± 0, (1) | 0 ± 0, (1) | 15.13 ± 46.64, (1) | 3.13 ± 18, (1) | 29.5 ± 25.9, (29.78) |
| 5546 | 9.07 ± 29.71, (1) | 5.97 ± 27.38, (1) | 35.49 ± 57.31, (1) | 2.56 ± 14.71, (1) | 29.7 ± 36.65, (26.71) |
| 5580 | 2.91 ± 16.45, (1) | 11.32 ± 35.97, (1) | 0 ± 0, (1) | 30.2 ± 50.91, (1) | 26.55 ± 26.89, (28.17) |
| 5609 | 11.2 ± 45.89, (1) | 5.92 ± 27.14, (1) | 6.44 ± 28.81, (1) | 64.35 ± 68.87, (1) | 43.22 ± 36.05, (41.12) |
| 5645 | 6.24 ± 24.62, (1) | 0 ± 0, (1) | 0 ± 0, (1) | 0 ± 0, (1) | 17.98 ± 24.35, (1) |
| 5676 | 0 ± 0, (1) | 0 ± 0, (1) | 4.85 ± 21.71, (1) | 0 ± 0, (1) | 21.37 ± 24.58, (1) |
| 5707 | 0 ± 0, (1) | 0 ± 0, (1) | 0 ± 0, (1) | 7.65 ± 31.44, (1) | 11.41 ± 20.57, (1) |
| 5737 | 7.77 ± 31.23, (1) | 80.99 ± 98.91, (1) | 50.03 ± 58.02, (1) | 119.46 ± 123.29, (140.43) | 48.63 ± 25.61, (49.95) |
| 5770 | 0 ± 0, (1) | 0 ± 0, (1) | 18.06 ± 37.37, (1) | 0 ± 0, (1) | 16.76 ± 26.03, (1) |
| 5816 | 0 ± 0, (1) | 0 ± 0, (1) | 16.49 ± 40.42, (1) | 7.16 ± 41.14, (1) | 26.9 ± 30.11, (23.46) |
| 5853 | 16.42 ± 44.42, (1) | 0 ± 0, (1) | 47.94 ± 73.06, (1) | 6.07 ± 34.87, (1) | 8.51 ± 20.75, (1) |
| 5888 | 1054.81 ± 627.53, (1017.01) | 2596.05 ± 1033.3, (2365.27) | 243.27 ± 400.35, (146.37) | 1850.13 ± 522.29, (1871.1) | 3039.98 ± 2229.66, (2770.16) |
| 5923 | 43.85 ± 68.4, (1) | 136.62 ± 146.38, (146.82) | 19.6 ± 40.94, (1) | 77.22 ± 122.39, (1) | 19.07 ± 30.64, (1) |
| 5957 | 44.6 ± 146.62, (1) | 8.1 ± 37.13, (1) | 33.3 ± 53.67, (1) | 5.01 ± 28.75, (1) | 32.91 ± 34.7, (38.99) |
| 5997 | 3.65 ± 20.63, (1) | 0 ± 0, (1) | 12.11 ± 37.67, (1) | 0 ± 0, (1) | 25.49 ± 30.66, (1) |
| 6028 | 0 ± 0, (1) | 0 ± 0, (1) | 0 ± 0, (1) | 0 ± 0, (1) | 30 ± 27.27, (33.02) |

FIG. 16A (CONT'D)

| Mass | Prostate | Breast | Bladder | Control | Prostate2 |
|---|---|---|---|---|---|
| 6062 | 0 ± 0, (1) | 0 ± 0, (1) | 0 ± 0, (1) | 0 ± 0, (1) | 39.85 ± 36.32, (38.44) |
| 6111 | 0 ± 0, (1) | 0 ± 0, (1) | 23.02 ± 56.78, (1) | 0 ± 0, (1) | 18.14 ± 25.35, (1) |
| 6152 | 30.22 ± 170.94, (1) | 0 ± 0, (1) | 4.64 ± 20.75, (1) | 0 ± 0, (1) | 9.8 ± 18.2, (1) |
| 6184 | 31.91 ± 135.88, (1) | 0 ± 0, (1) | 109.8 ± 93.62, (113.62) | 3.42 ± 19.64, (1) | 44.99 ± 78.14, (34.55) |
| 6220 | 4.03 ± 22.82, (1) | 0 ± 0, (1) | 0 ± 0, (1) | 0 ± 0, (1) | 53.39 ± 38.7, (57.8) |
| 6255 | 0 ± 0, (1) | 0 ± 0, (1) | 0 ± 0, (1) | 0 ± 0, (1) | 14.18 ± 22.35, (1) |
| 6294 | 0 ± 0, (1) | 0 ± 0, (1) | 0 ± 0, (1) | 3.54 ± 20.35, (1) | 34.29 ± 27.76, (35.76) |
| 6355 | 0 ± 0, (1) | 0 ± 0, (1) | 0 ± 0, (1) | 0 ± 0, (1) | 11.31 ± 22.24, (1) |
| 6393 | 32.21 ± 159.92, (1) | 0 ± 0, (1) | 6.6 ± 29.54, (1) | 7.23 ± 29.72, (1) | 3.79 ± 14.41, (1) |
| 6431 | 1785.43 ± 661.21, (1918.64) | 1198.12 ± 728.01, (1140.39) | 1636.3 ± 585.25, (1531.65) | 1467.32 ± 689.65, (1359.01) | 2575.38 ± 1238.98, (2661.47) |
| 6471 | 0 ± 0, (1) | 0 ± 0, (1) | 0 ± 0, (1) | 0 ± 0, (1) | 48.87 ± 48.98, (54.4) |
| 6512 | 0 ± 0, (1) | 0 ± 0, (1) | 0 ± 0, (1) | 0 ± 0, (1) | 33.07 ± 37.03, (34.48) |
| 6562 | 166.04 ± 494.09, (1) | 0 ± 0, (1) | 600.61 ± 912.06, (1) | 27.56 ± 111.57, (1) | 37.31 ± 157.96, (1) |
| 6598 | 4278.83 ± 1092.66, (4083.68) | 5065.09 ± 2141.4, (5437.47) | 3479.86 ± 938.98, (3601.64) | 4394.7 ± 1229.96, (4274.71) | 12282.42 ± 3582.39, (12660.9) |
| 6633 | 83.74 ± 162.03, (78.64) | 72.78 ± 68.57, (96.7) | 57.84 ± 50.19, (68.06) | 104.45 ± 188.19, (1) | 203.95 ± 195.41, (184.81) |
| 6670 | 9.64 ± 32.59, (1) | 4.43 ± 20.3, (1) | 0 ± 0, (1) | 5.19 ± 29.8, (1) | 106.85 ± 205.14, (1) |
| 6713 | 2.05 ± 11.61, (1) | 0 ± 0, (1) | 0 ± 0, (1) | 0 ± 0, (1) | 34.2 ± 33.35, (33.33) |
| 6754 | 0 ± 0, (1) | 15.13 ± 39.53, (1) | 0 ± 0, (1) | 0 ± 0, (1) | 4.71 ± 12.08, (1) |
| 6790 | 21.68 ± 55.54, (1) | 8.43 ± 26.74, (1) | 11.55 ± 29.7, (1) | 0 ± 0, (1) | 77.85 ± 136.53, (52.65) |
| 6826 | 0 ± 0, (1) | 0 ± 0, (1) | 0 ± 0, (1) | 0 ± 0, (1) | 7.06 ± 13.07, (1) |
| 6866 | 0 ± 0, (1) | 0 ± 0, (1) | 0 ± 0, (1) | 0 ± 0, (1) | 8.92 ± 14.34, (1) |
| 6906 | 0 ± 0, (1) | 0 ± 0, (1) | 0 ± 0, (1) | 0 ± 0, (1) | 21.7 ± 25.27, (22.03) |
| 6942 | 0 ± 0, (1) | 8.41 ± 26.75, (1) | 4.2 ± 18.78, (1) | 2.45 ± 14.07, (1) | 8.65 ± 13.41, (1) |
| 6981 | 1.81 ± 10.23, (1) | 4.68 ± 21.44, (1) | 0 ± 0, (1) | 2.99 ± 17.19, (1) | 13.33 ± 19.48, (1) |
| 7021 | 2.75 ± 15.56, (1) | 9.48 ± 30.31, (1) | 3.97 ± 17.77, (1) | 9.76 ± 26.99, (1) | 23.15 ± 22.22, (25.39) |
| 7060 | 0 ± 0, (1) | 0 ± 0, (1) | 0 ± 0, (1) | 6.52 ± 20.97, (1) | 15.15 ± 15.35, (17.33) |
| 7103 | 1.44 ± 8.14, (1) | 3.73 ± 17.08, (1) | 0 ± 0, (1) | 5.6 ± 18.12, (1) | 22.09 ± 17.42, (21.77) |
| 7142 | 3.18 ± 12.61, (1) | 0 ± 0, (1) | 0 ± 0, (1) | 1.96 ± 11.25, (1) | 22.11 ± 21.29, (20.23) |
| 7180 | 0 ± 0, (1) | 3.94 ± 18.06, (1) | 0 ± 0, (1) | 0 ± 0, (1) | 10.44 ± 14.54, (1) |
| 7219 | 0 ± 0, (1) | 0 ± 0, (1) | 0 ± 0, (1) | 0 ± 0, (1) | 17.24 ± 23.71, (16.23) |
| 7260 | 0 ± 0, (1) | 0 ± 0, (1) | 0 ± 0, (1) | 0 ± 0, (1) | 12.95 ± 13.05, (15.14) |

FIG. 16A (CONT'D)

| Mass | Prostate | Breast | Bladder | Control | Prostate2 |
|---|---|---|---|---|---|
| 7305 | 1.81 ± 10.25, (1) | 0 ± 0, (1) | 0 ± 0, (1) | 3.9 ± 15.62, (1) | 15.75 ± 16.07, (16.67) |
| 7345 | 1.72 ± 9.74, (1) | 0 ± 0, (1) | 0 ± 0, (1) | 0 ± 0, (1) | 15.25 ± 13.45, (17.15) |
| 7384 | 0 ± 0, (1) | 0 ± 0, (1) | 0 ± 0, (1) | 0 ± 0, (1) | 12.03 ± 15.34, (1) |
| 7427 | 0 ± 0, (1) | 0 ± 0, (1) | 0 ± 0, (1) | 0 ± 0, (1) | 12.27 ± 16.14, (10.13) |
| 7466 | 0 ± 0, (1) | 0 ± 0, (1) | 0 ± 0, (1) | 0 ± 0, (1) | 11.89 ± 13.46, (10.08) |
| 7510 | 0 ± 0, (1) | 0 ± 0, (1) | 0 ± 0, (1) | 0 ± 0, (1) | 12.79 ± 15.11, (9.66) |
| 7561 | 0 ± 0, (1) | 10.02 ± 45.9, (1) | 0 ± 0, (1) | 0 ± 0, (1) | 14.54 ± 13.19, (18) |
| 7607 | 4.76 ± 19.02, (1) | 0 ± 0, (1) | 0 ± 0, (1) | 4.17 ± 16.69, (1) | 18.64 ± 43.19, (1) |
| 7647 | 0 ± 0, (1) | 0 ± 0, (1) | 0 ± 0, (1) | 2 ± 11.47, (1) | 14.22 ± 15.96, (11.77) |
| 7688 | 9.77 ± 26.77, (1) | 0 ± 0, (1) | 10.71 ± 22.19, (1) | 0 ± 0, (1) | 1.89 ± 7.11, (1) |
| 7731 | 345.27 ± 118.66, (336.72) | 538.92 ± 173.84, (574.35) | 258.13 ± 84.27, (248.19) | 397.77 ± 130.31, (374.8) | 592.66 ± 294.22, (578.3) |
| 7771 | 22.25 ± 30.25, (1) | 69 ± 110.66, (66.8) | 8.63 ± 17.75, (1) | 24.71 ± 41.07, (1) | 8.11 ± 11.65, (1) |
| 7813 | 0 ± 0, (1) | 0 ± 0, (1) | 2.7 ± 12.05, (1) | 0 ± 0, (1) | 10.48 ± 15.81, (1) |
| 7854 | 0 ± 0, (1) | 0 ± 0, (1) | 0 ± 0, (1) | 0 ± 0, (1) | 7.04 ± 10.76, (1) |
| 7899 | 6.73 ± 30, (1) | 16.05 ± 34.92, (1) | 4.91 ± 15.44, (1) | 2.13 ± 12.24, (1) | 37.44 ± 46.51, (31.5) |
| 7956 | 0 ± 0, (1) | 0 ± 0, (1) | 0 ± 0, (1) | 0 ± 0, (1) | 7.82 ± 14.91, (1) |
| 7997 | 6.52 ± 25.7, (1) | 0 ± 0, (1) | 0 ± 0, (1) | 0 ± 0, (1) | 7.88 ± 10.69, (1) |
| 8043 | 7.08 ± 28.4, (1) | 0 ± 0, (1) | 18.27 ± 51.97, (1) | 0 ± 0, (1) | 5.58 ± 11.56, (1) |
| 8086 | 201.39 ± 388.31, (1) | 25.58 ± 87.48, (1) | 138.18 ± 113.05, (128.29) | 17.05 ± 57.79, (1) | 122.47 ± 768.06, (1) |
| 8128 | 57.06 ± 56.61, (55.84) | 108.06 ± 54.98, (113.79) | 18.7 ± 36.74, (1) | 41.84 ± 41, (50.89) | 180.78 ± 343.43, (71.96) |
| 8184 | 4.4 ± 19.58, (1) | 3.77 ± 17.26, (1) | 0 ± 0, (1) | 0 ± 0, (1) | 11.59 ± 17.8, (1) |
| 8232 | 2.07 ± 11.71, (1) | 0 ± 0, (1) | 0 ± 0, (1) | 0 ± 0, (1) | 22.55 ± 116.99, (1) |
| 8282 | 0 ± 0, (1) | 0 ± 0, (1) | 0 ± 0, (1) | 0 ± 0, (1) | 10.82 ± 15.04, (1) |
| 8337 | 0 ± 0, (1) | 0 ± 0, (1) | 0 ± 0, (1) | 0 ± 0, (1) | 5.02 ± 8.59, (1) |
| 8407 | 0 ± 0, (1) | 0 ± 0, (1) | 0 ± 0, (1) | 0 ± 0, (1) | 5.47 ± 8.57, (1) |
| 8486 | 0 ± 0, (1) | 0 ± 0, (1) | 0 ± 0, (1) | 0 ± 0, (1) | 4.66 ± 9.94, (1) |
| 8532 | 20.5 ± 74.68, (1) | 8.02 ± 36.74, (1) | 66.38 ± 205.58, (1) | 0 ± 0, (1) | 1.47 ± 5.34, (1) |
| 8597 | 276.1 ± 245.33, (215.18) | 370.25 ± 214.05, (301.2) | 376.5 ± 174.39, (381.01) | 247.21 ± 140.88, (235.88) | 498.37 ± 529.81, (315.16) |
| 8642 | 3.33 ± 18.81, (1) | 0 ± 0, (1) | 0 ± 0, (1) | 4.47 ± 25.69, (1) | 13.85 ± 26.86, (1) |
| 8717 | 5.97 ± 16.92, (1) | 9.23 ± 29.92, (1) | 0 ± 0, (1) | 4.44 ± 20.15, (1) | 3.9 ± 8.72, (1) |
| 8764 | 103.7 ± 88.69, (115.35) | 125.12 ± 90.08, (123.31) | 7.06 ± 31.57, (1) | 122.63 ± 71.01, (122.48) | 131.34 ± 90.16, (122.87) |

FIG. 16A (CONT'D)

| Mass | Prostate | Breast | Bladder | Control | Prostate2 |
|---|---|---|---|---|---|
| 8826 | 15.53 ± 45.6, (1) | 7.57 ± 24.73, (1) | 66.31 ± 74.08, (64.67) | 6.85 ± 22.43, (1) | 10 ± 16.33, (1) |
| 8877 | 47.3 ± 102.52, (1) | 11.89 ± 30.17, (1) | 335.77 ± 303.38, (304.71) | 8.18 ± 22.74, (1) | 9.52 ± 56.15, (1) |
| 8932 | 228.68 ± 152.1, (187.37) | 343.04 ± 207.75, (290.66) | 230.58 ± 306.51, (40.58) | 183.22 ± 81.94, (175.26) | 411.29 ± 537.14, (163.63) |
| 8988 | 0 ± 0, (1) | 0 ± 0, (1) | 0 ± 0, (1) | 0 ± 0, (1) | 6.51 ± 12.55, (1) |
| 9034 | 0 ± 0, (1) | 8.77 ± 40.18, (1) | 11.2 ± 50.11, (1) | 0 ± 0, (1) | 25.74 ± 80.68, (1) |
| 9085 | 0 ± 0, (1) | 25.53 ± 56.62, (1) | 3.48 ± 15.54, (1) | 0 ± 0, (1) | 16.72 ± 22.07, (1) |
| 9139 | 481.82 ± 383.47, (528.46) | 133.69 ± 283.48, (1) | 203.67 ± 217.35, (121.92) | 201.34 ± 319.85, (1) | 512.93 ± 387.44, (378) |
| 9234 | 117.72 ± 236.33, (1) | 277.39 ± 182.51, (308.78) | 105.72 ± 126.71, (33.1) | 317.15 ± 237.38, (366.16) | 1.24 ± 4.91, (1) |
| 9290 | 880.23 ± 381.87, (736.72) | 1376.35 ± 358.29, (1379.52) | 613.52 ± 282.95, (612.02) | 1230.99 ± 312.11, (1224.81) | 2246.26 ± 1362.94, (2107.21) |
| 9357 | 58.27 ± 158.5, (1) | 0 ± 0, (1) | 0 ± 0, (1) | 10.5 ± 60.32, (1) | 12.27 ± 34.17, (1) |
| 9405 | 89.04 ± 167.53, (1) | 61.94 ± 137.16, (1) | 71.03 ± 111.93, (1) | 10.96 ± 62.96, (1) | 241.94 ± 171.92, (178.42) |
| 9455 | 0.79 ± 3.68, (1) | 0 ± 0, (1) | 0 ± 0, (1) | 0.22 ± 1.29, (1) | 3.2 ± 7.42, (1) |
| 9504 | 0 ± 0, (1) | 0 ± 0, (1) | 0 ± 0, (1) | 0 ± 0, (1) | 7.83 ± 9.74, (6.45) |
| 9555 | 0 ± 0, (1) | 0 ± 0, (1) | 0 ± 0, (1) | 0 ± 0, (1) | 4.88 ± 7.3, (1) |
| 9611 | 1.5 ± 6.06, (1) | 1.6 ± 7.33, (1) | 0 ± 0, (1) | 0 ± 0, (1) | 9.44 ± 9.57, (9.41) |
| 9673 | 0 ± 0, (1) | 0 ± 0, (1) | 0 ± 0, (1) | 0 ± 0, (1) | 6.41 ± 6.77, (7.04) |
| 9748 | 0.2 ± 1.13, (1) | 0 ± 0, (1) | 0 ± 0, (1) | 0 ± 0, (1) | 2.95 ± 4.96, (1) |
| 9822 | 0.29 ± 1.63, (1) | 0.6 ± 2.75, (1) | 0 ± 0, (1) | 0.36 ± 2.09, (1) | 2.24 ± 5.33, (1) |
| 9884 | 1.24 ± 4.09, (1) | 2.73 ± 8.95, (1) | 0 ± 0, (1) | 1.48 ± 5.94, (1) | 2.15 ± 6.06, (1) |
| 9935 | 7.83 ± 12.15, (1) | 5.06 ± 11.54, (1) | 1.03 ± 4.63, (1) | 2.74 ± 9.3, (1) | 4.68 ± 8.39, (1) |
| 9992 | 1.06 ± 3.43, (1) | 1.44 ± 6.58, (1) | 2.59 ± 6.43, (1) | 0.49 ± 2.84, (1) | 2.11 ± 5.13, (1) |
| 10047 | 4.23 ± 10.41, (1) | 2.36 ± 7.73, (1) | 7.08 ± 11.17, (1) | 1.19 ± 4.78, (1) | 4.93 ± 21.22, (1) |
| 10106 | 1.53 ± 4.28, (1) | 4.9 ± 10.49, (1) | 1.59 ± 4.96, (1) | 2.42 ± 6.69, (1) | 2.76 ± 5.28, (1) |
| 10167 | 2.89 ± 7.37, (1) | 8.18 ± 15.75, (1) | 3.63 ± 6.63, (1) | 1.91 ± 8.21, (1) | 0.89 ± 4.09, (1) |
| 10228 | 19.06 ± 24.93, (16.63) | 51.21 ± 29.2, (50.21) | 11.19 ± 16.99, (4.61) | 66.97 ± 73.89, (40.58) | 31.87 ± 39.52, (17.47) |
| 10281 | 6.29 ± 8.45, (1) | 14.98 ± 14.87, (17.36) | 5.2 ± 7.76, (1) | 11.88 ± 10.54, (10.09) | 3.04 ± 4.75, (1) |
| 10335 | 5.5 ± 10.02, (1) | 9.68 ± 13.16, (1) | 4.69 ± 6.42, (1) | 4.1 ± 8.55, (1) | 4.16 ± 7.56, (1) |
| 10401 | 4.71 ± 6.71, (1) | 8.99 ± 12.13, (1) | 1.9 ± 3.94, (1) | 4.66 ± 7.81, (1) | 5.02 ± 4.77, (4.4) |
| 10455 | 2.38 ± 5.12, (1) | 12.98 ± 12.01, (17.88) | 1.27 ± 3.27, (1) | 3.31 ± 7.45, (1) | 3.86 ± 3.86, (4.2) |
| 10510 | 2.3 ± 5.06, (1) | 6.87 ± 9.06, (1) | 1.56 ± 3.28, (1) | 2.73 ± 5.96, (1) | 2.76 ± 3.7, (1) |
| 10568 | 3.86 ± 5.97, (1) | 4.93 ± 9.25, (1) | 2.74 ± 4.35, (1) | 3 ± 6.72, (1) | 3.62 ± 4.66, (3.37) |

FIG. 16A (CONT'D)

| Mass | Prostate | Breast | Bladder | Control | Prostate2 |
|---|---|---|---|---|---|
| 10626 | 5.36 ± 6.97, (1) | 10.44 ± 10.75, (13.65) | 19.23 ± 24.92, (14.59) | 3.39 ± 6.52, (1) | 11.84 ± 44.42, (3.73) |
| 10680 | 2.2 ± 4.39, (1) | 3.15 ± 6.76, (1) | 2.29 ± 4.16, (1) | 2.4 ± 6.09, (1) | 2.47 ± 3.1, (1) |
| 10735 | 3.62 ± 5.76, (1) | 4.46 ± 8.42, (1) | 1.45 ± 3.06, (1) | 1.81 ± 5.01, (1) | 2.24 ± 3.26, (1) |
| 10794 | 3.09 ± 5.37, (1) | 7.99 ± 9.76, (1) | 0 ± 0, (1) | 3.36 ± 6.23, (1) | 2.88 ± 4.09, (1) |
| 10849 | 2.25 ± 4.96, (1) | 6.46 ± 8.83, (1) | 2.69 ± 3.9, (1) | 3.59 ± 6.25, (1) | 2.36 ± 2.68, (1) |
| 10905 | 2.9 ± 4.58, (1) | 5.66 ± 9.35, (1) | 1.61 ± 3.35, (1) | 2.1 ± 4.78, (1) | 1.59 ± 2.58, (1) |
| 10962 | 3.34 ± 4.35, (1) | 3.37 ± 6.27, (1) | 3.5 ± 3.77, (2.66) | 5.1 ± 6.31, (1) | 2.01 ± 3.4, (1) |
| 11020 | 5.18 ± 4.99, (6.5) | 4.59 ± 8.51, (1) | 2.84 ± 3.93, (1) | 4.75 ± 5.67, (1) | 1.73 ± 3.3, (1) |
| 11077 | 8 ± 3.49, (8.5) | 30.54 ± 9.19, (28.61) | 5.26 ± 3.25, (5.98) | 10.26 ± 5.32, (9.92) | 3.92 ± 3.38, (3.54) |
| 11138 | 3.61 ± 4.34, (1) | 12.59 ± 9.73, (15.38) | 5.53 ± 2.45, (5.54) | 7.03 ± 5.26, (7.81) | 2.47 ± 3.2, (1) |
| 11198 | 5.07 ± 4.43, (6.92) | 5.23 ± 7.83, (1) | 3.79 ± 3.15, (4.51) | 6.11 ± 5.69, (6.94) | 2.35 ± 3.89, (1) |
| 11257 | 5.92 ± 4.42, (6.13) | 6.48 ± 8.64, (1) | 3.25 ± 3.95, (1) | 4.75 ± 4.85, (5.93) | 2.06 ± 2.73, (1) |
| 11315 | 3.97 ± 4.53, (1) | 10.34 ± 8.03, (12.81) | 3.85 ± 3.57, (4.85) | 6.35 ± 4.7, (7.26) | 1.98 ± 2.94, (1) |
| 11377 | 5.72 ± 3.77, (7.03) | 7.63 ± 7.79, (9.84) | 3.8 ± 3.06, (4.69) | 5.7 ± 5.17, (6.67) | 3.13 ± 3.41, (2.84) |
| 11442 | 5.46 ± 3.56, (6.72) | 9.59 ± 8.08, (13) | 5.33 ± 2.33, (5.47) | 6.47 ± 4.83, (7.34) | 1.72 ± 2.27, (1) |
| 11501 | 4.01 ± 4.13, (4.11) | 7.42 ± 7.58, (9.08) | 1.35 ± 2.49, (1) | 4.37 ± 4.56, (5.16) | 1.41 ± 2.71, (1) |
| 11560 | 6.1 ± 3.58, (6.96) | 10.92 ± 7.71, (13.06) | 4.76 ± 2.83, (5.25) | 5.15 ± 4.95, (6.22) | 3.2 ± 3.9, (2.4) |
| 11619 | 3.87 ± 4.4, (1) | 8.65 ± 7.32, (11.39) | 3.08 ± 3.5, (2.08) | 6.32 ± 4.9, (7.54) | 2.22 ± 2.66, (2.16) |
| 11678 | 3.17 ± 4.21, (1) | 4.08 ± 7.62, (1) | 1.94 ± 2.79, (1) | 2.64 ± 4.93, (1) | 1.1 ± 2.24, (1) |
| 11739 | 6.99 ± 3.8, (7.65) | 15.62 ± 4.65, (15.34) | 6.6 ± 2.63, (6.14) | 9.99 ± 3.26, (9.79) | 4.4 ± 4.59, (3.83) |
| 11802 | 2.97 ± 3.64, (1) | 6.77 ± 6.84, (10.06) | 3.35 ± 2.65, (4.22) | 5.54 ± 4.3, (5.7) | 2.41 ± 2.74, (2.06) |
| 11864 | 3.97 ± 3.69, (4.58) | 7.49 ± 6.83, (11.32) | 3.33 ± 3.28, (3.83) | 4.26 ± 4.64, (4.41) | 2.01 ± 3.06, (1) |
| 11929 | 4.83 ± 3.56, (5.38) | 7.54 ± 6.92, (10.68) | 3.38 ± 2.42, (4.19) | 5.39 ± 4.24, (5.66) | 2.02 ± 3.4, (1) |
| 11993 | 3.3 ± 3.3, (4.23) | 4.39 ± 5.8, (1) | 3.29 ± 2.72, (3.92) | 4.9 ± 3.71, (5.32) | 2.69 ± 3.31, (2.47) |
| 12056 | 2.86 ± 2.95, (3.46) | 7.89 ± 6.15, (9.45) | 2.54 ± 2.52, (3.28) | 3.85 ± 4.16, (4.42) | 1.86 ± 2.53, (1) |
| 12119 | 3.55 ± 3.3, (3.93) | 5.1 ± 6.27, (1) | 4.07 ± 2.12, (4.27) | 4.02 ± 4.07, (4.98) | 1.3 ± 1.77, (1) |
| 12188 | 3.7 ± 3.31, (4.06) | 5.95 ± 6.01, (7.03) | 2.62 ± 2.51, (3.33) | 4.04 ± 3.95, (4.55) | 1.27 ± 3.12, (1) |
| 12250 | 3.64 ± 3.3, (4.26) | 7.98 ± 6.31, (10.08) | 3.05 ± 2.64, (3.57) | 5.07 ± 3.69, (5.32) | 2.05 ± 3.44, (1) |
| 12316 | 3.23 ± 3.54, (2.02) | 7.06 ± 5.94, (8.79) | 2.58 ± 2.63, (3.18) | 4.55 ± 4.09, (6.02) | 1.85 ± 2.48, (1) |
| 12382 | 2.91 ± 4.09, (1) | 5.49 ± 7.7, (1) | 1.79 ± 2.58, (1) | 4.72 ± 4.72, (5.39) | 1.56 ± 2.62, (1) |
| 12450 | 8.74 ± 3.64, (8.16) | 13 ± 5.59, (13.45) | 4.9 ± 2.83, (4.8) | 7.19 ± 3.46, (7.12) | 5.59 ± 3.48, (4.86) |

FIG. 16A (CONT'D)

| Mass | Prostate | Breast | Bladder | Control | Prostate2 |
|---|---|---|---|---|---|
| 12516 | 3.58 ± 3.69, (3.84) | 5.41 ± 6.71, (1) | 1.61 ± 2.37, (1) | 3.11 ± 4.25, (1) | 1.95 ± 2.74, (1) |
| 12580 | 6.54 ± 3.05, (6.71) | 15.17 ± 4.36, (13.67) | 6.24 ± 4.11, (5.2) | 10.06 ± 3.24, (10.33) | 3.33 ± 3.24, (3.09) |
| 12662 | 3.94 ± 2.66, (4.71) | 8.25 ± 5.11, (9.21) | 2.66 ± 2.47, (3.15) | 5.87 ± 3.89, (5.84) | 1.72 ± 2.5, (1) |
| 12727 | 2.69 ± 2.95, (1.45) | 4.58 ± 5.05, (1) | 1.83 ± 1.94, (1.23) | 3.23 ± 3.42, (3.59) | 2.09 ± 2.77, (1) |
| 12793 | 3.06 ± 2.59, (3.5) | 8.35 ± 4.07, (9.08) | 3.41 ± 2.09, (3.42) | 4.57 ± 3.46, (4.89) | 2.12 ± 2.38, (2.15) |
| 12862 | 3.9 ± 2.52, (4.48) | 6.72 ± 4.72, (8.46) | 3.16 ± 1.56, (3.25) | 4.02 ± 3.2, (4.66) | 2.19 ± 3.26, (1) |
| 12932 | 3.63 ± 2.58, (4.03) | 7.91 ± 3.9, (8.38) | 3.01 ± 2.26, (3.25) | 4.47 ± 2.97, (4.48) | 1.91 ± 2.16, (2.06) |
| 13005 | 3.39 ± 2.58, (3.85) | 4.48 ± 4.48, (6.83) | 1.93 ± 1.9, (2.59) | 4.35 ± 3.16, (4.57) | 1.77 ± 2.18, (1) |
| 13082 | 3.54 ± 2.42, (4.01) | 4.76 ± 4.84, (6.68) | 2.3 ± 2.02, (3.32) | 4.03 ± 2.91, (4.24) | 1.98 ± 2.86, (1.84) |
| 13149 | 3.76 ± 2.05, (3.94) | 0.97 ± 3.07, (1) | 3.22 ± 1.74, (3.47) | 4.1 ± 3.17, (4.22) | 1.53 ± 1.99, (1) |
| 13222 | 3.04 ± 2.54, (3.19) | 8.61 ± 3.6, (8.57) | 2.78 ± 2.09, (3.28) | 3.66 ± 2.95, (3.96) | 2.27 ± 3, (2.08) |
| 13291 | 3.48 ± 2.56, (4.18) | 26.28 ± 13.54, (24.37) | 2.65 ± 1.98, (3) | 4.11 ± 3.19, (4.42) | 1.92 ± 2.55, (1) |
| 13359 | 3.44 ± 2.53, (4.13) | 10.88 ± 5.4, (11.89) | 1.98 ± 2.19, (1.33) | 4.36 ± 2.74, (4.55) | 1.9 ± 2.85, (1) |
| 13431 | 2.66 ± 2.55, (3.17) | 3.28 ± 5.47, (1) | 3.03 ± 1.77, (3.35) | 3.11 ± 3.14, (3.63) | 1.51 ± 2.85, (1) |
| 13506 | 4.27 ± 1.88, (4.37) | 5.38 ± 5.41, (7.46) | 4.46 ± 0.92, (4.24) | 4.98 ± 2.61, (5.24) | 1.76 ± 2.51, (1) |
| 13593 | 3.06 ± 2.46, (3.7) | 6.72 ± 4.53, (8.78) | 2.23 ± 2.05, (2.72) | 4.11 ± 2.84, (4.05) | 1.22 ± 1.68, (1) |
| 13669 | 3.44 ± 2.33, (3.89) | 5.8 ± 5.4, (7.74) | 2.26 ± 2.06, (2.98) | 4.28 ± 2.95, (4.6) | 2.11 ± 3.32, (1) |
| 13739 | 3.53 ± 2.33, (4.09) | 7.36 ± 4.48, (9.01) | 2.73 ± 1.6, (3.21) | 3.97 ± 2.59, (4.57) | 1.1 ± 2, (1) |
| 13814 | 3.6 ± 2.19, (4.1) | 8.3 ± 4.49, (9.74) | 2.47 ± 1.67, (2.85) | 4.45 ± 2.93, (4.84) | 2.57 ± 3.6, (2.13) |
| 13888 | 2.73 ± 2.51, (3.81) | 5.81 ± 6.05, (8.07) | 2.3 ± 2.15, (2.6) | 3.43 ± 2.87, (4.23) | 2.02 ± 4.13, (1) |
| 13964 | 3.26 ± 2.06, (3.63) | 7.03 ± 4.99, (8.96) | 2.59 ± 1.35, (2.85) | 4.06 ± 2.47, (4.17) | 1.85 ± 2.85, (1) |
| 14039 | 2.76 ± 2.29, (3.17) | 6.86 ± 4.68, (8.83) | 2.05 ± 2.04, (2.23) | 3.19 ± 2.85, (3.89) | 1.15 ± 1.66, (1) |
| 14115 | 3.69 ± 2.09, (3.7) | 6.77 ± 4.14, (8.37) | 2.82 ± 1.49, (3.05) | 4.42 ± 2.6, (4.4) | 2.2 ± 3.18, (1) |
| 14194 | 2.83 ± 2.07, (3.27) | 3.72 ± 4.78, (1) | 1.65 ± 1.66, (2.05) | 2.82 ± 2.49, (3.48) | 0.74 ± 1.82, (1) |
| 14267 | 3.5 ± 1.9, (3.44) | 6.96 ± 3.89, (7.67) | 2.75 ± 1.48, (2.81) | 3.99 ± 2.13, (4.17) | 1.41 ± 1.74, (1) |
| 14348 | 2.41 ± 2.15, (2.67) | 3.16 ± 4.27, (1) | 2.07 ± 1.69, (2.2) | 3.51 ± 2.31, (4.03) | 1.13 ± 2.21, (1) |
| 14426 | 3.59 ± 1.67, (3.78) | 5.83 ± 4.49, (7.42) | 2.76 ± 1.23, (2.86) | 3.97 ± 2.16, (3.79) | 2.15 ± 3.22, (1) |
| 14508 | 2.61 ± 2, (3.16) | 6.03 ± 4.58, (7.85) | 2 ± 1.74, (2.21) | 2.96 ± 2.35, (3.77) | 2.26 ± 3.34, (1) |
| 14590 | 2.46 ± 2.07, (2.79) | 5.97 ± 4.8, (7.15) | 2.11 ± 1.59, (2.58) | 3.54 ± 2.16, (3.84) | 1.25 ± 1.87, (1) |
| 14664 | 2.2 ± 1.93, (2.64) | 6.59 ± 4.1, (8.02) | 1.8 ± 1.57, (2.42) | 2.78 ± 2.39, (3.15) | 2.32 ± 3.37, (1.63) |
| 14740 | 2.57 ± 1.73, (2.9) | 5.26 ± 4.53, (6.55) | 2.23 ± 1.36, (2.42) | 3.43 ± 2.49, (3.63) | 1.7 ± 3.29, (1) |
| 14819 | 2.35 ± 2, (2.69) | 4.15 ± 4.21, (5.82) | 1.97 ± 1.46, (2.34) | 2.59 ± 2.26, (3.15) | 1.82 ± 3.02, (1) |
| 14896 | 2.41 ± 1.77, (2.69) | 6.15 ± 3.05, (6.62) | 2.39 ± 1.27, (2.63) | 2.96 ± 2.08, (3.34) | 2.47 ± 3.33, (1.98) |

FIG. 16A (CONT'D)

| Mass | Prostate | Breast | Bladder | Prostate2 | MultiClass (Kruskal-Wallis) |
|---|---|---|---|---|---|
| 702 | 0.915 | 0.0445 | 0.00316 | 0.000122 | 2.81E-05 |
| 707 | 0.787 | 0.434 | 0.104 | 8.44E-06 | 0.065 |
| 711 | 0.3 | 0.0578 | 0.745 | 0.821 | 0.0342 |
| 715 | 0.131 | 0.12 | 0.238 | 0.625 | 0.0115 |
| 719 | 0.179 | 0.0707 | 3.59E-10 | 0.0302 | 5.78E-11 |
| 725 | 0.000232 | 0.205 | 0.449 | 4.36E-05 | 1.29E-06 |
| 731 | 0.00246 | 0.0886 | 0.336 | 4.69E-16 | 8.13E-05 |
| 735 | 0.00274 | 0.785 | 0.0112 | 0.0352 | 7.39E-06 |
| 743 | 0.0179 | 0.223 | 3.01E-05 | 0.337 | 2.19E-07 |
| 749 | 2.36E-05 | 0.441 | 6.48E-05 | 0.448 | 1.25E-08 |
| 755 | 0.0126 | 0.39 | 0.75 | 0.711 | 0.0376 |
| 759 | 5.47E-05 | 3.14E-06 | 0.917 | 1.11E-07 | 5.46E-06 |
| 763 | 0.00408 | 0.0107 | 0.000532 | 0.0517 | 0.00957 |
| 766 | 7.80E-05 | 0.421 | 0.229 | 0.000397 | 0.00576 |
| 771 | 0.207 | 2.68E-05 | 0.000221 | 3.70E-16 | 2.00E-08 |
| 777 | 0.46 | 0.0289 | 1 | 1.83E-09 | 0.0471 |
| 783 | 0.226 | 0.882 | 4.72E-06 | 0.000965 | 6.42E-09 |
| 787 | 0.00274 | 1 | 1 | 0.471 | 0.0102 |
| 793 | 0.0306 | 0.000639 | 0.346 | 0.424 | 0.000158 |
| 798 | 4.66E-06 | 0.601 | 0.318 | 2.60E-11 | 2.82E-06 |
| 804 | 2.78E-08 | 0.0127 | 1.75E-13 | 0.871 | 1.55E-16 |
| 812 | 0.00114 | 0.149 | 1.97E-05 | 5.36E-07 | 1.67E-07 |
| 824 | 0.11 | 0.00742 | 1.30E-12 | 3.27E-06 | 3.24E-15 |
| 830 | 2.53E-05 | 0.558 | 1.06E-09 | 0.000121 | 1.85E-15 |
| 836 | 0.102 | 0.000875 | 0.148 | 0.185 | 0.00953 |
| 841 | 5.87E-06 | 0.245 | 0.000101 | 0.000753 | 2.73E-12 |
| 848 | 4.48E-08 | 0.278 | 2.21E-06 | 0.000101 | 1.03E-12 |
| 851 | 8.10E-05 | 1 | 0.688 | 0.578 | 8.32E-05 |
| 856 | 0.000489 | 0.000237 | 0.00962 | 0.00772 | 0.000105 |
| 862 | 0.621 | 0.887 | 0.254 | 1.18E-18 | 0.328 |
| 866 | 0.593 | 0.906 | 0.582 | 0.142 | 0.712 |
| 872 | 0.00675 | 0.00475 | 0.0767 | 0.0302 | 4.42E-06 |
| 881 | 0.0426 | 3.63E-07 | 0.154 | 0.794 | 7.01E-05 |
| 886 | 0.402 | 0.12 | 0.985 | 0.318 | 0.27 |
| 891 | 0.000155 | 0.00954 | 8.72E-10 | 0.808 | 1.64E-14 |
| 896 | 0.0124 | 0.126 | 0.632 | 0.000219 | 0.0333 |
| 904 | 2.23E-08 | 2.34E-06 | 0.0869 | 0.00166 | 7.26E-10 |
| 907 | 0.593 | 7.39E-10 | 3.12E-07 | 5.68E-07 | 3.65E-14 |
| 912 | 0.963 | 0.857 | 0.0303 | 0.0798 | 0.0676 |
| 916 | 0.288 | 0.245 | 0.582 | 2.94E-10 | 0.213 |

FIG. 16B

| Mass | Prostate | Breast | Bladder | Prostate2 | MultiClass (Kruskal-Wallis) |
|---|---|---|---|---|---|
| 922 | 0.0283 | 0.027 | 0.000775 | 0.00148 | 0.00435 |
| 929 | 0.616 | 0.0578 | 0.092 | 0.00523 | 0.0159 |
| 935 | 0.0103 | 0.434 | 0.0117 | 0.000336 | 0.016 |
| 940 | 0.288 | 1 | 0.314 | 0.00182 | 0.443 |
| 944 | 0.00101 | 3.56E-05 | 7.65E-13 | 9.67E-06 | 6.77E-21 |
| 949 | 0.0679 | 0.00466 | 0.8 | 0.00082 | 0.0269 |
| 956 | 0.0531 | 0.000875 | 0.000189 | 0.376 | 0.000162 |
| 960 | 0.471 | 1 | 0.0215 | 3.06E-06 | 0.0537 |
| 970 | 0.46 | 0.0837 | 1 | 0.000827 | 0.27 |
| 976 | 0.539 | 0.887 | 0.904 | 1.22E-15 | 0.841 |
| 980 | 0.0413 | 0.683 | 0.0252 | 7.66E-05 | 0.0363 |
| 984 | 0.294 | 0.389 | 0.595 | 0.306 | 0.555 |
| 992 | 3.53E-07 | 1.27E-06 | 0.586 | 0.00378 | 1.98E-11 |
| 995 | 5.69E-07 | 0.000204 | 1.23E-13 | 0.103 | 7.41E-14 |
| 1000 | 1.80E-05 | 9.72E-06 | 7.15E-09 | 1.60E-06 | 7.92E-09 |
| 1007 | 0.000143 | 0.0155 | 0.00637 | 4.50E-13 | 3.89E-08 |
| 1013 | 5.51E-07 | 8.92E-05 | 6.52E-07 | 2.14E-10 | 2.84E-08 |
| 1018 | 0.163 | 0.0645 | 0.000948 | 0.00138 | 0.000105 |
| 1023 | 1.34E-11 | 0.0323 | 2.80E-13 | 6.29E-13 | 1.67E-13 |
| 1031 | 0.362 | 0.986 | 0.254 | 0.348 | 0.206 |
| 1035 | 1.67E-07 | 1.68E-06 | 4.75E-10 | 2.46E-10 | 6.42E-11 |
| 1042 | 1.03E-06 | 0.0164 | 2.31E-05 | 2.63E-06 | 2.21E-06 |
| 1048 | 2.20E-11 | 0.00122 | 1.80E-13 | 8.34E-05 | 9.04E-24 |
| 1058 | 5.29E-07 | 0.00813 | 1.80E-13 | 2.35E-09 | 1.22E-13 |
| 1063 | 0.000489 | 1.03E-11 | 1.03E-12 | 0.272 | 9.04E-24 |
| 1066 | 1.87E-11 | 5.71E-05 | 6.60E-14 | 1.62E-26 | 8.87E-17 |
| 1069 | 0.46 | 0.00381 | 0.0488 | 1.26E-11 | 0.00229 |
| 1072 | 0.0561 | 0.389 | 0.314 | 0.00596 | 0.125 |
| 1079 | 2.94E-11 | 0.683 | 7.65E-13 | 9.69E-05 | 1.97E-14 |
| 1085 | 0.781 | 0.728 | 0.129 | 0.00523 | 0.159 |
| 1090 | 0.0561 | 0.17 | 0.0181 | 4.32E-09 | 0.142 |
| 1094 | 0.000844 | 0.000338 | 4.84E-10 | 2.33E-23 | 7.98E-06 |
| 1101 | 2.96E-06 | 0.0356 | 5.55E-08 | 0.665 | 7.10E-15 |
| 1106 | 0.192 | 0.17 | 0.0215 | 0.902 | 0.00467 |
| 1111 | 0.0235 | 1.81E-05 | 3.25E-10 | 2.41E-11 | 7.63E-08 |
| 1116 | 0.0124 | 0.605 | 2.56E-06 | 0.427 | 4.64E-06 |
| 1119 | 0.374 | 0.00439 | 0.292 | 0.349 | 0.00992 |
| 1126 | 6.84E-08 | 0.676 | 7.65E-13 | 0.000328 | 3.51E-18 |
| 1131 | 0.0516 | 1 | 1 | 5.16E-07 | 0.0426 |
| 1135 | 0.192 | 0.0104 | 0.0173 | 0.000112 | 0.00438 |
| 1139 | 0.39 | 0.901 | 0.0114 | 0.000191 | 0.0296 |
| 1144 | 0.46 | 0.609 | 0.0002 | 0.0436 | 2.00E-05 |
| 1150 | 0.688 | 0.00966 | 0.0195 | 0.371 | 0.000162 |
| 1153 | 0.0167 | 0.028 | 0.129 | 1.38E-08 | 0.0539 |

FIG. 16B (CONT'D)

| Mass | Prostate | Breast | Bladder | Prostate2 | MultiClass (Kruskal-Wallis) |
|---|---|---|---|---|---|
| 1156 | 0.0295 | 0.222 | 2.13E-08 | 0.000133 | 5.73E-07 |
| 1159 | 4.18E-08 | 0.625 | 5.43E-14 | 0.000225 | 2.43E-19 |
| 1162 | 0.145 | 0.00185 | 0.00142 | 0.00485 | 0.000271 |
| 1166 | 8.14E-12 | 1.59E-07 | 3.95E-13 | 8.93E-21 | 5.74E-20 |
| 1170 | 0.000282 | 0.0373 | 0.113 | 0.00623 | 0.0018 |
| 1174 | 1.25E-10 | 2.13E-05 | 0.0127 | 1.13E-15 | 1.86E-10 |
| 1177 | 0.149 | 0.422 | 1 | 0.373 | 0.208 |
| 1183 | 0.00185 | 0.00535 | 2.10E-14 | 7.55E-14 | 3.39E-09 |
| 1188 | 0.0167 | 0.028 | 0.314 | 1.11E-09 | 0.0324 |
| 1191 | 2.60E-10 | 0.000186 | 2.59E-11 | 1.10E-16 | 1.06E-14 |
| 1197 | 0.101 | 1.33E-07 | 0.858 | 0.0333 | 2.39E-09 |
| 1201 | 0.453 | 0.831 | 0.567 | 0.323 | 0.522 |
| 1206 | 0.0492 | 0.000141 | 7.68E-05 | 6.13E-05 | 9.98E-05 |
| 1209 | 4.18E-08 | 0.0654 | 1.30E-12 | 1.91E-10 | 1.31E-09 |
| 1214 | 0.000863 | 0.251 | 9.43E-08 | 4.13E-07 | 8.69E-11 |
| 1217 | 0.539 | 0.463 | 0.61 | 0.0651 | 0.81 |
| 1221 | 0.0019 | 0.00381 | 0.314 | 1.26E-25 | 0.00141 |
| 1226 | 0.102 | 0.17 | 1 | 1.26E-11 | 0.131 |
| 1231 | 0.523 | 0.867 | 1.10E-10 | 0.02 | 9.53E-11 |
| 1234 | 0.205 | 0.457 | 0.0179 | 0.0642 | 0.00748 |
| 1237 | 2.80E-05 | 0.0162 | 0.397 | 2.11E-09 | 0.0001 |
| 1240 | 0.0311 | 8.50E-05 | 1 | 2.27E-12 | 2.50E-05 |
| 1244 | 0.438 | 0.67 | 0.0899 | 0.991 | 0.315 |
| 1254 | 0.752 | 1.19E-09 | 0.00016 | 8.77E-05 | 1.57E-11 |
| 1262 | 0.0236 | 0.405 | 0.489 | 2.89E-06 | 0.113 |
| 1267 | 6.48E-17 | 2.75E-07 | 1.05E-10 | 4.47E-20 | 2.74E-16 |
| 1275 | 0.000143 | 0.012 | 0.802 | 4.85E-10 | 0.000264 |
| 1280 | 4.81E-09 | 0.434 | 1.95E-13 | 5.19E-13 | 5.74E-20 |
| 1292 | 0.0921 | 0.0208 | 0.129 | 2.90E-10 | 0.000453 |
| 1300 | 5.99E-06 | 1.35E-09 | 0.0015 | 0.000175 | 6.59E-10 |
| 1308 | 0.979 | 0.708 | 0.0458 | 1.27E-08 | 0.159 |
| 1314 | 0.193 | 0.834 | 2.94E-11 | 6.81E-05 | 2.40E-12 |
| 1318 | 0.402 | 0.665 | 0.0438 | 0.000843 | 0.0767 |
| 1323 | 0.135 | 0.602 | 0.73 | 0.012 | 0.204 |
| 1327 | 0.0377 | 0.607 | 0.667 | 6.80E-06 | 0.0115 |
| 1332 | 0.000846 | 1.09E-06 | 0.00938 | 1.38E-08 | 3.61E-05 |
| 1337 | 0.646 | 0.857 | 0.193 | 9.67E-08 | 0.29 |
| 1345 | 1 | 0.00175 | 0.00839 | 3.40E-07 | 0.000196 |
| 1354 | 1.01E-15 | 4.82E-05 | 4.50E-13 | 6.26E-17 | 1.38E-14 |
| 1362 | 0.0531 | 0.00535 | 0.449 | 7.14E-14 | 0.0119 |
| 1366 | 0.0196 | 0.126 | 0.0155 | 3.97E-15 | 0.0639 |
| 1370 | 9.73E-09 | 0.236 | 1 | 0.00737 | 3.29E-08 |
| 1375 | 0.166 | 0.857 | 0.00839 | 0.00737 | 0.0174 |
| 1383 | 0.245 | 5.56E-13 | 0.506 | 3.29E-07 | 6.74E-13 |

FIG. 16B (CONT'D)

| Mass | Prostate | Breast | Bladder | Prostate2 | MultiClass (Kruskal-Wallis) |
|---|---|---|---|---|---|
| 1393 | 6.99E-05 | 0.0147 | 0.449 | 1.36E-13 | 0.000659 |
| 1399 | 0.0167 | 0.389 | 0.00198 | 3.59E-07 | 0.00893 |
| 1406 | 0.191 | 1 | 0.37 | 0.39 | 0.0867 |
| 1415 | 0.0153 | 0.81 | 0.737 | 1.84E-05 | 0.0131 |
| 1421 | 0.13 | 0.0881 | 0.773 | 0.187 | 0.157 |
| 1427 | 5.65E-05 | 0.901 | 8.63E-06 | 6.96E-11 | 8.37E-11 |
| 1434 | 0.0521 | 0.000392 | 0.00439 | 1.10E-16 | 0.00171 |
| 1441 | 1 | 0.105 | 0.324 | 0.00492 | 0.211 |
| 1447 | 0.102 | 1 | 0.314 | 1.30E-05 | 0.113 |
| 1453 | 6.86E-07 | 0.852 | 6.37E-10 | 1.40E-12 | 1.98E-14 |
| 1458 | 0.288 | 0.028 | 1 | 0.142 | 0.0269 |
| 1463 | 0.000252 | 0.1 | 0.00763 | 1.84E-08 | 5.64E-05 |
| 1469 | 1.44E-05 | 0.128 | 1.25E-11 | 4.92E-08 | 1.88E-07 |
| 1476 | 0.516 | 0.852 | 0.212 | 0.00854 | 0.502 |
| 1488 | 0.208 | 0.321 | 0.00439 | 0.0582 | 0.000164 |
| 1494 | 0.288 | 1 | 1 | 1.26E-11 | 0.267 |
| 1502 | 0.0525 | 0.429 | 2.93E-15 | 1.71E-10 | 5.31E-15 |
| 1507 | 0.305 | 0.728 | 0.00172 | 0.418 | 0.00112 |
| 1516 | 0.0019 | 0.0107 | 2.10E-14 | 1.82E-21 | 2.09E-10 |
| 1523 | 2.20E-11 | 0.00104 | 2.16E-12 | 1.76E-18 | 1.18E-19 |
| 1534 | 0.977 | 0.864 | 9.76E-06 | 0.513 | 1.33E-05 |
| 1540 | 0.000108 | 0.000138 | 2.52E-10 | 1.26E-11 | 5.10E-12 |
| 1548 | 0.744 | 1.09E-06 | 0.0557 | 0.0364 | 5.58E-12 |
| 1555 | 0.00456 | 0.0445 | 9.77E-06 | 2.31E-06 | 2.12E-08 |
| 1561 | 0.46 | 1 | 1 | 0.24 | 0.582 |
| 1567 | 0.46 | 6.15E-10 | 0.0904 | 2.90E-10 | 3.64E-08 |
| 1573 | 0.0374 | 0.000392 | 0.7 | 1.50E-14 | 0.000601 |
| 1579 | 0.991 | 1 | 0.0146 | 0.0569 | 0.0899 |
| 1586 | 0.059 | 3.46E-06 | 1 | 0.000141 | 3.19E-07 |
| 1590 | 0.113 | 1 | 8.64E-07 | 2.07E-08 | 1.36E-06 |
| 1595 | 0.00762 | 0.794 | 0.0599 | 0.688 | 0.0116 |
| 1602 | 0.116 | 0.109 | 9.01E-05 | 0.0517 | 2.60E-05 |
| 1610 | 0.137 | 0.756 | 0.00053 | 0.572 | 0.0136 |
| 1618 | 0.023 | 0.0178 | 1.05E-10 | 0.000233 | 4.80E-09 |
| 1625 | 0.135 | 0.372 | 1 | 0.471 | 0.0442 |
| 1630 | 0.288 | 6.69E-12 | 1 | 0.821 | 4.28E-10 |
| 1635 | 0.0246 | 0.00216 | 1.12E-11 | 5.97E-07 | 4.10E-09 |
| 1642 | 0.083 | 0.162 | 0.00172 | 5.87E-07 | 4.91E-05 |
| 1655 | 0.789 | 0.0147 | 0.129 | 0.4 | 0.00748 |
| 1659 | 0.288 | 0.717 | 0.734 | 0.00164 | 0.618 |
| 1668 | 0.782 | 9.72E-06 | 0.262 | 0.583 | 5.82E-06 |
| 1672 | 0.363 | 1.32E-07 | 0.855 | 0.963 | 1.51E-08 |
| 1679 | 0.0665 | 0.00185 | 1.82E-05 | 9.73E-05 | 6.05E-05 |

FIG. 16B (CONT'D)

| Mass | Prostate | Breast | Bladder | Prostate2 | MultiClass (Kruskal-Wallis) |
|---|---|---|---|---|---|
| 1683 | 0.679 | 0.413 | 0.314 | 0.989 | 0.339 |
| 1691 | 7.71E-06 | 0.0045 | 1.05E-10 | 0.416 | 1.06E-07 |
| 1696 | 0.000169 | 0.4 | 8.73E-11 | 1.22E-15 | 4.77E-13 |
| 1706 | 2.21E-05 | 8.94E-05 | 0.0173 | 3.45E-12 | 3.67E-06 |
| 1710 | 0.453 | 3.78E-07 | 0.00904 | 0.0302 | 7.53E-10 |
| 1715 | 0.977 | 1 | 0.00192 | 1.55E-06 | 0.0007 |
| 1724 | 0.0378 | 0.0172 | 1.62E-08 | 3.28E-05 | 8.01E-09 |
| 1729 | 0.000556 | 0.852 | 0.265 | 3.51E-08 | 0.000231 |
| 1738 | 0.452 | 0.109 | 0.582 | 1.24E-07 | 0.117 |
| 1744 | 0.0758 | 3.92E-06 | 0.129 | 0.0835 | 2.84E-08 |
| 1750 | 0.46 | 1 | 1 | 0.00182 | 0.582 |
| 1757 | 0.0103 | 0.389 | 4.50E-13 | 0.000846 | 9.48E-13 |
| 1767 | 0.288 | 3.00E-11 | 7.48E-06 | 0.0521 | 2.32E-13 |
| 1776 | 0.0418 | 0.443 | 1.20E-07 | 0.189 | 3.05E-06 |
| 1782 | 5.29E-07 | 0.522 | 1.06E-09 | 1.18E-18 | 1.85E-15 |
| 1791 | 0.0185 | 0.000121 | 0.0316 | 1.89E-15 | 0.00259 |
| 1797 | 0.614 | 0.116 | 0.334 | 2.08E-05 | 0.106 |
| 1807 | 0.679 | 9.73E-05 | 1.95E-07 | 0.000167 | 3.54E-09 |
| 1813 | 1 | 0.329 | 0.0484 | 0.0211 | 0.158 |
| 1820 | 0.0394 | 6.69E-12 | 4.75E-07 | 0.0611 | 1.87E-10 |
| 1827 | 0.403 | 0.605 | 0.000238 | 0.838 | 0.00239 |
| 1832 | 0.305 | 0.000714 | 0.0015 | 0.116 | 5.15E-07 |
| 1838 | 0.117 | 0.375 | 0.134 | 0.0106 | 0.264 |
| 1845 | 0.166 | 0.39 | 2.19E-06 | 4.25E-07 | 6.75E-05 |
| 1853 | 0.593 | 4.70E-08 | 0.529 | 0.276 | 2.44E-05 |
| 1861 | 0.0259 | 0.625 | 0.000226 | 0.838 | 0.000106 |
| 1870 | 1.80E-05 | 1.39E-05 | 3.34E-11 | 1.18E-18 | 2.17E-19 |
| 1876 | 0.0374 | 0.434 | 2.31E-05 | 0.909 | 5.49E-06 |
| 1884 | 0.226 | 4.40E-09 | 0.314 | 0.000196 | 1.78E-06 |
| 1890 | 0.785 | 0.232 | 0.0929 | 2.95E-08 | 0.0688 |
| 1900 | 0.0153 | 1.04E-08 | 4.50E-13 | 6.05E-07 | 9.14E-17 |
| 1906 | 0.46 | 0.0728 | 1 | 2.27E-12 | 0.0624 |
| 1912 | 0.471 | 0.478 | 0.582 | 0.489 | 0.237 |
| 1918 | 0.258 | 9.66E-06 | 0.25 | 0.917 | 7.99E-06 |
| 1926 | 0.00328 | 6.38E-08 | 0.0153 | 1.79E-08 | 1.52E-06 |
| 1931 | 0.0241 | 0.12 | 6.60E-14 | 6.03E-09 | 1.47E-16 |
| 1939 | 0.151 | 1.79E-07 | 0.144 | 0.00347 | 2.57E-07 |
| 1945 | 1.03E-05 | 0.779 | 1.26E-06 | 7.99E-17 | 1.18E-09 |
| 1956 | 6.81E-09 | 5.56E-13 | 7.15E-09 | 1.10E-13 | 3.09E-16 |
| 1961 | 0.013 | 0.982 | 0.025 | 0.2 | 0.00855 |
| 1975 | 0.989 | 0.424 | 4.10E-09 | 4.41E-07 | 1.89E-10 |
| 1982 | 0.00215 | 0.683 | 7.70E-06 | 1.03E-07 | 1.15E-07 |
| 1990 | 0.213 | 0.00307 | 0.0284 | 0.269 | 4.93E-05 |
| 1995 | 1 | 1 | 0.632 | 0.00104 | 0.95 |

FIG. 16B (CONT'D)

| Mass | Prostate | Breast | Bladder | Prostate2 | MultiClass (Kruskal-Wallis) |
|---|---|---|---|---|---|
| 2001 | 1 | 0.00122 | 1 | 0.865 | 0.000676 |
| 2009 | 5.35E-05 | 0.25 | 0.0305 | 1.94E-07 | 3.10E-05 |
| 2016 | 0.000416 | 0.293 | 0.00192 | 1.69E-16 | 0.000223 |
| 2025 | 0.193 | 1 | 0.147 | 1.23E-08 | 0.041 |
| 2031 | 1 | 0.8 | 0.0181 | 0.648 | 0.0314 |
| 2038 | 0.879 | 0.0181 | 1 | 1.85E-06 | 0.00733 |
| 2048 | 0.65 | 0.0175 | 0.696 | 2.73E-07 | 0.0282 |
| 2058 | 0.000491 | 0.127 | 4.50E-13 | 2.43E-16 | 5.75E-12 |
| 2065 | 0.46 | 0.0728 | 1 | 1.26E-11 | 0.0624 |
| 2072 | 0.224 | 0.0104 | 0.406 | 2.08E-05 | 0.000617 |
| 2078 | 0.176 | 0.193 | 0.00299 | 5.10E-09 | 0.000227 |
| 2087 | 0.0942 | 0.814 | 0.723 | 6.13E-05 | 0.102 |
| 2095 | 1 | 0.0205 | 0.12 | 0.000679 | 0.003 |
| 2113 | 0.541 | 0.104 | 0.000213 | 0.0449 | 0.000822 |
| 2119 | 2.36E-07 | 8.19E-10 | 2.75E-11 | 6.62E-09 | 5.82E-18 |
| 2127 | 1 | 0.237 | 0.0171 | 0.00564 | 0.0567 |
| 2132 | 0.453 | 0.00466 | 0.639 | 2.69E-06 | 0.0286 |
| 2147 | 0.0189 | 5.27E-05 | 7.65E-13 | 0.131 | 3.45E-14 |
| 2153 | 1.39E-05 | 0.0645 | 4.03E-06 | 0.000339 | 4.12E-07 |
| 2164 | 0.513 | 6.04E-06 | 0.0021 | 4.57E-08 | 4.46E-06 |
| 2174 | 4.93E-06 | 3.69E-05 | 4.80E-05 | 1.27E-08 | 7.63E-08 |
| 2179 | 0.0959 | 0.453 | 0.181 | 0.00831 | 0.0256 |
| 2189 | 6.59E-07 | 1.49E-08 | 0.000221 | 1.65E-07 | 9.87E-11 |
| 2196 | 1 | 0.189 | 0.195 | 0.378 | 0.219 |
| 2214 | 0.00215 | 0.625 | 2.19E-05 | 4.63E-07 | 0.000137 |
| 2226 | 0.163 | 4.11E-08 | 0.224 | 0.788 | 6.02E-09 |
| 2235 | 0.645 | 0.059 | 0.988 | 0.821 | 0.0395 |
| 2242 | 0.71 | 0.434 | 0.988 | 2.68E-09 | 0.598 |
| 2250 | 0.745 | 2.03E-08 | 0.165 | 0.0765 | 1.41E-07 |
| 2256 | 0.0629 | 0.127 | 1.49E-11 | 0.471 | 3.29E-08 |
| 2262 | 0.207 | 1.35E-09 | 0.396 | 0.0368 | 1.50E-13 |
| 2273 | 7.63E-12 | 0.0981 | 5.29E-06 | 1.67E-13 | 3.08E-13 |
| 2280 | 0.0514 | 0.475 | 3.14E-07 | 4.31E-08 | 8.09E-07 |
| 2292 | 0.637 | 2.18E-08 | 0.526 | 0.0116 | 5.10E-07 |
| 2303 | 0.0947 | 0.848 | 0.0302 | 0.707 | 0.00289 |
| 2310 | 5.53E-08 | 1.09E-06 | 1.76E-05 | 5.44E-12 | 7.90E-10 |
| 2318 | 1 | 0.00435 | 0.0252 | 0.462 | 5.52E-05 |
| 2334 | 6.26E-05 | 0.175 | 0.165 | 5.07E-09 | 0.000507 |
| 2342 | 0.000307 | 0.00024 | 1.05E-10 | 0.000191 | 1.18E-11 |
| 2351 | 0.00158 | 4.72E-08 | 1.12E-11 | 0.0457 | 2.21E-19 |
| 2363 | 0.000368 | 4.07E-12 | 0.00439 | 5.38E-12 | 8.65E-13 |
| 2369 | 0.176 | 0.389 | 0.00649 | 0.00052 | 0.033 |
| 2376 | 0.46 | 1 | 1 | 0.418 | 0.582 |
| 2383 | 0.000437 | 1.26E-07 | 1.25E-10 | 8.74E-11 | 1.54E-16 |
| 2398 | 0.363 | 0.67 | 0.0237 | 5.49E-14 | 0.107 |

FIG. 16B (CONT'D)

| Mass | Prostate | Breast | Bladder | Prostate2 | MultiClass (Kruskal-Wallis) |
|---|---|---|---|---|---|
| 2414 | 0.000882 | 0.00677 | 3.52E-12 | 9.67E-06 | 7.39E-13 |
| 2423 | 0.0725 | 0.000368 | 0.117 | 0.448 | 0.00032 |
| 2434 | 0.116 | 0.68 | 0.0447 | 0.293 | 0.0219 |
| 2448 | 0.288 | 0.453 | 0.00161 | 2.68E-05 | 0.0445 |
| 2456 | 0.64 | 4.88E-07 | 0.396 | 0.794 | 4.49E-06 |
| 2471 | 2.09E-05 | 2.14E-06 | 0.000384 | 5.68E-07 | 4.77E-13 |
| 2477 | 0.36 | 2.78E-05 | 0.000186 | 0.959 | 7.44E-07 |
| 2483 | 0.0302 | 0.887 | 0.887 | 1.26E-11 | 0.0199 |
| 2498 | 2.21E-05 | 0.313 | 1.23E-12 | 3.06E-07 | 8.65E-17 |
| 2512 | 0.0101 | 5.56E-13 | 0.0929 | 1.74E-05 | 5.60E-14 |
| 2519 | 1 | 0.887 | 0.887 | 0.000159 | 1 |
| 2529 | 0.65 | 0.447 | 0.0169 | 1.18E-06 | 0.0941 |
| 2536 | 0.00274 | 0.0044 | 1 | 1.22E-15 | 0.000523 |
| 2543 | 0.176 | 0.0107 | 1 | 0.00596 | 0.0116 |
| 2551 | 0.471 | 0.434 | 0.0169 | 0.0731 | 0.00768 |
| 2558 | 0.163 | 0.0837 | 0.101 | 1.04E-08 | 0.128 |
| 2570 | 0.532 | 0.105 | 2.81E-07 | 9.19E-10 | 4.26E-13 |
| 2578 | 0.46 | 1 | 1 | 0.0853 | 0.582 |
| 2587 | 0.00535 | 0.625 | 0.0394 | 7.29E-08 | 0.0018 |
| 2595 | 0.46 | 1 | 1 | 0.24 | 0.582 |
| 2601 | 1 | 0.0107 | 0.314 | 1.30E-05 | 0.00133 |
| 2607 | 1.43E-08 | 2.08E-07 | 0.0317 | 6.55E-19 | 6.60E-10 |
| 2617 | 0.979 | 1.60E-11 | 0.708 | 3.45E-05 | 4.40E-10 |
| 2632 | 0.0235 | 0.887 | 3.31E-07 | 5.68E-07 | 8.19E-06 |
| 2651 | 0.192 | 0.91 | 6.60E-10 | 7.32E-08 | 3.60E-07 |
| 2658 | 0.288 | 1 | 0.314 | 0.0517 | 0.441 |
| 2664 | 0.0205 | 7.39E-12 | 0.254 | 1.76E-18 | 3.78E-08 |
| 2675 | 5.28E-06 | 0.0015 | 2.26E-07 | 0.00261 | 1.67E-11 |
| 2686 | 6.13E-05 | 1.03E-11 | 9.20E-08 | 1.14E-08 | 1.18E-18 |
| 2694 | 0.288 | 1 | 0.314 | 0.142 | 0.441 |
| 2700 | 1 | 0.0728 | 0.129 | 4.69E-16 | 0.0495 |
| 2714 | 0.0338 | 1.79E-07 | 0.0243 | 5.00E-09 | 2.17E-06 |
| 2720 | 1 | 0.0522 | 0.394 | 0.0348 | 0.016 |
| 2730 | 5.99E-06 | 0.000431 | 4.48E-09 | 3.88E-11 | 9.52E-13 |
| 2739 | 0.46 | 0.17 | 1 | 1 | 0.251 |
| 2745 | 0.0123 | 1.03E-11 | 0.00122 | 8.52E-06 | 1.64E-14 |
| 2761 | 0.605 | 0.533 | 1.95E-07 | 4.07E-08 | 3.06E-07 |
| 2773 | 0.0514 | 0.695 | 8.42E-11 | 0.0023 | 8.37E-11 |
| 2784 | 0.176 | 0.0728 | 0.129 | 0.0104 | 0.297 |
| 2792 | 6.47E-06 | 0.0175 | 0.000134 | 1.82E-21 | 2.34E-05 |
| 2799 | 0.46 | 0.389 | 0.314 | 0.0853 | 0.731 |
| 2806 | 0.46 | 1 | 0.314 | 1.82E-21 | 0.582 |

FIG. 16B (CONT'D)

| Mass | Prostate | Breast | Bladder | Prostate2 | MultiClass (Kruskal-Wallis) |
|---|---|---|---|---|---|
| 2822 | 0.00535 | 0.627 | 6.96E-15 | 2.05E-12 | 2.18E-15 |
| 2832 | 0.112 | 5.43E-09 | 0.0627 | 0.0333 | 8.88E-15 |
| 2841 | 0.452 | 0.245 | 0.0141 | 1.33E-05 | 0.0812 |
| 2849 | 2.23E-08 | 6.96E-08 | 3.49E-10 | 1.09E-09 | 5.74E-20 |
| 2858 | 1 | 1 | 1 | 1.27E-07 | 1 |
| 2866 | 0.000336 | 7.63E-05 | 0.287 | 5.33E-16 | 2.68E-07 |
| 2874 | 0.636 | 2.71E-11 | 0.149 | 0.152 | 1.39E-11 |
| 2888 | 8.79E-11 | 0.0802 | 0.632 | 5.90E-09 | 4.82E-08 |
| 2904 | 0.109 | 0.638 | 0.104 | 0.000569 | 0.0115 |
| 2917 | 0.645 | 0.547 | 1.14E-05 | 0.0117 | 2.82E-06 |
| 2937 | 0.416 | 0.937 | 4.19E-11 | 4.55E-08 | 5.39E-09 |
| 2948 | 0.796 | 0.722 | 0.287 | 0.126 | 0.635 |
| 2957 | 0.288 | 0.00953 | 8.64E-07 | 0.000753 | 8.01E-09 |
| 2966 | 0.288 | 0.389 | 0.314 | 1.30E-05 | 0.643 |
| 2981 | 0.285 | 8.60E-10 | 1.95E-13 | 3.01E-10 | 1.85E-13 |
| 2989 | 0.288 | 1 | 1 | 0.0517 | 0.267 |
| 2997 | 0.000283 | 7.28E-12 | 0.00178 | 2.17E-07 | 6.36E-17 |
| 3005 | 0.239 | 0.0368 | 0.0039 | 0.901 | 8.06E-05 |
| 3021 | 0.15 | 2.75E-07 | 0.567 | 1.23E-13 | 1.24E-06 |
| 3034 | 1.16E-15 | 6.24E-14 | 1.21E-06 | 6.55E-19 | 1.01E-22 |
| 3043 | 0.71 | 9.72E-06 | 0.224 | 0.591 | 3.97E-06 |
| 3051 | 2.71E-05 | 0.986 | 0.595 | 4.09E-08 | 0.00029 |
| 3059 | 2.59E-05 | 0.0707 | 2.20E-10 | 7.03E-11 | 1.51E-07 |
| 3071 | 0.176 | 0.389 | 0.129 | 2.89E-05 | 0.417 |
| 3080 | 0.787 | 0.279 | 0.396 | 1.34E-16 | 0.212 |
| 3092 | 0.0975 | 0.00136 | 0.000114 | 0.0573 | 7.92E-09 |
| 3101 | 0.956 | 0.109 | 1.14E-10 | 0.037 | 3.97E-06 |
| 3108 | 0.319 | 0.000162 | 0.358 | 4.02E-07 | 2.03E-05 |
| 3116 | 0.149 | 0.0245 | 0.534 | 1.23E-08 | 0.0163 |
| 3132 | 0.0426 | 0.625 | 0.582 | 2.65E-11 | 0.00492 |
| 3143 | 0.995 | 0.0449 | 0.254 | 6.55E-14 | 0.137 |
| 3157 | 2.88E-05 | 0.67 | 1.48E-06 | 5.89E-09 | 2.12E-08 |
| 3165 | 2.64E-12 | 0.198 | 7.04E-10 | 2.48E-15 | 1.74E-19 |
| 3173 | 0.176 | 1 | 1 | 0.142 | 0.103 |
| 3181 | 0.751 | 0.242 | 0.396 | 1.80E-10 | 0.0921 |
| 3188 | 0.0228 | 0.923 | 7.64E-09 | 7.31E-08 | 1.38E-09 |
| 3196 | 7.74E-07 | 0.499 | 1.95E-13 | 0.429 | 3.76E-17 |
| 3207 | 0.46 | 0.389 | 0.0181 | 2.27E-12 | 0.0349 |
| 3221 | 0.857 | 0.22 | 0.000459 | 0.211 | 0.000296 |
| 3229 | 0.00857 | 0.17 | 2.46E-11 | 4.87E-14 | 1.77E-09 |
| 3239 | 0.623 | 0.277 | 0.254 | 0.0683 | 0.0861 |
| 3246 | 0.316 | 0.906 | 0.82 | 1.67E-13 | 0.575 |

FIG. 16B (CONT'D)

| Mass | Prostate | Breast | Bladder | Prostate2 | MultiClass (Kruskal-Wallis) |
|---|---|---|---|---|---|
| 3259 | 0.189 | 0.262 | 2.24E-06 | 2.57E-14 | 6.21E-08 |
| 3267 | 7.63E-12 | 0.875 | 1.82E-13 | 0.0218 | 6.77E-21 |
| 3278 | 0.0122 | 0.887 | 2.44E-14 | 2.65E-11 | 2.82E-14 |
| 3295 | 0.239 | 0.67 | 0.775 | 1.07E-09 | 0.347 |
| 3307 | 0.41 | 0.779 | 1 | 2.09E-05 | 0.453 |
| 3320 | 0.0435 | 0.836 | 0.698 | 2.37E-06 | 0.0268 |
| 3328 | 0.0103 | 0.507 | 1.43E-07 | 0.000681 | 3.24E-06 |
| 3336 | 0.46 | 0.17 | 1 | 0.142 | 0.251 |
| 3345 | 0.0474 | 0.322 | 1 | 8.03E-06 | 0.00603 |
| 3357 | 0.00521 | 0.209 | 0.0234 | 1.38E-11 | 7.79E-05 |
| 3367 | 0.616 | 6.13E-05 | 0.149 | 1.14E-06 | 0.00748 |
| 3376 | 0.166 | 0.223 | 0.0812 | 0.143 | 0.018 |
| 3385 | 1 | 0.625 | 0.887 | 0.734 | 0.879 |
| 3393 | 1 | 0.478 | 0.449 | 3.55E-17 | 0.643 |
| 3409 | 0.0124 | 0.00305 | 1.14E-10 | 0.0529 | 4.11E-11 |
| 3434 | 0.081 | 0.000927 | 0.47 | 0.802 | 0.00245 |
| 3443 | 0.288 | 0.028 | 0.129 | 0.0853 | 0.0945 |
| 3452 | 0.193 | 2.79E-10 | 0.000141 | 6.78E-06 | 3.16E-14 |
| 3476 | 0.175 | 0.887 | 4.51E-09 | 8.93E-21 | 1.60E-10 |
| 3491 | 0.46 | 0.722 | 0.813 | 2.65E-11 | 0.55 |
| 3504 | 1 | 0.887 | 0.582 | 0.198 | 0.886 |
| 3512 | 0.0194 | 1.09E-09 | 0.0169 | 2.34E-06 | 9.04E-09 |
| 3523 | 1.66E-08 | 0.0215 | 3.59E-10 | 1.01E-11 | 6.45E-12 |
| 3532 | 0.0124 | 0.108 | 0.000144 | 0.157 | 1.16E-05 |
| 3547 | 0.416 | 0.443 | 0.182 | 0.00538 | 0.141 |
| 3558 | 0.3 | 0.789 | 0.396 | 0.458 | 0.288 |
| 3568 | 0.425 | 0.0024 | 0.0241 | 0.359 | 2.12E-05 |
| 3579 | 0.00578 | 0.681 | 0.583 | 0.0256 | 0.0175 |
| 3590 | 0.0391 | 9.72E-06 | 4.71E-06 | 0.00232 | 1.97E-06 |
| 3598 | 0.902 | 0.887 | 0.000119 | 0.011 | 4.12E-05 |
| 3610 | 0.338 | 0.00182 | 0.117 | 0.0155 | 5.21E-06 |
| 3618 | 0.592 | 0.434 | 0.37 | 0.000653 | 0.264 |
| 3626 | 1 | 0.253 | 0.396 | 0.227 | 0.408 |
| 3635 | 8.09E-06 | 3.92E-06 | 0.00274 | 0.192 | 2.74E-09 |
| 3646 | 1.97E-06 | 0.105 | 1 | 0.000745 | 1.21E-06 |
| 3656 | 0.46 | 0.722 | 0.988 | 2.42E-07 | 0.791 |
| 3671 | 0.0251 | 0.13 | 1 | 0.000146 | 0.0436 |
| 3689 | 1.89E-12 | 0.0175 | 2.96E-09 | 1.78E-08 | 2.73E-14 |
| 3698 | 0.46 | 0.457 | 0.134 | 5.53E-05 | 0.301 |
| 3709 | 1 | 0.789 | 0.0918 | 9.95E-05 | 0.207 |
| 3718 | 0.453 | 2.74E-05 | 0.644 | 9.35E-08 | 3.48E-06 |

FIG. 16B (CONT'D)

| Mass | Prostate | Breast | Bladder | Prostate2 | MultiClass (Kruskal-Wallis) |
| --- | --- | --- | --- | --- | --- |
| 3735 | 0.65 | 0.447 | 0.134 | 2.47E-08 | 0.17 |
| 3743 | 0.237 | 2.78E-05 | 0.605 | 0.00974 | 1.28E-05 |
| 3758 | 0.165 | 0.00531 | 0.729 | 8.17E-06 | 0.00528 |
| 3768 | 0.46 | 0.852 | 0.134 | 0.65 | 0.168 |
| 3778 | 3.03E-12 | 0.00389 | 3.15E-10 | 3.87E-10 | 1.07E-16 |
| 3787 | 1 | 0.434 | 0.396 | 0.0449 | 0.549 |
| 3798 | 0.821 | 1 | 0.0929 | 7.94E-07 | 0.386 |
| 3818 | 2.64E-12 | 0.00175 | 3.46E-11 | 2.90E-10 | 8.88E-15 |
| 3828 | 0.71 | 0.814 | 0.988 | 9.11E-07 | 0.932 |
| 3841 | 0.46 | 0.389 | 0.314 | 2.89E-05 | 0.731 |
| 3852 | 1 | 0.0107 | 1 | 1.26E-25 | 0.000109 |
| 3863 | 0.672 | 0.625 | 0.582 | 9.35E-15 | 0.55 |
| 3888 | 0.113 | 3.63E-07 | 6.49E-08 | 1.68E-08 | 1.80E-14 |
| 3897 | 0.452 | 0.887 | 0.582 | 0.000901 | 0.522 |
| 3908 | 0.3 | 0.447 | 0.396 | 0.48 | 0.102 |
| 3920 | 0.192 | 0.887 | 0.17 | 0.0449 | 0.29 |
| 3931 | 0.64 | 0.26 | 0.345 | 0.00206 | 0.468 |
| 3940 | 1 | 1 | 0.314 | 6.27E-11 | 0.301 |
| 3960 | 0.0514 | 0.546 | 1.48E-06 | 4.32E-07 | 4.78E-06 |
| 3977 | 1 | 0.29 | 5.98E-09 | 7.70E-08 | 2.68E-09 |
| 3989 | 0.0189 | 0.789 | 5.29E-06 | 3.55E-12 | 1.26E-05 |
| 3999 | 1 | 1 | 0.314 | 1 | 0.301 |
| 4008 | 0.46 | 1 | 1 | 0.142 | 0.582 |
| 4029 | 0.288 | 0.389 | 1 | 0.0104 | 0.455 |
| 4048 | 5.80E-11 | 0.00435 | 0.00211 | 1.31E-12 | 6.36E-10 |
| 4064 | 0.193 | 1 | 0.134 | 0.0551 | 0.159 |
| 4080 | 0.000374 | 0.0127 | 1.38E-10 | 3.78E-08 | 7.06E-11 |
| 4090 | 0.691 | 0.887 | 0.887 | 0.489 | 1 |
| 4104 | 0.46 | 1 | 1 | 1 | 0.582 |
| 4114 | 0.653 | 0.887 | 0.733 | 0.757 | 0.973 |
| 4130 | 0.946 | 0.276 | 0.254 | 0.754 | 0.277 |
| 4140 | 0.3 | 0.434 | 0.00439 | 5.92E-08 | 0.00138 |
| 4152 | 0.452 | 0.478 | 0.582 | 0.198 | 0.457 |
| 4161 | 0.46 | 1 | 1 | 1 | 0.582 |
| 4172 | 0.46 | 1 | 0.314 | 0.418 | 0.582 |
| 4182 | 0.00781 | 0.222 | 6.03E-11 | 1.93E-16 | 5.36E-09 |
| 4192 | 0.000573 | 0.105 | 1.95E-13 | 0.000414 | 3.89E-16 |
| 4202 | 0.288 | 0.389 | 1 | 1 | 0.451 |
| 4215 | 3.44E-05 | 0.324 | 4.10E-09 | 5.83E-15 | 1.13E-09 |
| 4237 | 0.46 | 1 | 0.314 | 0.418 | 0.582 |
| 4251 | 0.288 | 1 | 0.0181 | 1 | 0.0205 |

FIG. 16B (CONT'D)

| Mass | Prostate | Breast | Bladder | Prostate2 | MultiClass (Kruskal-Wallis) |
|---|---|---|---|---|---|
| 4262 | 1 | 0.625 | 0.0127 | 0.0731 | 0.000617 |
| 4272 | 0.000283 | 0.276 | 4.92E-09 | 5.54E-07 | 1.36E-09 |
| 4284 | 0.263 | 0.851 | 0.468 | 0.106 | 0.152 |
| 4295 | 1 | 0.836 | 0.396 | 0.909 | 0.703 |
| 4328 | 1 | 1 | 1 | 2.31E-06 | 1 |
| 4345 | 0.46 | 1 | 0.129 | 0.00335 | 0.219 |
| 4362 | 1 | 1 | 0.314 | 0.000965 | 0.301 |
| 4373 | 0.323 | 0.223 | 0.197 | 2.37E-06 | 0.149 |
| 4390 | 1 | 1 | 1 | 0.0183 | 1 |
| 4409 | 0.0019 | 0.115 | 3.28E-06 | 1.59E-10 | 9.32E-06 |
| 4429 | 0.288 | 0.773 | 0.226 | 0.119 | 0.139 |
| 4444 | 0.188 | 0.223 | 0.396 | 0.506 | 0.368 |
| 4455 | 0.71 | 0.532 | 0.0369 | 0.48 | 0.123 |
| 4468 | 1 | 0.17 | 1 | 0.142 | 0.0643 |
| 4480 | 1 | 1 | 1 | 0.00335 | 1 |
| 4490 | 0.46 | 0.389 | 1 | 0.142 | 0.598 |
| 4511 | 1 | 0.17 | 0.314 | 2.89E-05 | 0.182 |
| 4531 | 0.988 | 0.389 | 0.527 | 0.142 | 0.33 |
| 4556 | 0.491 | 0.999 | 0.82 | 8.55E-07 | 0.848 |
| 4566 | 0.175 | 0.625 | 0.425 | 0.0831 | 0.152 |
| 4583 | 0.46 | 1 | 1 | 0.0312 | 0.582 |
| 4614 | 0.0822 | 4.67E-05 | 2.10E-07 | 5.62E-19 | 4.58E-06 |
| 4631 | 0.00358 | 0.0323 | 3.33E-08 | 0.00248 | 4.27E-07 |
| 4641 | 0.46 | 1 | 0.129 | 0.418 | 0.212 |
| 4655 | 0.293 | 0.628 | 0.000336 | 6.52E-14 | 0.00855 |
| 4686 | 0.176 | 1 | 1 | 0.0104 | 0.103 |
| 4696 | 0.0869 | 0.975 | 0.245 | 1.75E-11 | 0.141 |
| 4721 | 0.835 | 0.683 | 0.632 | 0.012 | 0.72 |
| 4776 | 6.13E-05 | 0.0445 | 0.582 | 2.21E-18 | 5.16E-06 |
| 4804 | 0.766 | 1 | 0.0398 | 0.487 | 0.162 |
| 4836 | 1 | 1 | 0.314 | 7.19E-20 | 0.301 |
| 4864 | 1 | 1 | 1 | 5.63E-06 | 1 |
| 4889 | 0.46 | 1 | 1 | 2.31E-06 | 0.582 |
| 4917 | 1 | 0.389 | 1 | 3.59E-07 | 0.33 |
| 4950 | 0.841 | 1.10E-05 | 0.0101 | 0.0101 | 3.18E-09 |
| 4983 | 0.71 | 0.434 | 0.811 | 0.00977 | 0.591 |
| 5013 | 0.288 | 0.322 | 5.15E-14 | 2.63E-06 | 5.90E-18 |
| 5040 | 0.57 | 0.151 | 3.40E-05 | 2.58E-07 | 0.000506 |
| 5068 | 0.000863 | 0.424 | 5.52E-08 | 0.0799 | 1.35E-08 |
| 5108 | 1 | 1 | 1 | 0.0517 | 1 |

FIG. 16B (CONT'D)

| Mass | Prostate | Breast | Bladder | Prostate2 | MultiClass (Kruskal-Wallis) |
|---|---|---|---|---|---|
| 5145 | 0.0019 | 0.00553 | 0.0369 | 0.0981 | 2.58E-06 |
| 5175 | 1 | 0.389 | 0.314 | 0.0104 | 0.448 |
| 5204 | 1 | 1 | 1 | 0.000965 | 1 |
| 5238 | 0.288 | 0.389 | 1 | 4.87E-14 | 0.451 |
| 5267 | 0.46 | 1 | 1 | 0.00596 | 0.582 |
| 5294 | 1 | 1 | 1 | 0.24 | 1 |
| 5322 | 0.658 | 0.256 | 2.08E-08 | 4.54E-09 | 8.40E-08 |
| 5351 | 0.346 | 0.992 | 2.16E-12 | 0.0102 | 1.11E-14 |
| 5383 | 0.176 | 1 | 0.0488 | 1.27E-07 | 0.1 |
| 5413 | 1 | 0.625 | 6.52E-07 | 0.0185 | 8.37E-13 |
| 5441 | 0.288 | 1 | 0.0488 | 1.38E-08 | 0.096 |
| 5477 | 0.3 | 0.789 | 0.396 | 3.53E-06 | 0.288 |
| 5509 | 0.471 | 0.625 | 0.397 | 1.77E-07 | 0.208 |
| 5546 | 0.46 | 0.887 | 0.00949 | 6.80E-06 | 0.0156 |
| 5580 | 0.0223 | 0.289 | 0.0252 | 0.307 | 0.00733 |
| 5609 | 0.000882 | 0.00248 | 0.00249 | 0.808 | 3.71E-06 |
| 5645 | 0.288 | 1 | 1 | 6.34E-05 | 0.267 |
| 5676 | 1 | 1 | 0.314 | 5.63E-06 | 0.301 |
| 5707 | 0.3 | 0.434 | 0.396 | 0.0449 | 0.288 |
| 5737 | 7.25E-05 | 0.389 | 0.113 | 0.609 | 0.000176 |
| 5770 | 1 | 1 | 0.0181 | 0.00052 | 0.000659 |
| 5816 | 0.471 | 0.625 | 0.226 | 7.31E-06 | 0.0488 |
| 5853 | 0.316 | 0.625 | 0.00542 | 0.0831 | 0.0021 |
| 5888 | 5.28E-06 | 0.0186 | 1.25E-11 | 0.0449 | 1.90E-19 |
| 5923 | 0.444 | 0.17 | 0.0623 | 0.0517 | 0.0086 |
| 5957 | 0.298 | 0.887 | 0.0169 | 3.00E-06 | 0.0467 |
| 5997 | 0.46 | 1 | 0.129 | 2.31E-06 | 0.212 |
| 6028 | 1 | 1 | 1 | 1.38E-08 | 1 |
| 6062 | 1 | 1 | 1 | 1.11E-09 | 1 |
| 6111 | 1 | 1 | 0.0488 | 6.34E-05 | 0.00681 |
| 6152 | 0.46 | 1 | 0.314 | 0.00335 | 0.582 |
| 6184 | 0.452 | 0.625 | 1.15E-08 | 4.10E-07 | 1.29E-12 |
| 6220 | 0.46 | 1 | 1 | 2.27E-12 | 0.582 |
| 6255 | 1 | 1 | 1 | 0.00052 | 1 |
| 6294 | 0.471 | 0.625 | 0.582 | 1.96E-08 | 0.598 |
| 6355 | 1 | 1 | 1 | 0.00596 | 1 |
| 6393 | 1 | 0.434 | 1 | 0.909 | 0.791 |
| 6431 | 0.15 | 0.262 | 0.482 | 9.69E-05 | 0.0269 |
| 6471 | 1 | 1 | 1 | 1.38E-08 | 1 |
| 6512 | 1 | 1 | 1 | 9.11E-07 | 1 |
| 6562 | 0.233 | 0.434 | 0.00936 | 0.314 | 0.00396 |

FIG. 16B (CONT'D)

| Mass | Prostate | Breast | Bladder | Prostate2 | MultiClass (Kruskal-Wallis) |
|---|---|---|---|---|---|
| 6598 | 0.605 | 0.192 | 0.00722 | 4.95E-15 | 0.00629 |
| 6633 | 0.906 | 0.72 | 0.971 | 0.00692 | 0.799 |
| 6670 | 0.463 | 0.92 | 0.582 | 0.00133 | 0.548 |
| 6713 | 0.46 | 1 | 1 | 1.11E-09 | 0.582 |
| 6754 | 1 | 0.0728 | 1 | 0.0312 | 0.00965 |
| 6790 | 0.0561 | 0.17 | 0.0488 | 2.33E-23 | 0.185 |
| 6826 | 1 | 1 | 1 | 0.00335 | 1 |
| 6866 | 1 | 1 | 1 | 0.00052 | 1 |
| 6906 | 1 | 1 | 1 | 4.31E-08 | 1 |
| 6942 | 0.471 | 0.507 | 0.849 | 0.00379 | 0.44 |
| 6981 | 1 | 0.92 | 0.582 | 0.00113 | 0.891 |
| 7021 | 0.338 | 0.975 | 0.551 | 0.000269 | 0.618 |
| 7060 | 0.192 | 0.322 | 0.287 | 0.000342 | 0.117 |
| 7103 | 0.46 | 0.801 | 0.287 | 1.38E-06 | 0.55 |
| 7142 | 0.712 | 0.625 | 0.582 | 1.34E-09 | 0.566 |
| 7180 | 1 | 0.389 | 1 | 2.89E-05 | 0.33 |
| 7219 | 1 | 1 | 1 | 4.31E-08 | 1 |
| 7260 | 1 | 1 | 1 | 3.59E-07 | 1 |
| 7305 | 0.705 | 0.434 | 0.396 | 4.13E-05 | 0.569 |
| 7345 | 0.46 | 1 | 1 | 1.11E-09 | 0.582 |
| 7384 | 1 | 1 | 1 | 1.30E-05 | 1 |
| 7427 | 1 | 1 | 1 | 9.11E-07 | 1 |
| 7466 | 1 | 1 | 1 | 9.11E-07 | 1 |
| 7510 | 1 | 1 | 1 | 9.11E-07 | 1 |
| 7561 | 1 | 0.389 | 1 | 1.38E-08 | 0.33 |
| 7607 | 1 | 0.434 | 0.396 | 0.00162 | 0.549 |
| 7647 | 0.471 | 0.625 | 0.582 | 1.67E-05 | 0.598 |
| 7688 | 0.102 | 1 | 0.0181 | 0.142 | 0.0342 |
| 7731 | 0.316 | 0.000963 | 2.70E-05 | 0.000298 | 3.10E-09 |
| 7771 | 0.979 | 0.0941 | 0.226 | 0.486 | 0.0238 |
| 7813 | 1 | 1 | 0.314 | 0.00013 | 0.301 |
| 7854 | 1 | 1 | 1 | 0.000263 | 1 |
| 7899 | 0.691 | 0.117 | 0.449 | 6.53E-17 | 0.265 |
| 7956 | 1 | 1 | 1 | 0.000965 | 1 |
| 7997 | 0.288 | 1 | 1 | 6.34E-05 | 0.267 |
| 8043 | 0.288 | 1 | 0.0181 | 0.00596 | 0.0214 |
| 8086 | 0.0041 | 0.996 | 9.42E-08 | 0.895 | 4.04E-07 |
| 8128 | 0.605 | 1.54E-05 | 0.0825 | 0.000855 | 1.98E-06 |
| 8184 | 0.288 | 0.389 | 1 | 2.89E-05 | 0.453 |
| 8232 | 0.46 | 1 | 1 | 0.00182 | 0.582 |
| 8282 | 1 | 1 | 1 | 2.31E-06 | 1 |

FIG. 16B (CONT'D)

| Mass | Prostate | Breast | Bladder | Prostate2 | MultiClass (Kruskal-Wallis) |
|---|---|---|---|---|---|
| 8337 | 1 | 1 | 1 | 0.000965 | 1 |
| 8407 | 1 | 1 | 1 | 0.00052 | 1 |
| 8486 | 1 | 1 | 1 | 0.0104 | 1 |
| 8532 | 0.176 | 0.389 | 0.129 | 0.142 | 0.393 |
| 8597 | 0.847 | 0.0873 | 0.00994 | 0.0166 | 0.0104 |
| 8642 | 1 | 0.625 | 0.582 | 0.000615 | 0.801 |
| 8717 | 0.562 | 0.814 | 0.396 | 0.157 | 0.506 |
| 8764 | 0.539 | 1 | 3.56E-08 | 0.946 | 3.24E-06 |
| 8826 | 0.744 | 1 | 2.19E-05 | 0.0239 | 2.33E-06 |
| 8877 | 0.163 | 0.887 | 5.35E-07 | 0.504 | 1.88E-07 |
| 8932 | 0.383 | 0.000285 | 0.439 | 0.471 | 0.00725 |
| 8988 | 1 | 1 | 1 | 0.00335 | 1 |
| 9034 | 1 | 0.389 | 0.314 | 0.00052 | 0.448 |
| 9085 | 1 | 0.028 | 0.314 | 2.31E-06 | 0.00749 |
| 9139 | 0.00978 | 0.613 | 0.84 | 1.84E-05 | 0.00103 |
| 9234 | 0.00386 | 0.613 | 0.00412 | 1.59E-10 | 0.000202 |
| 9290 | 0.000416 | 0.256 | 2.03E-09 | 0.00013 | 1.71E-11 |
| 9357 | 0.288 | 0.625 | 0.582 | 0.0519 | 0.123 |
| 9405 | 0.0338 | 0.0226 | 0.0169 | 8.93E-21 | 0.0653 |
| 9455 | 0.691 | 0.625 | 0.582 | 0.0363 | 0.557 |
| 9504 | 1 | 1 | 1 | 9.11E-07 | 1 |
| 9555 | 1 | 1 | 1 | 2.89E-05 | 1 |
| 9611 | 0.288 | 0.389 | 1 | 1.38E-08 | 0.455 |
| 9673 | 1 | 1 | 1 | 1.27E-07 | 1 |
| 9748 | 0.46 | 1 | 1 | 0.000965 | 0.582 |
| 9822 | 1 | 0.887 | 0.582 | 0.0456 | 0.886 |
| 9884 | 0.824 | 0.836 | 0.396 | 0.142 | 0.631 |
| 9935 | 0.0419 | 0.5 | 0.729 | 0.0319 | 0.0256 |
| 9992 | 0.463 | 0.887 | 0.212 | 0.0297 | 0.503 |
| 10047 | 0.285 | 0.836 | 0.0169 | 0.0641 | 0.0639 |
| 10106 | 1 | 0.608 | 0.913 | 0.349 | 0.791 |
| 10167 | 0.421 | 0.14 | 0.138 | 0.896 | 0.283 |
| 10228 | 2.80E-05 | 1 | 8.64E-07 | 0.000672 | 7.82E-10 |
| 10281 | 0.0674 | 0.728 | 0.0486 | 1.34E-05 | 0.0269 |
| 10335 | 0.605 | 0.228 | 0.459 | 0.327 | 0.507 |
| 10401 | 0.922 | 0.412 | 0.396 | 0.129 | 0.325 |
| 10455 | 0.993 | 0.00386 | 0.75 | 0.0116 | 0.000251 |
| 10510 | 1 | 0.137 | 1 | 0.132 | 0.173 |
| 10568 | 0.522 | 0.676 | 0.747 | 0.0102 | 0.862 |
| 10626 | 0.404 | 0.0323 | 0.000147 | 0.00671 | 0.000675 |
| 10680 | 0.815 | 0.887 | 0.707 | 0.0409 | 1 |

FIG. 16B (CONT'D)

| Mass | Prostate | Breast | Bladder | Prostate2 | MultiClass (Kruskal-Wallis) |
|---|---|---|---|---|---|
| 10735 | 0.227 | 0.386 | 0.745 | 0.032 | 0.409 |
| 10794 | 1 | 0.151 | 0.0398 | 0.264 | 0.0101 |
| 10849 | 0.497 | 0.427 | 1 | 0.529 | 0.361 |
| 10905 | 0.46 | 0.39 | 1 | 0.387 | 0.572 |
| 10962 | 0.46 | 0.478 | 0.641 | 0.134 | 0.661 |
| 11020 | 0.882 | 0.625 | 0.358 | 0.0312 | 0.397 |
| 11077 | 0.0575 | 5.56E-13 | 9.32E-05 | 2.13E-08 | 3.51E-18 |
| 11138 | 0.0282 | 0.0353 | 0.129 | 8.83E-05 | 0.00171 |
| 11198 | 0.672 | 0.625 | 0.181 | 0.00409 | 0.508 |
| 11257 | 0.54 | 0.975 | 0.396 | 0.0282 | 0.426 |
| 11315 | 0.163 | 0.0522 | 0.0438 | 7.48E-05 | 0.00282 |
| 11377 | 0.988 | 0.475 | 0.181 | 0.035 | 0.233 |
| 11442 | 0.41 | 0.154 | 0.13 | 1.04E-05 | 0.103 |
| 11501 | 0.8 | 0.232 | 0.0285 | 0.00692 | 0.0254 |
| 11560 | 0.593 | 0.00553 | 0.61 | 0.1 | 0.00558 |
| 11619 | 0.102 | 0.166 | 0.0235 | 0.000592 | 0.0058 |
| 11678 | 0.556 | 0.891 | 1 | 0.78 | 0.831 |
| 11739 | 0.00675 | 1.32E-07 | 7.93E-05 | 5.25E-11 | 6.99E-13 |
| 11802 | 0.0575 | 0.625 | 0.0555 | 0.00213 | 0.0564 |
| 11864 | 0.998 | 0.152 | 0.61 | 0.0633 | 0.206 |
| 11929 | 0.797 | 0.386 | 0.0679 | 0.00045 | 0.128 |
| 11993 | 0.192 | 0.79 | 0.0937 | 0.00422 | 0.357 |
| 12056 | 0.482 | 0.0186 | 0.396 | 0.0633 | 0.00828 |
| 12119 | 0.779 | 0.831 | 1 | 0.00644 | 1 |
| 12188 | 0.92 | 0.39 | 0.303 | 0.000726 | 0.341 |
| 12250 | 0.295 | 0.102 | 0.0484 | 0.000182 | 0.00855 |
| 12316 | 0.288 | 0.132 | 0.0949 | 0.00445 | 0.0212 |
| 12382 | 0.193 | 1 | 0.0353 | 0.00255 | 0.184 |
| 12450 | 0.298 | 9.72E-06 | 0.00191 | 0.00308 | 9.04E-09 |
| 12516 | 0.8 | 0.259 | 0.47 | 0.745 | 0.291 |
| 12580 | 7.62E-05 | 1.73E-05 | 3.45E-06 | 8.49E-13 | 2.56E-16 |
| 12662 | 0.0536 | 0.0266 | 0.00263 | 3.45E-06 | 2.12E-05 |
| 12727 | 0.676 | 0.457 | 0.226 | 0.236 | 0.355 |
| 12793 | 0.182 | 0.000875 | 0.206 | 0.00177 | 3.14E-06 |
| 12862 | 0.896 | 0.0272 | 0.17 | 0.0189 | 0.0101 |
| 12932 | 0.406 | 0.000887 | 0.0442 | 0.000108 | 7.99E-06 |
| 13005 | 0.305 | 0.858 | 0.00366 | 0.000133 | 0.0416 |
| 13082 | 0.482 | 0.676 | 0.0315 | 0.000596 | 0.143 |
| 13149 | 0.686 | 0.00034 | 0.295 | 0.000191 | 5.64E-05 |
| 13222 | 0.471 | 1.27E-06 | 0.255 | 0.0227 | 4.01E-08 |
| 13291 | 0.513 | 1.45E-10 | 0.078 | 0.00385 | 9.34E-12 |

FIG. 16B (CONT'D)

| Mass | Prostate | Breast | Bladder | Prostate2 | MultiClass (Kruskal-Wallis) |
|---|---|---|---|---|---|
| 13359 | 0.338 | 5.53E-06 | 0.00305 | 6.34E-05 | 1.38E-08 |
| 13431 | 0.601 | 0.676 | 0.887 | 0.0207 | 0.646 |
| 13506 | 0.36 | 0.874 | 0.447 | 1.23E-06 | 0.749 |
| 13593 | 0.288 | 0.0169 | 0.0239 | 8.00E-06 | 0.000604 |
| 13669 | 0.308 | 0.39 | 0.00714 | 0.000569 | 0.0324 |
| 13739 | 0.46 | 0.00137 | 0.024 | 1.28E-06 | 0.000147 |
| 13814 | 0.202 | 0.000237 | 0.00421 | 0.00145 | 1.66E-06 |
| 13888 | 0.363 | 0.331 | 0.184 | 0.00584 | 0.237 |
| 13964 | 0.272 | 0.0233 | 0.00505 | 8.88E-05 | 0.000823 |
| 14039 | 0.582 | 0.00331 | 0.212 | 0.00137 | 0.0014 |
| 14115 | 0.209 | 0.012 | 0.0022 | 9.73E-05 | 9.86E-05 |
| 14194 | 0.975 | 0.852 | 0.0812 | 0.000118 | 0.307 |
| 14267 | 0.3 | 0.00075 | 0.00879 | 6.20E-07 | 1.75E-05 |
| 14348 | 0.114 | 0.67 | 0.0159 | 2.09E-05 | 0.152 |
| 14426 | 0.46 | 0.0897 | 0.0104 | 0.000726 | 0.0102 |
| 14508 | 0.593 | 0.0175 | 0.149 | 0.101 | 0.00975 |
| 14590 | 0.074 | 0.0643 | 0.00759 | 1.21E-05 | 0.00228 |
| 14664 | 0.395 | 0.000549 | 0.149 | 0.163 | 9.38E-05 |
| 14740 | 0.193 | 0.162 | 0.0469 | 0.000726 | 0.0392 |
| 14819 | 0.747 | 0.391 | 0.329 | 0.0739 | 0.463 |
| 14896 | 0.301 | 2.70E-05 | 0.137 | 0.0948 | 1.51E-06 |

FIG. 16B (CONT'D)

Fold Change – Median

| Mass | Prostate | Breast | Bladder | Prostate2 |
|---|---|---|---|---|
| 702 | 1.00 | 1.00 | 65.86 | 13.64 |
| 707 | 1.00 | 1.00 | 1.00 | 4.46 |
| 711 | 1.21 | 0.67 | 0.88 | 1.05 |
| 715 | 1.29 | 1.26 | 0.01 | 0.74 |
| 719 | 1.26 | 0.02 | 2.86 | 0.05 |
| 725 | 1.90 | 0.81 | 0.94 | 1.76 |
| 731 | 1.31 | 0.81 | 0.95 | 0.31 |
| 735 | 1.41 | 0.88 | 0.71 | 0.72 |
| 743 | 1.27 | 0.85 | 1.68 | 1.03 |
| 749 | 1.56 | 0.96 | 1.79 | 0.75 |
| 755 | 80.10 | 60.18 | 1.00 | 3.26 |
| 759 | 0.66 | 0.65 | 0.95 | 0.53 |
| 763 | 1.00 | 1.00 | 1.00 | 1.00 |
| 766 | 1.52 | 1.05 | 1.13 | 0.41 |
| 771 | 1.09 | 0.73 | 0.70 | 0.31 |
| 777 | 0.99 | 0.73 | 0.91 | 0.26 |
| 783 | 1.24 | 0.95 | 2.44 | 0.63 |
| 787 | 1.38 | 1.03 | 0.38 | 0.74 |
| 793 | 87.38 | 96.65 | 1.00 | 15.99 |
| 798 | 1.47 | 0.86 | 0.88 | 0.48 |
| 804 | 1.63 | 1.40 | 2.48 | 0.36 |
| 812 | 1.29 | 0.91 | 1.32 | 0.62 |
| 824 | 1.15 | 0.76 | 4.66 | 0.52 |
| 830 | 1.57 | 0.95 | 8.32 | 0.58 |
| 836 | 1.23 | 1.42 | 1.11 | 0.36 |
| 841 | 1.49 | 1.04 | 0.01 | 0.33 |
| 848 | 1.62 | 0.95 | 1.75 | 0.63 |
| 851 | 1.63 | 1.04 | 0.93 | 1.07 |
| 856 | 1.50 | 1.33 | 1.27 | 0.46 |
| 862 | 0.96 | 1.06 | 1.13 | 0.23 |
| 866 | 1.00 | 1.00 | 1.00 | 1.00 |
| 872 | 1.26 | 0.81 | 0.82 | 0.79 |
| 881 | 1.47 | 1.97 | 1.33 | 0.61 |
| 886 | 1.00 | 1.00 | 1.00 | 1.00 |
| 891 | 1.46 | 0.76 | 2.03 | 1.03 |
| 896 | 1.00 | 1.00 | 1.00 | 4.68 |

FIG. 16C

| Mass | Prostate | Breast | Bladder | Prostate2 |
|---|---|---|---|---|
| 904 | 347.31 | 434.09 | 144.31 | 172.32 |
| 907 | 1.06 | 1.62 | 0.79 | 2.09 |
| 912 | 1.00 | 1.00 | 471.31 | 37.21 |
| 916 | 1.00 | 1.00 | 1.00 | 31.50 |
| 922 | 1.25 | 1.66 | 1.57 | 1.81 |
| 929 | 0.95 | 1.50 | 0.01 | 1.48 |
| 935 | 1.00 | 1.00 | 59.52 | 30.62 |
| 940 | 1.00 | 1.00 | 1.00 | 1.00 |
| 944 | 1.74 | 0.58 | 5.18 | 2.01 |
| 949 | 1.00 | 114.34 | 1.00 | 45.01 |
| 956 | 1.43 | 1.57 | 1.80 | 0.24 |
| 960 | 1.05 | 0.94 | 1.43 | 0.57 |
| 970 | 0.89 | 0.86 | 1.00 | 0.70 |
| 976 | 1.08 | 0.97 | 1.02 | 0.20 |
| 980 | 1.00 | 1.00 | 1.00 | 13.94 |
| 984 | 1.00 | 1.00 | 1.00 | 1.00 |
| 992 | 1.94 | 1.54 | 0.95 | 2.20 |
| 995 | 167.57 | 186.65 | 409.88 | 1.00 |
| 1000 | 121.34 | 147.00 | 256.16 | 27.41 |
| 1007 | 0.64 | 0.84 | 1.50 | 0.32 |
| 1013 | 354.69 | 202.11 | 202.64 | 335.19 |
| 1018 | 1.70 | 1.70 | 0.24 | 2.03 |
| 1023 | 0.28 | 0.47 | 0.28 | 0.15 |
| 1031 | 0.01 | 0.01 | 1.14 | 0.23 |
| 1035 | 1.89 | 2.22 | 2.35 | 1.88 |
| 1042 | 178.80 | 1.00 | 117.78 | 11.05 |
| 1048 | 0.42 | 0.83 | 0.18 | 0.40 |
| 1058 | 226.73 | 1.00 | 1050.72 | 191.06 |
| 1063 | 0.77 | 1.90 | 0.43 | 1.16 |
| 1066 | 0.00 | 0.55 | 0.00 | 0.00 |
| 1069 | 1.00 | 1.00 | 1.00 | 25.74 |
| 1072 | 1.00 | 1.00 | 1.00 | 1.00 |
| 1079 | 0.54 | 0.95 | 0.50 | 0.59 |
| 1085 | 1.00 | 1.00 | 1.00 | 59.32 |
| 1090 | 1.00 | 1.00 | 1.00 | 6.86 |
| 1094 | 1.00 | 1.00 | 142.67 | 42.78 |
| 1101 | 1.43 | 0.81 | 2.29 | 0.99 |
| 1106 | 139.55 | 160.37 | 1.00 | 33.97 |
| 1111 | 1.00 | 161.06 | 142.89 | 22.73 |
| 1116 | 1.48 | 1.47 | 2.09 | 0.59 |
| 1119 | 146.80 | 234.56 | 152.31 | 44.87 |

FIG. 16C (CONT'D)

| Mass | Prostate | Breast | Bladder | Prostate2 |
|---|---|---|---|---|
| 1126 | 0.42 | 0.87 | 0.25 | 0.28 |
| 1131 | 1.00 | 1.00 | 1.00 | 40.34 |
| 1135 | 0.83 | 0.01 | 0.57 | 0.22 |
| 1139 | 0.89 | 0.90 | 0.00 | 0.40 |
| 1144 | 1.20 | 0.96 | 2.70 | 0.37 |
| 1150 | 1.00 | 169.49 | 1.00 | 30.19 |
| 1153 | 1.00 | 1.00 | 1.00 | 9.88 |
| 1156 | 1.00 | 1.00 | 213.15 | 21.39 |
| 1159 | 199.59 | 1.00 | 263.54 | 56.23 |
| 1162 | 0.01 | 0.01 | 0.01 | 0.01 |
| 1166 | 0.54 | 0.68 | 0.00 | 0.20 |
| 1170 | 151.01 | 1.00 | 50.22 | 27.34 |
| 1174 | 199.74 | 149.64 | 1.00 | 79.51 |
| 1177 | 1.00 | 1.00 | 1.00 | 34.83 |
| 1183 | 1.00 | 1.00 | 182.75 | 40.58 |
| 1188 | 1.00 | 1.00 | 1.00 | 15.59 |
| 1191 | 0.48 | 0.69 | 0.00 | 0.27 |
| 1197 | 159.26 | 278.24 | 1.00 | 64.44 |
| 1201 | 1.00 | 1.00 | 1.00 | 1.00 |
| 1206 | 1.00 | 290.73 | 178.45 | 77.22 |
| 1209 | 0.50 | 0.69 | 0.44 | 0.19 |
| 1214 | 7.86 | 0.01 | 10.80 | 7.39 |
| 1217 | 1.00 | 1.00 | 1.00 | 1.00 |
| 1221 | 1.00 | 1.00 | 1.00 | 247.69 |
| 1226 | 1.00 | 1.00 | 1.00 | 16.58 |
| 1231 | 0.90 | 1.24 | 5.66 | 0.33 |
| 1234 | 0.01 | 1.31 | 0.01 | 0.26 |
| 1237 | 57.89 | 1.00 | 1.00 | 36.38 |
| 1240 | 1.00 | 1.00 | 1.00 | 38.07 |
| 1244 | 1.00 | 1.00 | 1.00 | 33.40 |
| 1254 | 1.04 | 1.65 | 0.01 | 0.54 |
| 1262 | 1.00 | 1.00 | 1.00 | 69.02 |
| 1267 | 0.20 | 0.23 | 0.24 | 0.11 |
| 1275 | 145.83 | 1.00 | 1.00 | 69.48 |
| 1280 | 251.92 | 1.00 | 1406.33 | 231.96 |
| 1292 | 0.92 | 1.38 | 1.22 | 0.44 |
| 1300 | 164.59 | 265.47 | 168.89 | 114.01 |
| 1308 | 0.96 | 1.04 | 0.01 | 0.37 |
| 1314 | 1.00 | 1.00 | 634.96 | 21.25 |
| 1318 | 0.89 | 1.09 | 0.41 | 0.57 |
| 1323 | 1.00 | 1.00 | 1.00 | 44.90 |

FIG. 16C (CONT'D)

| Mass | Prostate | Breast | Bladder | Prostate2 |
|------|----------|--------|---------|-----------|
| 1327 | 1.00 | 1.00 | 1.00 | 28.21 |
| 1332 | 1.00 | 186.86 | 1.00 | 67.26 |
| 1337 | 0.95 | 1.13 | 1.28 | 0.32 |
| 1345 | 1.00 | 177.17 | 64.05 | 45.37 |
| 1354 | 0.47 | 0.35 | 0.46 | 0.25 |
| 1362 | 1.00 | 1.00 | 1.00 | 43.57 |
| 1366 | 1.00 | 1.00 | 1.00 | 78.23 |
| 1370 | 240.69 | 1.00 | 1.00 | 94.02 |
| 1375 | 1.00 | 1.00 | 123.34 | 23.67 |
| 1383 | 0.90 | 4.34 | 0.83 | 0.42 |
| 1393 | 0.81 | 0.82 | 0.92 | 0.65 |
| 1399 | 1.00 | 1.00 | 1.00 | 6.97 |
| 1406 | 1.17 | 1.12 | 0.83 | 0.67 |
| 1415 | 0.69 | 1.11 | 0.95 | 0.30 |
| 1421 | 0.79 | 0.01 | 0.46 | 0.65 |
| 1427 | 0.67 | 1.10 | 3.22 | 0.40 |
| 1434 | 1.00 | 1.00 | 1.00 | 89.56 |
| 1441 | 1.00 | 1.00 | 1.00 | 15.06 |
| 1447 | 1.00 | 1.00 | 1.00 | 1.00 |
| 1453 | 1885.15 | 437.78 | 2646.51 | 2217.87 |
| 1458 | 1.00 | 1.00 | 1.00 | 1.00 |
| 1463 | 0.00 | 0.55 | 0.00 | 0.00 |
| 1469 | 0.66 | 0.80 | 0.55 | 0.33 |
| 1476 | 1.00 | 1.00 | 1.00 | 36.20 |
| 1488 | 0.01 | 1.67 | 3.44 | 0.64 |
| 1494 | 1.00 | 1.00 | 1.00 | 16.93 |
| 1502 | 1.00 | 1.00 | 809.48 | 98.91 |
| 1507 | 1.45 | 0.01 | 0.01 | 0.93 |
| 1516 | 1.00 | 1.00 | 206.28 | 111.62 |
| 1523 | 0.38 | 0.58 | 0.15 | 0.33 |
| 1534 | 0.97 | 0.95 | 2.61 | 0.73 |
| 1540 | 0.58 | 0.54 | 0.00 | 0.31 |
| 1548 | 1.00 | 310.95 | 1.00 | 162.04 |
| 1555 | 126.61 | 1.00 | 196.45 | 80.36 |
| 1561 | 1.00 | 1.00 | 1.00 | 1.00 |
| 1567 | 0.79 | 0.54 | 1.13 | 0.60 |
| 1573 | 1.00 | 1.00 | 1.00 | 48.71 |
| 1579 | 1.00 | 1.00 | 113.26 | 26.57 |
| 1586 | 1.00 | 256.70 | 1.00 | 21.65 |
| 1590 | 1.00 | 1.00 | 182.20 | 64.09 |
| 1595 | 1.43 | 0.01 | 1.31 | 0.81 |

FIG. 16C (CONT'D)

| Mass | Prostate | Breast | Bladder | Prostate2 |
|------|----------|--------|---------|-----------|
| 1602 | 0.01 | 1.34 | 0.01 | 0.59 |
| 1610 | 1.53 | 0.01 | 1.87 | 0.78 |
| 1618 | 0.65 | 0.58 | 0.34 | 0.55 |
| 1625 | 1.00 | 1.00 | 1.00 | 1.00 |
| 1630 | 1.09 | 2.78 | 0.88 | 0.89 |
| 1635 | 0.81 | 0.00 | 0.00 | 0.42 |
| 1642 | 0.84 | 1.15 | 1.24 | 0.46 |
| 1655 | 1.00 | 141.92 | 1.00 | 44.62 |
| 1659 | 1.00 | 1.00 | 1.00 | 58.87 |
| 1668 | 0.01 | 2.76 | 0.01 | 0.46 |
| 1672 | 1.00 | 331.42 | 1.00 | 24.05 |
| 1679 | 1.00 | 169.63 | 140.83 | 56.69 |
| 1683 | 1.00 | 1.00 | 44.53 | 28.32 |
| 1691 | 1.92 | 2.62 | 2.35 | 0.84 |
| 1696 | 4.05 | 1.01 | 6.85 | 4.92 |
| 1706 | 5.10 | 2.32 | 2.74 | 4.75 |
| 1710 | 0.01 | 4.02 | 0.01 | 0.01 |
| 1715 | 1.00 | 1.00 | 39.06 | 22.29 |
| 1724 | 0.81 | 1.45 | 0.64 | 0.61 |
| 1729 | 113.20 | 1.00 | 1.00 | 87.93 |
| 1738 | 1.00 | 1.00 | 1.00 | 22.46 |
| 1744 | 0.75 | 2.76 | 0.66 | 1.23 |
| 1750 | 1.00 | 1.00 | 1.00 | 1.00 |
| 1757 | 1.82 | 1.36 | 5.70 | 1.34 |
| 1767 | 1.62 | 3.16 | 0.01 | 1.18 |
| 1776 | 147.62 | 1.00 | 219.86 | 40.57 |
| 1782 | 4.37 | 0.96 | 7.70 | 6.79 |
| 1791 | 2.39 | 2.30 | 2.88 | 5.47 |
| 1797 | 1.00 | 1.00 | 1.00 | 67.13 |
| 1807 | 1.00 | 171.84 | 252.34 | 79.02 |
| 1813 | 1.00 | 1.00 | 1.00 | 46.65 |
| 1820 | 1.59 | 2.74 | 2.37 | 1.12 |
| 1827 | 0.01 | 0.01 | 0.01 | 0.66 |
| 1832 | 0.01 | 2.28 | 0.01 | 0.53 |
| 1838 | 1.00 | 1.00 | 1.00 | 26.22 |
| 1845 | 1.00 | 1.00 | 170.72 | 62.97 |
| 1853 | 1.19 | 2.59 | 1.14 | 0.95 |
| 1861 | 1.00 | 1.00 | 155.44 | 1.00 |
| 1870 | 2.18 | 0.30 | 3.33 | 3.89 |
| 1876 | 1.00 | 1.00 | 304.82 | 1.00 |
| 1884 | 1.00 | 227.61 | 1.00 | 55.19 |

FIG. 16C (CONT'D)

| Mass | Prostate | Breast | Bladder | Prostate2 |
|---|---|---|---|---|
| 1890 | 1.00 | 1.00 | 1.00 | 191.10 |
| 1900 | 1.27 | 2.95 | 3.33 | 1.97 |
| 1906 | 1.00 | 1.00 | 1.00 | 19.25 |
| 1912 | 1.00 | 1.00 | 1.00 | 1.00 |
| 1918 | 0.01 | 2.14 | 1.81 | 0.84 |
| 1926 | 120.52 | 207.96 | 58.20 | 75.75 |
| 1931 | 78.66 | 1.00 | 671.27 | 158.45 |
| 1939 | 1.00 | 226.08 | 1.00 | 51.41 |
| 1945 | 157.72 | 1.00 | 140.58 | 146.86 |
| 1956 | 174.88 | 305.53 | 135.54 | 162.96 |
| 1961 | 1.00 | 1.00 | 1.00 | 36.51 |
| 1975 | 1.00 | 1.00 | 640.68 | 52.59 |
| 1982 | 1.38 | 0.87 | 1.73 | 1.52 |
| 1990 | 1.00 | 127.61 | 1.00 | 1.00 |
| 1995 | 1.00 | 1.00 | 1.00 | 38.43 |
| 2001 | 1.00 | 160.91 | 1.00 | 1.00 |
| 2009 | 482.05 | 239.32 | 329.08 | 617.58 |
| 2016 | 1.00 | 1.00 | 1.00 | 1320.49 |
| 2025 | 1.05 | 0.93 | 0.86 | 1.80 |
| 2031 | 1.00 | 1.00 | 264.99 | 1.00 |
| 2038 | 1.00 | 1.00 | 1.00 | 44.45 |
| 2048 | 1.00 | 120.15 | 1.00 | 103.96 |
| 2058 | 105.06 | 1.00 | 306.00 | 137.69 |
| 2065 | 1.00 | 1.00 | 1.00 | 9.12 |
| 2072 | 1.00 | 131.95 | 1.00 | 61.28 |
| 2078 | 1.81 | 0.01 | 0.01 | 3.16 |
| 2087 | 1.47 | 0.91 | 0.92 | 1.80 |
| 2095 | 1.00 | 145.21 | 1.00 | 68.99 |
| 2113 | 1.14 | 0.72 | 0.61 | 1.22 |
| 2119 | 3.22 | 10.61 | 12.23 | 2.84 |
| 2127 | 0.02 | 0.02 | 0.02 | 1.34 |
| 2132 | 1.00 | 70.98 | 1.00 | 49.46 |
| 2147 | 1.74 | 1.93 | 6.89 | 1.28 |
| 2153 | 1.56 | 1.71 | 2.46 | 1.37 |
| 2164 | 0.77 | 1.60 | 0.01 | 0.14 |
| 2174 | 1.89 | 2.81 | 1.71 | 2.03 |
| 2179 | 1.00 | 1.00 | 1.00 | 20.92 |
| 2189 | 1.71 | 2.83 | 1.79 | 2.17 |
| 2196 | 1.00 | 1.00 | 1.00 | 1.00 |
| 2214 | 1.72 | 1.56 | 2.07 | 1.99 |
| 2226 | 1.39 | 3.33 | 0.72 | 0.86 |

FIG. 16C (CONT'D)

| Mass | Prostate | Breast | Bladder | Prostate2 |
|---|---|---|---|---|
| 2235 | 0.02 | 2.19 | 1.06 | 0.98 |
| 2242 | 1.00 | 1.00 | 1.00 | 23.86 |
| 2250 | 0.44 | 2.59 | 0.01 | 0.81 |
| 2256 | 1.34 | 1.80 | 3.24 | 0.89 |
| 2262 | 1.00 | 175.95 | 1.00 | 1.00 |
| 2273 | 4.58 | 1.46 | 2.64 | 6.30 |
| 2280 | 0.60 | 1.25 | 0.01 | 0.01 |
| 2292 | 1.03 | 2.35 | 0.78 | 1.30 |
| 2303 | 1.00 | 1.00 | 73.06 | 1.00 |
| 2310 | 3.75 | 3.49 | 2.56 | 2.82 |
| 2318 | 1.00 | 127.69 | 1.00 | 1.00 |
| 2334 | 108.78 | 1.00 | 55.85 | 90.33 |
| 2342 | 1.75 | 2.10 | 4.87 | 1.58 |
| 2351 | 0.01 | 2.42 | 0.01 | 0.73 |
| 2363 | 99.81 | 531.10 | 72.58 | 112.76 |
| 2369 | 1.00 | 1.00 | 1.00 | 1.00 |
| 2376 | 1.00 | 1.00 | 1.00 | 1.00 |
| 2383 | 1.57 | 1.71 | 0.22 | 3.46 |
| 2398 | 1.00 | 1.00 | 1.00 | 36.37 |
| 2414 | 96.71 | 109.24 | 2124.24 | 64.14 |
| 2423 | 1.31 | 1.68 | 0.51 | 1.10 |
| 2434 | 1.40 | 0.02 | 0.02 | 0.55 |
| 2448 | 1.00 | 1.00 | 54.96 | 29.32 |
| 2456 | 0.02 | 3.07 | 1.17 | 0.78 |
| 2471 | 1.77 | 1.85 | 0.62 | 3.42 |
| 2477 | 1.00 | 234.02 | 96.22 | 20.64 |
| 2483 | 1.00 | 1.00 | 1.00 | 22.80 |
| 2498 | 0.46 | 1.03 | 0.17 | 0.44 |
| 2512 | 1.38 | 7.96 | 1.20 | 1.69 |
| 2519 | 1.00 | 1.00 | 1.00 | 1.00 |
| 2529 | 1.00 | 1.00 | 19.19 | 21.25 |
| 2536 | 133.88 | 125.64 | 1.00 | 241.36 |
| 2543 | 1.00 | 1.00 | 1.00 | 1.00 |
| 2551 | 1.00 | 1.00 | 1.00 | 1.00 |
| 2558 | 1.35 | 1.50 | 1.31 | 2.69 |
| 2570 | 1.00 | 1.00 | 901.87 | 170.85 |
| 2578 | 1.00 | 1.00 | 1.00 | 1.00 |
| 2587 | 88.45 | 1.00 | 75.44 | 73.94 |
| 2595 | 1.00 | 1.00 | 1.00 | 1.00 |
| 2601 | 1.00 | 1.00 | 1.00 | 1.00 |
| 2607 | 2.84 | 4.73 | 2.30 | 5.86 |

FIG. 16C (CONT'D)

| Mass | Prostate | Breast | Bladder | Prostate2 |
|---|---|---|---|---|
| 2617 | 1.00 | 218.19 | 1.00 | 94.95 |
| 2632 | 2.24 | 1.07 | 0.26 | 2.01 |
| 2651 | 1.00 | 1.00 | 136.37 | 61.22 |
| 2658 | 1.00 | 1.00 | 1.00 | 1.00 |
| 2664 | 1.37 | 2.45 | 1.18 | 3.26 |
| 2675 | 2.23 | 1.92 | 0.01 | 2.69 |
| 2686 | 2.11 | 2.74 | 0.01 | 2.69 |
| 2694 | 1.00 | 1.00 | 1.00 | 1.00 |
| 2700 | 1.00 | 1.00 | 1.00 | 25.21 |
| 2714 | 60.51 | 133.14 | 49.16 | 66.16 |
| 2720 | 1.00 | 1.00 | 1.00 | 1.00 |
| 2730 | 1.75 | 1.64 | 6.17 | 3.64 |
| 2739 | 1.00 | 1.00 | 1.00 | 1.00 |
| 2745 | 1.65 | 2.79 | 0.01 | 1.74 |
| 2761 | 1.11 | 1.22 | 12.35 | 5.42 |
| 2773 | 0.77 | 0.98 | 0.03 | 1.61 |
| 2784 | 1.00 | 1.00 | 1.00 | 1.00 |
| 2792 | 70.34 | 1.00 | 16.25 | 77.12 |
| 2799 | 1.00 | 1.00 | 1.00 | 1.00 |
| 2806 | 1.00 | 1.00 | 1.00 | 22.05 |
| 2822 | 68.20 | 1.00 | 222.55 | 86.93 |
| 2832 | 1.00 | 166.86 | 1.00 | 30.22 |
| 2841 | 1.00 | 1.00 | 1.00 | 3.07 |
| 2849 | 2.42 | 2.26 | 0.02 | 3.58 |
| 2858 | 1.00 | 1.00 | 1.00 | 3.51 |
| 2866 | 31.17 | 82.44 | 1.00 | 72.32 |
| 2874 | 0.02 | 7.71 | 1.13 | 0.72 |
| 2888 | 1.68 | 1.51 | 1.02 | 1.95 |
| 2904 | 79.23 | 1.00 | 1.00 | 77.50 |
| 2917 | 0.02 | 0.02 | 2.55 | 1.52 |
| 2937 | 1.24 | 0.97 | 0.13 | 2.32 |
| 2948 | 1.00 | 1.00 | 1.00 | 1.00 |
| 2957 | 0.30 | 1.39 | 0.00 | 1.64 |
| 2966 | 1.00 | 1.00 | 1.00 | 1.00 |
| 2981 | 1.00 | 121.10 | 168.41 | 33.24 |
| 2989 | 1.00 | 1.00 | 1.00 | 1.00 |
| 2997 | 1.69 | 3.15 | 0.02 | 2.30 |
| 3005 | 0.02 | 1.90 | 0.02 | 0.77 |
| 3021 | 1.00 | 85.34 | 1.00 | 57.92 |
| 3034 | 149.42 | 168.72 | 54.45 | 119.18 |
| 3043 | 1.00 | 83.76 | 1.00 | 1.00 |
| 3051 | 72.10 | 1.00 | 17.05 | 73.01 |

FIG. 16C (CONT'D)

| Mass | Prostate | Breast | Bladder | Prostate2 |
|---|---|---|---|---|
| 3059 | 65.29 | 1.00 | 81.48 | 48.90 |
| 3071 | 1.00 | 1.00 | 1.00 | 1.00 |
| 3080 | 1.00 | 1.00 | 1.00 | 38.98 |
| 3092 | 0.02 | 2.66 | 0.02 | 1.01 |
| 3101 | 1.00 | 0.02 | 0.02 | 1.28 |
| 3108 | 1.00 | 95.13 | 1.00 | 53.18 |
| 3116 | 1.00 | 54.67 | 1.00 | 62.94 |
| 3132 | 1.00 | 1.00 | 1.00 | 25.52 |
| 3143 | 1.00 | 65.41 | 21.72 | 143.51 |
| 3157 | 1.83 | 0.02 | 2.45 | 0.02 |
| 3165 | 3.43 | 1.33 | 10.68 | 4.23 |
| 3173 | 1.00 | 1.00 | 1.00 | 1.00 |
| 3181 | 1.00 | 1.00 | 1.00 | 42.27 |
| 3188 | 0.74 | 1.00 | 6.26 | 0.01 |
| 3196 | 0.52 | 0.94 | 0.00 | 0.94 |
| 3207 | 1.00 | 1.00 | 1.00 | 44.46 |
| 3221 | 1.25 | 1.34 | 0.50 | 1.26 |
| 3229 | 1.00 | 1.00 | 116.01 | 18.47 |
| 3239 | 1.00 | 1.00 | 1.00 | 1.00 |
| 3246 | 1.00 | 1.00 | 1.00 | 194.98 |
| 3259 | 0.70 | 1.51 | 0.01 | 0.01 |
| 3267 | 0.33 | 0.92 | 0.08 | 0.74 |
| 3278 | 1.00 | 1.00 | 1277.00 | 399.45 |
| 3295 | 1.00 | 1.00 | 1.00 | 78.19 |
| 3307 | 1.00 | 1.00 | 1.00 | 84.75 |
| 3320 | 1.61 | 1.05 | 0.91 | 2.64 |
| 3328 | 1.00 | 1.00 | 126.49 | 1.00 |
| 3336 | 1.00 | 1.00 | 1.00 | 1.00 |
| 3345 | 1.00 | 1.00 | 1.00 | 10.15 |
| 3357 | 2.73 | 1.88 | 0.71 | 3.41 |
| 3367 | 1.17 | 1.52 | 1.37 | 1.65 |
| 3376 | 0.03 | 1.31 | 0.03 | 0.95 |
| 3385 | 1.00 | 1.00 | 1.00 | 1.00 |
| 3393 | 1.00 | 1.00 | 1.00 | 21.41 |
| 3409 | 0.02 | 2.11 | 0.02 | 0.84 |
| 3434 | 1.15 | 1.65 | 0.82 | 0.95 |
| 3443 | 1.00 | 1.00 | 1.00 | 1.00 |
| 3452 | 0.94 | 1.79 | 0.60 | 0.65 |
| 3476 | 1.00 | 1.00 | 52.54 | 22.44 |
| 3491 | 1.00 | 1.00 | 1.00 | 18.99 |
| 3504 | 1.00 | 1.00 | 1.00 | 1.00 |

FIG. 16C (CONT'D)

| Mass | Prostate | Breast | Bladder | Prostate2 |
|---|---|---|---|---|
| 3512 | 3.08 | 2.72 | 0.03 | 1.85 |
| 3523 | 3.81 | 2.37 | 4.77 | 4.06 |
| 3532 | 36.21 | 1.00 | 35.70 | 1.00 |
| 3547 | 1.00 | 1.00 | 1.00 | 18.61 |
| 3558 | 1.00 | 1.00 | 1.00 | 1.00 |
| 3568 | 1.00 | 46.82 | 1.00 | 14.30 |
| 3579 | 1.00 | 1.00 | 1.00 | 12.55 |
| 3590 | 31.95 | 52.32 | 32.23 | 21.53 |
| 3598 | 1.00 | 1.00 | 28.30 | 4.41 |
| 3610 | 1.00 | 34.55 | 1.00 | 11.17 |
| 3618 | 1.00 | 1.00 | 1.00 | 12.96 |
| 3626 | 1.00 | 1.00 | 1.00 | 1.00 |
| 3635 | 1.67 | 1.83 | 0.73 | 1.12 |
| 3646 | 42.77 | 1.00 | 1.00 | 14.72 |
| 3656 | 1.00 | 1.00 | 1.00 | 14.82 |
| 3671 | 12.97 | 1.00 | 1.00 | 16.51 |
| 3689 | 2.89 | 2.59 | 5.43 | 2.60 |
| 3698 | 1.00 | 1.00 | 1.00 | 9.45 |
| 3709 | 1.00 | 1.00 | 1.00 | 3.03 |
| 3718 | 1.00 | 45.59 | 1.00 | 16.06 |
| 3735 | 1.00 | 1.00 | 1.00 | 14.61 |
| 3743 | 1.00 | 46.37 | 1.00 | 15.19 |
| 3758 | 1.00 | 35.75 | 1.00 | 19.52 |
| 3768 | 1.00 | 1.00 | 1.00 | 1.00 |
| 3778 | 4.44 | 2.27 | 7.01 | 3.12 |
| 3787 | 1.00 | 1.00 | 1.00 | 1.00 |
| 3798 | 1.00 | 1.00 | 1.00 | 13.26 |
| 3818 | 3.14 | 2.02 | 3.68 | 2.94 |
| 3828 | 1.00 | 1.00 | 1.00 | 5.99 |
| 3841 | 1.00 | 1.00 | 1.00 | 1.00 |
| 3852 | 1.00 | 1.00 | 1.00 | 13.25 |
| 3863 | 1.00 | 1.00 | 1.00 | 12.13 |
| 3888 | 1.13 | 1.60 | 0.48 | 1.84 |
| 3897 | 1.00 | 1.00 | 1.00 | 1.00 |
| 3908 | 1.00 | 1.00 | 1.00 | 1.00 |
| 3920 | 1.00 | 1.00 | 1.00 | 25.61 |
| 3931 | 1.11 | 1.51 | 1.10 | 0.02 |
| 3940 | 1.00 | 1.00 | 1.00 | 147.49 |
| 3960 | 1.33 | 0.87 | 2.46 | 1.88 |
| 3977 | 1.00 | 1.00 | 957.31 | 302.46 |
| 3989 | 1.00 | 1.00 | 32.35 | 17.57 |

FIG. 16C (CONT'D)

| Mass | Prostate | Breast | Bladder | Prostate2 |
|------|---------|--------|---------|-----------|
| 3999 | 1.00 | 1.00 | 1.00 | 1.00 |
| 4008 | 1.00 | 1.00 | 1.00 | 1.00 |
| 4029 | 1.00 | 1.00 | 1.00 | 1.00 |
| 4048 | 2.30 | 1.60 | 1.74 | 2.94 |
| 4064 | 1.00 | 1.00 | 1.00 | 1.00 |
| 4080 | 0.51 | 0.77 | 0.00 | 0.34 |
| 4090 | 1.00 | 1.00 | 1.00 | 1.00 |
| 4104 | 1.00 | 1.00 | 1.00 | 1.00 |
| 4114 | 1.00 | 1.00 | 1.00 | 1.00 |
| 4130 | 1.00 | 1.00 | 1.00 | 1.00 |
| 4140 | 1.00 | 1.00 | 1.00 | 99.82 |
| 4152 | 1.00 | 1.00 | 1.00 | 1.00 |
| 4161 | 1.00 | 1.00 | 1.00 | 1.00 |
| 4172 | 1.00 | 1.00 | 1.00 | 1.00 |
| 4182 | 0.64 | 0.84 | 0.00 | 0.00 |
| 4192 | 0.70 | 1.34 | 0.00 | 1.51 |
| 4202 | 1.00 | 1.00 | 1.00 | 1.00 |
| 4215 | 0.00 | 0.66 | 0.00 | 0.00 |
| 4237 | 1.00 | 1.00 | 1.00 | 1.00 |
| 4251 | 1.00 | 1.00 | 1.00 | 1.00 |
| 4262 | 1.00 | 1.00 | 1.00 | 1.00 |
| 4272 | 661.24 | 205.45 | 2851.85 | 753.39 |
| 4284 | 1.00 | 1.00 | 1.00 | 1.00 |
| 4295 | 1.00 | 1.00 | 1.00 | 1.00 |
| 4328 | 1.00 | 1.00 | 1.00 | 1.00 |
| 4345 | 1.00 | 1.00 | 1.00 | 1.00 |
| 4362 | 1.00 | 1.00 | 1.00 | 1.00 |
| 4373 | 1.00 | 1.00 | 1.00 | 91.75 |
| 4390 | 1.00 | 1.00 | 1.00 | 1.00 |
| 4409 | 0.01 | 0.01 | 0.01 | 0.01 |
| 4429 | 0.73 | 0.91 | 1.12 | 0.44 |
| 4444 | 136.65 | 164.97 | 1.00 | 1.00 |
| 4455 | 1.00 | 1.00 | 1.00 | 1.00 |
| 4468 | 1.00 | 1.00 | 1.00 | 1.00 |
| 4480 | 1.00 | 1.00 | 1.00 | 1.00 |
| 4490 | 1.00 | 1.00 | 1.00 | 1.00 |
| 4511 | 1.00 | 1.00 | 1.00 | 1.00 |
| 4531 | 1.00 | 1.00 | 1.00 | 1.00 |
| 4556 | 1.00 | 1.00 | 1.00 | 192.51 |
| 4566 | 1.00 | 1.00 | 1.00 | 1.00 |
| 4583 | 1.00 | 1.00 | 1.00 | 1.00 |

FIG. 16C (CONT'D)

| Mass | Prostate | Breast | Bladder | Prostate2 |
|------|----------|--------|---------|-----------|
| 4614 | 0.17 | 0.69 | 0.00 | 0.00 |
| 4631 | 0.69 | 0.83 | 0.63 | 1.45 |
| 4641 | 1.00 | 1.00 | 1.00 | 1.00 |
| 4655 | 0.18 | 0.97 | 0.56 | 0.00 |
| 4686 | 1.00 | 1.00 | 1.00 | 1.00 |
| 4696 | 1.00 | 1.00 | 1.00 | 272.25 |
| 4721 | 1.00 | 1.00 | 1.00 | 1.00 |
| 4776 | 149.39 | 1.00 | 1.00 | 205.80 |
| 4804 | 1.00 | 1.00 | 1.00 | 1.00 |
| 4836 | 1.00 | 1.00 | 1.00 | 61.66 |
| 4864 | 1.00 | 1.00 | 1.00 | 1.00 |
| 4889 | 1.00 | 1.00 | 1.00 | 1.00 |
| 4917 | 1.00 | 1.00 | 1.00 | 32.03 |
| 4950 | 1.00 | 301.26 | 1.00 | 75.25 |
| 4983 | 1.00 | 1.00 | 1.00 | 1.00 |
| 5013 | 1.00 | 1.00 | 739.13 | 63.32 |
| 5040 | 0.95 | 0.01 | 0.01 | 0.01 |
| 5068 | 0.77 | 0.92 | 0.00 | 0.84 |
| 5108 | 1.00 | 1.00 | 1.00 | 1.00 |
| 5145 | 0.52 | 0.58 | 1.46 | 0.57 |
| 5175 | 1.00 | 1.00 | 1.00 | 1.00 |
| 5204 | 1.00 | 1.00 | 1.00 | 1.00 |
| 5238 | 1.00 | 1.00 | 1.00 | 53.59 |
| 5267 | 1.00 | 1.00 | 1.00 | 1.00 |
| 5294 | 1.00 | 1.00 | 1.00 | 1.00 |
| 5322 | 1.22 | 1.18 | 0.30 | 2.83 |
| 5351 | 1.00 | 1.00 | 199.61 | 1.00 |
| 5383 | 1.00 | 1.00 | 1.00 | 30.16 |
| 5413 | 1.00 | 1.00 | 195.84 | 1.00 |
| 5441 | 1.00 | 1.00 | 1.00 | 32.62 |
| 5477 | 1.00 | 1.00 | 1.00 | 36.23 |
| 5509 | 1.00 | 1.00 | 1.00 | 29.78 |
| 5546 | 1.00 | 1.00 | 1.00 | 26.71 |
| 5580 | 1.00 | 1.00 | 1.00 | 28.17 |
| 5609 | 1.00 | 1.00 | 1.00 | 41.12 |
| 5645 | 1.00 | 1.00 | 1.00 | 1.00 |
| 5676 | 1.00 | 1.00 | 1.00 | 1.00 |
| 5707 | 1.00 | 1.00 | 1.00 | 1.00 |
| 5737 | 0.01 | 0.01 | 0.01 | 0.36 |
| 5770 | 1.00 | 1.00 | 1.00 | 1.00 |
| 5816 | 1.00 | 1.00 | 1.00 | 23.46 |

FIG. 16C (CONT'D)

| Mass | Prostate | Breast | Bladder | Prostate2 |
|---|---|---|---|---|
| 5853 | 1.00 | 1.00 | 1.00 | 1.00 |
| 5888 | 0.54 | 1.26 | 0.08 | 1.48 |
| 5923 | 1.00 | 146.82 | 1.00 | 1.00 |
| 5957 | 1.00 | 1.00 | 1.00 | 38.99 |
| 5997 | 1.00 | 1.00 | 1.00 | 1.00 |
| 6028 | 1.00 | 1.00 | 1.00 | 33.02 |
| 6062 | 1.00 | 1.00 | 1.00 | 38.44 |
| 6111 | 1.00 | 1.00 | 1.00 | 1.00 |
| 6152 | 1.00 | 1.00 | 1.00 | 1.00 |
| 6184 | 1.00 | 1.00 | 113.62 | 34.55 |
| 6220 | 1.00 | 1.00 | 1.00 | 57.80 |
| 6255 | 1.00 | 1.00 | 1.00 | 1.00 |
| 6294 | 1.00 | 1.00 | 1.00 | 35.76 |
| 6355 | 1.00 | 1.00 | 1.00 | 1.00 |
| 6393 | 1.00 | 1.00 | 1.00 | 1.00 |
| 6431 | 1.41 | 0.84 | 1.13 | 1.96 |
| 6471 | 1.00 | 1.00 | 1.00 | 54.40 |
| 6512 | 1.00 | 1.00 | 1.00 | 34.48 |
| 6562 | 1.00 | 1.00 | 1.00 | 1.00 |
| 6598 | 0.96 | 1.27 | 0.84 | 2.96 |
| 6633 | 78.64 | 96.70 | 68.06 | 184.81 |
| 6670 | 1.00 | 1.00 | 1.00 | 1.00 |
| 6713 | 1.00 | 1.00 | 1.00 | 33.33 |
| 6754 | 1.00 | 1.00 | 1.00 | 1.00 |
| 6790 | 1.00 | 1.00 | 1.00 | 52.65 |
| 6826 | 1.00 | 1.00 | 1.00 | 1.00 |
| 6866 | 1.00 | 1.00 | 1.00 | 1.00 |
| 6906 | 1.00 | 1.00 | 1.00 | 22.03 |
| 6942 | 1.00 | 1.00 | 1.00 | 1.00 |
| 6981 | 1.00 | 1.00 | 1.00 | 1.00 |
| 7021 | 1.00 | 1.00 | 1.00 | 25.39 |
| 7060 | 1.00 | 1.00 | 1.00 | 17.33 |
| 7103 | 1.00 | 1.00 | 1.00 | 21.77 |
| 7142 | 1.00 | 1.00 | 1.00 | 20.23 |
| 7180 | 1.00 | 1.00 | 1.00 | 1.00 |
| 7219 | 1.00 | 1.00 | 1.00 | 16.23 |
| 7260 | 1.00 | 1.00 | 1.00 | 15.14 |
| 7305 | 1.00 | 1.00 | 1.00 | 16.67 |
| 7345 | 1.00 | 1.00 | 1.00 | 17.15 |
| 7384 | 1.00 | 1.00 | 1.00 | 1.00 |
| 7427 | 1.00 | 1.00 | 1.00 | 10.13 |

FIG. 16C (CONT'D)

| Mass | Prostate | Breast | Bladder | Prostate2 |
|---|---|---|---|---|
| 7466 | 1.00 | 1.00 | 1.00 | 10.08 |
| 7510 | 1.00 | 1.00 | 1.00 | 9.66 |
| 7561 | 1.00 | 1.00 | 1.00 | 18.00 |
| 7607 | 1.00 | 1.00 | 1.00 | 1.00 |
| 7647 | 1.00 | 1.00 | 1.00 | 11.77 |
| 7688 | 1.00 | 1.00 | 1.00 | 1.00 |
| 7731 | 0.90 | 1.53 | 0.66 | 1.54 |
| 7771 | 1.00 | 66.80 | 1.00 | 1.00 |
| 7813 | 1.00 | 1.00 | 1.00 | 1.00 |
| 7854 | 1.00 | 1.00 | 1.00 | 1.00 |
| 7899 | 1.00 | 1.00 | 1.00 | 31.50 |
| 7956 | 1.00 | 1.00 | 1.00 | 1.00 |
| 7997 | 1.00 | 1.00 | 1.00 | 1.00 |
| 8043 | 1.00 | 1.00 | 1.00 | 1.00 |
| 8086 | 1.00 | 1.00 | 128.29 | 1.00 |
| 8128 | 1.10 | 2.24 | 0.02 | 1.41 |
| 8184 | 1.00 | 1.00 | 1.00 | 1.00 |
| 8232 | 1.00 | 1.00 | 1.00 | 1.00 |
| 8282 | 1.00 | 1.00 | 1.00 | 1.00 |
| 8337 | 1.00 | 1.00 | 1.00 | 1.00 |
| 8407 | 1.00 | 1.00 | 1.00 | 1.00 |
| 8486 | 1.00 | 1.00 | 1.00 | 1.00 |
| 8532 | 1.00 | 1.00 | 1.00 | 1.00 |
| 8597 | 0.91 | 1.28 | 1.62 | 1.34 |
| 8642 | 1.00 | 1.00 | 1.00 | 1.00 |
| 8717 | 1.00 | 1.00 | 1.00 | 1.00 |
| 8764 | 0.94 | 1.01 | 0.01 | 1.00 |
| 8826 | 1.00 | 1.00 | 64.67 | 1.00 |
| 8877 | 1.00 | 1.00 | 304.71 | 1.00 |
| 8932 | 1.07 | 1.66 | 0.23 | 0.93 |
| 8988 | 1.00 | 1.00 | 1.00 | 1.00 |
| 9034 | 1.00 | 1.00 | 1.00 | 1.00 |
| 9085 | 1.00 | 1.00 | 1.00 | 1.00 |
| 9139 | 528.46 | 1.00 | 121.92 | 378.00 |
| 9234 | 0.00 | 0.84 | 0.09 | 0.00 |
| 9290 | 0.60 | 1.13 | 0.50 | 1.72 |
| 9357 | 1.00 | 1.00 | 1.00 | 1.00 |
| 9405 | 1.00 | 1.00 | 1.00 | 178.42 |
| 9455 | 1.00 | 1.00 | 1.00 | 1.00 |
| 9504 | 1.00 | 1.00 | 1.00 | 6.45 |
| 9555 | 1.00 | 1.00 | 1.00 | 1.00 |
| 9611 | 1.00 | 1.00 | 1.00 | 9.41 |

FIG. 16C (CONT'D)

| Mass | Prostate | Breast | Bladder | Prostate2 |
|---|---|---|---|---|
| 9673 | 1.00 | 1.00 | 1.00 | 7.04 |
| 9748 | 1.00 | 1.00 | 1.00 | 1.00 |
| 9822 | 1.00 | 1.00 | 1.00 | 1.00 |
| 9884 | 1.00 | 1.00 | 1.00 | 1.00 |
| 9935 | 1.00 | 1.00 | 1.00 | 1.00 |
| 9992 | 1.00 | 1.00 | 1.00 | 1.00 |
| 10047 | 1.00 | 1.00 | 1.00 | 1.00 |
| 10106 | 1.00 | 1.00 | 1.00 | 1.00 |
| 10167 | 1.00 | 1.00 | 1.00 | 1.00 |
| 10228 | 0.41 | 1.24 | 0.11 | 0.43 |
| 10281 | 0.10 | 1.72 | 0.10 | 0.10 |
| 10335 | 1.00 | 1.00 | 1.00 | 1.00 |
| 10401 | 1.00 | 1.00 | 1.00 | 4.40 |
| 10455 | 1.00 | 17.88 | 1.00 | 4.20 |
| 10510 | 1.00 | 1.00 | 1.00 | 1.00 |
| 10568 | 1.00 | 1.00 | 1.00 | 3.37 |
| 10626 | 1.00 | 13.65 | 14.59 | 3.73 |
| 10680 | 1.00 | 1.00 | 1.00 | 1.00 |
| 10735 | 1.00 | 1.00 | 1.00 | 1.00 |
| 10794 | 1.00 | 1.00 | 1.00 | 1.00 |
| 10849 | 1.00 | 1.00 | 1.00 | 1.00 |
| 10905 | 1.00 | 1.00 | 1.00 | 1.00 |
| 10962 | 1.00 | 1.00 | 2.66 | 1.00 |
| 11020 | 6.50 | 1.00 | 1.00 | 1.00 |
| 11077 | 0.86 | 2.88 | 0.60 | 0.36 |
| 11138 | 0.13 | 1.97 | 0.71 | 0.13 |
| 11198 | 1.00 | 0.14 | 0.65 | 0.14 |
| 11257 | 1.03 | 0.17 | 0.17 | 0.17 |
| 11315 | 0.14 | 1.76 | 0.67 | 0.14 |
| 11377 | 1.05 | 1.48 | 0.70 | 0.43 |
| 11442 | 0.92 | 1.77 | 0.75 | 0.14 |
| 11501 | 0.80 | 1.76 | 0.19 | 0.19 |
| 11560 | 1.12 | 2.10 | 0.84 | 0.39 |
| 11619 | 0.13 | 1.51 | 0.28 | 0.29 |
| 11678 | 1.00 | 1.00 | 1.00 | 1.00 |
| 11739 | 0.78 | 1.57 | 0.63 | 0.39 |
| 11802 | 0.18 | 1.76 | 0.74 | 0.36 |
| 11864 | 1.04 | 2.57 | 0.87 | 0.23 |
| 11929 | 0.95 | 1.89 | 0.74 | 0.18 |
| 11993 | 0.79 | 0.19 | 0.74 | 0.46 |
| 12056 | 0.78 | 2.14 | 0.74 | 0.23 |
| 12119 | 0.79 | 0.20 | 0.86 | 0.20 |

FIG. 16C (CONT'D)

| Mass | Prostate | Breast | Bladder | Prostate2 |
|---|---|---|---|---|
| 12188 | 0.89 | 1.54 | 0.73 | 0.22 |
| 12250 | 0.80 | 1.89 | 0.67 | 0.19 |
| 12316 | 0.34 | 1.46 | 0.53 | 0.17 |
| 12382 | 0.19 | 0.19 | 0.19 | 0.19 |
| 12450 | 1.15 | 1.89 | 0.67 | 0.68 |
| 12516 | 3.84 | 1.00 | 1.00 | 1.00 |
| 12580 | 0.65 | 1.32 | 0.50 | 0.30 |
| 12662 | 0.81 | 1.58 | 0.54 | 0.17 |
| 12727 | 0.41 | 0.28 | 0.34 | 0.28 |
| 12793 | 0.72 | 1.86 | 0.70 | 0.44 |
| 12862 | 0.96 | 1.82 | 0.70 | 0.21 |
| 12932 | 0.90 | 1.87 | 0.73 | 0.46 |
| 13005 | 0.84 | 1.50 | 0.57 | 0.22 |
| 13082 | 0.95 | 1.58 | 0.78 | 0.43 |
| 13149 | 0.93 | 0.24 | 0.82 | 0.24 |
| 13222 | 0.81 | 2.17 | 0.83 | 0.52 |
| 13291 | 0.95 | 5.51 | 0.68 | 0.23 |
| 13359 | 0.91 | 2.61 | 0.29 | 0.22 |
| 13431 | 0.87 | 0.28 | 0.92 | 0.28 |
| 13506 | 0.83 | 1.43 | 0.81 | 0.19 |
| 13593 | 0.91 | 2.17 | 0.67 | 0.25 |
| 13669 | 0.85 | 1.68 | 0.65 | 0.22 |
| 13739 | 0.90 | 1.97 | 0.70 | 0.22 |
| 13814 | 0.85 | 2.01 | 0.59 | 0.44 |
| 13888 | 0.90 | 1.91 | 0.61 | 0.24 |
| 13964 | 0.87 | 2.15 | 0.68 | 0.24 |
| 14039 | 0.82 | 2.27 | 0.57 | 0.26 |
| 14115 | 0.84 | 1.90 | 0.69 | 0.23 |
| 14194 | 0.94 | 0.29 | 0.59 | 0.29 |
| 14267 | 0.82 | 1.84 | 0.67 | 0.24 |
| 14348 | 0.66 | 0.25 | 0.54 | 0.25 |
| 14426 | 1.00 | 1.96 | 0.75 | 0.26 |
| 14508 | 0.84 | 2.08 | 0.59 | 0.27 |
| 14590 | 0.73 | 1.86 | 0.67 | 0.26 |

FIG. 16C (CONT'D)

| Mass | Prostate | Breast | Bladder | Prostate2 |
|---|---|---|---|---|
| 14664 | 0.84 | 2.55 | 0.77 | 0.52 |
| 14740 | 0.80 | 1.81 | 0.67 | 0.28 |
| 14819 | 0.85 | 1.85 | 0.74 | 0.32 |
| 14896 | 0.80 | 1.98 | 0.79 | 0.59 |

FIG. 16C (CONT'D)

| M/Z-value | Binary Comparisons Mean ± STD (Median) | | | Controls |
|---|---|---|---|---|
| | Prostate (14) | Breast (14) | Bladder (58) | |
| 824 | 252.99 ± 173.92, (204.02) | 160.11 ± 69.57, (135.22) | 1064.54 ± 726.55, (829.12) | 195.36 ± 80.69, (177.91) |
| 830 | 254.8 ± 166.72, (233.97) | 143.99 ± 43.67, (142.23) | 1156.92 ± 703.1, (1243.67) | 176.1 ± 127.5, (149.42) |
| 891 | 594.67 ± 338.63, (543.63) | 309.71 ± 123.02, (280.38) | 778.16 ± 225.79, (752.41) | 404.31 ± 117.45, (371.2) |
| 907 | 4561.2 ± 1727.3, (4511.86) | 7338.56 ± 2182.97, (6910.05) | 3272.39 ± 767.81, (3381.28) | 4369.04 ± 539.06, (4265.11) |
| 944 | 1161.36 ± 752.6, (943.64) | 332.25 ± 102.72, (313.79) | 2817.62 ± 707.49, (2808.31) | 643.38 ± 420.99, (542) |
| 1023 | 1581.47 ± 1259.27, (1121.19) | 2769.8 ± 1905.14, (1894) | 1207.52 ± 762.91, (1116.83) | 4016.7 ± 464.05, (4018.76) |
| 1048 | 444.12 ± 245.1, (371.99) | 763.89 ± 221.41, (743.79) | 155.23 ± 151.88, (160.86) | 1002.57 ± 279.33, (894.87) |
| 1058 | 274.25 ± 299.72, (226.73) | 181.78 ± 247.01, (1) | 939.21 ± 493.65, (1050.72) | 25.32 ± 61.91, (1) |
| 1063 | 2911.33 ± 1457.22, (3074.48) | 8192.98 ± 2705.77, (7566.57) | 1746.85 ± 958.92, (1694.1) | 4216.94 ± 790.82, (3972.51) |
| 1079 | 1880.88 ± 1044.4, (2014.18) | 3688.8 ± 1709.02, (3515.63) | 1909.45 ± 528.38, (1833.42) | 3664.76 ± 401.86, (3702.34) |
| 1101 | 438.06 ± 226.06, (362.24) | 186.9 ± 89.59, (204.22) | 600.4 ± 292.61, (581) | 254.91 ± 72.11, (253.33) |
| 1126 | 252.64 ± 146.67, (214.62) | 477.82 ± 166.46, (445.61) | 115.07 ± 77.82, (128.27) | 521.36 ± 195.04, (515.14) |
| 1209 | 2259.24 ± 1661.17, (2267.99) | 3437.89 ± 2294.84, (3107.73) | 2171.06 ± 864.61, (1970.59) | 4558.92 ± 641.12, (4517.21) |
| 1214 | 1460.59 ± 1300.61, (1391.49) | 205.32 ± 398.04, (1) | 2038.25 ± 989.02, (1912.04) | 483.85 ± 741.93, (177.1) |
| 1231 | 142.29 ± 127.3, (162.25) | 177.67 ± 111.17, (222.86) | 967.3 ± 495, (1016.21) | 173.62 ± 133.9, (179.55) |
| 1267 | 908.3 ± 670.36, (638.46) | 1200.4 ± 1082.93, (755.41) | 988.66 ± 727.44, (785.8) | 3187.09 ± 640.76, (3271.91) |
| 1280 | 315.68 ± 237.5, (251.92) | 84.09 ± 166.11, (1) | 1446.41 ± 708.12, (1406.33) | 73.44 ± 278.74, (1) |
| 1314 | 106.62 ± 251.67, (1) | 36.1 ± 77.88, (1) | 715.63 ± 501.13, (634.96) | 38.84 ± 129.6, (1) |
| 1354 | 2080.48 ± 1235.52, (2102.44) | 2153.51 ± 1680.56, (1571.81) | 2107.42 ± 835.37, (2086.29) | 4545.13 ± 463.86, (4496.6) |
| 1383 | 145.8 ± 87.14, (164.77) | 781.38 ± 358.17, (795.73) | 192.51 ± 178.45, (151.76) | 173.54 ± 76.32, (183.51) |
| 1427 | 193.04 ± 195.89, (174.45) | 277.17 ± 80.82, (286.87) | 1103.34 ± 806.59, (840.46) | 320.38 ± 250.78, (261.41) |
| 1453 | 2159.29 ± 1380.63, (1885.15) | 390.67 ± 177.43, (437.78) | 2751.62 ± 1140.1, (2646.51) | 565.13 ± 755.93, (1) |
| 1469 | 3240.85 ± 1805.38, (3378.1) | 3949.53 ± 2241.27, (4081.59) | 2915.25 ± 948.24, (2834.33) | 5117.08 ± 720.94, (5133.73) |
| 1502 | 100.31 ± 147.84, (1) | 67.74 ± 113.81, (1) | 831.64 ± 535, (809.48) | 29.71 ± 81.34, (1) |
| 1523 | 688.1 ± 334.43, (598.26) | 1047.44 ± 452.72, (911.47) | 269.71 ± 299.37, (242.68) | 1465.61 ± 330.44, (1583.23) |
| 1534 | 888.53 ± 546.08, (768.39) | 944.93 ± 726.19, (746) | 1915.21 ± 742.33, (2058.15) | 866.59 ± 492.35, (788.51) |
| 1540 | 511.92 ± 415.35, (568.44) | 548.63 ± 337.96, (526.19) | 63.06 ± 247.7, (1) | 904.68 ± 283.76, (979.16) |
| 1567 | 866.76 ± 701.1, (620.9) | 448.06 ± 107.93, (424.35) | 1121.01 ± 631.83, (892.96) | 769.93 ± 167, (788.67) |
| 1618 | 494.63 ± 434.51, (345.33) | 411.56 ± 270.5, (308.13) | 183.73 ± 118.29, (179.97) | 565.78 ± 195.43, (533.41) |

FIG. 17A

| | | | |
|---|---|---|---|
| 1630 | 284.69 ± 140.7, (298.72) | 810.04 ± 377.15, (764.04) | 318.86 ± 183.28, (240.99) | 249.83 ± 113.53, (274.41) |
| 1696 | 1190.9 ± 1175.42, (795.86) | 158.28 ± 125, (197.94) | 1801.44 ± 1248.81, (1346.59) | 264.99 ± 200.67, (196.44) |
| 1744 | 868.29 ± 507.68, (764.05) | 2528.75 ± 1182.77, (2817.04) | 904.21 ± 659.21, (669.96) | 985.98 ± 272.35, (1020.07) |
| 1757 | 175.76 ± 150.02, (199.37) | 139.54 ± 140.04, (149.67) | 660.76 ± 269.38, (625.98) | 90.96 ± 76.14, (109.77) |
| 1782 | 1755.48 ± 1517.47, (1015.47) | 206.3 ± 110.37, (222.49) | 2209.42 ± 1326.83, (1789.4) | 348.39 ± 261.82, (232.33) |
| 1870 | 3335.21 ± 1759.63, (2660.63) | 444.93 ± 164.29, (369.54) | 3975.98 ± 897.39, (4057.03) | 1387.84 ± 932.62, (1219.19) |
| 1900 | 1159.19 ± 551.08, (1042.22) | 2549.48 ± 1183.38, (2415.09) | 2569.25 ± 761.88, (2732.08) | 817.45 ± 243.86, (819.5) |
| 1931 | 182.49 ± 219.7, (78.66) | 6.36 ± 29.14, (1) | 694.31 ± 390.38, (671.27) | 40.47 ± 95.75, (1) |
| 1975 | 45.77 ± 110.64, (1) | 56.5 ± 85.43, (1) | 749.54 ± 588.68, (640.68) | 31.52 ± 79, (1) |
| 1982 | 465.51 ± 303.8, (401.9) | 253.16 ± 94.16, (252.61) | 509.78 ± 192.1, (503.42) | 280.44 ± 83.61, (291.52) |
| 2119 | 423.08 ± 416.02, (307.12) | 938.9 ± 524.4, (1011.77) | 1196.66 ± 694.48, (1166) | 104.39 ± 139.48, (95.37) |
| 2147 | 147.6 ± 116.77, (147.98) | 175.22 ± 110.49, (164.93) | 566.47 ± 246.56, (587.13) | 88.45 ± 42.79, (85.25) |
| 2189 | 444.65 ± 193.51, (399.04) | 700.19 ± 340.28, (659.4) | 442.72 ± 223.55, (418.33) | 248.71 ± 72.2, (233.35) |
| 2273 | 1179.54 ± 966.02, (810.1) | 396.38 ± 501.88, (258.68) | 578.94 ± 448.48, (467.27) | 198.98 ± 126.21, (176.84) |
| 2342 | 225.26 ± 140.74, (197.02) | 235.01 ± 143.67, (236.19) | 771.06 ± 852.04, (548.12) | 118.8 ± 96.8, (112.58) |
| 2363 | 179.83 ± 285.35, (99.81) | 534.86 ± 312.47, (531.1) | 75.2 ± 76.55, (72.58) | 26.81 ± 49.77, (1) |
| 2383 | 602.55 ± 380.24, (549.5) | 628.11 ± 218.93, (600.55) | 98.26 ± 72.59, (76.29) | 329.12 ± 105.17, (350.32) |
| 2414 | 207.25 ± 264.92, (96.71) | 97.34 ± 70.28, (109.24) | 1818.24 ± 1301.3, (2124.24) | 84.07 ± 281.49, (1) |
| 2512 | 215.6 ± 379.84, (160.91) | 854.57 ± 405.59, (928.01) | 151.76 ± 74.32, (140.08) | 102.04 ± 60.83, (116.58) |
| 2570 | 63.36 ± 287.03, (1) | 0 ± 0, (1) | 960.6 ± 826.63, (901.87) | 54.15 ± 259.92, (1) |
| 2607 | 565.34 ± 322.95, (476.37) | 686.64 ± 335.04, (792.37) | 389.77 ± 315.07, (385.25) | 182.64 ± 73.01, (167.56) |
| 2730 | 310.64 ± 437.03, (162.51) | 152.86 ± 60.24, (152.26) | 530.95 ± 268.79, (573.43) | 109.58 ± 77.01, (92.98) |
| 2761 | 162.39 ± 302.21, (98.96) | 83.07 ± 70.13, (109.19) | 1333.1 ± 1073.2, (1104.71) | 107.96 ± 178.88, (89.45) |
| 2773 | 1374.94 ± 769.55, (1402.29) | 1729.28 ± 915.47, (1767.74) | 230.77 ± 460.16, (57.11) | 1844.05 ± 626.78, (1810.76) |
| 2937 | 2849.34 ± 1600.28, (3138.65) | 2460.84 ± 1085.04, (2461.74) | 449 ± 566.03, (327.68) | 2535.87 ± 532.94, (2536.62) |
| 3165 | 490.75 ± 219.94, (460.99) | 218.04 ± 232.1, (178.22) | 1378.69 ± 774.81, (1435.63) | 146.55 ± 76.97, (134.48) |
| 3188 | 185.07 ± 351.68, (96.45) | 116.96 ± 71.53, (130.31) | 994.5 ± 724.4, (814.41) | 146.72 ± 110.92, (130.05) |
| 3196 | 1230.27 ± 914.13, (1140.9) | 1968.93 ± 882.4, (2048.72) | 163.96 ± 352.72, (1) | 2238.86 ± 540.43, (2188.87) |
| 3267 | 1694.49 ± 1337.71, (1340.86) | 3845.22 ± 1607.33, (3737.23) | 363.36 ± 435.27, (308.7) | 4053.35 ± 608.94, (4055.38) |
| 3278 | 241 ± 545.8, (1) | 109.86 ± 331.01, (1) | 1187.65 ± 600.05, (1277) | 35.09 ± 153.42, (1) |
| 3960 | 1089.65 ± 699.43, (905.2) | 693.97 ± 377.07, (590.35) | 1740.34 ± 956.75, (1677.38) | 694.26 ± 210.11, (682.01) |

FIG. 17A (CONT'D)

| 3977 | 92.08 ± 242.92, (1) | 274.17 ± 624.47, (1) | 1142.42 ± 880.3, (957.31) | 81.4 ± 165.25, (1) |
|---|---|---|---|---|
| 4192 | 885.71 ± 594.73, (876.96) | 1599.54 ± 367.22, (1684.09) | 68.51 ± 256.55, (1) | 1384.26 ± 345.28, (1260.57) |
| 4272 | 815.44 ± 772.4, (661.24) | 461.83 ± 1014.05, (205.45) | 2619.7 ± 1488.91, (2851.85) | 268.04 ± 572.24, (1) |
| 4631 | 950.45 ± 378.46, (819.99) | 994.7 ± 271.21, (986.77) | 664.56 ± 335.09, (747.07) | 1191.67 ± 292.57, (1194.98) |
| 5013 | 188.71 ± 488.44, (1) | 0 ± 0, (1) | 828.21 ± 487.82, (739.13) | 41.29 ± 139.31, (1) |
| 5068 | 431.3 ± 291.5, (440.99) | 547.41 ± 189.68, (524.93) | 229.54 ± 409.22, (1) | 606.09 ± 264.85, (571.51) |
| 5888 | 1054.81 ± 627.53, (1017.01) | 2596.05 ± 1033.3, (2365.27) | 243.27 ± 400.35, (146.37) | 1850.13 ± 522.29, (1871.1) |
| 9290 | 880.23 ± 381.87, (736.72) | 1376.35 ± 358.29, (1379.52) | 613.52 ± 282.95, (612.02) | 1230.99 ± 312.11, (1224.81) |

FIG. 17A (CONT'D)

| M/Z | p-value Prostate | Breast | Bladder | Prostate2 | Multiclass |
|---|---|---|---|---|---|
| 824 | 0.11 | 7.42E-03 | 1.30E-12 | 3.27E-06 | 3.24E-15 |
| 830 | 2.53E-05 | 0.558 | 1.06E-09 | 1.21E-04 | 1.85E-15 |
| 891 | 1.55E-04 | 9.54E-03 | 8.72E-10 | 0.808 | 1.64E-14 |
| 907 | 0.593 | 7.39E-10 | 3.12E-07 | 5.68E-07 | 3.65E-14 |
| 944 | 1.01E-03 | 3.56E-05 | 7.65E-13 | 9.67E-06 | 6.77E-21 |
| 1023 | 1.34E-11 | 0.0323 | 2.80E-13 | 6.29E-13 | 1.67E-13 |
| 1048 | 2.20E-11 | 1.22E-03 | 1.80E-13 | 8.34E-05 | 9.04E-24 |
| 1058 | 5.29E-07 | 8.13E-03 | 1.80E-13 | 2.35E-09 | 1.22E-13 |
| 1063 | 4.89E-04 | 1.03E-11 | 1.03E-12 | 0.272 | 9.04E-24 |
| 1079 | 2.94E-11 | 0.683 | 7.65E-13 | 9.69E-05 | 1.97E-14 |
| 1101 | 2.96E-06 | 0.0356 | 5.55E-08 | 0.665 | 7.10E-15 |
| 1126 | 6.84E-08 | 0.676 | 7.65E-13 | 3.28E-04 | 3.51E-18 |
| 1209 | 4.18E-08 | 0.0654 | 1.30E-12 | 1.91E-10 | 1.31E-09 |
| 1214 | 8.63E-04 | 0.251 | 9.43E-08 | 4.13E-07 | 8.69E-11 |
| 1231 | 0.523 | 0.867 | 1.10E-10 | 0.02 | 9.53E-11 |
| 1267 | 6.48E-17 | 2.75E-07 | 1.05E-10 | 4.47E-20 | 2.74E-16 |
| 1280 | 4.81E-09 | 0.434 | 1.95E-13 | 5.19E-13 | 5.74E-20 |
| 1314 | 0.193 | 0.834 | 2.94E-11 | 6.81E-05 | 2.40E-12 |
| 1354 | 1.01E-15 | 4.82E-05 | 4.50E-13 | 6.26E-17 | 1.38E-14 |
| 1383 | 0.245 | 5.56E-13 | 0.506 | 3.29E-07 | 6.74E-13 |
| 1427 | 5.65E-05 | 0.901 | 8.63E-06 | 6.96E-11 | 8.37E-11 |
| 1453 | 6.86E-07 | 0.852 | 6.37E-10 | 1.40E-12 | 1.98E-14 |
| 1469 | 1.44E-05 | 0.128 | 1.25E-11 | 4.92E-08 | 1.88E-07 |
| 1502 | 0.0525 | 0.429 | 2.93E-15 | 1.71E-10 | 5.31E-15 |
| 1523 | 2.20E-11 | 1.04E-03 | 2.16E-12 | 1.76E-18 | 1.18E-19 |
| 1534 | 0.977 | 0.864 | 9.76E-06 | 0.513 | 1.33E-05 |
| 1540 | 1.08E-04 | 1.38E-04 | 2.52E-10 | 1.26E-11 | 5.10E-12 |
| 1567 | 0.46 | 6.15E-10 | 0.0904 | 2.90E-10 | 3.64E-08 |
| 1618 | 0.023 | 0.0178 | 1.05E-10 | 2.33E-04 | 4.80E-09 |
| 1630 | 0.288 | 6.69E-12 | 1 | 0.821 | 4.28E-10 |
| 1696 | 1.69E-04 | 0.4 | 8.73E-11 | 1.22E-15 | 4.77E-13 |
| 1744 | 0.0758 | 3.92E-06 | 0.129 | 0.0835 | 2.84E-08 |
| 1757 | 0.0103 | 0.389 | 4.50E-13 | 8.46E-04 | 9.48E-13 |
| 1782 | 5.29E-07 | 0.522 | 1.06E-09 | 1.18E-18 | 1.85E-15 |
| 1870 | 1.80E-05 | 1.39E-05 | 3.34E-11 | 1.18E-18 | 2.17E-19 |
| 1900 | 0.0153 | 1.04E-08 | 4.50E-13 | 6.05E-07 | 9.14E-17 |
| 1931 | 0.0241 | 0.12 | 6.60E-14 | 6.03E-09 | 1.47E-16 |
| 1975 | 0.989 | 0.424 | 4.10E-09 | 4.41E-07 | 1.89E-10 |

FIG. 17B

| M/Z | Prostate | Breast | Bladder | Prostate2 | Multiclass |
|---|---|---|---|---|---|
| 1982 | 2.15E-03 | 0.683 | 7.70E-06 | 1.03E-07 | 1.15E-07 |
| 2119 | 2.36E-07 | 8.19E-10 | 2.75E-11 | 6.62E-09 | 5.82E-18 |
| 2147 | 0.0189 | 5.27E-05 | 7.65E-13 | 0.131 | 3.45E-14 |
| 2189 | 6.59E-07 | 1.49E-08 | 2.21E-04 | 1.65E-07 | 9.87E-11 |
| 2273 | 7.63E-12 | 0.0981 | 5.29E-06 | 1.67E-13 | 3.08E-13 |
| 2342 | 3.07E-04 | 2.40E-04 | 1.05E-10 | 1.91E-04 | 1.18E-11 |
| 2363 | 3.68E-04 | 4.07E-12 | 4.39E-03 | 5.38E-12 | 8.65E-13 |
| 2383 | 4.37E-04 | 1.26E-07 | 1.25E-10 | 8.74E-11 | 1.54E-16 |
| 2414 | 8.82E-04 | 6.77E-03 | 3.52E-12 | 9.67E-06 | 7.39E-13 |
| 2512 | 0.0101 | 5.56E-13 | 0.0929 | 1.74E-05 | 5.60E-14 |
| 2570 | 0.532 | 0.105 | 2.81E-07 | 9.19E-10 | 4.26E-13 |
| 2607 | 1.43E-08 | 2.08E-07 | 0.0317 | 6.55E-19 | 6.60E-10 |
| 2730 | 5.99E-06 | 4.31E-04 | 4.48E-09 | 3.88E-11 | 9.52E-13 |
| 2761 | 0.605 | 0.533 | 1.95E-07 | 4.07E-08 | 3.06E-07 |
| 2773 | 0.0514 | 0.695 | 8.42E-11 | 2.30E-03 | 8.37E-11 |
| 2937 | 0.416 | 0.937 | 4.19E-11 | 4.55E-08 | 5.39E-09 |
| 3165 | 2.64E-12 | 0.198 | 7.04E-10 | 2.48E-15 | 1.74E-19 |
| 3188 | 0.0228 | 0.923 | 7.64E-09 | 7.31E-08 | 1.38E-09 |
| 3196 | 7.74E-07 | 0.499 | 1.95E-13 | 0.429 | 3.76E-17 |
| 3267 | 7.63E-12 | 0.875 | 1.82E-13 | 0.0218 | 6.77E-21 |
| 3278 | 0.0122 | 0.887 | 2.44E-14 | 2.65E-11 | 2.82E-14 |
| 3960 | 0.0514 | 0.546 | 1.48E-06 | 4.32E-07 | 4.78E-06 |
| 3977 | 1 | 0.29 | 5.98E-09 | 7.70E-08 | 2.68E-09 |
| 4192 | 5.73E-04 | 0.105 | 1.95E-13 | 4.14E-04 | 3.89E-16 |
| 4272 | 2.83E-04 | 0.276 | 4.92E-09 | 5.54E-07 | 1.36E-09 |
| 4631 | 3.58E-03 | 0.0323 | 3.33E-08 | 2.48E-03 | 4.27E-07 |
| 5013 | 0.288 | 0.322 | 5.15E-14 | 2.63E-06 | 5.90E-18 |
| 5068 | 8.63E-04 | 0.424 | 5.52E-08 | 0.0799 | 1.35E-08 |
| 5888 | 5.28E-06 | 0.0186 | 1.25E-11 | 0.0449 | 1.90E-19 |
| 9290 | 4.16E-04 | 0.256 | 2.03E-09 | 1.30E-04 | 1.71E-11 |

FIG. 17B (CONT'D)

| M/Z | Ratio: Group/Control | | | |
|---|---|---|---|---|
| | Prostate | Breast | Bladder | Prostate2 |
| 824 | 1.15 | 0.76 | 4.66 | 0.52 |
| 830 | 1.57 | 0.95 | 8.32 | 0.58 |
| 891 | 1.46 | 0.76 | 2.03 | 1.03 |
| 907 | 1.06 | 1.62 | 0.79 | 2.09 |
| 944 | 1.74 | 0.58 | 5.18 | 2.01 |
| 1023 | 0.28 | 0.47 | 0.28 | 0.15 |
| 1048 | 0.42 | 0.83 | 0.18 | 0.40 |
| 1058 | 226.73 | 1.00 | 1050.72 | 191.06 |
| 1063 | 0.77 | 1.90 | 0.43 | 1.16 |
| 1079 | 0.54 | 0.95 | 0.50 | 0.59 |
| 1101 | 1.43 | 0.81 | 2.29 | 0.99 |
| 1126 | 0.42 | 0.87 | 0.25 | 0.28 |
| 1209 | 0.50 | 0.69 | 0.44 | 0.19 |
| 1214 | 7.86 | 0.01 | 10.80 | 7.39 |
| 1231 | 0.90 | 1.24 | 5.66 | 0.33 |
| 1267 | 0.20 | 0.23 | 0.24 | 0.11 |
| 1280 | 251.92 | 1.00 | 1406.33 | 231.96 |
| 1314 | 1.00 | 1.00 | 634.96 | 21.25 |
| 1354 | 0.47 | 0.35 | 0.46 | 0.25 |
| 1383 | 0.90 | 4.34 | 0.83 | 0.42 |
| 1427 | 0.67 | 1.10 | 3.22 | 0.40 |
| 1453 | 1885.15 | 437.78 | 2646.51 | 2217.87 |
| 1469 | 0.66 | 0.80 | 0.55 | 0.33 |
| 1502 | 1.00 | 1.00 | 809.48 | 98.91 |
| 1523 | 0.38 | 0.58 | 0.15 | 0.33 |
| 1534 | 0.97 | 0.95 | 2.61 | 0.73 |
| 1540 | 0.58 | 0.54 | 0.00 | 0.31 |
| 1567 | 0.79 | 0.54 | 1.13 | 0.60 |
| 1618 | 0.65 | 0.58 | 0.34 | 0.55 |
| 1630 | 1.09 | 2.78 | 0.88 | 0.89 |
| 1696 | 4.05 | 1.01 | 6.85 | 4.92 |
| 1744 | 0.75 | 2.76 | 0.66 | 1.23 |
| 1757 | 1.82 | 1.36 | 5.70 | 1.34 |
| 1782 | 4.37 | 0.96 | 7.70 | 6.79 |
| 1870 | 2.18 | 0.30 | 3.33 | 3.89 |
| 1900 | 1.27 | 2.95 | 3.33 | 1.97 |
| 1931 | 78.66 | 1.00 | 671.27 | 158.45 |
| 1975 | 1.00 | 1.00 | 640.68 | 52.59 |
| 1982 | 1.38 | 0.87 | 1.73 | 1.52 |

FIG. 17C

| M/Z | Prostate | Breast | Bladder | Prostate2 |
|---|---|---|---|---|
| 2119 | 3.22 | 10.61 | 12.23 | 2.84 |
| 2147 | 1.74 | 1.93 | 6.89 | 1.28 |
| 2189 | 1.71 | 2.83 | 1.79 | 2.17 |
| 2273 | 4.58 | 1.46 | 2.64 | 6.30 |
| 2342 | 1.75 | 2.10 | 4.87 | 1.58 |
| 2363 | 99.81 | 531.10 | 72.58 | 112.76 |
| 2383 | 1.57 | 1.71 | 0.22 | 3.46 |
| 2414 | 96.71 | 109.24 | 2124.24 | 64.14 |
| 2512 | 1.38 | 7.96 | 1.20 | 1.69 |
| 2570 | 1.00 | 1.00 | 901.87 | 170.85 |
| 2607 | 2.84 | 4.73 | 2.30 | 5.86 |
| 2730 | 1.75 | 1.64 | 6.17 | 3.64 |
| 2761 | 1.11 | 1.22 | 12.35 | 5.42 |
| 2773 | 0.77 | 0.98 | 0.03 | 1.61 |
| 2937 | 1.24 | 0.97 | 0.13 | 2.32 |
| 3165 | 3.43 | 1.33 | 10.68 | 4.23 |
| 3188 | 0.74 | 1.00 | 6.26 | 0.01 |
| 3196 | 0.52 | 0.94 | 0.00 | 0.94 |
| 3267 | 0.33 | 0.92 | 0.08 | 0.74 |
| 3278 | 1.00 | 1.00 | 1277.00 | 399.45 |
| 3960 | 1.33 | 0.87 | 2.46 | 1.88 |
| 3977 | 1.00 | 1.00 | 957.31 | 302.46 |
| 4192 | 0.70 | 1.34 | 0.00 | 1.51 |
| 4272 | 661.24 | 205.45 | 2851.85 | 753.39 |
| 4631 | 0.69 | 0.83 | 0.63 | 1.45 |
| 5013 | 1.00 | 1.00 | 739.13 | 63.32 |
| 5068 | 0.77 | 0.92 | 0.00 | 0.84 |
| 5888 | 0.54 | 1.26 | 0.08 | 1.48 |
| 9290 | 0.60 | 1.13 | 0.50 | 1.72 |

FIG. 17C (CONT'D)

ORIGIN
    1 ypfalfyrhy lfyketylih lfhtftglsi ayfnfgnqly hsllcivlqf lilrlmgrti
   61 tavlttfcfq mayllagyyy tatgnydikw tmphcvltlk liglavdyfd ggkdqnslss
  121 eqqkyairgv psllevagfs yfygaflvgp qfsmnhymkl vqgelidipg kipnsiipal
  181 krlslglfyl vgytllsphi tedylltedy dnhpfwfrcm ymliwgkfvl ykyvtcwlvt
  241 egvciltglg fngfeekgka kwdacanmkv wlfetnprft gtiasfnint nawvaryifk
  301 rlkflgnkel sqglsllfla lwhglhsgyl vcfqmkfliv iverqaarli qesptlskla
  361 aitvlqpfyy lvqqtihwlf mgysmtafcl ftwdkwlkvy ksiyflghif flsllfilpy
  421 ihkamvprke klkkme

FIG. 18

ORIGIN
      1 mkpprpvrtc skvlvllsll aihqtttaek ngidiysltv dsrvssrfah tvvtsrvvnr
     61 antvqeatfq melpkkafit nfsmnidgmt ypgiikekae aqaqysaava kgksaglvka
    121 tgrnmeqfqv svsvapnaki tfelvyeell krrlgvyell lkvrpqqlvk hlqmdihife
    181 pqgisflete stfmtnqlvd alttwqnktk ahirfkptls qqqkspeqqe tvldgnliir
    241 ydvdraisgg siqiengyfv hyfapegltt mpknvvfvid ksgsmsgrki qqtrealiki
    301 lddlsprdqf nlivfsteat qwrpslvpas aenvnkarsf aagiqalggt nindamlmav
    361 qlldssnqee rlpegsvsli illtdgdptv getnprsiqn nvreavsgry slfclgfgfd
    421 vsyaflekla ldngglarri hedsdsalql qdfyqevanp lltavtfeyp snaveevtqn
    481 nfrllfkgse mvvagklqdr gpdvltatvs gklptqnitf qtessvaeqe aefqspkyif
    541 hnfmerlway ltiqqlleqt vsasdadqqa lrnqalnlsl aysfvtplts mvvtkpddqe
    601 qsqvaekpme gesrnrnvhs gstffkyylq gakipkpeas fsprrgwnrq agaagsrmnf
    661 rpgvlssrql glpgppdvpd haayhpfrrl ailpasappa tsnpdpavsr vmnmkieett
    721 mttqtpapiq apsailplpg qsverlcvdp rhrqgpvnll sdpeqgvevt gqyerekagf
    781 swievtfknp lvwvhaspeh vvvtrnrrss aykwketlfs vmpglkmtmd ktglllsdp
    841 dkvtigllfw dgrgeglrll lrdtdrfssh vggtlgqfyq evlwgspaas ddgrrtlrvq
    901 gndhsatrer rldyqegppg veiscwsvel

FIG. 19

ORIGIN
      1 mmktllllfvg llltwesgqv lgdqtvsdne lqemsnqgsk yvnkeiqnav ngvkqiktli
     61 ektneerktl lsnleeakkk kedalnetre setklkelpg vcnetmmalw eeckpclkqt
    121 cmkfyarvcr sgsglvgrql eeflnqsspf yfwmngdrid sllendrqqt hmldvmqdhf
    181 srassiidel fqdrfftrep qdtyhylpfs lphrrphfff pksrivrslm pfspyeplnf
    241 hamfqpflem iheaqqamdi hfhspafqhp ptefiregdd drtvcreirh nstgclrmkd
    301 qcdkcreils vdcstnnpsq aklrreldes lqvaerltrk ynellksyqw kmlntsslle
    361 qlneqfnwvs rlanltqged qyylrvttva shtsdsdvps gvtevvvklf dsdpitvtvp
    421 vevsrknpkf metvaekalq eyrkkhr

FIG. 20

ORIGIN
        1 gqyasptakr ccqdgvtrlp mmrsceqraa rvqqpdcrep flsccqfaes lrkksrdkgq
       61 aglqraleil qeedlidedd ipvrsffpen wlwrvetvdr fqiltlwlpd slttweihgl
      121 slsktkglcv atpvqlrvfr efhlhlrlpm svrrfeqlel rpvlynyldk nltvsvhvsp
      181 veglclaggg glaqqvlvpa gsarpvafsv vptaatavsl kvvargsfef pvgdavskvl
      241 qiekegaihr eelvyelnpl dhrgrtleip gnsdpnmipd gdfnsyvrvt asdpldtlgs
      301 egalspggva sllrlprgcg eqtmiylapt laasryldkt eqwstlppet kdhavdliqk
      361 gymriqqfrk adgsyaawls rgsstwltaf vlkvlslaqe qvggspeklq etsnwllsqq
      421 qadgsfqdpc pvldrsmqgg lvgndetval tafvtialhh glavfqdega eplkqrveas
      481 iskaxsflge kasagllgah aaaitayalt ltkapvdllg vahnnlmama qetg

FIG. 21

ORIGIN
    1 mfsmrivclv lsvvgtawta dsgegdflae gggvrgprvv erhqsackds dwpfcsdedw
   61 nykcpsgcrm kglidevnqd ftnrinklkn slfeyqknnk dshslttnim eilrgdfssa
  121 nnrdntynrv sedlrsriev lkrkviekvq hiqllqknvr aqlvdmkrle vdidikirsc
  181 rgscsralar evdlkdyedq qkqleqviak dllpsrdrqh lplikmkpvp dlvpgnfksq
  241 lqkvppewka ltdmpqmrme lerpggneit rggstsygtg setesprnps sagswnsgss
  301 gpgstgnrnp gssgtggtat wkpgssgpgs tgswnsgssg tgstgnqnpg sprpgstgtw
  361 npgssergsa ghwtsessvs gstgqwhses gsfrpdspgs gnarpnnpdw gtfeevsgnv
  421 spgtrreyht eklvtskgdk elrtgkekvt sgsttttrrs csktvtktvi gpdghkevtk
  481 evvtsedgsd cpeamdlgtl sgigtldgfr hrhpdeaaff dtastgktfp gffspmlgef
  541 vsetesrgse sgiftntkes sshhpgiaef psrgksssys kqftsstsyn rgdstfesks
  601 ykmadeagse adhegthstk rghaksrpvr gihtsplgkp slsp

FIG. 22

ORIGIN
    1 mklitilflc srlllsltqe sqseeidcnd kdlfkavdaa lkkynsqnqs nnqfvlyrit
   61 eatktvgsdt fysfkyeike gdcpvqsgkt wqdceykdaa kaatgectat vgkrsstkfs
  121 vatqtcqitp aegpvvtaqy dclgcvhpis tqspdlepil rhgiqyfnnn tqhsslfmln
  181 evkraqrqvv aglnfritys ivqtncsken flfltpdcks lwngdtgect dnayidiqlr
  241 iasfsqncdi ypgkdfvqpp tkicvgcprd iptnspelee tlthtitkln aennatfyfk
  301 idnvkkarvq vvagkkyfid fvarettcsk esneeltesc etkklgqsld cnaevyvvpw
  361 ekkiyptvnc qplgmislmk rppgfspfrs srigeikeet tvspphtsma paqdeerdsg
  421 keqghtrrhd wghekqrkhn lghghkherd qghghqrghg lghgheqqhg lghghkfkld
  481 ddlehqgghv ldhghkhkhg hghgkhknkg kkngkhngwk tehlasssed sttpsaqtqe
  541 ktegptpips lakpgvtvtf sdfqdsdlia tmmppispap iqsdddwipd iqtdpnglsf
  601 npisdfpdtt spkcpgrpwk svseinpttq mkesyyfdlt dgls

FIG. 23

```
MFSMRIVCLVLSVVGTAWTADSGEGDFLAEGGGVRGPRVVERHQSACKDSDWP
FCSDEDWNYKCPSGCRMKGLIDEVNQDFTNRINKLKNSLFEYQKNNKDSHSLTT
NIMEILRGDFSSANNRDNTYNRVSEDLRSRIEVLKRKVIEKVQHIQLLQKNVRAQ
LVDMKRLEVDIDIKIRSCRGSCSRALAREVDLKDYEDQQKQLEQVIAKDLLPSRD
RQHLPLIKMKPVPDLVPGNFKSQLQKVPPEWKALTDMPQMRMELERPGGNEITR
GGSTSYGTGSETESPRNPSSAGSWNSGSSGPGSTGNRNPGSSGTGGTATWKPGSS
GPGSTGSWNSGSSGTGSTGNQNPGSPRPGSTGTWNPGSSERGSAGHWTSESSVS
GSTGQWHSESGSFRPDSPGSGNARPNNPDWGTFEEVSGNVSPGTRREYHTEKLV
TSKGDKELRTGKEKVTSGSTTTTRRSCSKTVTKTVIGPDGHKEVTKEVVTSEDGS
DCPEAMDLGTLSGIGTLDGFRHRHPDEAAFFDTASTGKTFPGFFSPMLGEFVSET
ESRGSESGIFTNTKESSSHHPGIAEFPSRGKSSSYSKQFTSSTSYNRGDSTFESKSY
KMADEAGSEADHEGTHSTKRGHAKSRPVRGIHTSPLGKPSLSP
```

FIG. 24

MKAAVLTLAVLFLTGSQARHFWQQDEPPQSPWDRVKDLATVYVDVLKDSGRD
YVSQFEGSALGKQLNLKLLDNWDSVTSTFSKLREQLGPVTQEFWDNLEKETEGL
RQEMSKDLEEVKAKVQPYLDDFQKKWQEEMELYRQKVEPLRAELQEGARQKL
HELQEKLSPLGEEMRDRARAHVDALRTHLAPYSDELRQRLAARLEALKENGGA
RLAEYHAKATEHLSTLSEKAKPALEDLRQGLLPVLESFKVSFLSALEEYTKKLNT
Q

FIG. 25

MFLKAVVLTLALVAVAGARAEVSADQVATVMWDYFSQLSNNAKEAVEHLQKS
ELTQQLNALFQDKLGEVNTYAGDLQKKLVPFATELHERLAKDSEKLKEEIGKEL
EELRARLLPHANEVSQKIGDNLRELQQRLEPYADQLRTQVNTQAEQLRRQLTPY
AQRMERVLRENADSLQASLRPHADELKAKIDQNVEELKGRLTPYADEFKVKIDQ
TVEELRRSLAPYAQDTQEKLNHQLEGLTFQMKKNAEELKARISASAEELRQRLA
PLAEDVRGNLRGNTEGLQKSLAELGGHLDQQVEEFRRRVEPYGENFNKALVQQ
MEQLRTKLGPHAGDVEGHLSFLEKDLRDKVNSFFSTFKEKESQDKTLSLPELEQQ
QEQHQEQQQEQVQMLAPLES

FIG. 26

MKVLWAALLVTFLAGCQAKVEQAVETEPEPELRQQTEWQSGQRWELALGRFW
DYLRWVQTLSEQVQEELLSSQVTQELRALMDETMKELKAYKSELEEQLTPVAEE
TRARLSKELQAAQARLGADMEDVCGRLVQYRGEVQAMLGQSTEELRVRLASHL
RKLRKRLLRDADDLQKRLAVYQAGAREGAERGLSAIRERLGPLVEQGRVRAAT
VGSLAGQPLQERAQAWGERLRARMEEMGSRTRDRLDEVKEQVAEVRAKLEEQ
AQQIRLQAEAFQARLKSWFEPLVEDMQRQWAGLVEKVQAAVGTSAAPVPSDN
H

FIG. 27

MKLITILFLCSRLLLSLTQESQSEEIDCNDKDLFKAVDAALKKYNSQNQSNNQFV
LYRITEATKTVGSDTFYSFKYEIKEGDCPVQSGKTWQDCEYKDAAKAATGECTA
TVGKRSSTKFSVATQTCQITPAEGPVVTAQYDCLGCVHPISTQSPDLEPILRHGIQ
YFNNNTQHSSLFMLNEVKRAQRQVVAGLNFRITYSIVQTNCSKENFLFLTPDCKS
LWNGDTGECTDNAYIDIQLRIASFSQNCDIYPGKDFVQPPTKICVGCPRDIPTNSP
ELEETLTHTITKLNAENNATFYFKIDNVKKARVQVVAGKKYFIDFVARETTCSKE
SNEELTESCETKKLGQSLDCNAEVYVVPWEKKIYPTVNCQPLGMISLMKRPPGFS
PFRSSRIGEIKEETTSHLRSCEYKGRPPKAGAEPASEREVS

FIG. 28

MSETSRTAFGGRRAVPPNNSNAAEDDLPTVELQGVVPRGVNLQEFLNVTSVHLF
KERWDTNKVDHHTDKYENNKLIVRRGQSFYVQIDLSRPYDPRRDLFRVEYVIGR
YPQENKGTYIPVPIVSELQSGKWGAKIVMREDRSVRLSIQSSPKCIVGKFRMYVA
VWTPYGVLRTSRNPETDTYILFNPWCEDDAVYLDNEKEREEYVLNDIGVIFYGE
VNDIKTRSWSYGQFEDGILDTCLYVMDRAQMDLSGRGNPIKVSRVGSAMVNAK
DDEGVLVGSWDNIYAYGVPPSAWTGSVDILLEYRSSENPVRYGQCWVFAGVFN
TFLRCLGIPARIVTNYFSAHDNDANLQMDIFLEEDGNVNSKLTKDSVWNYHCWN
EAWMTRPDLPVGFGGWQAVDSTPQENSDGMYRCGPASVQAIKHGHVCFQFDA
PFVFAEVNSDLIYITAKKDGTHVVENVDATHIGKLIVTKQIGGDGMMDITDTYKF
QEGQEEERLALETALMYGAKKPLNTEGVMKSRSNVDMDFEVENAVLGKDFKLS
ITFRNNSHNRYTITAYLSANITFYTGVPKAEFKKETFDVTLEPLSFKKEAVLIQAG
EYMGQLLEQASLHFFVTARINETRDVLAKQKSTVLTIPEIIIKVRGTQVVGSDMTV
TVQFTNPLKETLRNVWVHLDGPGVTRPMKKMFREIRPNSTVQWEEVCRPWVSG
HRKLIASMSSDSLRHVYGELDVQIQRRPSM

FIG. 29

MASHRLLLLCLAGLVFVSEAGPTGTGESKCPLMVKVLDAVRGSPAINVAVHVFR
KAADDTWEPFASGKTSESGELHGLTTEEEFVEGIYKVEIDTKSYWKALGISPFHE
HAEVVFTANDSGPRRYTIAALLSPYSYSTTAVVTNPKE

FIG. 30

Non-degradable, $^{13}$C- or $^{13}$C/$^{15}$N-labeled Synthetic Peptides:

| MH+ marker | AA sequence | Surrogate |
|---|---|---|
| Fibrinopeptide A (FPA); NCBI # 229185 | | |
| 758.41 | LAEGGGVR | P-   (BL-) |
| 905.48 | FLAEGGGVR | B+(BL-) |
| 1020.51 | DFLAEGGGVR | P-   (BL-)(T-) |
| 1077.53 | GDFLAEGGGVR | P-   (BL-) |
| 1206.58 | EGDFLAEGGGVR | P-   (BL-)(T-) |
| 1263.59 | GEGDFLAEGGGVR | P-B-(BL-)(T-) |
| 1350.63 | SGEGDFLAEGGGVR | P-B-(BL-)(T-) |
| 1465.65 | DSGEGDFLAEGGGVR | P-   (BL-)(T-) |
| 1536.69 | ADSGEGDFLAEGGGVR  (=FPA) | P-B-(BL-) |
| Fibrinogen alpha; NCBI # 4033511 | | |
| | (Res. 548-574) | |
| 2816.25 | GSESGIFTNTKESSSHHPGIAEFPSRG | (BL-) |
| | (Res. 576-604) | |
| 2768.22 | SSSYSKQFTSSTSYNRGDSTFESKS.... | (BL-)(T-) |
| 2931.28 | SSSYSKQFTSSTSYNRGDSTFESKSY... | (BL-)(T-) |
| 3190.42 | SSSYSKQFTSSTSYNRGDSTFESKSYKM. | P-   (BL-)(T-) |
| 3261.45 | SSSYSKQFTSSTSYNRGDSTFESKSYKMA | P-   (BL-)(T-) |
| 2379.03 | .SSYSKQFTSSTSYNRGDSTFE | B+(BL-) |
| | (Res. 605-629) | |
| 2659.24 | DEAGSEADHEGTHSTKRGHAKSRPV | B+ |

FIG. 31

**\*Complement C3f; NCBI #226159 (\*complete series has been synthesized)**

| | | |
|---|---|---|
| 942.47 (BL+) (T+) | HWESASLL. | B- |
| 1055.55 (BL+) | IHWESASLL. | P+ |
| 1211.65 (BL+) (T+) | RIHWESASLL. | P+B- |
| 1348.71 | HRIHWESASLL. | --- |
| 1449.76 (BL+) (T+) | THRIHWESASLL. | P+ |
| 1562.84 | ITHRIHWESASLL. | B- |
| 1690.93 (BL+) (T+) | KITHRIHWESASLL. | P+ |
| 1777.97 (BL+) (T+) | SKITHRIHWESASLL. | P+ |
| 1864.99 (BL+) (T+) | SSKITHRIHWESASLL. | P+B- |
| 2021.10 | SSKITHRIHWESASLLR (=C3f) | --- |

Complement C4 precursor; NCBI # 20141171

(Res. 1337-1352)

| | | |
|---|---|---|
| 1228.64 | NGFKSHALQLN..... | (BL+) |
| 1498.78 | NGFKSHALQLNNR... | (BL+) |
| 1626.84 | NGFKSHALQLNNRQ.. | B+ |
| 1739.92 | NGFKSHALQLNNRQI. | B+ |
| 1896.02 | NGFKSHALQLNNRQIR | B+ (BL+) |

(Res. 1353-1382)

| | | |
|---|---|---|
| 1762.92 | GLEEELQFSLGSKINV | B+ (BL-) |
| 2305.19 | GLEEELQFSLGSKINVKVGGNS | P+B+ (BL+) |
| 2704.44 | GLEEELQFSLGSKINVKVGGNSKGTL | B+ |

FIG. 31 (CONT'D)

Inter-alpha-trypsin inhibitor heavy chain H4 (ITIH4); NCBI # 13432192
(Res. 650-688)

| | | |
|---|---|---|
| 842.39 (BL−) | HAAYHPF. | P+ |
| 1519.69 (BL−) | GPPDVPDHAAYHPF. | P+ |
| 1616.74 | PGPPDVPDHAAYHPF. | --- |
| 1786.85 | GLPGPPDVPDHAAYHPF. | B+ |
| 2027.99 | QLGLPGPPDVPDHAAYHPF. | --- |
| 2271.12 (BL+) | SRQLGLPGPPDVPDHAAYHPF. | P+ |
| 2358.15 | SSRQLGLPGPPDVPDHAAYHPF. | B+ |
| 2627.34 (BL−) | GVLSSRQLGLPGPPDVPDHAAYHPF. | |
| 2724.38 (BL+) | PGVLSSRQLGLPGPPDVPDHAAYHPF. | P+ |
| 3272.63 (BL+) | MNFRPGVLSSRQLGLPGPPDVPDHAAYHPF. | |
| 2184.09 | QLGLPGPPDVPDHAAYHPFR | P+B+ |
| 998.49 | HAAYHPFR | P+B+ (BL+) |

(Res. 617-644)

3156.61      NVHSGSTFFKYYLQGAKIPKPEASFSPR      P+   (BL+)

ITIH4 splice variant: PRO1851; NCBI # 7770149
(Res. 347-367)

2115.04      NVHSAGAAGSRMNFRPGVLSS      P+B+(BL+)

Apolipoprotein A-I; NCBI # 4557321
(Res. 220-238)

2053.07 (BL+)      ATEHLSTLSEKAKPALEDL (Res. 240-267)

3182.72 (BL+)      QGLLPVLESFKVSFLSALEEYTKKLNTQ 1971.04 (BL+)      VSFLSALEEYTKKLNTQ

Apolipoprotein A-IV; NCBI # 114006
(Res. 256-278)

2508.35      ISASAEELRQRLAPLAEDVRGNL      B+

(Res. 280-304)

1771.84 (BL+)      SLAELGGHLDQQVEEF.

2755.35 (BL+)      GNTEGLQKSLAELGGHLDQQVEEFR 1927.94 (BL+)      SLAELGGHLDQQVEEFR

FIG. 31 (CONT'D)

Apolipoprotein E; NCBI # 114039
              (Res. 210-233)
2409.26                AATVGSLAGQPLQERAQAWGERL.
(BL+)
2565.36                AATVGSLAGQPLQERAQAWGERLR
(BL+)

CLUSTERIN precursor; NCBI # 42716297
              (Res. 267-278)
 822.43               ..HFFFPK....
(BL+)
1277.71                ..HFFFPKSRIV                      P+
(BL+)
1530.86                RPHFFFPKSRIV
(BL+)

Bradykinin; des-Arg bradykinin
 904.46                RPPGFSPF.                           B+(BL-)
1060.57                RPPGFSPFR                           B+(BL-)

HMW Kininogen; NCBI # 125507
              (Res. 438-456)
1943.90                NLGHGHKHERDQGHGHQ           P+
(BL+)
2209.05                KHNLGHGHKHERDQGHGHQ
(BL+)

FACTOR XIIIa precursor; NCBI 119720
              (Res. 14-38)
2602.30                AVPPNNSNAAEDDLPTVELQGVVPR       P+B+

TRANSTHYRETIN precursor; NCBI # 136464
              (Res. 101-123)
2451.19                ALGISPFHEHAEVVFTANDSGPR         B+

---

All amino acids are <u>D-stereo-isomers</u>, except for the isotope-containing (L-isomer).
<u>Isotope-labeled amino acids:</u> L, $^{13}$C(6)-Leu; F, $^{13}$C(6-ring)-Phe; V, $^{13}$C(5)/$^{15}$N(1)-Val.
(Note: isotope labels result in a molecular mass increase by 6 Da for each peptide).

<u>Surrogate marker code</u>: P, prostate cancer; B, breast cancer; BL, bladder cancer; T, thyroid cancer; +, median ion intensity of this particular peptide in MALDI-TOF MS is higher in cancer samples than in controls; -, median ion intensity lower in cancer than controls (12).

FIG. 31 (CONT'D)

MALDI-based, relative quantitation of serum peptides
Normalized Ion Intensities

Relative Quantitation (using added REF peptides)

Isotope-labeled [$^{13}$C- or $^{13}$C/$^{15}$N-AA] Peptide Substrates for Blood Protease Assays.

| MH+ | AA sequence |
|---|---|

1) Fibrinopeptide A (FPA); NCBI # 229185
    1536.69        ADSGEGDFLAEGGGVR 2) Fibrinogen alpha; NCBI # 4033511 (Res. 576-604)
    3261.45        SSSYSKQFTSSTSYNRGDSTFESKSYKMA 3) Fibrinogen alpha (Res. 605-629)
    3239.51        SYKMADEAGSEADHEGTHSTKRGHAKSRPV 4) Complement C3f (C3f); NCBI #226159
    2021.10        SSKITHRIHWESASLLR  (peptide available with single label)

5) Complement C4 precursor; NCBI # 20141171 (Res. 1337-1352)
    1896.02        NGFKSHALQLNNRQIR 6) C4 precursor (Res. 1353-1382)
    3200.79        GLEEELQFSLGSKINVKVGGNSKGTLKVLR 7) ITIH4; NCBI # 13432192 (Res. 650-688)
    2880.48        PGVLSSRQLGLPGPPDVPDHAAYHPFR  (note: non-degradable)
                       .GVLSSRQLGLPGPPDVPDHAAYHPFR  ***
                       ..VLSSRQLGLPGPPDVPDHAAYHPFR  ***
                       ...LSSRQLGLPGPPDVPDHAAYHPFR  ***
                       ....SSRQLGLPGPPDVPDHAAYHPFR  ***
                       .......QLGLPGPPDVPDHAAYHPFR  ***
    ***Five 'test' founder peptides (N-t: G, V, L, S, Q)

8) Alpha-1-antitrypsin precursor;
    NCBI # 15080499('D') (C-t)
    2489.30        LMIDQNTKSPLFMGKVVNPTQK
    NCBI # 50363221('E') (C-t)
    2503.33        LMIEQNTKSPLFMGKVVNPTQK 9) Apolipoprotein A-I; NCBI # 4557321 (Res. 240-267)
    1971.04        VSFLSALEEYTKKLNTQ 10) Apolipoprotein A-IV; NCBI # 114006 (Res. 280-304)
    1927.94        SLAELGGHLDQQVEEFR

FIG. 33

11) CLUSTERIN precursor; NCBI # 42716297 (Res. 267-278)
   1277.71            HFFFPKSRIV
   1530.86            RPHFFFPKSRIV 12) TRANSTHYRETIN precursor; NCBI # 136464 (Res. 125-147)
   2645.37            RYTIAALLSPYSYSTTAVVTNPKE
   2489.27            .YTIAALLSPYSYSTTAVVTNPKE

---

Total 15 syntheses, including 2 (#7 and 11) or more multi-samplings; ≥18 cleavages, purifications, QC and quantitation. Isotope-labeled amino acids: L, $^{13}$C(6)-Leu; F, $^{13}$C(6-ring)-Phe; V, $^{13}$C(5)/$^{15}$N(1)-Val; A, $^{13}$C(3)/$^{15}$N(1)-Ala; resulting in molecular mass increase of 12 Da per peptide.

FIG. 33 (CONT'D)

```
                         SEQUENCE LISTING

<160> NUMBER OF SEQ ID NOS: 148

<210> SEQ ID NO 1
    <211> LENGTH: 15
    <212> TYPE: PRT
    <213> ORGANISM: Homo sapiens

<400> SEQUENCE: 1

Asp Ser Gly Glu Gly Asp Phe Leu Ala Glu Gly Gly Gly Val Arg
    1               5                   10                  15

<210> SEQ ID NO 2
    <211> LENGTH: 14
    <212> TYPE: PRT
    <213> ORGANISM: Homo sapiens

<400> SEQUENCE: 2

Ser Gly Glu Gly Asp Phe Leu Ala Glu Gly Gly Gly Val Arg
    1               5                   10

<210> SEQ ID NO 3
    <211> LENGTH: 13
    <212> TYPE: PRT
    <213> ORGANISM: Homo sapiens

<400> SEQUENCE: 3

Gly Glu Gly Asp Phe Leu Ala Glu Gly Gly Gly Val Arg
    1               5                   10

<210> SEQ ID NO 4
    <211> LENGTH: 12
    <212> TYPE: PRT
    <213> ORGANISM: Homo sapiens

<400> SEQUENCE: 4

Glu Gly Asp Phe Leu Ala Glu Gly Gly Gly Val Arg
    1               5                   10

<210> SEQ ID NO 5
    <211> LENGTH: 11
    <212> TYPE: PRT
    <213> ORGANISM: Homo sapiens

<400> SEQUENCE: 5

Gly Asp Phe Leu Ala Glu Gly Gly Gly Val Arg
    1               5                   10

<210> SEQ ID NO 6
    <211> LENGTH: 10
    <212> TYPE: PRT
    <213> ORGANISM: Homo sapiens

<400> SEQUENCE: 6

Asp Phe Leu Ala Glu Gly Gly Gly Val Arg
```

```
1               5                   10
```

<210> SEQ ID NO 7
<211> LENGTH: 16
<212> TYPE: PRT
<213> ORGANISM: Homo sapiens

<400> SEQUENCE: 7

```
Glu Glu Glu Leu Gln Phe Ser Gly Leu Ser Phe Asn Val Lys Val Ser
1               5                   10                  15
```

<210> SEQ ID NO 8
<211> LENGTH: 16
<212> TYPE: PRT
<213> ORGANISM: Homo sapiens

<400> SEQUENCE: 8

```
Ser Ser Lys Ile Thr His Arg Ile His Trp Glu Ser Ala Ser Leu Leu
1               5                   10                  15
```

<210> SEQ ID NO 9
<211> LENGTH: 15
<212> TYPE: PRT
<213> ORGANISM: Homo sapiens

<400> SEQUENCE: 9

```
Ser Lys Ile Thr His Arg Ile His Trp Glu Ser Ala Ser Leu Leu
1               5                   10                  15
```

<210> SEQ ID NO 10
<211> LENGTH: 14
<212> TYPE: PRT
<213> ORGANISM: Homo sapiens

<400> SEQUENCE: 10

```
Lys Ile Thr His Arg Ile His Trp Glu Ser Ala Ser Leu Leu
1               5                   10
```

<210> SEQ ID NO 11
<211> LENGTH: 12
<212> TYPE: PRT
<213> ORGANISM: Homo sapiens

<400> SEQUENCE: 11

```
Thr His Arg Ile His Trp Glu Ser Ala Ser Leu Leu
1               5                   10
```

<210> SEQ ID NO 12
<211> LENGTH: 8
<212> TYPE: PRT
<213> ORGANISM: Homo sapiens

<400> SEQUENCE: 12

```
His Trp Glu Ser Ala Ser Leu Leu
1               5
```

<210> SEQ ID NO 13
<211> LENGTH: 26
<212> TYPE: PRT
<213> ORGANISM: Homo sapiens

<400> SEQUENCE: 13

```
Pro Gly Val Leu Ser Ser Arg Gln Leu Gly Leu Pro Gly Pro Pro Asp
1               5                   10                  15

Val Pro Asp His Ala Ala Tyr His Pro Phe
```

20                  25

<210> SEQ ID NO 14
<211> LENGTH: 25
<212> TYPE: PRT
<213> ORGANISM: Homo sapiens

<400> SEQUENCE: 14

Gly Val Leu Ser Ser Arg Gln Leu Gly Leu Pro Gly Pro Pro Asp Val
1               5                   10                  15

Pro Asp His Ala Ala Tyr His Pro Phe
            20                  25

<210> SEQ ID NO 15
<211> LENGTH: 21
<212> TYPE: PRT
<213> ORGANISM: Homo sapiens

<400> SEQUENCE: 15

Ser Arg Gln Leu Gly Leu Pro Gly Pro Pro Asp Val Pro Asp His Ala
1               5                   10                  15

Ala Tyr His Pro Phe
            20

<210> SEQ ID NO 16
<211> LENGTH: 17
<212> TYPE: PRT
<213> ORGANISM: Homo sapiens

<400> SEQUENCE: 16

Gly Leu Pro Gly Pro Pro Asp Val Pro Asp His Ala Ala Tyr His Pro
1               5                   10                  15

Phe

<210> SEQ ID NO 17
<211> LENGTH: 10
<212> TYPE: PRT
<213> ORGANISM: Homo sapiens

<400> SEQUENCE: 17

His Phe Phe Phe Pro Lys Ser Arg Ile Val
1               5                   10

<210> SEQ ID NO 18
<211> LENGTH: 6
<212> TYPE: PRT
<213> ORGANISM: Homo sapiens

<400> SEQUENCE: 18

His Phe Phe Phe Pro Lys
1               5

<210> SEQ ID NO 19
<211> LENGTH: 9
<212> TYPE: PRT
<213> ORGANISM: Homo sapiens

<400> SEQUENCE: 19

Arg Pro Pro Gly Phe Ser Pro Phe Arg
1               5

<210> SEQ ID NO 20
<211> LENGTH: 8
<212> TYPE: PRT

<213> ORGANISM: Homo sapiens

<400> SEQUENCE: 20

Arg Pro Pro Gly Phe Ser Pro Phe
1               5

<210> SEQ ID NO 21
<211> LENGTH: 16
<212> TYPE: PRT
<213> ORGANISM: Homo sapiens

<400> SEQUENCE: 21

Arg Asn Gly Phe Lys Ser His Ala Leu Gln Leu Asn Asn Arg Gln Ile
1               5                   10                  15

<210> SEQ ID NO 22
<211> LENGTH: 15
<212> TYPE: PRT
<213> ORGANISM: Homo sapiens

<400> SEQUENCE: 22

Asn Gly Phe Lys Ser His Ala Leu Gln Leu Asn Asn Arg Gln Ile
1               5                   10                  15

<210> SEQ ID NO 23
<211> LENGTH: 22
<212> TYPE: PRT
<213> ORGANISM: Homo sapiens

<400> SEQUENCE: 23

Gly Leu Glu Glu Glu Leu Gln Phe Ser Leu Gly Ser Lys Ile Asn Val
1               5                   10                  15

Lys Val Gly Gly Asn Ser
            20

<210> SEQ ID NO 24
<211> LENGTH: 9
<212> TYPE: PRT
<213> ORGANISM: Homo sapiens

<400> SEQUENCE: 24

Phe Leu Ala Glu Gly Gly Gly Val Arg
1               5

<210> SEQ ID NO 25
<211> LENGTH: 8
<212> TYPE: PRT
<213> ORGANISM: Homo sapiens

<400> SEQUENCE: 25

Leu Ala Glu Gly Gly Gly Val Arg
1               5

<210> SEQ ID NO 26
<211> LENGTH: 13
<212> TYPE: PRT
<213> ORGANISM: Homo sapiens

<400> SEQUENCE: 26

Ile Thr His Arg Ile His Trp Glu Ser Ala Ser Leu Leu
1               5                   10

<210> SEQ ID NO 27
<211> LENGTH: 10
<212> TYPE: PRT

<213> ORGANISM: Homo sapiens

<400> SEQUENCE: 27

Arg Ile His Trp Glu Ser Ala Ser Leu Leu
1               5                   10

<210> SEQ ID NO 28
<211> LENGTH: 9
<212> TYPE: PRT
<213> ORGANISM: Homo sapiens

<400> SEQUENCE: 28

Ile His Trp Glu Ser Ala Ser Leu Leu
1               5

<210> SEQ ID NO 29
<211> LENGTH: 15
<212> TYPE: PRT
<213> ORGANISM: Homo sapiens

<400> SEQUENCE: 29

Ser Ser Lys Ile Thr His Arg Ile His Trp Glu Ser Ala Ser Leu
1               5                   10                  15

<210> SEQ ID NO 30
<211> LENGTH: 14
<212> TYPE: PRT
<213> ORGANISM: Homo sapiens

<400> SEQUENCE: 30

Asn Gly Phe Lys Ser His Ala Leu Gln Leu Asn Asn Arg Gln
1               5                   10

<210> SEQ ID NO 31
<211> LENGTH: 13
<212> TYPE: PRT
<213> ORGANISM: Homo sapiens

<400> SEQUENCE: 31

Asn Gly Phe Lys Ser His Ala Leu Gln Leu Asn Asn Arg
1               5                   10

<210> SEQ ID NO 32
<211> LENGTH: 26
<212> TYPE: PRT
<213> ORGANISM: Homo sapiens

<400> SEQUENCE: 32

Gly Leu Glu Glu Glu Leu Gln Phe Ser Leu Gly Ser Lys Ile Asn Val
1               5                   10                  15

Lys Val Gly Gly Asn Ser Lys Gly Thr Leu
            20                  25

<210> SEQ ID NO 33
<211> LENGTH: 16
<212> TYPE: PRT
<213> ORGANISM: Homo sapiens

<400> SEQUENCE: 33

Gly Leu Glu Glu Glu Leu Gln Phe Ser Leu Gly Ser Lys Ile Asn Val
1               5                   10                  15

<210> SEQ ID NO 34
<211> LENGTH: 8
<212> TYPE: PRT

<213> ORGANISM: Homo sapiens

<400> SEQUENCE: 34

His Ala Ala Tyr His Pro Phe Arg
1               5

<210> SEQ ID NO 35
<211> LENGTH: 20
<212> TYPE: PRT
<213> ORGANISM: Homo sapiens

<400> SEQUENCE: 35

Gln Leu Gly Leu Pro Gly Pro Pro Asp Val Pro Asp His Ala Ala Tyr
1               5                   10                  15

His Pro Phe Arg
            20

<210> SEQ ID NO 36
<211> LENGTH: 38
<212> TYPE: PRT
<213> ORGANISM: Homo sapiens

<400> SEQUENCE: 36

Gln Ala Gly Ala Ala Gly Ser Arg Met Asn Phe Arg Pro Gly Val Leu
1               5                   10                  15

Ser Ser Arg Gln Leu Gly Leu Pro Gly Pro Pro Asp Val Pro Asp His
            20                  25                  30

Ala Ala Tyr His Pro Phe
        35

<210> SEQ ID NO 37
<211> LENGTH: 30
<212> TYPE: PRT
<213> ORGANISM: Homo sapiens

<400> SEQUENCE: 37

Met Asn Phe Arg Pro Gly Val Leu Ser Ser Arg Gln Leu Gly Leu Pro
1               5                   10                  15

Gly Pro Pro Asp Val Pro Asp His Ala Ala Tyr His Pro Phe
            20                  25                  30

<210> SEQ ID NO 38
<211> LENGTH: 22
<212> TYPE: PRT
<213> ORGANISM: Homo sapiens

<400> SEQUENCE: 38

Ser Ser Arg Gln Leu Gly Leu Pro Gly Pro Pro Asp Val Pro Asp His
1               5                   10                  15

Ala Ala Tyr His Pro Phe
            20

<210> SEQ ID NO 39
<211> LENGTH: 7
<212> TYPE: PRT
<213> ORGANISM: Homo sapiens

<400> SEQUENCE: 39

His Ala Ala Tyr His Pro Phe
1               5

<210> SEQ ID NO 40
<211> LENGTH: 28

```
<212> TYPE: PRT
<213> ORGANISM: Homo sapiens

<400> SEQUENCE: 40

Asn Val His Ser Gly Ser Thr Phe Phe Lys Tyr Tyr Leu Gln Gly Ala
1               5                   10                  15

Lys Ile Pro Lys Pro Glu Ala Ser Phe Ser Pro Arg
            20                  25

<210> SEQ ID NO 41
<211> LENGTH: 21
<212> TYPE: PRT
<213> ORGANISM: Homo sapiens

<400> SEQUENCE: 41

Asn Val His Ser Ala Gly Ala Ala Gly Ser Arg Met Asn Phe Arg Pro
1               5                   10                  15

Gly Val Leu Ser Ser
            20

<210> SEQ ID NO 42
<211> LENGTH: 28
<212> TYPE: PRT
<213> ORGANISM: Homo sapiens

<400> SEQUENCE: 42

Gln Gly Leu Leu Pro Val Leu Glu Ser Phe Lys Val Ser Phe Leu Ser
1               5                   10                  15

Ala Leu Glu Glu Tyr Thr Lys Lys Leu Asn Thr Gln
            20                  25

<210> SEQ ID NO 43
<211> LENGTH: 17
<212> TYPE: PRT
<213> ORGANISM: Homo sapiens

<400> SEQUENCE: 43

Val Ser Phe Leu Ser Ala Leu Glu Glu Tyr Thr Lys Lys Leu Asn Thr
1               5                   10                  15

Gln

<210> SEQ ID NO 44
<211> LENGTH: 19
<212> TYPE: PRT
<213> ORGANISM: Homo sapiens

<400> SEQUENCE: 44

Ala Thr Glu His Leu Ser Thr Leu Ser Glu Lys Ala Lys Pro Ala Leu
1               5                   10                  15

Glu Asp Leu

<210> SEQ ID NO 45
<211> LENGTH: 23
<212> TYPE: PRT
<213> ORGANISM: Homo sapiens

<400> SEQUENCE: 45

Ile Ser Ala Ser Ala Glu Glu Leu Arg Gln Arg Leu Ala Pro Leu Ala
1               5                   10                  15

Glu Asp Val Arg Gly Asn Leu
            20
```

```
<210> SEQ ID NO 46
<211> LENGTH: 25
<212> TYPE: PRT
<213> ORGANISM: Homo sapiens

<400> SEQUENCE: 46

Gly Asn Thr Glu Gly Leu Gln Lys Ser Leu Ala Glu Leu Gly Gly His
1               5                   10                  15

Leu Asp Gln Gln Val Glu Glu Phe Arg
            20                  25

<210> SEQ ID NO 47
<211> LENGTH: 17
<212> TYPE: PRT
<213> ORGANISM: Homo sapiens

<400> SEQUENCE: 47

Ser Leu Ala Glu Leu Gly Gly His Leu Asp Gln Gln Val Glu Glu Phe
1               5                   10                  15

Arg

<210> SEQ ID NO 48
<211> LENGTH: 16
<212> TYPE: PRT
<213> ORGANISM: Homo sapiens

<400> SEQUENCE: 48

Ser Leu Ala Glu Leu Gly Gly His Leu Asp Gln Gln Val Glu Glu Phe
1               5                   10                  15

<210> SEQ ID NO 49
<211> LENGTH: 24
<212> TYPE: PRT
<213> ORGANISM: Homo sapiens

<400> SEQUENCE: 49

Ala Ala Thr Val Gly Ser Leu Ala Gly Gln Pro Leu Gln Glu Arg Ala
1               5                   10                  15

Gln Ala Trp Gly Glu Arg Leu Arg
            20

<210> SEQ ID NO 50
<211> LENGTH: 23
<212> TYPE: PRT
<213> ORGANISM: Homo sapiens

<400> SEQUENCE: 50

Ala Ala Thr Val Gly Ser Leu Ala Gly Gln Pro Leu Gln Glu Arg Ala
1               5                   10                  15

Gln Ala Trp Gly Glu Arg Leu
            20

<210> SEQ ID NO 51
<211> LENGTH: 19
<212> TYPE: PRT
<213> ORGANISM: Homo sapiens

<400> SEQUENCE: 51

Lys His Asn Leu Gly His Gly His Lys His Glu Arg Asp Gln Gly His
1               5                   10                  15

Gly His Gln

<210> SEQ ID NO 52
```

```
<211> LENGTH: 17
<212> TYPE: PRT
<213> ORGANISM: Homo sapiens

<400> SEQUENCE: 52

Asn Leu Gly His Gly His Lys His Glu Arg Asp Gln Gly His Gly His
 1               5                  10                  15

Gln

<210> SEQ ID NO 53
<211> LENGTH: 25
<212> TYPE: PRT
<213> ORGANISM: Homo sapiens

<400> SEQUENCE: 53

Ala Val Pro Pro Asn Asn Ser Asn Ala Ala Glu Asp Asp Leu Pro Thr
 1               5                  10                  15

Val Glu Leu Gln Gly Val Val Pro Arg
            20                  25

<210> SEQ ID NO 54
<211> LENGTH: 23
<212> TYPE: PRT
<213> ORGANISM: Homo sapiens

<400> SEQUENCE: 54

Ala Leu Gly Ile Ser Pro Phe His Glu His Ala Glu Val Val Phe Thr
 1               5                  10                  15

Ala Asn Asp Ser Gly Pro Arg
            20

<210> SEQ ID NO 55
<211> LENGTH: 29
<212> TYPE: PRT
<213> ORGANISM: Homo sapiens

<400> SEQUENCE: 55

Ser Ser Ser Tyr Ser Lys Gln Phe Thr Ser Ser Thr Ser Tyr Asn Arg
 1               5                  10                  15

Gly Asp Ser Thr Phe Glu Ser Lys Ser Tyr Lys Met Ala
            20                  25

<210> SEQ ID NO 56
<211> LENGTH: 28
<212> TYPE: PRT
<213> ORGANISM: Homo sapiens

<400> SEQUENCE: 56

Ser Ser Ser Tyr Ser Lys Gln Phe Thr Ser Ser Thr Ser Tyr Asn Arg
 1               5                  10                  15

Gly Asp Ser Thr Phe Glu Ser Lys Ser Tyr Lys Met
            20                  25

<210> SEQ ID NO 57
<211> LENGTH: 26
<212> TYPE: PRT
<213> ORGANISM: Homo sapiens

<400> SEQUENCE: 57

Ser Ser Ser Tyr Ser Lys Gln Phe Thr Ser Ser Thr Ser Tyr Asn Arg
 1               5                  10                  15

Gly Asp Ser Thr Phe Glu Ser Lys Ser Tyr
            20                  25
```

```
<210> SEQ ID NO 58
<211> LENGTH: 25
<212> TYPE: PRT
<213> ORGANISM: Homo sapiens

<400> SEQUENCE: 58

Ser Ser Ser Tyr Ser Lys Gln Phe Thr Ser Ser Thr Ser Tyr Asn Arg
1               5                   10                  15

Gly Asp Ser Thr Phe Glu Ser Lys Ser
            20                  25

<210> SEQ ID NO 59
<211> LENGTH: 25
<212> TYPE: PRT
<213> ORGANISM: Homo sapiens

<400> SEQUENCE: 59

Gly Leu Glu Glu Glu Leu Gln Phe Ser Leu Gly Ser Lys Ile Asn Val
1               5                   10                  15

Lys Gly Gly Asn Ser Lys Gly Thr Ile
            20                  25

<210> SEQ ID NO 60
<211> LENGTH: 21
<212> TYPE: PRT
<213> ORGANISM: Homo sapiens

<400> SEQUENCE: 60

Ser Ser Tyr Ser Lys Gln Phe Thr Ser Ser Thr Ser Tyr Asn Arg Gly
1               5                   10                  15

Asp Ser Thr Phe Glu
            20

<210> SEQ ID NO 61
<211> LENGTH: 27
<212> TYPE: PRT
<213> ORGANISM: Homo sapiens

<400> SEQUENCE: 61

Gly Ser Glu Ser Gly Ile Phe Thr Asn Thr Lys Glu Ser Ser Ser His
1               5                   10                  15

His Pro Gly Ile Ala Glu Phe Pro Ser Arg Gly
            20                  25

<210> SEQ ID NO 62
<211> LENGTH: 25
<212> TYPE: PRT
<213> ORGANISM: Homo sapiens

<400> SEQUENCE: 62

Asp Glu Ala Gly Ser Glu Ala Asp His Glu Gly Thr His Ser Thr Lys
1               5                   10                  15

Arg Gly His Ala Lys Ser Arg Pro Val
            20                  25

<210> SEQ ID NO 63
<211> LENGTH: 436
<212> TYPE: PRT
<213> ORGANISM: Homo sapiens

<400> SEQUENCE: 63

Tyr Pro Phe Ala Leu Phe Tyr Arg His Tyr Leu Phe Tyr Lys Glu Thr
```

-continued

```
1               5               10              15
Tyr Leu Ile His Leu Phe His Thr Phe Thr Gly Leu Ser Ile Ala Tyr
                20                  25                  30
Phe Asn Phe Gly Asn Gln Leu Tyr His Ser Leu Leu Cys Ile Val Leu
            35                  40                  45
Gln Phe Leu Ile Leu Arg Leu Met Gly Arg Thr Ile Thr Ala Val Leu
        50                  55                  60
Thr Thr Phe Cys Phe Gln Met Ala Tyr Leu Leu Ala Gly Tyr Tyr Tyr
65                  70                  75                  80
Thr Ala Thr Gly Asn Tyr Asp Ile Lys Trp Thr Met Pro His Cys Val
                85                  90                  95
Leu Thr Leu Lys Leu Ile Gly Leu Ala Val Asp Tyr Phe Asp Gly Gly
            100                 105                 110
Lys Asp Gln Asn Ser Leu Ser Ser Glu Gln Lys Tyr Ala Ile Arg
        115                 120                 125
Gly Val Pro Ser Leu Leu Glu Val Ala Gly Phe Ser Tyr Phe Tyr Gly
        130                 135                 140
Ala Phe Leu Val Gly Pro Gln Phe Ser Met Asn His Tyr Met Lys Leu
145                 150                 155                 160
Val Gln Gly Glu Leu Ile Asp Ile Pro Gly Lys Ile Pro Asn Ser Ile
                165                 170                 175
Ile Pro Ala Leu Lys Arg Leu Ser Leu Gly Leu Phe Tyr Leu Val Gly
            180                 185                 190
Tyr Thr Leu Leu Ser Pro His Ile Thr Glu Asp Tyr Leu Leu Thr Glu
        195                 200                 205
Asp Tyr Asp Asn His Pro Phe Trp Phe Arg Cys Met Tyr Met Leu Ile
        210                 215                 220
Trp Gly Lys Phe Val Leu Tyr Lys Tyr Val Thr Cys Trp Leu Val Thr
225                 230                 235                 240
Glu Gly Val Cys Ile Leu Thr Gly Leu Gly Phe Asn Gly Phe Glu Glu
                245                 250                 255
Lys Gly Lys Ala Lys Trp Asp Ala Cys Ala Asn Met Lys Val Trp Leu
            260                 265                 270
Phe Glu Thr Asn Pro Arg Phe Thr Gly Thr Ile Ala Ser Phe Asn Ile
        275                 280                 285
Asn Thr Asn Ala Trp Val Ala Arg Tyr Ile Phe Lys Arg Leu Lys Phe
        290                 295                 300
Leu Gly Asn Lys Glu Leu Ser Gln Gly Leu Ser Leu Phe Leu Ala
305                 310                 315                 320
Leu Trp His Gly Leu His Ser Gly Tyr Leu Val Cys Phe Gln Met Lys
                325                 330                 335
Phe Leu Ile Val Ile Val Glu Arg Gln Ala Ala Arg Leu Ile Gln Glu
            340                 345                 350
Ser Pro Thr Leu Ser Lys Leu Ala Ala Ile Thr Val Leu Gln Pro Phe
        355                 360                 365
Tyr Tyr Leu Val Gln Gln Thr Ile His Trp Leu Phe Met Gly Tyr Ser
        370                 375                 380
Met Thr Ala Phe Cys Leu Phe Thr Trp Asp Lys Trp Leu Lys Val Tyr
385                 390                 395                 400
Lys Ser Ile Tyr Phe Leu Gly His Ile Phe Phe Leu Ser Leu Leu Phe
                405                 410                 415
Ile Leu Pro Tyr Ile His Lys Ala Met Val Pro Arg Lys Glu Lys Leu
            420                 425                 430
```

```
Lys Lys Met Glu
        435

<210> SEQ ID NO 64
<211> LENGTH: 930
<212> TYPE: PRT
<213> ORGANISM: Homo sapiens

<400> SEQUENCE: 64

Met Lys Pro Pro Arg Pro Val Arg Thr Cys Ser Lys Val Leu Val Leu
1               5                   10                  15

Leu Ser Leu Leu Ala Ile His Gln Thr Thr Ala Glu Lys Asn Gly
            20                  25                  30

Ile Asp Ile Tyr Ser Leu Thr Val Asp Ser Arg Val Ser Ser Arg Phe
            35                  40                  45

Ala His Thr Val Val Thr Ser Arg Val Val Asn Arg Ala Asn Thr Val
        50                  55                  60

Gln Glu Ala Thr Phe Gln Met Glu Leu Pro Lys Lys Ala Phe Ile Thr
65                  70                  75                  80

Asn Phe Ser Met Asn Ile Asp Gly Met Thr Tyr Pro Gly Ile Ile Lys
                85                  90                  95

Glu Lys Ala Glu Ala Gln Ala Gln Tyr Ser Ala Ala Val Ala Lys Gly
            100                 105                 110

Lys Ser Ala Gly Leu Val Lys Ala Thr Gly Arg Asn Met Glu Gln Phe
        115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

His Ile Phe Glu Pro Gln Gly Ile Ser Phe Leu Glu Thr Glu Ser Thr
            180                 185                 190

Phe Met Thr Asn Gln Leu Val Asp Ala Leu Thr Thr Trp Gln Asn Lys
        195                 200                 205

Thr Lys Ala His Ile Arg Phe Lys Pro Thr Leu Ser Gln Gln Gln Lys
    210                 215                 220

Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
                245                 250                 255

Gly Tyr Phe Val His Tyr Phe Ala Pro Glu Gly Leu Thr Thr Met Pro
            260                 265                 270

Lys Asn Val Val Phe Val Ile Asp Lys Ser Gly Ser Met Ser Gly Arg
        275                 280                 285

Lys Ile Gln Gln Thr Arg Glu Ala Leu Ile Lys Ile Leu Asp Asp Leu
    290                 295                 300

Ser Pro Arg Asp Gln Phe Asn Leu Ile Val Phe Ser Thr Glu Ala Thr
305                 310                 315                 320

Gln Trp Arg Pro Ser Leu Val Pro Ala Ser Ala Glu Asn Val Asn Lys
                325                 330                 335

Ala Arg Ser Phe Ala Ala Gly Ile Gln Ala Leu Gly Gly Thr Asn Ile
            340                 345                 350

Asn Asp Ala Met Leu Met Ala Val Gln Leu Leu Asp Ser Ser Asn Gln
        355                 360                 365
```

-continued

```
Glu Glu Arg Leu Pro Glu Gly Ser Val Ser Leu Ile Ile Leu Leu Thr
    370                 375                 380

Asp Gly Asp Pro Thr Val Gly Glu Thr Asn Pro Arg Ser Ile Gln Asn
385                 390                 395                 400

Asn Val Arg Glu Ala Val Ser Gly Arg Tyr Ser Leu Phe Cys Leu Gly
                405                 410                 415

Phe Gly Phe Asp Val Ser Tyr Ala Phe Leu Glu Lys Leu Ala Leu Asp
            420                 425                 430

Asn Gly Gly Leu Ala Arg Arg Ile His Glu Asp Ser Asp Ser Ala Leu
        435                 440                 445

Gln Leu Gln Asp Phe Tyr Gln Glu Val Ala Asn Pro Leu Leu Thr Ala
    450                 455                 460

Val Thr Phe Glu Tyr Pro Ser Asn Ala Val Glu Glu Val Thr Gln Asn
465                 470                 475                 480

Asn Phe Arg Leu Leu Phe Lys Gly Ser Glu Met Val Val Ala Gly Lys
                485                 490                 495

Leu Gln Asp Arg Gly Pro Asp Val Leu Thr Ala Thr Val Ser Gly Lys
            500                 505                 510

Leu Pro Thr Gln Asn Ile Thr Phe Gln Thr Glu Ser Ser Val Ala Glu
        515                 520                 525

Gln Glu Ala Glu Phe Gln Ser Pro Lys Tyr Ile Phe His Asn Phe Met
    530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
                565                 570                 575

Asn Leu Ser Leu Ala Tyr Ser Phe Val Thr Pro Leu Thr Ser Met Val
            580                 585                 590

Val Thr Lys Pro Asp Asp Gln Glu Gln Ser Gln Val Ala Glu Lys Pro
        595                 600                 605

Met Glu Gly Glu Ser Arg Asn Arg Asn Val His Ser Gly Ser Thr Phe
    610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
                645                 650                 655

Arg Met Asn Phe Arg Pro Gly Val Leu Ser Ser Arg Gln Leu Gly Leu
            660                 665                 670

Pro Gly Pro Pro Asp Val Pro Asp His Ala Ala Tyr His Pro Phe Arg
        675                 680                 685

Arg Leu Ala Ile Leu Pro Ala Ser Ala Pro Pro Ala Thr Ser Asn Pro
    690                 695                 700

Asp Pro Ala Val Ser Arg Val Met Asn Met Lys Ile Glu Glu Thr Thr
705                 710                 715                 720

Met Thr Thr Gln Thr Pro Ala Pro Ile Gln Ala Pro Ser Ala Ile Leu
                725                 730                 735

Pro Leu Pro Gly Gln Ser Val Glu Arg Leu Cys Val Asp Pro Arg His
            740                 745                 750

Arg Gln Gly Pro Val Asn Leu Leu Ser Asp Pro Glu Gln Gly Val Glu
        755                 760                 765

Val Thr Gly Gln Tyr Glu Arg Glu Lys Ala Gly Phe Ser Trp Ile Glu
    770                 775                 780

Val Thr Phe Lys Asn Pro Leu Val Trp Val His Ala Ser Pro Glu His
785                 790                 795                 800
```

```
Val Val Val Thr Arg Asn Arg Arg Ser Ser Ala Tyr Lys Trp Lys Glu
            805                 810                 815

Thr Leu Phe Ser Val Met Pro Gly Leu Lys Met Thr Met Asp Lys Thr
            820                 825                 830

Gly Leu Leu Leu Leu Ser Asp Pro Asp Lys Val Thr Ile Gly Leu Leu
            835                 840                 845

Phe Trp Asp Gly Arg Gly Glu Gly Leu Arg Leu Leu Arg Asp Thr
            850                 855                 860

Asp Arg Phe Ser His Val Gly Gly Thr Leu Gly Gln Phe Tyr Gln
865                 870                 875                 880

Glu Val Leu Trp Gly Ser Pro Ala Ala Ser Asp Gly Arg Thr
                    885                 890                 895

Leu Arg Val Gln Gly Asn Asp His Ser Ala Thr Arg Gly Arg Arg Leu
            900                 905                 910

Asp Tyr Gln Glu Gly Pro Pro Gly Val Glu Ile Ser Cys Trp Ser Val
            915                 920                 925

Glu Leu
    930

<210> SEQ ID NO 65
<211> LENGTH: 447
<212> TYPE: PRT
<213> ORGANISM: Homo sapiens

<400> SEQUENCE: 65

Met Met Lys Thr Leu Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
            35                  40                  45

Ala Val Asn Gly Val Lys Gln Ile Lys Thr Leu Ile Glu Lys Thr Asn
    50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
            115                 120                 125

Cys Arg Ser Gly Ser Gly Leu Val Gly Arg Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
            195                 200                 205

Phe Ser Leu Pro His Arg Arg Pro His Phe Phe Pro Lys Ser Arg
    210                 215                 220

Ile Val Arg Ser Leu Met Pro Phe Ser Pro Tyr Glu Pro Leu Asn Phe
225                 230                 235                 240
```

```
His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
                260                 265                 270

Glu Phe Ile Arg Glu Gly Asp Asp Arg Thr Val Cys Arg Glu Ile
                275                 280                 285

Arg His Asn Ser Thr Gly Cys Leu Arg Met Lys Asp Gln Cys Asp Lys
290                 295                 300

Cys Arg Glu Ile Leu Ser Val Asp Cys Ser Thr Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
                340                 345                 350

Leu Asn Thr Ser Ser Leu Leu Glu Gln Leu Asn Glu Gln Phe Asn Trp
                355                 360                 365

Val Ser Arg Leu Ala Asn Leu Thr Gln Gly Glu Asp Gln Tyr Tyr Leu
                370                 375                 380

Arg Val Thr Thr Val Ala Ser His Thr Ser Asp Ser Asp Val Pro Ser
385                 390                 395                 400

Gly Val Thr Glu Val Val Lys Leu Phe Asp Ser Asp Pro Ile Thr
                405                 410                 415

Val Thr Val Pro Val Glu Val Ser Arg Lys Asn Pro Lys Phe Met Glu
                420                 425                 430

Thr Val Ala Glu Lys Ala Leu Gln Glu Tyr Arg Lys Lys His Arg
                435                 440                 445

<210> SEQ ID NO 66
<211> LENGTH: 534
<212> TYPE: PRT
<213> ORGANISM: Homo sapiens
<220> FEATURE:
<221> NAME/KEY: MOD_RES
<222> LOCATION: (485)..(485)
<223> OTHER INFORMATION: Any amino acid

<400> SEQUENCE: 66

Gly Gln Tyr Ala Ser Pro Thr Ala Lys Arg Cys Cys Gln Asp Gly Val
1               5                   10                  15

Thr Arg Leu Pro Met Met Arg Ser Cys Glu Gln Arg Ala Ala Arg Val
                20                  25                  30

Gln Gln Pro Asp Cys Arg Glu Pro Phe Leu Ser Cys Cys Gln Phe Ala
                35                  40                  45

Glu Ser Leu Arg Lys Lys Ser Arg Asp Lys Gly Gln Ala Gly Leu Gln
                50                  55                  60

Arg Ala Leu Glu Ile Leu Gln Glu Asp Leu Ile Asp Glu Asp Asp
65                  70                  75                  80

Ile Pro Val Arg Ser Phe Phe Pro Glu Asn Trp Leu Trp Arg Val Glu
                85                  90                  95

Thr Val Asp Arg Phe Gln Ile Leu Thr Leu Trp Leu Pro Asp Ser Leu
                100                 105                 110

Thr Thr Trp Glu Ile His Gly Leu Ser Leu Ser Lys Thr Lys Gly Leu
                115                 120                 125

Cys Val Ala Thr Pro Val Gln Leu Arg Val Phe Arg Glu Phe His Leu
130                 135                 140

His Leu Arg Leu Pro Met Ser Val Arg Arg Phe Glu Gln Leu Glu Leu
```

```
            145                 150                 155                 160
Arg Pro Val Leu Tyr Asn Tyr Leu Asp Lys Asn Leu Thr Val Ser Val
                    165                 170                 175

His Val Ser Pro Val Glu Gly Leu Cys Leu Ala Gly Gly Gly Gly Leu
                180                 185                 190

Ala Gln Gln Val Leu Val Pro Ala Gly Ser Ala Arg Pro Val Ala Phe
            195                 200                 205

Ser Val Pro Thr Ala Ala Thr Ala Val Ser Leu Lys Val Val Ala
        210                 215                 220

Arg Gly Ser Phe Glu Phe Pro Val Gly Asp Ala Val Ser Lys Val Leu
225                 230                 235                 240

Gln Ile Glu Lys Glu Gly Ala Ile His Arg Glu Leu Val Tyr Glu
                245                 250                 255

Leu Asn Pro Leu Asp His Arg Gly Arg Thr Leu Glu Ile Pro Gly Asn
                260                 265                 270

Ser Asp Pro Asn Met Ile Pro Asp Gly Asp Phe Asn Ser Tyr Val Arg
            275                 280                 285

Val Thr Ala Ser Asp Pro Leu Asp Thr Leu Gly Ser Glu Gly Ala Leu
        290                 295                 300

Ser Pro Gly Gly Val Ala Ser Leu Leu Arg Leu Pro Arg Gly Cys Gly
305                 310                 315                 320

Glu Gln Thr Met Ile Tyr Leu Ala Pro Thr Leu Ala Ala Ser Arg Tyr
                325                 330                 335

Leu Asp Lys Thr Glu Gln Trp Ser Thr Leu Pro Pro Glu Thr Lys Asp
                340                 345                 350

His Ala Val Asp Leu Ile Gln Lys Gly Tyr Met Arg Ile Gln Gln Phe
            355                 360                 365

Arg Lys Ala Asp Gly Ser Tyr Ala Ala Trp Leu Ser Arg Gly Ser Ser
        370                 375                 380

Thr Trp Leu Thr Ala Phe Val Leu Lys Val Leu Ser Leu Ala Gln Glu
385                 390                 395                 400

Gln Val Gly Gly Ser Pro Glu Lys Leu Gln Glu Thr Ser Asn Trp Leu
                405                 410                 415

Leu Ser Gln Gln Gln Ala Asp Gly Ser Phe Gln Asp Pro Cys Pro Val
            420                 425                 430

Leu Asp Arg Ser Met Gln Gly Gly Leu Val Gly Asn Asp Glu Thr Val
        435                 440                 445

Ala Leu Thr Ala Phe Val Thr Ile Ala Leu His His Gly Leu Ala Val
    450                 455                 460

Phe Gln Asp Glu Gly Ala Glu Pro Leu Lys Gln Arg Val Glu Ala Ser
465                 470                 475                 480

Ile Ser Lys Ala Xaa Ser Phe Leu Gly Glu Lys Ala Ser Ala Gly Leu
                485                 490                 495

Leu Gly Ala His Ala Ala Ala Ile Thr Ala Tyr Ala Leu Thr Leu Thr
            500                 505                 510

Lys Ala Pro Val Asp Leu Leu Gly Val Ala His Asn Asn Leu Met Ala
        515                 520                 525

Met Ala Gln Glu Thr Gly
    530

<210> SEQ ID NO 67
<211> LENGTH: 644
<212> TYPE: PRT
<213> ORGANISM: Homo sapiens
```

<400> SEQUENCE: 67

```
Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
        355                 360                 365

Ser Ala Gly His Trp Thr Ser Glu Ser Ser Val Ser Gly Ser Thr Gly
370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415
```

```
Ser Gly Asn Val Ser Pro Gly Thr Arg Arg Glu Tyr His Thr Glu Lys
            420                 425                 430

Leu Val Thr Ser Lys Gly Asp Lys Glu Leu Arg Thr Gly Lys Glu Lys
        435                 440                 445

Val Thr Ser Gly Ser Thr Thr Thr Thr Arg Arg Ser Cys Ser Lys Thr
450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
        515                 520                 525

Phe Pro Gly Phe Phe Ser Pro Met Leu Gly Glu Phe Val Ser Glu Thr
    530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
        595                 600                 605

Ser Glu Ala Asp His Glu Gly Thr His Ser Thr Lys Arg Gly His Ala
    610                 615                 620

Lys Ser Arg Pro Val Arg Gly Ile His Thr Ser Pro Leu Gly Lys Pro
625                 630                 635                 640

Ser Leu Ser Pro

<210> SEQ ID NO 68
<211> LENGTH: 644
<212> TYPE: PRT
<213> ORGANISM: Homo sapiens

<400> SEQUENCE: 68

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
        35                  40                  45

Gln Ser Asn Asn Gln Phe Val Leu Tyr Arg Ile Thr Glu Ala Thr Lys
    50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
                85                  90                  95

Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
        115                 120                 125

Thr Pro Ala Glu Gly Pro Val Val Thr Ala Gln Tyr Asp Cys Leu Gly
    130                 135                 140

Cys Val His Pro Ile Ser Thr Gln Ser Pro Asp Leu Glu Pro Ile Leu
```

-continued

```
            145                 150                 155                 160
Arg His Gly Ile Gln Tyr Phe Asn Asn Thr Gln His Ser Ser Leu
            165                 170                 175
Phe Met Leu Asn Glu Val Lys Arg Ala Gln Arg Gln Val Val Ala Gly
            180                 185                 190
Leu Asn Phe Arg Ile Thr Tyr Ser Ile Val Gln Thr Asn Cys Ser Lys
            195                 200                 205
Glu Asn Phe Leu Phe Leu Thr Pro Asp Cys Lys Ser Leu Trp Asn Gly
            210                 215                 220
Asp Thr Gly Glu Cys Thr Asp Asn Ala Tyr Ile Asp Ile Gln Leu Arg
225                 230                 235                 240
Ile Ala Ser Phe Ser Gln Asn Cys Asp Ile Tyr Pro Gly Lys Asp Phe
            245                 250                 255
Val Gln Pro Pro Thr Lys Ile Cys Val Gly Cys Pro Arg Asp Ile Pro
            260                 265                 270
Thr Asn Ser Pro Glu Leu Glu Glu Thr Leu Thr His Thr Ile Thr Lys
            275                 280                 285
Leu Asn Ala Glu Asn Asn Ala Thr Phe Tyr Phe Lys Ile Asp Asn Val
            290                 295                 300
Lys Lys Ala Arg Val Gln Val Val Ala Gly Lys Lys Tyr Phe Ile Asp
305                 310                 315                 320
Phe Val Ala Arg Glu Thr Thr Cys Ser Lys Glu Ser Asn Glu Glu Leu
            325                 330                 335
Thr Glu Ser Cys Glu Thr Lys Lys Leu Gly Gln Ser Leu Asp Cys Asn
            340                 345                 350
Ala Glu Val Tyr Val Val Pro Trp Glu Lys Lys Ile Tyr Pro Thr Val
            355                 360                 365
Asn Cys Gln Pro Leu Gly Met Ile Ser Leu Met Lys Arg Pro Pro Gly
            370                 375                 380
Phe Ser Pro Phe Arg Ser Ser Arg Ile Gly Glu Ile Lys Glu Glu Thr
385                 390                 395                 400
Thr Val Ser Pro Pro His Thr Ser Met Ala Pro Ala Gln Asp Glu Glu
            405                 410                 415
Arg Asp Ser Gly Lys Glu Gln Gly His Thr Arg Arg His Asp Trp Gly
            420                 425                 430
His Glu Lys Gln Arg Lys His Asn Leu Gly His Gly His Lys His Glu
            435                 440                 445
Arg Asp Gln Gly His Gly His Gln Arg Gly His Gly Leu Gly His Gly
            450                 455                 460
His Glu Gln Gln His Gly Leu Gly His Gly His Lys Phe Lys Leu Asp
465                 470                 475                 480
Asp Asp Leu Glu His Gln Gly Gly His Val Leu Asp His Gly His Lys
            485                 490                 495
His Lys His Gly His Gly His Gly Lys His Lys Asn Lys Gly Lys Lys
            500                 505                 510
Asn Gly Lys His Asn Gly Trp Lys Thr Glu His Leu Ala Ser Ser Ser
            515                 520                 525
Glu Asp Ser Thr Thr Pro Ser Ala Gln Thr Gln Glu Lys Thr Glu Gly
            530                 535                 540
Pro Thr Pro Ile Pro Ser Leu Ala Lys Pro Gly Val Thr Val Thr Phe
545                 550                 555                 560
Ser Asp Phe Gln Asp Ser Asp Leu Ile Ala Thr Met Met Pro Pro Ile
            565                 570                 575
```

```
Ser Pro Ala Pro Ile Gln Ser Asp Asp Trp Ile Pro Asp Ile Gln
            580                 585                 590

Thr Asp Pro Asn Gly Leu Ser Phe Asn Pro Ile Ser Asp Phe Pro Asp
        595                 600                 605

Thr Thr Ser Pro Lys Cys Pro Gly Arg Pro Trp Lys Ser Val Ser Glu
    610                 615                 620

Ile Asn Pro Thr Thr Gln Met Lys Glu Ser Tyr Tyr Phe Asp Leu Thr
625                 630                 635                 640

Asp Gly Leu Ser

<210> SEQ ID NO 69
<211> LENGTH: 644
<212> TYPE: PRT
<213> ORGANISM: Homo sapiens

<400> SEQUENCE: 69

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Glu Arg His Gln Ser Ala Cys Lys
        35                  40                  45

Asp Ser Asp Trp Pro Phe Cys Ser Asp Glu Asp Trp Asn Tyr Lys Cys
    50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Gly Thr Ala Thr
```

```
            305                 310                 315                 320
Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
        355                 360                 365

Ser Ala Gly His Trp Thr Ser Glu Ser Ser Val Ser Gly Ser Thr Gly
    370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
            420                 425                 430

Leu Val Thr Ser Lys Gly Asp Lys Glu Leu Arg Thr Gly Lys Glu Lys
        435                 440                 445

Val Thr Ser Gly Ser Thr Thr Thr Thr Arg Arg Ser Cys Ser Lys Thr
    450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
                485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
        515                 520                 525

Phe Pro Gly Phe Phe Ser Pro Met Leu Gly Glu Phe Val Ser Glu Thr
    530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
        595                 600                 605

Ser Glu Ala Asp His Glu Gly Thr His Ser Thr Lys Arg Gly His Ala
    610                 615                 620

Lys Ser Arg Pro Val Arg Gly Ile His Thr Ser Pro Leu Gly Lys Pro
625                 630                 635                 640

Ser Leu Ser Pro

<210> SEQ ID NO 70
<211> LENGTH: 267
<212> TYPE: PRT
<213> ORGANISM: Homo sapiens

<400> SEQUENCE: 70

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45
```

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
                100                 105                 110

Asp Leu Glu Glu Val Lys Ala Lys Val Gln Pro Tyr Leu Asp Asp Phe
                115                 120                 125

Gln Lys Lys Trp Gln Glu Glu Met Glu Leu Tyr Arg Gln Lys Val Glu
130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
                180                 185                 190

Glu Leu Arg Gln Arg Leu Ala Ala Arg Leu Glu Ala Leu Lys Glu Asn
                195                 200                 205

Gly Gly Ala Arg Leu Ala Glu Tyr His Ala Lys Ala Thr Glu His Leu
210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
                260                 265

<210> SEQ ID NO 71
<211> LENGTH: 396
<212> TYPE: PRT
<213> ORGANISM: Homo sapiens

<400> SEQUENCE: 71

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
                35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
                100                 105                 110

Leu Leu Pro His Ala Asn Glu Val Ser Gln Lys Ile Gly Asp Asn Leu
                115                 120                 125

Arg Glu Leu Gln Gln Arg Leu Glu Pro Tyr Ala Asp Gln Leu Arg Thr
                130                 135                 140

Gln Val Asn Thr Gln Ala Glu Gln Leu Arg Arg Gln Leu Thr Pro Tyr
145                 150                 155                 160

```
Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Arg Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Thr Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Gln His Gln Glu Gln Gln
    370                 375                 380

Gln Glu Gln Val Gln Met Leu Ala Pro Leu Glu Ser
385                 390                 395

<210> SEQ ID NO 72
<211> LENGTH: 317
<212> TYPE: PRT
<213> ORGANISM: Homo sapiens

<400> SEQUENCE: 72

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140
```

```
Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Leu Gln Lys Arg
            165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
            195                 200                 205

Arg Ala Ala Thr Val Gly Ser Leu Ala Gly Gln Pro Leu Gln Glu Arg
210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
            245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
            290                 295                 300

Val Gly Thr Ser Ala Ala Pro Val Pro Ser Asp Asn His
305                 310                 315

<210> SEQ ID NO 73
<211> LENGTH: 427
<212> TYPE: PRT
<213> ORGANISM: Homo sapiens

<400> SEQUENCE: 73

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
            35                  40                  45

Gln Ser Asn Asn Gln Phe Val Leu Tyr Arg Ile Thr Glu Ala Thr Lys
50                  55                  60

Thr Val Gly Ser Asp Thr Phe Tyr Ser Phe Lys Tyr Glu Ile Lys Glu
65                  70                  75                  80

Gly Asp Cys Pro Val Gln Ser Gly Lys Thr Trp Gln Asp Cys Glu Tyr
            85                  90                  95

Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
            115                 120                 125

Thr Pro Ala Glu Gly Pro Val Val Thr Ala Gln Tyr Asp Cys Leu Gly
            130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Asn Thr Gln His Ser Ser Leu
            165                 170                 175

Phe Met Leu Asn Glu Val Lys Arg Ala Gln Arg Gln Val Val Ala Gly
            180                 185                 190

Leu Asn Phe Arg Ile Thr Tyr Ser Ile Val Gln Thr Asn Cys Ser Lys
            195                 200                 205
```

-continued

```
Glu Asn Phe Leu Phe Leu Thr Pro Asp Cys Lys Ser Leu Trp Asn Gly
    210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
            260                 265                 270

Thr Asn Ser Pro Glu Leu Glu Thr Leu Thr His Thr Ile Thr Lys
        275                 280                 285

Leu Asn Ala Glu Asn Asn Ala Thr Phe Tyr Phe Lys Ile Asp Asn Val
    290                 295                 300

Lys Lys Ala Arg Val Gln Val Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335

Thr Glu Ser Cys Glu Thr Lys Lys Leu Gly Gln Ser Leu Asp Cys Asn
            340                 345                 350

Ala Glu Val Tyr Val Val Pro Trp Glu Lys Lys Ile Tyr Pro Thr Val
        355                 360                 365

Asn Cys Gln Pro Leu Gly Met Ile Ser Leu Met Lys Arg Pro Pro Gly
    370                 375                 380

Phe Ser Pro Phe Arg Ser Ser Arg Ile Gly Glu Ile Lys Glu Glu Thr
385                 390                 395                 400

Thr Ser His Leu Arg Ser Cys Glu Tyr Lys Gly Arg Pro Pro Lys Ala
                405                 410                 415

Gly Ala Glu Pro Ala Ser Glu Arg Glu Val Ser
            420                 425

<210> SEQ ID NO 74
<211> LENGTH: 732
<212> TYPE: PRT
<213> ORGANISM: Homo sapiens

<400> SEQUENCE: 74

Met Ser Glu Thr Ser Arg Thr Ala Phe Gly Gly Arg Arg Ala Val Pro
1               5                   10                  15

Pro Asn Asn Ser Asn Ala Ala Glu Asp Asp Leu Pro Thr Val Glu Leu
            20                  25                  30

Gln Gly Val Val Pro Arg Gly Val Asn Leu Gln Glu Phe Leu Asn Val
        35                  40                  45

Thr Ser Val His Leu Phe Lys Glu Arg Trp Asp Thr Asn Lys Val Asp
    50                  55                  60

His His Thr Asp Lys Tyr Glu Asn Asn Lys Leu Ile Val Arg Arg Gly
65                  70                  75                  80

Gln Ser Phe Tyr Val Gln Ile Asp Leu Ser Arg Pro Tyr Asp Pro Arg
                85                  90                  95

Arg Asp Leu Phe Arg Val Glu Tyr Val Ile Gly Arg Tyr Pro Gln Glu
            100                 105                 110

Asn Lys Gly Thr Tyr Ile Pro Val Pro Ile Val Ser Glu Leu Gln Ser
        115                 120                 125

Gly Lys Trp Gly Ala Lys Ile Val Met Arg Glu Asp Arg Ser Val Arg
    130                 135                 140

Leu Ser Ile Gln Ser Ser Pro Lys Cys Ile Val Gly Lys Phe Arg Met
145                 150                 155                 160
```

-continued

```
Tyr Val Ala Val Trp Thr Pro Tyr Gly Val Leu Arg Thr Ser Arg Asn
                165                 170                 175
Pro Glu Thr Asp Thr Tyr Ile Leu Phe Asn Pro Trp Cys Glu Asp Asp
            180                 185                 190
Ala Val Tyr Leu Asp Asn Glu Lys Glu Arg Glu Tyr Val Leu Asn
        195                 200                 205
Asp Ile Gly Val Ile Phe Tyr Gly Val Asn Asp Ile Lys Thr Arg
    210                 215                 220
Ser Trp Ser Tyr Gly Gln Phe Glu Asp Gly Ile Leu Asp Thr Cys Leu
225                 230                 235                 240
Tyr Val Met Asp Arg Ala Gln Met Asp Leu Ser Gly Arg Gly Asn Pro
                245                 250                 255
Ile Lys Val Ser Arg Val Gly Ser Ala Met Val Asn Ala Lys Asp Asp
                260                 265                 270
Glu Gly Val Leu Val Gly Ser Trp Asp Asn Ile Tyr Ala Tyr Gly Val
            275                 280                 285
Pro Pro Ser Ala Trp Thr Gly Ser Val Asp Ile Leu Leu Glu Tyr Arg
        290                 295                 300
Ser Ser Glu Asn Pro Val Arg Tyr Gly Gln Cys Trp Val Phe Ala Gly
305                 310                 315                 320
Val Phe Asn Thr Phe Leu Arg Cys Leu Gly Ile Pro Ala Arg Ile Val
                325                 330                 335
Thr Asn Tyr Phe Ser Ala His Asp Asn Asp Ala Asn Leu Gln Met Asp
                340                 345                 350
Ile Phe Leu Glu Glu Asp Gly Asn Val Asn Ser Lys Leu Thr Lys Asp
            355                 360                 365
Ser Val Trp Asn Tyr His Cys Trp Asn Glu Ala Trp Met Thr Arg Pro
        370                 375                 380
Asp Leu Pro Val Gly Phe Gly Gly Trp Gln Ala Val Asp Ser Thr Pro
385                 390                 395                 400
Gln Glu Asn Ser Asp Gly Met Tyr Arg Cys Gly Pro Ala Ser Val Gln
                405                 410                 415
Ala Ile Lys His Gly His Val Cys Phe Gln Phe Asp Ala Pro Phe Val
                420                 425                 430
Phe Ala Glu Val Asn Ser Asp Leu Ile Tyr Ile Thr Ala Lys Lys Asp
            435                 440                 445
Gly Thr His Val Glu Asn Val Asp Ala Thr His Ile Gly Lys Leu
        450                 455                 460
Ile Val Thr Lys Gln Ile Gly Gly Asp Gly Met Met Asp Ile Thr Asp
465                 470                 475                 480
Thr Tyr Lys Phe Gln Glu Gly Gln Glu Glu Arg Leu Ala Leu Glu
                485                 490                 495
Thr Ala Leu Met Tyr Gly Ala Lys Lys Pro Leu Asn Thr Glu Gly Val
                500                 505                 510
Met Lys Ser Arg Ser Asn Val Asp Met Asp Phe Glu Val Glu Asn Ala
            515                 520                 525
Val Leu Gly Lys Asp Phe Lys Leu Ser Ile Thr Phe Arg Asn Asn Ser
        530                 535                 540
His Asn Arg Tyr Thr Ile Thr Ala Tyr Leu Ser Ala Asn Ile Thr Phe
545                 550                 555                 560
Tyr Thr Gly Val Pro Lys Ala Glu Phe Lys Lys Glu Thr Phe Asp Val
                565                 570                 575
Thr Leu Glu Pro Leu Ser Phe Lys Lys Glu Ala Val Leu Ile Gln Ala
```

```
                    580                 585                 590
Gly Glu Tyr Met Gly Gln Leu Leu Glu Gln Ala Ser Leu His Phe Phe
                595                 600                 605

Val Thr Ala Arg Ile Asn Glu Thr Arg Asp Val Leu Ala Lys Gln Lys
            610                 615                 620

Ser Thr Val Leu Thr Ile Pro Glu Ile Ile Lys Val Arg Gly Thr
625                 630                 635                 640

Gln Val Val Gly Ser Asp Met Thr Val Gln Phe Thr Asn Pro
                645                 650                 655

Leu Lys Glu Thr Leu Arg Asn Val Trp Val His Leu Asp Gly Pro Gly
            660                 665                 670

Val Thr Arg Pro Met Lys Lys Met Phe Arg Glu Ile Arg Pro Asn Ser
            675                 680                 685

Thr Val Gln Trp Glu Glu Val Cys Arg Pro Trp Val Ser Gly His Arg
            690                 695                 700

Lys Leu Ile Ala Ser Met Ser Ser Asp Ser Leu Arg His Val Tyr Gly
705                 710                 715                 720

Glu Leu Asp Val Gln Ile Gln Arg Arg Pro Ser Met
                725                 730

<210> SEQ ID NO 75
<211> LENGTH: 147
<212> TYPE: PRT
<213> ORGANISM: Homo sapiens

<400> SEQUENCE: 75

Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145

<210> SEQ ID NO 76
<211> LENGTH: 17
<212> TYPE: PRT
<213> ORGANISM: Homo sapiens

<400> SEQUENCE: 76

Arg Asn Gly Phe Lys Ser His Ala Leu Gln Leu Asn Asn Arg Gln Ile
1               5                   10                  15

Arg
```

<210> SEQ ID NO 77
<211> LENGTH: 16
<212> TYPE: PRT
<213> ORGANISM: Homo sapiens

<400> SEQUENCE: 77

Asn Gly Phe Lys Ser His Ala Leu Gln Leu Asn Asn Arg Gln Ile Arg
1               5                   10                  15

<210> SEQ ID NO 78
<211> LENGTH: 31
<212> TYPE: PRT
<213> ORGANISM: Homo sapiens

<400> SEQUENCE: 78

Arg Gly Leu Glu Glu Glu Leu Gln Phe Ser Leu Gly Ser Lys Ile Asn
1               5                   10                  15

Val Lys Val Gly Gly Asn Ser Lys Gly Thr Leu Lys Val Leu Arg
            20                  25                  30

<210> SEQ ID NO 79
<211> LENGTH: 27
<212> TYPE: PRT
<213> ORGANISM: Homo sapiens

<400> SEQUENCE: 79

Arg Gly Leu Glu Glu Glu Leu Gln Phe Ser Leu Gly Ser Lys Ile Asn
1               5                   10                  15

Val Lys Val Gly Gly Asn Ser Lys Gly Thr Leu
            20                  25

<210> SEQ ID NO 80
<211> LENGTH: 23
<212> TYPE: PRT
<213> ORGANISM: Homo sapiens

<400> SEQUENCE: 80

Arg Gly Leu Glu Glu Glu Leu Gln Phe Ser Leu Gly Ser Lys Ile Asn
1               5                   10                  15

Val Lys Val Gly Gly Asn Ser
            20

<210> SEQ ID NO 81
<211> LENGTH: 17
<212> TYPE: PRT
<213> ORGANISM: Homo sapiens

<400> SEQUENCE: 81

Arg Gly Leu Glu Glu Glu Leu Gln Phe Ser Leu Gly Ser Lys Ile Asn
1               5                   10                  15

Val

<210> SEQ ID NO 82
<211> LENGTH: 39
<212> TYPE: PRT
<213> ORGANISM: Homo sapiens

<400> SEQUENCE: 82

Arg Gln Ala Gly Ala Ala Gly Ser Arg Met Asn Phe Arg Pro Gly Val
1               5                   10                  15

Leu Ser Ser Arg Gln Leu Gly Leu Pro Gly Pro Pro Asp Val Pro Asp
            20                  25                  30

His Ala Ala Tyr His Pro Phe
           35

<210> SEQ ID NO 83
<211> LENGTH: 19
<212> TYPE: PRT
<213> ORGANISM: Homo sapiens

<400> SEQUENCE: 83

Gln Leu Gly Leu Pro Gly Pro Pro Asp Val Pro Asp His Ala Ala Tyr
1               5                   10                  15

His Pro Phe

<210> SEQ ID NO 84
<211> LENGTH: 29
<212> TYPE: PRT
<213> ORGANISM: Homo sapiens

<400> SEQUENCE: 84

Arg Asn Val His Ser Gly Ser Thr Phe Phe Lys Tyr Tyr Leu Gln Gly
1               5                   10                  15

Ala Lys Ile Pro Lys Pro Glu Ala Ser Phe Ser Pro Arg
            20                  25

<210> SEQ ID NO 85
<211> LENGTH: 23
<212> TYPE: PRT
<213> ORGANISM: Homo sapiens

<400> SEQUENCE: 85

Arg Asn Val His Ser Ala Gly Ala Ala Gly Ser Arg Met Asn Phe Arg
1               5                   10                  15

Pro Gly Val Leu Ser Ser Arg
            20

<210> SEQ ID NO 86
<211> LENGTH: 31
<212> TYPE: PRT
<213> ORGANISM: Homo sapiens
<220> FEATURE:
<221> NAME/KEY: MOD_RES
<222> LOCATION: (26)..(26)
<223> OTHER INFORMATION: Oxidated Met

<400> SEQUENCE: 86

Arg Ala Glu Leu Gln Glu Gly Ala Arg Gln Lys Leu His Glu Leu Gln
1               5                   10                  15

Glu Lys Leu Ser Pro Leu Gly Glu Glu Met Arg Asp Arg Ala Arg
            20                  25                  30

<210> SEQ ID NO 87
<211> LENGTH: 15
<212> TYPE: PRT
<213> ORGANISM: Homo sapiens

<400> SEQUENCE: 87

Glu Leu Gln Glu Gly Ala Arg Gln Lys Leu His Glu Leu Gln Glu
1               5                   10                  15

<210> SEQ ID NO 88
<211> LENGTH: 29
<212> TYPE: PRT
<213> ORGANISM: Homo sapiens

<400> SEQUENCE: 88

```
Arg Gln Gly Leu Leu Pro Val Leu Glu Ser Phe Lys Val Ser Phe Leu
 1               5                  10                  15

Ser Ala Leu Glu Glu Tyr Thr Lys Lys Leu Asn Thr Gln
                20                  25
```

<210> SEQ ID NO 89
<211> LENGTH: 21
<212> TYPE: PRT
<213> ORGANISM: Homo sapiens

<400> SEQUENCE: 89

```
Lys Ala Thr Glu His Leu Ser Thr Leu Ser Glu Lys Ala Lys Pro Ala
 1               5                  10                  15

Leu Glu Asp Leu Arg
                20
```

<210> SEQ ID NO 90
<211> LENGTH: 24
<212> TYPE: PRT
<213> ORGANISM: Homo sapiens

<400> SEQUENCE: 90

```
Ile Ser Ala Ser Ala Glu Glu Leu Arg Gln Arg Leu Ala Pro Leu Ala
 1               5                  10                  15

Glu Asp Val Arg Gly Asn Leu Lys
                20
```

<210> SEQ ID NO 91
<211> LENGTH: 26
<212> TYPE: PRT
<213> ORGANISM: Homo sapiens

<400> SEQUENCE: 91

```
Lys Gly Asn Thr Glu Gly Leu Gln Lys Ser Leu Ala Glu Leu Gly Gly
 1               5                  10                  15

His Leu Asp Gln Gln Val Glu Glu Phe Arg
                20                  25
```

<210> SEQ ID NO 92
<211> LENGTH: 25
<212> TYPE: PRT
<213> ORGANISM: Homo sapiens

<400> SEQUENCE: 92

```
Arg Ala Ala Thr Val Gly Ser Leu Ala Gly Gln Pro Leu Gln Glu Arg
 1               5                  10                  15

Ala Gln Ala Trp Gly Glu Arg Leu Arg
                20                  25
```

<210> SEQ ID NO 93
<211> LENGTH: 24
<212> TYPE: PRT
<213> ORGANISM: Homo sapiens

<400> SEQUENCE: 93

```
Arg Ala Ala Thr Val Gly Ser Leu Ala Gly Gln Pro Leu Gln Glu Arg
 1               5                  10                  15

Ala Gln Ala Trp Gly Glu Arg Leu
                20
```

<210> SEQ ID NO 94
<211> LENGTH: 11

```
<212> TYPE: PRT
<213> ORGANISM: Homo sapiens

<400> SEQUENCE: 94

His Phe Phe Phe Pro Lys Ser Arg Ile Val Arg
1               5                   10

<210> SEQ ID NO 95
<211> LENGTH: 21
<212> TYPE: PRT
<213> ORGANISM: Homo sapiens

<400> SEQUENCE: 95

Arg Lys His Asn Leu Gly His Gly His Lys His Glu Arg Asp Gln Gly
1               5                   10                  15

His Gly His Gln Arg
            20

<210> SEQ ID NO 96
<211> LENGTH: 18
<212> TYPE: PRT
<213> ORGANISM: Homo sapiens

<400> SEQUENCE: 96

Asn Leu Gly His Gly His Lys His Glu Arg Asp Gln Gly His Gly His
1               5                   10                  15

Gln Arg

<210> SEQ ID NO 97
<211> LENGTH: 22
<212> TYPE: PRT
<213> ORGANISM: Homo sapiens

<400> SEQUENCE: 97

Arg Gly His Gly Leu Gly His Gly His Glu Gln Gln His Gly Leu Gly
1               5                   10                  15

His Gly His Lys Phe Lys
            20

<210> SEQ ID NO 98
<211> LENGTH: 26
<212> TYPE: PRT
<213> ORGANISM: Homo sapiens

<400> SEQUENCE: 98

Arg Ala Val Pro Pro Asn Asn Ser Asn Ala Ala Glu Asp Asp Leu Pro
1               5                   10                  15

Thr Val Glu Leu Gln Gly Val Val Pro Arg
            20                  25

<210> SEQ ID NO 99
<211> LENGTH: 24
<212> TYPE: PRT
<213> ORGANISM: Homo sapiens

<400> SEQUENCE: 99

Lys Ala Leu Gly Ile Ser Pro Phe His Glu His Ala Glu Val Val Phe
1               5                   10                  15

Thr Ala Asn Asp Ser Gly Pro Arg
            20

<210> SEQ ID NO 100
<211> LENGTH: 21
```

```
<212> TYPE: PRT
<213> ORGANISM: Homo sapiens

<400> SEQUENCE: 100

Gly Leu Glu Glu Glu Leu Gln Phe Ser Leu Gly Ser Lys Ile Asn Val
1               5                   10                  15

Lys Gly Gly Asn Ser
            20

<210> SEQ ID NO 101
<211> LENGTH: 30
<212> TYPE: PRT
<213> ORGANISM: Homo sapiens

<400> SEQUENCE: 101

Lys Ser Ser Ser Tyr Ser Lys Gln Phe Thr Ser Thr Ser Tyr Asn
1               5                   10                  15

Arg Gly Asp Ser Thr Phe Glu Ser Lys Ser Tyr Lys Met Ala
                20                  25                  30

<210> SEQ ID NO 102
<211> LENGTH: 57
<212> TYPE: PRT
<213> ORGANISM: Homo sapiens

<400> SEQUENCE: 102

Gly Ser Glu Ser Gly Ile Phe Thr Asn Thr Lys Glu Ser Ser His
1               5                   10                  15

His Pro Gly Ile Ala Glu Phe Pro Ser Arg Gly Lys Ser Ser Tyr
                20                  25                  30

Ser Lys Gln Phe Thr Ser Ser Thr Ser Tyr Asn Arg Gly Asp Ser Thr
            35                  40                  45

Phe Glu Ser Lys Ser Tyr Lys Met Ala
    50                  55

<210> SEQ ID NO 103
<211> LENGTH: 19
<212> TYPE: PRT
<213> ORGANISM: Homo sapiens

<400> SEQUENCE: 103

Arg Gly Leu Glu Glu Glu Leu Gln Phe Ser Leu Gly Ser Lys Ile Asn
1               5                   10                  15

Val Lys Val

<210> SEQ ID NO 104
<211> LENGTH: 24
<212> TYPE: PRT
<213> ORGANISM: Homo sapiens

<400> SEQUENCE: 104

Arg Thr Leu Glu Ile Pro Gly Asn Ser Asp Pro Asn Met Ile Pro Asp
1               5                   10                  15

Gly Asp Phe Asn Ser Tyr Val Arg
            20

<210> SEQ ID NO 105
<211> LENGTH: 25
<212> TYPE: PRT
<213> ORGANISM: Homo sapiens

<400> SEQUENCE: 105
```

```
Lys Gly Asn Thr Glu Gly Leu Gln Lys Ser Leu Ala Glu Leu Gly Gly
1               5                   10                  15

His Leu Asp Gln Gln Val Glu Glu Phe
            20                  25
```

<210> SEQ ID NO 106
<211> LENGTH: 26
<212> TYPE: PRT
<213> ORGANISM: Homo sapiens

<400> SEQUENCE: 106

```
Asp Val Ser Ser Ala Leu Asp Lys Leu Lys Glu Phe Gly Asn Thr Leu
1               5                   10                  15

Glu Asp Lys Ala Arg Glu Leu Ile Ser Arg
            20                  25
```

<210> SEQ ID NO 107
<211> LENGTH: 21
<212> TYPE: PRT
<213> ORGANISM: Homo sapiens

<400> SEQUENCE: 107

```
Thr Val Gly Ser Leu Ala Gly Gln Pro Leu Gln Glu Arg Ala Gln Ala
1               5                   10                  15

Trp Gly Glu Arg Leu
            20
```

<210> SEQ ID NO 108
<211> LENGTH: 644
<212> TYPE: PRT
<213> ORGANISM: Homo sapiens

<400> SEQUENCE: 108

```
Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                  40                  45

Asp Ser Asp Trp Pro Phe Cys Ser Asp Glu Asp Trp Asn Tyr Lys Cys
50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205
```

```
Ala Lys Asp Leu Leu Pro Ser Arg Asp Arg Gln His Leu Pro Leu Ile
    210                 215                 220
Lys Met Lys Pro Val Pro Asp Leu Val Pro Gly Asn Phe Lys Ser Gln
225                 230                 235                 240
Leu Gln Lys Val Pro Pro Glu Trp Lys Ala Leu Thr Asp Met Pro Gln
                245                 250                 255
Met Arg Met Glu Leu Glu Arg Pro Gly Gly Asn Glu Ile Thr Arg Gly
            260                 265                 270
Gly Ser Thr Ser Tyr Gly Thr Gly Ser Glu Thr Glu Ser Pro Arg Asn
        275                 280                 285
Pro Ser Ser Ala Gly Ser Trp Asn Ser Gly Ser Ser Gly Pro Gly Ser
    290                 295                 300
Thr Gly Asn Arg Asn Pro Gly Ser Ser Gly Thr Gly Gly Thr Ala Thr
305                 310                 315                 320
Trp Lys Pro Gly Ser Ser Gly Pro Gly Ser Thr Gly Ser Trp Asn Ser
                325                 330                 335
Gly Ser Ser Gly Thr Gly Ser Thr Gly Asn Gln Asn Pro Gly Ser Pro
            340                 345                 350
Arg Pro Gly Ser Thr Gly Thr Trp Asn Pro Gly Ser Ser Glu Arg Gly
        355                 360                 365
Ser Ala Gly His Trp Thr Ser Glu Ser Ser Val Ser Gly Ser Thr Gly
    370                 375                 380
Gln Trp His Ser Glu Ser Gly Ser Phe Arg Pro Asp Ser Pro Gly Ser
385                 390                 395                 400
Gly Asn Ala Arg Pro Asn Asn Pro Asp Trp Gly Thr Phe Glu Glu Val
                405                 410                 415
Ser Gly Asn Val Ser Pro Gly Thr Arg Arg Glu Tyr His Thr Glu Lys
            420                 425                 430
Leu Val Thr Ser Lys Gly Asp Lys Glu Leu Arg Thr Gly Lys Glu Lys
        435                 440                 445
Val Thr Ser Gly Ser Thr Thr Thr Arg Arg Ser Cys Ser Lys Thr
    450                 455                 460
Val Thr Lys Thr Val Ile Gly Pro Asp Gly His Lys Glu Val Thr Lys
465                 470                 475                 480
Glu Val Val Thr Ser Glu Asp Gly Ser Asp Cys Pro Glu Ala Met Asp
                485                 490                 495
Leu Gly Thr Leu Ser Gly Ile Gly Thr Leu Asp Gly Phe Arg His Arg
            500                 505                 510
His Pro Asp Glu Ala Ala Phe Phe Asp Thr Ala Ser Thr Gly Lys Thr
        515                 520                 525
Phe Pro Gly Phe Phe Ser Pro Met Leu Gly Glu Phe Val Ser Glu Thr
    530                 535                 540
Glu Ser Arg Gly Ser Glu Ser Gly Ile Phe Thr Asn Thr Lys Glu Ser
545                 550                 555                 560
Ser Ser His His Pro Gly Ile Ala Glu Phe Pro Ser Arg Gly Lys Ser
                565                 570                 575
Ser Ser Tyr Ser Lys Gln Phe Thr Ser Ser Thr Ser Tyr Asn Arg Gly
            580                 585                 590
Asp Ser Thr Phe Glu Ser Lys Ser Tyr Lys Met Ala Asp Glu Ala Gly
        595                 600                 605
Ser Glu Ala Asp His Glu Gly Thr His Ser Thr Lys Arg Gly His Ala
    610                 615                 620
Lys Ser Arg Pro Val Arg Gly Ile His Thr Ser Pro Leu Gly Lys Pro
```

-continued

<210> SEQ ID NO 109
<211> LENGTH: 1663
<212> TYPE: PRT
<213> ORGANISM: Homo sapiens

<400> SEQUENCE: 109

```
Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
            20                  25                  30

Ile Leu Arg Leu Glu Ser Glu Glu Thr Met Val Leu Glu Ala His Asp
            35                  40                  45

Ala Gln Gly Asp Val Pro Val Thr Val Thr Val His Asp Phe Pro Gly
        50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Leu Val Ser Leu Gln Ser Gly
        115                 120                 125

Tyr Leu Phe Ile Gln Thr Asp Lys Thr Ile Tyr Thr Pro Gly Ser Thr
        130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Pro Ile Glu Asp Gly Ser Gly Glu Val Val Leu Ser Arg
    290                 295                 300

Lys Val Leu Leu Asp Gly Val Gln Asn Leu Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
            340                 345                 350

Tyr Gln Ile His Phe Thr Lys Thr Pro Lys Tyr Phe Lys Pro Gly Met
        355                 360                 365
```

```
Pro Phe Asp Leu Met Val Phe Val Thr Asn Pro Asp Gly Ser Pro Ala
    370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
                405                 410                 415

Gln Lys Pro Leu Ser Ile Thr Val Arg Thr Lys Lys Gln Glu Leu Ser
            420                 425                 430

Glu Ala Glu Gln Ala Thr Arg Thr Met Gln Ala Leu Pro Tyr Ser Thr
        435                 440                 445

Val Gly Asn Ser Asn Asn Tyr Leu His Leu Ser Val Leu Arg Thr Glu
    450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                485                 490                 495

Lys Gly Arg Leu Leu Lys Ala Gly Arg Gln Val Arg Glu Pro Gly Gln
            500                 505                 510

Asp Leu Val Val Leu Pro Leu Ser Ile Thr Thr Asp Phe Ile Pro Ser
        515                 520                 525

Phe Arg Leu Val Ala Tyr Tyr Thr Leu Ile Gly Ala Ser Gly Gln Arg
    530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
            580                 585                 590

Val Val Leu Val Ala Val Asp Lys Gly Val Phe Val Leu Asn Lys Lys
        595                 600                 605

Asn Lys Leu Thr Gln Ser Lys Ile Trp Asp Val Val Glu Lys Ala Asp
    610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Ser Gly Gln Gln Thr Ala Gln
                645                 650                 655

Arg Ala Glu Leu Gln Cys Pro Gln Pro Ala Ala Arg Arg Arg Arg Ser
            660                 665                 670

Val Gln Leu Thr Glu Lys Arg Met Asp Lys Val Gly Lys Tyr Pro Lys
        675                 680                 685

Glu Leu Arg Lys Cys Cys Glu Asp Gly Met Arg Glu Asn Pro Met Arg
    690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
            740                 745                 750

Glu Asp Ile Ile Ala Glu Glu Asn Ile Val Ser Arg Ser Glu Phe Pro
        755                 760                 765

Glu Ser Trp Leu Trp Asn Val Glu Asp Leu Lys Glu Pro Pro Lys Asn
    770                 775                 780

Gly Ile Ser Thr Lys Leu Met Asn Ile Phe Leu Lys Asp Ser Ile Thr
```

-continued

```
                785                 790                 795                 800
Thr Trp Glu Ile Leu Ala Val Ser Met Ser Asp Lys Lys Gly Ile Cys
                    805                 810                 815
Val Ala Asp Pro Phe Glu Val Thr Val Met Gln Asp Phe Phe Ile Asp
                    820                 825                 830
Leu Arg Leu Pro Tyr Ser Val Arg Asn Glu Gln Val Glu Ile Arg
                    835                 840                 845
Ala Val Leu Tyr Asn Tyr Arg Gln Asn Gln Glu Leu Lys Val Arg Val
                    850                 855                 860
Glu Leu Leu His Asn Pro Ala Phe Cys Ser Leu Ala Thr Thr Lys Arg
865                 870                 875                 880
Arg His Gln Gln Thr Val Thr Ile Pro Pro Lys Ser Ser Leu Ser Val
                    885                 890                 895
Pro Tyr Val Ile Val Pro Leu Lys Thr Gly Leu Gln Glu Val Glu Val
                    900                 905                 910
Lys Ala Ala Val Tyr His His Phe Ile Ser Asp Gly Val Arg Lys Ser
                    915                 920                 925
Leu Lys Val Val Pro Glu Gly Ile Arg Met Asn Lys Thr Val Ala Val
                    930                 935                 940
Arg Thr Leu Asp Pro Glu Arg Leu Gly Arg Glu Gly Val Gln Lys Glu
945                 950                 955                 960
Asp Ile Pro Pro Ala Asp Leu Ser Asp Gln Val Pro Asp Thr Glu Ser
                    965                 970                 975
Glu Thr Arg Ile Leu Leu Gln Gly Thr Pro Val Ala Gln Met Thr Glu
                    980                 985                 990
Asp Ala Val Asp Ala Glu Arg Leu Lys His Leu Ile Val  Thr Pro Ser
                    995                 1000                1005
Gly Cys  Gly Glu Gln Asn Met  Ile Gly Met Thr Pro  Thr Val Ile
    1010                1015                1020
Ala Val  His Tyr Leu Asp Glu  Thr Glu Gln Trp Glu  Lys Phe Gly
    1025                1030                1035
Leu Glu  Lys Arg Gln Gly Ala  Leu Glu Leu Ile Lys  Lys Gly Tyr
    1040                1045                1050
Thr Gln  Gln Leu Ala Phe Arg  Gln Pro Ser Ser Ala  Phe Ala Ala
    1055                1060                1065
Phe Val  Lys Arg Ala Pro Ser  Thr Trp Leu Thr Ala  Tyr Val Val
    1070                1075                1080
Lys Val  Phe Ser Leu Ala Val  Asn Leu Ile Ala Ile  Asp Ser Gln
    1085                1090                1095
Val Leu  Cys Gly Ala Val Lys  Trp Leu Ile Leu Glu  Lys Gln Lys
    1100                1105                1110
Pro Asp  Gly Val Phe Gln Glu  Asp Ala Pro Val Ile  His Gln Glu
    1115                1120                1125
Met Ile  Gly Gly Leu Arg Asn  Asn Asn Glu Lys Asp  Met Ala Leu
    1130                1135                1140
Thr Ala  Phe Val Leu Ile Ser  Leu Gln Glu Ala Lys  Asp Ile Cys
    1145                1150                1155
Glu Glu  Gln Val Asn Ser Leu  Pro Gly Ser Ile Thr  Lys Ala Gly
    1160                1165                1170
Asp Phe  Leu Glu Ala Asn Tyr  Met Asn Leu Gln Arg  Ser Tyr Thr
    1175                1180                1185
Val Ala  Ile Ala Gly Tyr Ala  Leu Ala Gln Met Gly  Arg Leu Lys
    1190                1195                1200
```

```
                        -continued

Gly Pro  Leu Leu Asn Lys Phe  Leu Thr Thr Ala Lys  Asp Lys Asn
    1205             1210                 1215

Arg Trp  Glu Asp Pro Gly Lys  Gln Leu Tyr Asn Val  Glu Ala Thr
    1220             1225                 1230

Ser Tyr  Ala Leu Leu Ala Leu  Leu Gln Leu Lys Asp  Phe Asp Phe
    1235             1240                 1245

Val Pro  Pro Val Val Arg Trp  Leu Asn Glu Gln Arg  Tyr Tyr Gly
    1250             1255                 1260

Gly Gly  Tyr Gly Ser Thr Gln  Ala Thr Phe Met Val  Phe Gln Ala
    1265             1270                 1275

Leu Ala  Gln Tyr Gln Lys Asp  Ala Pro Asp His Gln  Glu Leu Asn
    1280             1285                 1290

Leu Asp  Val Ser Leu Gln Leu  Pro Ser Arg Ser Ser  Lys Ile Thr
    1295             1300                 1305

His Arg  Ile His Trp Glu Ser  Ala Ser Leu Leu Arg  Ser Glu Glu
    1310             1315                 1320

Thr Lys  Glu Asn Glu Gly Phe  Thr Val Thr Ala Glu  Gly Lys Gly
    1325             1330                 1335

Gln Gly  Thr Leu Ser Val Val  Thr Met Tyr His Ala  Lys Ala Lys
    1340             1345                 1350

Asp Gln  Leu Thr Cys Asn Lys  Phe Asp Leu Lys Val  Thr Ile Lys
    1355             1360                 1365

Pro Ala  Pro Glu Thr Glu Lys  Arg Pro Gln Asp Ala  Lys Asn Thr
    1370             1375                 1380

Met Ile  Leu Glu Ile Cys Thr  Arg Tyr Arg Gly Asp  Gln Asp Ala
    1385             1390                 1395

Thr Met  Ser Ile Leu Asp Ile  Ser Met Met Thr Gly  Phe Ala Pro
    1400             1405                 1410

Asp Thr  Asp Asp Leu Lys Gln  Leu Ala Asn Gly Val  Asp Arg Tyr
    1415             1420                 1425

Ile Ser  Lys Tyr Glu Leu Asp  Lys Ala Phe Ser Asp  Arg Asn Thr
    1430             1435                 1440

Leu Ile  Ile Tyr Leu Asp Lys  Val Ser His Ser Glu  Asp Asp Cys
    1445             1450                 1455

Leu Ala  Phe Lys Val His Gln  Tyr Phe Asn Val Glu  Leu Ile Gln
    1460             1465                 1470

Pro Gly  Ala Val Lys Val Tyr  Ala Tyr Tyr Asn Leu  Glu Glu Ser
    1475             1480                 1485

Cys Thr  Arg Phe Tyr His Pro  Glu Lys Glu Asp Gly  Lys Leu Asn
    1490             1495                 1500

Lys Leu  Cys Arg Asp Glu Leu  Cys Arg Cys Ala Glu  Glu Asn Cys
    1505             1510                 1515

Phe Ile  Gln Lys Ser Asp Asp  Lys Val Thr Leu Glu  Glu Arg Leu
    1520             1525                 1530

Asp Lys  Ala Cys Glu Pro Gly  Val Asp Tyr Val Tyr  Lys Thr Arg
    1535             1540                 1545

Leu Val  Lys Val Gln Leu Ser  Asn Asp Phe Asp Glu  Tyr Ile Met
    1550             1555                 1560

Ala Ile  Glu Gln Thr Ile Lys  Ser Gly Ser Asp Glu  Val Gln Val
    1565             1570                 1575

Gly Gln  Gln Arg Thr Phe Ile  Ser Pro Ile Lys Cys  Arg Glu Ala
    1580             1585                 1590

Leu Lys  Leu Glu Glu Lys Lys  His Tyr Leu Met Trp  Gly Leu Ser
    1595             1600                 1605
```

Ser Asp Phe Trp Gly Glu Lys Pro Asn Leu Ser Tyr Ile Ile Gly
    1610                1615                1620

Lys Asp Thr Trp Val Glu His Trp Pro Glu Glu Asp Glu Cys Gln
    1625                1630                1635

Asp Glu Glu Asn Gln Lys Gln Cys Gln Asp Leu Gly Ala Phe Thr
    1640                1645                1650

Glu Ser Met Val Val Phe Gly Cys Pro Asn
    1655                1660

<210> SEQ ID NO 110
<211> LENGTH: 1744
<212> TYPE: PRT
<213> ORGANISM: Homo sapiens

<400> SEQUENCE: 110

Met Arg Leu Leu Trp Gly Leu Ile Trp Ala Ser Ser Phe Phe Thr Leu
1               5                   10                  15

Ser Leu Gln Lys Pro Arg Leu Leu Leu Phe Ser Pro Ser Val Val His
                20                  25                  30

Leu Gly Val Pro Leu Ser Val Gly Val Gln Leu Gln Asp Val Pro Arg
            35                  40                  45

Gly Gln Val Val Lys Gly Ser Val Phe Leu Arg Asn Pro Ser Arg Asn
        50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
    130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
    210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
        275                 280                 285

Glu Asp Gly Lys Lys Thr Phe Phe Arg Gly Leu Glu Ser Gln Thr Lys
    290                 295                 300

Leu Val Asn Gly Gln Ser His Ile Ser Leu Ser Lys Ala Glu Phe Gln
305                 310                 315                 320

```
Asp Ala Leu Glu Lys Leu Asn Met Gly Ile Thr Asp Leu Gln Gly Leu
            325                 330                 335

Arg Leu Tyr Val Ala Ala Ile Ile Glu Ser Pro Gly Gly Glu Met
            340                 345                 350

Glu Glu Ala Glu Leu Thr Ser Trp Tyr Phe Val Ser Ser Pro Phe Ser
            355                 360                 365

Leu Asp Leu Ser Lys Thr Lys Arg His Leu Val Pro Gly Ala Pro Phe
            370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
            405                 410                 415

Glu Val Gln Asp Ile Gln Gln Asn Thr Asp Gly Ser Gly Gln Val Ser
            420                 425                 430

Ile Pro Ile Ile Ile Pro Gln Thr Ile Ser Glu Leu Gln Leu Ser Val
            435                 440                 445

Ser Ala Gly Ser Pro His Pro Ala Ile Ala Arg Leu Thr Val Ala Ala
            450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
            485                 490                 495

Gly Ser Gly Ala Thr Phe Ser His Tyr Tyr Tyr Met Ile Leu Ser Arg
            500                 505                 510

Gly Gln Ile Val Phe Met Asn Arg Glu Pro Lys Arg Thr Leu Thr Ser
            515                 520                 525

Val Ser Val Phe Val Asp His His Leu Ala Pro Ser Phe Tyr Phe Val
            530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
            565                 570                 575

Gly Ala Lys Gln Tyr Arg Asn Gly Glu Ser Val Lys Leu His Leu Glu
            580                 585                 590

Thr Asp Ser Leu Ala Leu Val Ala Leu Gly Ala Leu Asp Thr Ala Leu
            595                 600                 605

Tyr Ala Ala Gly Ser Lys Ser His Lys Pro Leu Asn Met Gly Lys Val
            610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
            645                 650                 655

Gly Asp Gln Trp Thr Leu Ser Arg Lys Arg Leu Ser Cys Pro Lys Glu
            660                 665                 670

Lys Thr Thr Arg Lys Lys Arg Asn Val Asn Phe Gln Lys Ala Ile Asn
            675                 680                 685

Glu Lys Leu Gly Gln Tyr Ala Ser Pro Thr Ala Lys Arg Cys Cys Gln
            690                 695                 700

Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
            725                 730                 735

Gln Phe Ala Glu Ser Leu Arg Lys Lys Ser Arg Asp Lys Gly Gln Ala
```

```
                     740                 745                 750
Gly Leu Gln Arg Ala Leu Glu Ile Leu Gln Glu Glu Asp Leu Ile Asp
                 755                 760                 765
Glu Asp Asp Ile Pro Val Arg Ser Phe Phe Pro Glu Asn Trp Leu Trp
             770                 775                 780
Arg Val Glu Thr Val Asp Arg Phe Gln Ile Leu Thr Leu Trp Leu Pro
785                 790                 795                 800
Asp Ser Leu Thr Thr Trp Glu Ile His Gly Leu Ser Leu Ser Lys Thr
                 805                 810                 815
Lys Gly Leu Cys Val Ala Thr Pro Val Gln Leu Arg Val Phe Arg Glu
             820                 825                 830
Phe His Leu His Leu Arg Leu Pro Met Ser Val Arg Arg Phe Glu Gln
             835                 840                 845
Leu Glu Leu Arg Pro Val Leu Tyr Asn Tyr Leu Asp Lys Asn Leu Thr
             850                 855                 860
Val Ser Val His Val Ser Pro Val Glu Gly Leu Cys Leu Ala Gly Gly
865                 870                 875                 880
Gly Gly Leu Ala Gln Gln Val Leu Val Pro Ala Gly Ser Ala Arg Pro
                 885                 890                 895
Val Ala Phe Ser Val Val Pro Thr Ala Ala Ala Val Ser Leu Lys
                 900                 905                 910
Val Val Ala Arg Gly Ser Phe Glu Phe Pro Val Gly Asp Ala Val Ser
             915                 920                 925
Lys Val Leu Gln Ile Glu Lys Glu Gly Ala Ile His Arg Glu Glu Leu
             930                 935                 940
Val Tyr Glu Leu Asn Pro Leu Asp His Arg Gly Arg Thr Leu Glu Ile
945                 950                 955                 960
Pro Gly Asn Ser Asp Pro Asn Met Ile Pro Asp Gly Asp Phe Asn Ser
                 965                 970                 975
Tyr Val Arg Val Thr Ala Ser Asp Pro Leu Asp Thr Leu Gly Ser Glu
             980                 985                 990
Gly Ala Leu Ser Pro Gly Gly Val Ala Ser Leu Leu Arg Leu Pro Arg
             995                 1000                1005
Gly Cys Gly Glu Gln Thr Met Ile Tyr Leu Ala Pro Thr Leu Ala
             1010                1015                1020
Ala Ser Arg Tyr Leu Asp Lys Thr Glu Gln Trp Ser Thr Leu Pro
             1025                1030                1035
Pro Glu Thr Lys Asp His Ala Val Asp Leu Ile Gln Lys Gly Tyr
             1040                1045                1050
Met Arg Ile Gln Gln Phe Arg Lys Ala Asp Gly Ser Tyr Ala Ala
             1055                1060                1065
Trp Leu Ser Arg Asp Ser Ser Thr Trp Leu Thr Ala Phe Val Leu
             1070                1075                1080
Lys Val Leu Ser Leu Ala Gln Glu Gln Val Gly Gly Ser Pro Glu
             1085                1090                1095
Lys Leu Gln Glu Thr Ser Asn Trp Leu Leu Ser Gln Gln Gln Ala
             1100                1105                1110
Asp Gly Ser Phe Gln Asp Pro Cys Pro Val Leu Asp Arg Ser Met
             1115                1120                1125
Gln Gly Gly Leu Val Gly Asn Asp Glu Thr Val Ala Leu Thr Ala
             1130                1135                1140
Phe Val Thr Ile Ala Leu His His Gly Leu Ala Val Phe Gln Asp
             1145                1150                1155
```

```
Glu Gly Ala Glu Pro Leu Lys Gln Arg Val Glu Ala Ser Ile Ser
1160            1165                1170

Lys Ala Asn Ser Phe Leu Gly Glu Lys Ala Ser Ala Gly Leu Leu
1175            1180                1185

Gly Ala His Ala Ala Ala Ile Thr Ala Tyr Ala Leu Ser Leu Thr
1190            1195                1200

Lys Ala Pro Val Asp Leu Leu Gly Val Ala His Asn Asn Leu Met
1205            1210                1215

Ala Met Ala Gln Glu Thr Gly Asp Asn Leu Tyr Trp Gly Ser Val
1220            1225                1230

Thr Gly Ser Gln Ser Asn Ala Val Ser Pro Thr Pro Ala Pro Arg
1235            1240                1245

Asn Pro Ser Asp Pro Met Pro Gln Ala Pro Ala Leu Trp Ile Glu
1250            1255                1260

Thr Thr Ala Tyr Ala Leu Leu His Leu Leu His Glu Gly Lys
1265            1270                1275

Ala Glu Met Ala Asp Gln Ala Ser Ala Trp Leu Thr Arg Gln Gly
1280            1285                1290

Ser Phe Gln Gly Gly Phe Arg Ser Thr Gln Asp Thr Val Ile Ala
1295            1300                1305

Leu Asp Ala Leu Ser Ala Tyr Trp Ile Ala Ser His Thr Thr Glu
1310            1315                1320

Glu Arg Gly Leu Asn Val Thr Leu Ser Ser Thr Gly Arg Asn Gly
1325            1330                1335

Phe Lys Ser His Ala Leu Gln Leu Asn Asn Arg Gln Ile Arg Gly
1340            1345                1350

Leu Glu Glu Glu Leu Gln Phe Ser Leu Gly Ser Lys Ile Asn Val
1355            1360                1365

Lys Val Gly Gly Asn Ser Lys Gly Thr Leu Lys Val Leu Arg Thr
1370            1375                1380

Tyr Asn Val Leu Asp Met Lys Asn Thr Thr Cys Gln Asp Leu Gln
1385            1390                1395

Ile Glu Val Thr Val Lys Gly His Val Glu Tyr Thr Met Glu Ala
1400            1405                1410

Asn Glu Asp Tyr Glu Asp Tyr Glu Tyr Asp Glu Leu Pro Ala Lys
1415            1420                1425

Asp Asp Pro Asp Ala Pro Leu Gln Pro Val Thr Pro Leu Gln Leu
1430            1435                1440

Phe Glu Gly Arg Arg Asn Arg Arg Arg Arg Glu Ala Pro Lys Val
1445            1450                1455

Val Glu Glu Gln Glu Ser Arg Val His Tyr Thr Val Cys Ile Trp
1460            1465                1470

Arg Asn Gly Lys Val Gly Leu Ser Gly Met Ala Ile Ala Asp Val
1475            1480                1485

Thr Leu Leu Ser Gly Phe His Ala Leu Arg Ala Asp Leu Glu Lys
1490            1495                1500

Leu Thr Ser Leu Ser Asp Arg Tyr Val Ser His Phe Glu Thr Glu
1505            1510                1515

Gly Pro His Val Leu Leu Tyr Phe Asp Ser Val Pro Thr Ser Arg
1520            1525                1530

Glu Cys Val Gly Phe Glu Ala Val Gln Glu Val Pro Val Gly Leu
1535            1540                1545

Val Gln Pro Ala Ser Ala Thr Leu Tyr Asp Tyr Tyr Asn Pro Glu
1550            1555                1560
```

-continued

Arg Arg Cys Ser Val Phe Tyr Gly Ala Pro Ser Lys Ser Arg Leu
1565                1570                1575

Leu Ala Thr Leu Cys Ser Ala Glu Val Cys Gln Cys Ala Glu Gly
1580                1585                1590

Lys Cys Pro Arg Gln Arg Arg Ala Leu Glu Arg Gly Leu Gln Asp
1595                1600                1605

Glu Asp Gly Tyr Arg Met Lys Phe Ala Cys Tyr Tyr Pro Arg Val
1610                1615                1620

Glu Tyr Gly Phe Gln Val Lys Val Leu Arg Glu Asp Ser Arg Ala
1625                1630                1635

Ala Phe Arg Leu Phe Glu Thr Lys Ile Thr Gln Val Leu His Phe
1640                1645                1650

Thr Lys Asp Val Lys Ala Ala Asn Gln Met Arg Asn Phe Leu
1655                1660                1665

Val Arg Ala Ser Cys Arg Leu Arg Leu Glu Pro Gly Lys Glu Tyr
1670                1675                1680

Leu Ile Met Gly Leu Asp Gly Ala Thr Tyr Asp Leu Glu Gly His
1685                1690                1695

Pro Gln Tyr Leu Leu Asp Ser Asn Ser Trp Ile Glu Glu Met Pro
1700                1705                1710

Ser Glu Arg Leu Cys Arg Ser Thr Arg Gln Arg Ala Ala Cys Ala
1715                1720                1725

Gln Leu Asn Asp Phe Leu Gln Glu Tyr Gly Thr Gln Gly Cys Gln
1730                1735                1740

Val

<210> SEQ ID NO 111
<211> LENGTH: 930
<212> TYPE: PRT
<213> ORGANISM: Homo sapiens

<400> SEQUENCE: 111

Met Lys Pro Pro Arg Pro Val Arg Thr Cys Ser Lys Val Leu Val Leu
1               5                   10                  15

Leu Ser Leu Leu Ala Ile His Gln Thr Thr Ala Glu Lys Asn Gly
                20                  25                  30

Ile Asp Ile Tyr Ser Leu Thr Val Asp Ser Arg Val Ser Ser Arg Phe
                35                  40                  45

Ala His Thr Val Val Thr Ser Arg Val Val Asn Arg Ala Asn Thr Val
            50                  55                  60

Gln Glu Ala Thr Phe Gln Met Glu Leu Pro Lys Lys Ala Phe Ile Thr
65                  70                  75                  80

Asn Phe Ser Met Asn Ile Asp Gly Met Thr Tyr Pro Gly Ile Ile Lys
                85                  90                  95

Glu Lys Ala Glu Ala Gln Ala Gln Tyr Ser Ala Ala Val Ala Lys Gly
                100                 105                 110

Lys Ser Ala Gly Leu Val Lys Ala Thr Gly Arg Asn Met Glu Gln Phe
            115                 120                 125

Gln Val Ser Val Ser Val Ala Pro Asn Ala Lys Ile Thr Phe Glu Leu
        130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

-continued

```
His Ile Phe Glu Pro Gln Gly Ile Ser Phe Leu Glu Thr Glu Ser Thr
            180                 185                 190

Phe Met Thr Asn Gln Leu Val Asp Ala Leu Thr Thr Trp Gln Asn Lys
        195                 200                 205

Thr Lys Ala His Ile Arg Phe Lys Pro Thr Leu Ser Gln Gln Gln Lys
210                 215                 220

Ser Pro Glu Gln Gln Glu Thr Val Leu Asp Gly Asn Leu Ile Ile Arg
225                 230                 235                 240

Tyr Asp Val Asp Arg Ala Ile Ser Gly Gly Ser Ile Gln Ile Glu Asn
                245                 250                 255

Gly Tyr Phe Val His Tyr Phe Ala Pro Glu Gly Leu Thr Met Pro
            260                 265                 270

Lys Asn Val Val Phe Val Ile Asp Lys Ser Gly Ser Met Ser Gly Arg
        275                 280                 285

Lys Ile Gln Gln Thr Arg Glu Ala Leu Ile Lys Ile Leu Asp Asp Leu
290                 295                 300

Ser Pro Arg Asp Gln Phe Asn Leu Ile Val Phe Ser Thr Glu Ala Thr
305                 310                 315                 320

Gln Trp Arg Pro Ser Leu Val Pro Ala Ser Ala Glu Asn Val Asn Lys
                325                 330                 335

Ala Arg Ser Phe Ala Ala Gly Ile Gln Ala Leu Gly Gly Thr Asn Ile
            340                 345                 350

Asn Asp Ala Met Leu Met Ala Val Gln Leu Leu Asp Ser Ser Asn Gln
        355                 360                 365

Glu Glu Arg Leu Pro Glu Gly Ser Val Ser Leu Ile Ile Leu Leu Thr
370                 375                 380

Asp Gly Asp Pro Thr Val Gly Glu Thr Asn Pro Arg Ser Ile Gln Asn
385                 390                 395                 400

Asn Val Arg Glu Ala Val Ser Gly Arg Tyr Ser Leu Phe Cys Leu Gly
                405                 410                 415

Phe Gly Phe Asp Val Ser Tyr Ala Phe Leu Glu Lys Leu Ala Leu Asp
            420                 425                 430

Asn Gly Gly Leu Ala Arg Arg Ile His Glu Asp Ser Asp Ser Ala Leu
        435                 440                 445

Gln Leu Gln Asp Phe Tyr Gln Glu Val Ala Asn Pro Leu Leu Thr Ala
450                 455                 460

Val Thr Phe Glu Tyr Pro Ser Asn Ala Val Glu Glu Val Thr Gln Asn
465                 470                 475                 480

Asn Phe Arg Leu Leu Phe Lys Gly Ser Glu Met Val Val Ala Gly Lys
                485                 490                 495

Leu Gln Asp Arg Gly Pro Asp Val Leu Thr Ala Thr Val Ser Gly Lys
            500                 505                 510

Leu Pro Thr Gln Asn Ile Thr Phe Gln Thr Glu Ser Ser Val Ala Glu
        515                 520                 525

Gln Glu Ala Glu Phe Gln Ser Pro Lys Tyr Ile Phe His Asn Phe Met
530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
                565                 570                 575

Asn Leu Ser Leu Ala Tyr Ser Phe Val Thr Pro Leu Thr Ser Met Val
            580                 585                 590

Val Thr Lys Pro Asp Asp Gln Gln Ser Gln Val Ala Glu Lys Pro
        595                 600                 605
```

```
Met Glu Gly Glu Ser Arg Asn Arg Asn Val His Ser Gly Ser Thr Phe
610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
                645                 650                 655

Arg Met Asn Phe Arg Pro Gly Val Leu Ser Ser Arg Gln Leu Gly Leu
            660                 665                 670

Pro Gly Pro Pro Asp Val Pro Asp His Ala Ala Tyr His Pro Phe Arg
            675                 680                 685

Arg Leu Ala Ile Leu Pro Ala Ser Ala Pro Ala Thr Ser Asn Pro
690                 695                 700

Asp Pro Ala Val Ser Arg Val Met Asn Met Lys Ile Glu Glu Thr Thr
705                 710                 715                 720

Met Thr Thr Gln Thr Pro Ala Pro Ile Gln Ala Pro Ser Ala Ile Leu
                725                 730                 735

Pro Leu Pro Gly Gln Ser Val Glu Arg Leu Cys Val Asp Pro Arg His
            740                 745                 750

Arg Gln Gly Pro Val Asn Leu Leu Ser Asp Pro Glu Gln Gly Val Glu
            755                 760                 765

Val Thr Gly Gln Tyr Glu Arg Glu Lys Ala Gly Phe Ser Trp Ile Glu
770                 775                 780

Val Thr Phe Lys Asn Pro Leu Val Trp Val His Ala Ser Pro Glu His
785                 790                 795                 800

Val Val Val Thr Arg Asn Arg Arg Ser Ser Ala Tyr Lys Trp Lys Glu
                805                 810                 815

Thr Leu Phe Ser Val Met Pro Gly Leu Lys Met Thr Met Asp Lys Thr
            820                 825                 830

Gly Leu Leu Leu Leu Ser Asp Pro Asp Lys Val Thr Ile Gly Leu Leu
            835                 840                 845

Phe Trp Asp Gly Arg Gly Glu Gly Leu Arg Leu Leu Leu Arg Asp Thr
850                 855                 860

Asp Arg Phe Ser Ser His Val Gly Gly Thr Leu Gly Gln Phe Tyr Gln
865                 870                 875                 880

Glu Val Leu Trp Gly Ser Pro Ala Ala Ser Asp Asp Gly Arg Arg Thr
                885                 890                 895

Leu Arg Val Gln Gly Asn Asp His Ser Ala Thr Arg Glu Arg Arg Leu
            900                 905                 910

Asp Tyr Gln Glu Gly Pro Pro Gly Val Glu Ile Ser Cys Trp Ser Val
            915                 920                 925

Glu Leu
    930

<210> SEQ ID NO 112
<211> LENGTH: 644
<212> TYPE: PRT
<213> ORGANISM: Homo sapiens

<400> SEQUENCE: 112

Met Pro Lys Asn Val Val Phe Val Ile Asp Lys Ser Gly Ser Met Ser
1               5                   10                  15

Gly Arg Lys Ile Gln Gln Thr Arg Glu Ala Leu Ile Lys Ile Leu Asp
            20                  25                  30

Asp Leu Ser Pro Arg Asp Gln Phe Asn Leu Ile Val Phe Ser Thr Glu
        35                  40                  45
```

```
Ala Thr Gln Trp Arg Pro Ser Leu Val Pro Ala Ser Ala Glu Asn Val
     50                  55                  60

Asn Lys Ala Arg Ser Phe Ala Ala Gly Ile Gln Ala Leu Gly Gly Thr
65                  70                  75                  80

Asn Ile Asn Asp Ala Met Leu Met Ala Val Gln Leu Leu Asp Ser Ser
                    85                  90                  95

Asn Gln Glu Glu Arg Leu Pro Glu Gly Ser Val Ser Leu Ile Ile Leu
                100                 105                 110

Leu Thr Asp Gly Asp Pro Thr Val Gly Glu Thr Asn Pro Arg Ser Ile
            115                 120                 125

Gln Asn Asn Val Arg Glu Ala Val Ser Gly Arg Tyr Ser Leu Phe Cys
        130                 135                 140

Leu Gly Phe Gly Phe Asp Val Ser Tyr Ala Phe Leu Glu Lys Leu Ala
145                 150                 155                 160

Leu Asp Asn Gly Gly Leu Ala Arg Arg Ile His Glu Asp Ser Asp Ser
                165                 170                 175

Ala Leu Gln Leu Gln Asp Phe Tyr Gln Glu Val Ala Asn Pro Leu Leu
                180                 185                 190

Thr Ala Val Thr Phe Glu Tyr Pro Ser Asn Ala Val Glu Glu Val Thr
            195                 200                 205

Gln Asn Asn Phe Arg Leu Leu Phe Lys Gly Ser Glu Met Val Val Ala
        210                 215                 220

Gly Lys Leu Gln Asp Arg Gly Pro Asp Val Leu Thr Ala Thr Val Ser
225                 230                 235                 240

Gly Lys Leu Pro Thr Gln Asn Ile Thr Phe Gln Thr Glu Ser Ser Val
                245                 250                 255

Ala Glu Gln Glu Ala Glu Phe Gln Ser Pro Lys Tyr Ile Phe His Asn
                260                 265                 270

Phe Met Glu Arg Leu Trp Ala Tyr Leu Thr Ile Gln Gln Leu Leu Glu
            275                 280                 285

Gln Thr Val Ser Ala Ser Asp Ala Asp Gln Gln Ala Leu Arg Asn Gln
        290                 295                 300

Ala Leu Asn Leu Ser Leu Ala Tyr Ser Phe Val Thr Pro Leu Thr Ser
305                 310                 315                 320

Met Val Val Thr Lys Pro Asp Asp Gln Glu Gln Ser Gln Val Ala Glu
                325                 330                 335

Lys Pro Met Glu Gly Glu Ser Arg Asn Arg Asn Val His Ser Ala Gly
            340                 345                 350

Ala Ala Gly Ser Arg Met Asn Phe Arg Pro Gly Val Leu Ser Ser Arg
        355                 360                 365

Gln Leu Gly Leu Pro Gly Pro Pro Asp Val Pro Asp His Ala Ala Tyr
    370                 375                 380

His Pro Phe Arg Arg Leu Ala Ile Leu Pro Ala Ser Ala Pro Ala
385                 390                 395                 400

Thr Ser Asn Pro Asp Pro Ala Val Ser Arg Val Met Asn Met Lys Ile
                405                 410                 415

Glu Glu Thr Thr Met Thr Thr Gln Thr Pro Ala Cys Pro Ser Cys Ser
            420                 425                 430

Arg Ser Arg Ala Pro Ala Val Pro Ala Pro Ile Gln Ala Pro Ser Ala
        435                 440                 445

Ile Leu Pro Leu Pro Gly Gln Ser Val Glu Arg Leu Cys Val Asp Pro
450                 455                 460

Arg His Arg Gln Gly Pro Val Asn Leu Leu Ser Asp Pro Glu Gln Gly
```

```
                465                 470                 475                 480
Val Glu Val Thr Gly Gln Tyr Glu Arg Glu Lys Ala Gly Phe Ser Trp
                    485                 490                 495

Ile Glu Val Thr Phe Lys Asn Pro Leu Val Trp Val His Ala Ser Pro
                    500                 505                 510

Glu His Val Val Thr Arg Asn Arg Arg Ser Ser Ala Tyr Lys Trp
                515                 520                 525

Lys Glu Thr Leu Phe Ser Val Met Pro Gly Leu Lys Met Thr Met Asp
                530                 535                 540

Lys Thr Gly Leu Leu Leu Ser Asp Pro Asp Lys Val Thr Ile Gly
545                 550                 555                 560

Leu Leu Phe Trp Asp Gly Arg Gly Glu Gly Leu Arg Leu Leu Arg
                    565                 570                 575

Asp Thr Asp Arg Phe Ser Ser His Val Gly Gly Thr Leu Gly Gln Phe
                    580                 585                 590

Tyr Gln Glu Val Leu Trp Gly Ser Pro Ala Ala Ser Asp Asp Gly Arg
                595                 600                 605

Arg Thr Leu Arg Val Gln Gly Asn Asp His Ser Ala Thr Arg Glu Arg
                610                 615                 620

Arg Leu Asp Tyr Gln Glu Gly Pro Pro Gly Val Glu Ile Ser Cys Trp
625                 630                 635                 640

Ser Val Glu Leu

<210> SEQ ID NO 113
<211> LENGTH: 267
<212> TYPE: PRT
<213> ORGANISM: Homo sapiens

<400> SEQUENCE: 113

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
                20                  25                  30

Asp Arg Val Lys Asp Leu Ala Thr Val Tyr Val Asp Val Leu Lys Asp
                35                  40                  45

Ser Gly Arg Asp Tyr Val Ser Gln Phe Glu Gly Ser Ala Leu Gly Lys
            50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
                100                 105                 110

Asp Leu Glu Glu Val Lys Ala Lys Val Gln Pro Tyr Leu Asp Asp Phe
            115                 120                 125

Gln Lys Lys Trp Gln Glu Glu Met Glu Leu Tyr Arg Gln Lys Val Glu
        130                 135                 140

Pro Leu Arg Ala Glu Leu Gly Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
                180                 185                 190

Glu Leu Arg Gln Arg Leu Ala Ala Arg Leu Glu Ala Leu Lys Glu Asn
            195                 200                 205
```

```
Gly Gly Ala Arg Leu Ala Glu Tyr His Ala Lys Ala Thr Glu His Leu
            210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                    245                 250                 255

Leu Glu Glu Tyr Thr Lys Lys Leu Asn Thr Gln
            260                 265

<210> SEQ ID NO 114
<211> LENGTH: 396
<212> TYPE: PRT
<213> ORGANISM: Homo sapiens

<400> SEQUENCE: 114

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
            20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
    50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95

Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
            115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
            195                 200                 205

Lys Val Lys Ile Asp Gln Thr Val Glu Glu Leu Arg Arg Ser Leu Ala
    210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
            275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320
```

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Gln Gln Gln
370                 375                 380

Gln Glu Gln Val Gln Met Leu Ala Pro Glu Leu Ser
385                 390                 395

<210> SEQ ID NO 115
<211> LENGTH: 317
<212> TYPE: PRT
<213> ORGANISM: Homo sapiens

<400> SEQUENCE: 115

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
290                 295                 300

Val Gly Thr Ser Ala Ala Pro Val Pro Ser Asp Asn His
305                 310                 315

<210> SEQ ID NO 116
<211> LENGTH: 16
<212> TYPE: PRT
<213> ORGANISM: Homo sapiens

<400> SEQUENCE: 116

Ala Asp Ser Gly Glu Gly Asp Phe Leu Ala Glu Gly Gly Gly Val Arg
1               5                   10                  15

<210> SEQ ID NO 117
<211> LENGTH: 16
<212> TYPE: PRT
<213> ORGANISM: Homo sapiens

<400> SEQUENCE: 117

Ala Asp Ser Gly Glu Gly Asp Phe Leu Ala Glu Gly Gly Gly Val Arg
1               5                   10                  15

<210> SEQ ID NO 118
<211> LENGTH: 16
<212> TYPE: PRT
<213> ORGANISM: Homo sapiens

<400> SEQUENCE: 118

Ala Asp Ser Gly Glu Gly Asp Phe Leu Ala Glu Gly Gly Gly Val Arg
1               5                   10                  15

<210> SEQ ID NO 119
<211> LENGTH: 30
<212> TYPE: PRT
<213> ORGANISM: Homo sapiens

<400> SEQUENCE: 119

Lys Ser Ser Ser Tyr Ser Lys Gln Phe Thr Ser Ser Thr Ser Tyr Asn
1               5                   10                  15

Arg Gly Asp Ser Thr Phe Glu Ser Lys Ser Tyr Lys Met Ala
            20                  25                  30

<210> SEQ ID NO 120
<211> LENGTH: 29
<212> TYPE: PRT
<213> ORGANISM: Homo sapiens

<400> SEQUENCE: 120

Lys Ser Ser Ser Tyr Ser Lys Gln Phe Thr Ser Ser Thr Ser Tyr Asn
1               5                   10                  15

Arg Gly Asp Ser Thr Phe Glu Ser Lys Ser Tyr Lys Met
            20                  25

<210> SEQ ID NO 121
<211> LENGTH: 27
<212> TYPE: PRT
<213> ORGANISM: Homo sapiens

<400> SEQUENCE: 121

Lys Ser Ser Ser Tyr Ser Lys Gln Phe Thr Ser Ser Thr Ser Tyr Asn
1               5                   10                  15

Arg Gly Asp Ser Thr Phe Glu Ser Lys Ser Tyr
            20                  25

<210> SEQ ID NO 122
<211> LENGTH: 26
<212> TYPE: PRT
<213> ORGANISM: Homo sapiens

<400> SEQUENCE: 122

Lys Ser Ser Ser Tyr Ser Lys Gln Phe Thr Ser Ser Thr Ser Tyr Asn
1               5                   10                  15

Arg Gly Asp Ser Thr Phe Glu Ser Lys Ser
            20                  25

<210> SEQ ID NO 123
<211> LENGTH: 24
<212> TYPE: PRT
<213> ORGANISM: Homo sapiens

<400> SEQUENCE: 123

Lys Ser Ser Ser Tyr Ser Lys Gln Phe Thr Ser Ser Thr Ser Tyr Asn
1               5                   10                  15

Arg Gly Asp Ser Thr Phe Glu Ser
            20

<210> SEQ ID NO 124
<211> LENGTH: 29
<212> TYPE: PRT
<213> ORGANISM: Homo sapiens

<400> SEQUENCE: 124

Arg Gly Ser Glu Ser Gly Ile Phe Thr Asn Thr Lys Glu Ser Ser Ser
1               5                   10                  15

His His Pro Gly Ile Ala Glu Phe Pro Ser Arg Gly Lys
            20                  25

<210> SEQ ID NO 125
<211> LENGTH: 31
<212> TYPE: PRT
<213> ORGANISM: Homo sapiens

<400> SEQUENCE: 125

Ser Tyr Lys Met Ala Asp Glu Ala Gly Ser Glu Ala Asp His Glu Gly
1               5                   10                  15

Thr His Ser Thr Lys Arg Gly His Ala Lys Ser Arg Pro Val Arg
            20                  25                  30

<210> SEQ ID NO 126
<211> LENGTH: 26
<212> TYPE: PRT
<213> ORGANISM: Homo sapiens

<400> SEQUENCE: 126

Asp Glu Ala Gly Ser Glu Ala Asp His Glu Gly Thr His Ser Thr Lys
1               5                   10                  15

Arg Gly His Ala Lys Ser Arg Pro Val Arg
            20                  25

<210> SEQ ID NO 127
<211> LENGTH: 17
<212> TYPE: PRT
<213> ORGANISM: Homo sapiens

<400> SEQUENCE: 127

Ser Ser Lys Ile Thr His Arg Ile His Trp Glu Ser Ala Ser Leu Leu
1               5                   10                  15

Arg

<210> SEQ ID NO 128
<211> LENGTH: 11
<212> TYPE: PRT
<213> ORGANISM: Homo sapiens

<400> SEQUENCE: 128

His Arg Ile His Trp Glu Ser Ala Ser Leu Leu
1               5                   10

<210> SEQ ID NO 129
<211> LENGTH: 18
<212> TYPE: PRT
<213> ORGANISM: Homo sapiens

<400> SEQUENCE: 129

Ser Ser Lys Ile Thr His Arg Ile His Val Ile Glu Ser Ala Ser Leu
1               5                   10                  15

Leu Arg

<210> SEQ ID NO 130
<211> LENGTH: 11
<212> TYPE: PRT
<213> ORGANISM: Homo sapiens

<400> SEQUENCE: 130

Asn Gly Phe Lys Ser His Ala Leu Gln Leu Asn
1               5                   10

<210> SEQ ID NO 131
<211> LENGTH: 14
<212> TYPE: PRT
<213> ORGANISM: Homo sapiens

<400> SEQUENCE: 131

Gly Pro Pro Asp Val Pro Asp His Ala Ala Tyr His Pro Phe
1               5                   10

<210> SEQ ID NO 132
<211> LENGTH: 15
<212> TYPE: PRT
<213> ORGANISM: Homo sapiens

<400> SEQUENCE: 132

Pro Gly Pro Pro Asp Val Pro Asp His Ala Ala Tyr His Pro Phe
1               5                   10                  15

<210> SEQ ID NO 133
<211> LENGTH: 29
<212> TYPE: PRT
<213> ORGANISM: Homo sapiens

<400> SEQUENCE: 133

Met Phe Arg Pro Gly Val Leu Ser Ser Arg Gln Leu Gly Leu Pro Gly
1               5                   10                  15

Pro Pro Asp Val Pro Asp His Ala Ala Tyr His Pro Phe
            20                  25

<210> SEQ ID NO 134
<211> LENGTH: 12
<212> TYPE: PRT
<213> ORGANISM: Homo sapiens

<400> SEQUENCE: 134

```
Arg Pro His Phe Phe Pro Lys Ser Arg Ile Val
1               5                   10
```

<210> SEQ ID NO 135
<211> LENGTH: 30
<212> TYPE: PRT
<213> ORGANISM: Homo sapiens

<400> SEQUENCE: 135

```
Ser Tyr Lys Met Ala Asp Glu Ala Gly Ser Glu Ala Asp His Glu Gly
1               5                   10                  15

Thr His Ser Thr Lys Arg Gly His Ala Lys Ser Arg Pro Val
            20                  25                  30
```

<210> SEQ ID NO 136
<211> LENGTH: 30
<212> TYPE: PRT
<213> ORGANISM: Homo sapiens

<400> SEQUENCE: 136

```
Gly Leu Glu Glu Glu Leu Gln Phe Ser Leu Gly Ser Lys Ile Asn Val
1               5                   10                  15

Lys Val Gly Gly Asn Ser Lys Gly Thr Leu Lys Val Leu Arg
            20                  25                  30
```

<210> SEQ ID NO 137
<211> LENGTH: 27
<212> TYPE: PRT
<213> ORGANISM: Homo sapiens

<400> SEQUENCE: 137

```
Pro Gly Val Leu Ser Ser Arg Gln Leu Gly Leu Pro Gly Pro Pro Asp
1               5                   10                  15

Val Pro Asp His Ala Ala Tyr His Pro Phe Arg
            20                  25
```

<210> SEQ ID NO 138
<211> LENGTH: 26
<212> TYPE: PRT
<213> ORGANISM: Homo sapiens

<400> SEQUENCE: 138

```
Gly Val Leu Ser Ser Arg Gln Leu Gly Leu Pro Gly Pro Pro Asp Val
1               5                   10                  15

Pro Asp His Ala Ala Tyr His Pro Phe Arg
            20                  25
```

<210> SEQ ID NO 139
<211> LENGTH: 25
<212> TYPE: PRT
<213> ORGANISM: Homo sapiens

<400> SEQUENCE: 139

```
Val Leu Ser Ser Arg Gln Leu Gly Leu Pro Gly Pro Pro Asp Val Pro
1               5                   10                  15

Asp His Ala Ala Tyr His Pro Phe Arg
            20                  25
```

<210> SEQ ID NO 140
<211> LENGTH: 24
<212> TYPE: PRT
<213> ORGANISM: Homo sapiens

```
<400> SEQUENCE: 140

Leu Ser Ser Arg Gln Leu Gly Leu Pro Gly Pro Pro Asp Val Pro Asp
1               5                   10                  15

His Ala Ala Tyr His Pro Phe Arg
            20

<210> SEQ ID NO 141
<211> LENGTH: 23
<212> TYPE: PRT
<213> ORGANISM: Homo sapiens

<400> SEQUENCE: 141

Ser Ser Arg Gln Leu Gly Leu Pro Gly Pro Pro Asp Val Pro Asp His
1               5                   10                  15

Ala Ala Tyr His Pro Phe Arg
            20

<210> SEQ ID NO 142
<211> LENGTH: 22
<212> TYPE: PRT
<213> ORGANISM: Homo sapiens

<400> SEQUENCE: 142

Leu Met Ile Asp Gln Asn Thr Lys Ser Pro Leu Phe Met Gly Lys Val
1               5                   10                  15

Val Asn Pro Thr Gln Lys
            20

<210> SEQ ID NO 143
<211> LENGTH: 22
<212> TYPE: PRT
<213> ORGANISM: Homo sapiens

<400> SEQUENCE: 143

Leu Met Ile Glu Gln Asn Thr Lys Ser Pro Leu Phe Met Gly Lys Val
1               5                   10                  15

Val Asn Pro Thr Gln Lys
            20

<210> SEQ ID NO 144
<211> LENGTH: 24
<212> TYPE: PRT
<213> ORGANISM: Homo sapiens

<400> SEQUENCE: 144

Arg Tyr Thr Ile Ala Ala Leu Leu Ser Pro Tyr Ser Tyr Ser Thr Thr
1               5                   10                  15

Ala Val Val Thr Asn Pro Lys Glu
            20

<210> SEQ ID NO 145
<211> LENGTH: 23
<212> TYPE: PRT
<213> ORGANISM: Homo sapiens

<400> SEQUENCE: 145

Tyr Thr Ile Ala Ala Leu Leu Ser Pro Tyr Ser Tyr Ser Thr Thr Ala
1               5                   10                  15

Val Val Thr Asn Pro Lys Glu
            20

<210> SEQ ID NO 146
```

```
-continued
<211> LENGTH: 10
<212> TYPE: PRT
<213> ORGANISM: Homo sapiens

<400> SEQUENCE: 146

Arg Ile His Trp Glu Ser Ala Ala Leu Leu
1               5                   10

<210> SEQ ID NO 147
<211> LENGTH: 13
<212> TYPE: PRT
<213> ORGANISM: Homo sapiens

<400> SEQUENCE: 147

Ile Thr His Arg Ile His Trp Glu Ser Ala Ala Leu Leu
1               5                   10

<210> SEQ ID NO 148
<211> LENGTH: 16
<212> TYPE: PRT
<213> ORGANISM: Homo sapiens

<400> SEQUENCE: 148

Ser Ser Lys Ile Thr His Arg Ile His Trp Glu Ser Ala Ala Leu Leu
1               5                   10                  15
```

METHODS OF DETECTION OF CANCER USING PEPTIDE PROFILES

CROSS-REFERENCE TO RELATED APPLICATIONS/PATENTS & INCORPORATION BY REFERENCE

This application is the U.S. national phase application, pursuant to 35 U.S.C. §371, of PCT international application Ser. No. PCT/US2006/031957, filed Aug. 16, 2006, designating the United States and published in English on Feb. 22, 2007, as publication WO 2007/022248 A2, which claims priority to U.S. Provisional application Ser. No. 60/708,676, filed Aug. 16, 2005. The entire contents of the aforementioned patent applications are incorporated herein by this reference.

Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List before the paragraphs, or in the text itself; and, each of these documents or references ("herein-cited references"), as well as each document or reference cited in each of the herein-cited references (including any manufacturer's specifications, instructions, etc.), is hereby expressly incorporated herein by reference.

STATEMENT OF GOVERNMENTAL SUPPORT

This work was funded by NIH grant nos. 1 R21 CA1119425, 5 P30 CA08748 and 5 P50 CA 92629. The government may have certain rights to this invention.

BACKGROUND OF THE INVENTION

Serum biomarkers are used for diagnosis of disease and for predicting and monitoring response to treatment (Sidransky, D. 2002. *Nat Rev Cancer* 2:210-219; Bidart, J. M., et al. 1999. *Clin Chem* 45:1695-1707). Most clinically useful markers, to date, have been plasma proteins that require individual immunoassays for quantitation (Jortani, S. A., et al. 2004. *Clin Chem* 50:265-278; Watts, N. B. 1999. *Clin Chem* 45:1359-1368). Human serum also contains smaller peptides that constitute an entity known as the serum 'peptidome'. Advances in mass spectrometry (MS) now permit the display of hundreds of small to medium sized peptides from microliter volumes of serum (Koomen, J. M., et al., 2005. *J Proteome Res* 4:972-981; Villanueva, et al., 2004. *Anal Chem* 76:1560-1570). Several recent reports have advocated the use of MS-based serum peptide profiling to determine qualitative and quantitative patterns, or 'signatures', that indicate the presence/absence of disease such as cancer (Petricoin, E. F., et al., 2002. *Lancet* 359:572-577; Adam, B. L., et al., 2002. *Cancer Res* 62:3609-3614; Li, J., et al., 2002. *Clin Chem* 48:1296-1304; Ebert, M. P., et al., 2004. *J Proteome Res* 3:1261-1266; Ornstein, D. K., et al. 2004. *J Urol* 172:1302-1305; Conrads, T. P., et al., 2004. *Endocr Relat Cancer* 11:163-178). To date, it has neither been accomplished to independently reproduce entire peptidomic patterns, nor has it been shown that the highly discriminatory peptides have the same amino acid sequences.

TOF-MS is the most efficient mass analysis technique in terms of detection sensitivity and readily achieves high mass analysis at good mass accuracy (R. J. Cotter, Anal. Chem. 64 (21), 1027 (1992)). It is one of the few analysis techniques that combines high sensitivity, selectivity and specificity with speed of analysis. For example, TOF-MS can record a complete mass spectrum on a microsecond timescale.

Advances in MS-based serum peptide profiling can have important implications for cancer diagnostics.

SUMMARY OF THE INVENTION

It has now been determined that distinctive peptide patterns that correlate with clinically relevant outcomes can be established through mass spectrometry (MS). Methods of the present invention employ serum peptide profiles to identify various types of cancer.

The present invention provides peptide markers that are differentially present in the samples of cancer subjects and in the samples of control subjects. Measurement of these markers, alone or in combination, in patient samples provides information correlating with a probable diagnosis of human cancer or a negative diagnosis (e.g., normal or disease-free). Accordingly, further disclosed are methods and kits that employ these markers in diagnosing and monitoring cancer.

In one aspect, the present invention provides methods of diagnosing or monitoring cancer in a subject comprising measuring at least one peptide marker in a sample from the subject. The cancer can be cancer of the prostate, bladder, breast or thyroid. Peptide markers of the invention include but are not limited to complement C3f, ITIH4, clusterin, complement C4-alpha, fibrinopeptideA, bradykinin, APO A-I, APOA-IV, APO E, kininogen, factor XIII, transthyretin and fibrinogenA. Preferably, peptide markers for ITIH4, clusterin, complement C4-alpha, APO A-I, APO A-IV, APO E, kininogen, factor XIII, transthyretin and fibrinogenA are present in the serum as peptide fragments.

In one embodiment, peptide marker levels are detected in a combination of two or more of the aforementioned peptide markers. Thus, the number of individual peptide markers measured in a sample can range from about 2 to 10, 10 to 15, 15 to 20, 20 to 25, 25 to 30, 30 to 35, 35 to 40, 40 to 45, 45 to 50 and greater than about 50. In specific embodiments, at least about 20 of the peptide markers are measured.

In one embodiment, the invention provides a method of identifying cancer of the prostate in a subject comprising detecting an increase in a complement C3f peptide or a fragment thereof, a ITIH4, clusterin, complement C4-alpha, kininogen or factor XIII peptide fragment, or any combination thereof in a biological sample obtained from the subject, thereby identifying cancer of the prostate in the subject. The method can further comprise detecting a decrease in fibrinopeptideA peptide or a fragment thereof, or a fibrinogen-alpha peptide fragment, or any combination thereof in a biological sample obtained from the subject.

In another embodiment, the invention provides a method of identifying cancer of the bladder in a subject comprising detecting an increase in a complement C3f peptide or a fragment thereof, a ITIH4, clusterin, complement C4-alpha, fibrinogen-alpha, APO A-I, APO A-IV, APO E or kininogen peptide fragment, or any combination thereof in a biological sample obtained from the subject, thereby identifying cancer of the bladder in the subject. The method can further comprise detecting a decrease in a fibrinopeptideA peptide, bradykinin peptide, or a fragment thereof, a C4-alpha, ITIH4, or fibrinogen-alpha peptide fragment, or any combination thereof in a biological sample obtained from the subject.

In yet another embodiment, the invention provides a method of identifying cancer of the breast in a subject comprising detecting an increase in a fibrinopeptideA peptide, bradykinin peptide, or a fragment thereof, a ITIH4, complement C4-alpha, fibrinogen-alpha, APO A-IV, factorXIII or transthyretin peptide fragment, or any combination thereof in a biological sample obtained from the subject, thereby identifying cancer of the breast in the subject. The method can further comprise detecting a decrease in a fibrinopeptideA peptide, complement C3f peptide, or a fragment thereof, or any combination thereof in a biological sample obtained from the subject.

In yet another embodiment, the invention provides a method of identifying cancer of the prostate in a subject comprising detecting a decrease in a fibrinopeptideA peptide or a fragment thereof and a fibrinogen-alpha peptide fragment and an increase in a complement C3f peptide or a fragment thereof, a ITIH4, clusterin, complement C4-alpha, kininogen and factor XIII peptide fragment in a biological sample obtained from the subject, thereby identifying cancer of the prostate in the subject.

In yet another embodiment, the invention is provides a method of identifying cancer of the bladder in a subject comprising detecting a decrease in a fibrinopeptideA peptide, bradykinin peptide, or a fragment thereof, a C4-alpha, ITIH4, and fibrinogen-alpha peptide fragment and an increase in a complement C3f or a fragment thereof, a ITIH4, clusterin, complement C4-alpha, fibrinogen-alpha, APO A-I, APO A-IV, APO E and kininogen peptide fragment in a biological sample obtained from the subject, thereby identifying cancer of the bladder in the subject.

In yet another embodiment, the invention provides a method of identifying cancer of the breast in a subject comprising detecting a decrease in a fibrinopeptideA peptide and complement C3f peptide, or a fragment thereof, and an increase in a fibrinopeptideA peptide, bradykinin peptide, or a fragment thereof, a ITIH4, complement C4-alpha, fibrinogen-alpha, APO A-IV, factorXIII and transthyretin peptide fragment in a biological sample obtained from the subject, thereby identifying cancer of the breast in the subject.

In specific embodiments of the invention concerning cancer of the prostate, the fibrinopeptideA peptide fragment includes but is not limited to DSGEGDFLAEGGGVR (SEQ ID NO. 1), SGEGDFLAEGGGVR (SEQ ID NO. 2), GEGDFLAEGGGVR (SEQ ID NO. 3), EGDFLAEGGGVR (SEQ ID NO. 4), GDFLAEGGGVR (SEQ ID NO. 5), DFLAEGGGVR (SEQ ID NO. 6) or LAEGGGVR (SEQ ID NO. 25).

In other specific embodiments of the invention concerning cancer of the bladder, the fibrinopeptideA peptide fragment includes but is not limited to DSGEGDFLAEGGGVR (SEQ ID NO. 1), SGEGDFLAEGGGVR (SEQ ID NO. 2), GEGDFLAEGGGVR (SEQ ID NO. 3), EGDFLAEGGGVR (SEQ ID NO. 4), GDFLAEGGGVR (SEQ ID NO. 5), DFLAEGGGVR (SEQ ID NO. 6) FLAEGGGVR (SEQ ID NO. 24) or LAEGGGIVR (SEQ ID NO. 25).

In other specific embodiments of the invention concerning cancer of the breast, the fibrinopeptideA peptide fragment that is decreased includes but is not limited to SGEGDFLAEGGGVR (SEQ ID NO. 2) or GEGDFLAEGGGVR (SEQ ID NO. 3) and the fibrinopeptideA peptide fragment that is increased is FLAEGGGVR (SEQ ID NO. 24).

In other specific embodiments of the invention concerning cancer of the prostate, the complement C3f peptide fragment that is increased includes but is not limited to SSKITHRIHWESASLL (SEQ ID NO. 8), SKITHRIHWESASLL (SEQ ID NO. 9), KITHRIHWESASLL (SEQ ID NO. 10), THRIHWESASLL (SEQ ID NO. 11) or IHWESASLL (SEQ ID NO. 28).

In other specific embodiments of the invention concerning cancer of the bladder, the complement C3f peptide fragment that is increased includes but is not limited to SSKITHRIHWESASLL (SEQ ID NO. 8), SKITHRIHWESASLL (SEQ ID NO. 9), KITHRIHWESASLL (SEQ ID NO. 10), THRIHWESASLL (SEQ ID NO. 11), HWESASLL (SEQ ID NO. 12), RIHWESASLL (SEQ ID NO. 27), IHWESASLL (SEQ ID NO. 28) or SSKITHRIHWESASL (SEQ ID NO. 29).

In other specific embodiments of the invention concerning cancer of the breast, the complement C3f peptide fragment that is decreased includes but is not limited to SSKITHRIHWESASLL (SEQ ID NO. 8), HWESASLL (SEQ ID NO. 12) or ITHRIHWESASLL (SEQ ID NO. 26).

In other specific embodiments of the invention concerning cancer of the prostate, ITIH4 peptide fragment that is increased includes but is not limited to PGVLSSRQLGLPGPPDVPDHAAYHPF (SEQ ID NO. 13), SRQLGLPGPPDVPDHAAYHPF (SEQ ID NO. 15), HAAYHPFR (SEQ ID NO. 34), QLGLPGPPDVPDHAAYHPFR (SEQ ID NO. 35), HAAYHPF (SEQ ID NO. 39), NVHSGSTFFKYYLQGAKIPKPEASFSPR (SEQ ID NO. 40) or NVHSAGAAGSRMNFRPGVLSS (SEQ ID NO. 41).

In other specific embodiments of the invention concerning cancer of the bladder, the ITIH4 peptide fragment that is increased includes but is not limited to PGVLSSRQLGLPGPPDVPDHAAYHPF (SEQ ID NO. 13), SRQLGLPGPPDVPDHAAYHPF (SEQ ID NO. 15), HAAYHPFR (SEQ ID NO. 34), QAGAAGSRMNFRPGVLSSRQLGLPGPPDVPDHAAYHPF (SEQ ID NO. 36), MNFRPGVLSSRQLGLPGPPDVPDHAAYHPF (SEQ ID NO. 37), NVHSGSTFFKYYLQGAKIPKPEASFSPR (SEQ ID NO. 40) or NVHSAGAAGSRMNFRPGVLSS (SEQ ID NO. 41) and the ITIH4 peptide fragment that is decreased includes but is not limited to GVLSSRQLGLPGPPDVPDHAAYHPF (SEQ ID NO. 14) or HAAYHPF (SEQ ID NO. 39).

In other specific embodiments of the invention concerning cancer of the breast, the ITIH4 peptide fragment that is increased includes but is not limited to GLPGPPDVPDHAAYHPF (SEQ ID NO. 16), HAAYHPFR (SEQ ID NO. 34), QLGLPGPPDVPDHAAYHPFR (SEQ ID NO. 35), SSRQLGLPGPPDVPDHAAYHPF (SEQ ID NO. 38) or NVHSAGAAGSRMNFRPGVLSS (SEQ ID NO. 41).

In other specific embodiments of the invention concerning cancer of the prostate, the clusterin peptide fragment includes but is not limited to HFFFPKSRIV (SEQ ID NO. 17).

In other specific embodiments of the invention concerning cancer of the bladder, the clusterin peptide fragment that is increased includes but is not limited to HFFFPKSRIV (SEQ ID NO. 17) or HFFFPK (SEQ ID NO. 18).

In other specific embodiments of the invention concerning cancer of the bladder, the bradykinin peptide fragment that is decreased includes but is not limited to RPPGFSPFR (SEQ ID NO. 19) or RPPGFSPF (SEQ ID NO. 20).

In other specific embodiments of the invention concerning cancer of the breast, the bradykinin peptide fragment that is increased includes but is not limited to RPPGFSPFR (SEQ ID NO. 19) or RPPGFSPF (SEQ ID NO. 20).

In other specific embodiments of the invention concerning cancer of the prostate, the complement C4-alpha peptide fragment that is increased includes but is not limited to GLEEELQFSLGSKINVKVGGNS (SEQ ID NO. 23).

In other specific embodiments of the invention concerning cancer of the bladder, the complement C4-alpha peptide fragment that is increased includes but is not limited to RNGFK- SHALQLNNRQI (SEQ ID NO. 21), GLEEELQFSLGSKINVKVGGNS (SEQ ID NO. 23), or NGFKSHALQLNNR (SEQ ID NO. 31) and the complement C4-alpha peptide fragment that is decreased is GLEEELQFSLGSKINV (SEQ ID NO. 33).

In other specific embodiments of the invention concerning cancer of the breast, the complement C4-alpha peptide fragment that is increased includes but is not limited to RNGFKSHALQLNNRQI (SEQ ID NO. 21), NGFKSHALQLNNRQI (SEQ ID NO. 22), GLEEELQFSLGSKINVKVGGNS (SEQ ID NO. 23), NGFKSHALQLNNRQ (SEQ ID NO. 30), GLEEELQFSLGSKINVKVGGNSKGTL (SEQ ID NO. 32) or GLEEELQFSLGSKINV (SEQ ID NO. 33).

In other specific embodiments of the invention concerning cancer of the prostate, the fibrinogen-alpha peptide fragment that is decreased includes but is not limited to SSSYSKQFTSSTSYNRGDSTFESKSYKMA (SEQ ID NO. 55) or SSSYSKQFTSSTSYNRGDSTFESKSYKM (SEQ ID NO. 56).

In other specific embodiments of the invention concerning cancer of the bladder, the fibrinogen-alpha peptide fragment that is increased includes but is not limited to SSSYSKQFTSSTSYNRGDSTFESKSYKMA (SEQ ID NO. 55), SSSYSKQFTSSTSYNRGDSTFESKSYKM (SEQ ID NO. 56), SSSYSKQFTSSTSYNRGDSTFESKSY (SEQ ID NO. 57), SSSYSKQFTSSTSYNRGDSTFESKS (SEQ ID NO. 58), or SSYSKQFTSSTSYNRGDSTFE (SEQ ID NO. 60), and the fibrinogen-alpha peptide fragment that is decreased is GSESGIFTNTKESSSHHPGIAEFPSRG (SEQ ID NO. 61).

In other specific embodiments of the invention concerning cancer of the breast, the fibrinogen-alpha peptide fragment that is increased includes but is not limited to SSYSKQFTSSTSYNRGDSTFE (SEQ ID NO. 60) or DEAGSEADHEGTHSTKRGHAKSRPV (SEQ ID NO. 62).

In other specific embodiments of the invention concerning cancer of the prostate, the kininogen peptide fragment is NLGHGHKHERDQGHGHQ (SEQ ID NO. 52).

In other specific embodiments of the invention concerning cancer of the bladder, the kininogen peptide fragment that is increased includes but is not limited to KHNLGHGHKHERDQGHGHQ (SEQ ID NO. 51) or NLGHGHKHERDQGHGHQ (SEQ ID NO. 52).

In other specific embodiments of the invention concerning cancer of the bladder, the APO A-I peptide fragment that is increased includes but is not limited to QGLLPVLESFKVSFLSALEEYTKKLNTQ (SEQ ID NO. 42), VSFLSALEEYTKKLNTQ (SEQ ID NO. 43) or ATEHLSTLSEKAKPALEDL (SEQ ID NO. 44).

In other specific embodiments of the invention concerning cancer of the bladder, the APO A-IV peptide fragment that is increased includes but is not limited to GNTEGLQKSLAELGGHLDQQVEEFR (SEQ ID NO. 46), SLAELGGHLDQQVEEFR (SEQ ID NO. 47) or SLAELGGHLDQQVEEF (SEQ ID NO. 48).

In other specific embodiments of the invention concerning cancer of the breast, the APO A-IV peptide fragment that is increased is ISASAEELRQRLAPLAEDVRGNL (SEQ ID NO. 45).

In other specific embodiments of the invention concerning cancer of the bladder, the APO E peptide fragment that is increased includes but is not limited to AATVGSLAGQPLQERAQAWGERLR (SEQ ID NO. 49) or AATVGSLAGQPLQERAQAWGERL (SEQ ID NO. 50).

In other specific embodiments of the invention concerning cancer of the prostate, the factor XIII peptide fragment that is increased is AVPPNNSNAAEDDLPTVELQGVVPR (SEQ ID NO. 53).

In other specific embodiments of the invention concerning cancer of the breast, the factor XIII peptide fragment that is increased is AVPPNNSNAAEDDLPTVELQGVVPR (SEQ ID NO. 53).

In other specific embodiments of the invention concerning cancer of the breast, the transthyretin peptide fragment that is increased is ALGISPFHEHAEVVFTANDSGPR (SEQ ID NO. 54).

In practicing the methods of the invention, the biological sample can comprise plasma or serum or a preparation thereof. Detection can comprise analyzing the biological sample, or a preparation thereof using mass spectrometry. The mass spectrometry can be MALDI TOF, Fourier-transform ion cyclotron resonance, electrospray ionization mass spectrometry, or combinations thereof. In another aspect, detection can comprise analyzing the biological sample, or a preparation thereof on a solid support, wherein peptides in the sample bind to the solid support.

In another aspect, the invention provides peptide profiles indicative of cancer of the prostate, bladder, and breast.

In one embodiment, the invention provides an isolated or identified peptide profile indicating cancer of the prostate comprising an increased amount of peptides or peptide fragments of SSKITHRIHWESASLL (SEQ ID NO. 8), SKITHRIHWESASLL (SEQ ID NO. 9), KITHRIHWESASLL (SEQ ID NO. 10), THRIHWESASLL (SEQ ID NO. 11), PGVLSSRQLGLPGPPDVPDHAAYHPF (SEQ ID NO. 13), SRQLGLPGPPDVPDHAAYHPF (SEQ ID NO. 15), HFFFPKSRIV (SEQ ID NO. 17), GLEEELQFSLGSKINVKVGGNS (SEQ ID NO. 23), IHWESASLL (SEQ ID NO. 28), HAAYHPFR (SEQ ID NO. 34), QLGLPGPPDVPDHAAYHPFR (SEQ ID NO. 35), HAAYHPF (SEQ ID NO. 39), NVHSGSTFFKYYLQGAKIPKPEASFSPR (SEQ ID NO. 40), NVHSAGAAGSRMNFRPGVLSS (SEQ ID NO. 41), NLGHGHKHERDQGHGHQ (SEQ ID NO. 52), AVPPNNSNAAEDDLPTVELQGVVPR (SEQ ID NO. 53), or combinations thereof. In an additional embodiment, the isolated or identified peptide profile indicating cancer of the prostate comprises a decreased amount of peptides or peptide fragments of DSGEGDFLAEGGGVR (SEQ ID NO. 1), SGEGDFLAEGGGVR (SEQ ID NO. 2), GEGDFLAEGGGVR (SEQ ID NO. 3), EGDFLAEGGGVR (SEQ ID NO. 4), GDFLAEGGGVR (SEQ ID NO. 5), DFLAEGGGVR (SEQ ID NO. 6), LAEGGGVR (SEQ ID NO. 25), SSSYSKQFTSSTSYNRGDSTFESKSYKMA (SEQ ID NO. 55), SSSYSKQFTSSTSYNRGDSTFESKSYKM (SEQ ID NO. 56), or combinations thereof.

In another embodiment, the invention provides an isolated or identified peptide profile indicating cancer of the bladder comprising an increased amount of peptides or peptide fragments of SSKITHRIHWESASLL (SEQ ID NO. 8), SKITHRIHWESASLL (SEQ ID NO. 9), KITHRIHWESASLL (SEQ ID NO. 10), THRIHWESASLL (SEQ ID NO. 11), HWESASLL (SEQ ID NO. 12), PGVLSSRQLGLPGPPDVPDHAAYHPF (SEQ ID NO. 13), SRQLGLPGPPDVPDHAAYHPF (SEQ ID NO. 15), HFFFPKSRIV (SEQ ID NO. 17), HFFFPK (SEQ ID NO. 18), RNGFKSHALQLNNRQI (SEQ ID NO. 21), GLEEELQFSLGSKINVKVGGNS (SEQ ID NO. 23), (SEQ ID NO. 27), IHWESASLL (SEQ ID NO. 28), SSKITHRIHWESASL (SEQ ID NO. 29), NGFKSHALQLNNR (SEQ ID NO. 31), HAAYHPFR (SEQ ID NO. 34), QAGAAGSRMNFRPGVLSSRQLGLPGPPDVPDHAAYHPF (SEQ ID NO. 36), MNFRPGVLSS- RQLGLPGPPDVPDHAAYHPF (SEQ ID NO. 37), NVHSGSTFFKYYLQGAKIPKPEASFSPR (SEQ ID NO. 40), NVHSAGAAGSRMNFRPGVLSS (SEQ ID NO. 41), QGLLPVLESFKVSFLSALEEYTKKLNTQ (SEQ ID NO. 42), VSFLSALEEYTKKLNTQ (SEQ ID NO. 43), ATEHLSTLSEKAKPALEDL (SEQ ID NO. 44), GNTEGLQKSLAELGGHLDQQVEEFR (SEQ ID NO. 46), SLAELGGHLDQQVEEFR (SEQ ID NO. 47), SLAELGGHLDQQVEEF (SEQ ID NO. 48), AATVGSLAGQPLQERAQAWGERLR (SEQ ID NO. 49), AATVGSLAGQPLQERAQAWGERL (SEQ ID NO. 50), KHNLGHGHKHERDQGHGHQ (SEQ ID NO. 51), NLGHGHKHERDQGHGHQ (SEQ ID NO. 52), GSESGIFTNTKESSSHHPGIAEFPSRG (SEQ ID NO. 61), or combinations thereof. In an additional embodiment, the isolated or identified peptide profile indicating cancer of the bladder comprises a decreased amount of peptides or peptide fragments of DSGEGDFLAEGGGVR (SEQ ID NO. 1), SGEGDFLAEGGGVR (SEQ ID NO. 2), GEGDFLAEGGGVR (SEQ ID NO. 3), EGDFLAEGGGVR (SEQ ID NO. 4), GDFLAEGGGVR (SEQ ID NO. 5), DFLAEGGGVR (SEQ ID NO. 6), GVLSSRQLGLPGPPDVPDHAAYHPF (SEQ ID NO. 14), RPPGFSPFR (SEQ ID NO. 19), RPPGFSPF (SEQ ID NO. 20), FLAEGGGIR (SEQ ID NO. 24), LAEGGGVR (SEQ ID NO. 25), GLEEELQFSLGSKINV (SEQ ID NO. 33), HAAYHPF (SEQ ID NO. 39), SSSYSKQFTSSTSYNRGDSTFESKSYKMA (SEQ ID NO. 55), SSSYSKQFTSSTSYNRGDSTFESKSYKM (SEQ ID NO. 56), SSSYSKQFTSSTSYNRGDSTFESKSY (SEQ ID NO. 57), SSSYSKQFTSSTSYNRGDSTFESKS (SEQ ID NO. 58), SSYSKQFTSSTSYNRGDSTFE (SEQ ID NO. 60), or combinations thereof.

In yet another embodiment, the invention is directed to an isolated or identified peptide profile indicating cancer of the breast comprising an increased amount of peptides or peptide fragments of GLPGPPDVPDHAAYHPF (SEQ ID NO. 16), RPPGFSPFR (SEQ ID NO. 19), RPPGFSPF (SEQ ID NO. 20), RNGFKSHALQLNNRQI (SEQ ID NO. 21), NGFKSHALQLNNRQI (SEQ ID NO. 22), GLEEELQFSLGSKINVKVGGNS (SEQ ID NO. 23), FLAEGGGVR (SEQ ID NO. 24), NGFKSHALQLNNRQ (SEQ ID NO. 30), GLEEELQFSLGSKINVKVGGNSKGTL (SEQ ID NO. 32), GLEEELQFSLGSKINV (SEQ ID NO. 33), HAAYHPFR (SEQ ID NO. 34), QLGLPGPPDVPDHAAYHPFR (SEQ ID NO. 35), SSRQLGLPGPPDVPDHAAYHPF (SEQ ID NO. 38), NVHSAGAAGSRMNFRPGVLSS (SEQ ID NO. 41), ISASAEELRQRLAPLAEDVRGNL (SEQ ID NO. 45), AVPPNNSNAAEDDLPTVELQGVVPR (SEQ ID NO. 53), ALGISPFHEHAEWFTANDSGPR (SEQ ID NO. 54), SSYSKQFTSSTSYNRGDSTFE (SEQ ID NO. 60), DEAGSEADHEGTHSTKRGHAKSRPV (SEQ ID NO. 62), or combinations thereof. In an additional embodiment, the isolated or identified peptide profile indicating cancer of the breast comprises a decreased amount of peptides or peptide fragments of SGEGDFLAEGGGVR (SEQ ID NO. 2), GEGDFLAEGGGVR (SEQ ID NO. 3), SSKITHRIHWESASLL (SEQ ID NO. 8), HWESASLL (SEQ ID NO. 12), ITHRIHWESASLL (SEQ ID NO. 26), or combinations thereof.

In one embodiment of the peptide profile of the invention, the profile is present in an isolated biological sample. In another embodiment, the identified profile is stored by electronic means.

In one aspect, the invention provides a method of generating a peptide profile of a subject having, or at risk of having, cancer of the prostate, comprising the steps of:

i) combining an exogenous peptide including but not limited to a complement C3f, ITIH4, clusterin, complement C4-alpha, fibrinopeptide A, kininogen, factor XIII, and fibrinogenA peptide or a combination thereof with a biological sample from the subject; and ii) proteolytically digesting a peptide of step i), thereby generating a peptide profile of the subject.

In additional embodiments of the invention, the peptide profile indicates that the subject has or is at risk of having cancer of the prostate.

In one aspect, the invention provides a method of generating a peptide profile of a subject having, or at risk of having, cancer of the bladder, comprising the steps of:

i) combining an exogenous peptide including but not limited to a complement C3f, ITIH4, clusterin, complement C4-alpha, fibrinopeptide A, bradykinin, APO A-I, APO A-IV, APO E, kininogen, and fibrinogenA peptide or a combination thereof with a biological sample from the subject; and ii) proteolytically digesting a peptide of step i), thereby generating a peptide profile of the subject.

In an additional embodiment of the invention, the peptide profile indicates that the subject has or is at risk of having cancer of the bladder.

In one aspect, the invention provides a method of generating a peptide profile of a subject having, or at risk of having, cancer of the breast, comprising the steps of:

i) combining an exogenous peptide including but not limited to a ITIH4, bradykinin, complement C4-alpha, fibrinopeptide A, complement C3f, APO A-IV, factor XIII, transthyretin and fibrinogenA peptide or a combination thereof with a biological sample from the subject; and ii) proteolytically digesting a peptide of step i), thereby generating a peptide profile of the subject.

In an additional embodiment of the invention, the peptide profile indicates that the subject has or is at risk of having cancer of the breast.

In one aspect, the invention is provides a method of generating a peptide profile of a subject having, or at risk of having, cancer of the thyroid, comprising the steps of:

i) combining an exogenous peptide selected from the group consisting of a fibrinopeptide A, fibrinogenA, complement C3f peptide and combinations thereof with a biological sample from the subject, and ii) proteolytically digesting a peptide of step i), thereby generating a peptide profile of the subject.

In an additional embodiment of the invention, the peptide profile indicates that the subject has or is at risk of having cancer of the thyroid.

In further embodiments of the invention, the exogenous peptide is labeled with an isotope. In yet further embodiments of the invention, the biological sample is serum or plasma. In yet further embodiments of the invention, the exogenous peptide is a synthetic peptide. In yet further embodiments of the invention, the exogenous peptide is comprised of D-amino acids. In yet further embodiments of the invention, the proteolytic digest is analyzed, for example, using mass spectrometry.

Methods of the invention can further comprise the step of obtaining the exogenous peptide.

In yet another aspect, the invention provides a kit for generating a peptide profile of a subject having, or at risk of having, cancer of the bladder, breast, prostate or thyroid comprising an exogenous peptide or peptide fragment selected from the group consisting of complement C3f peptide, ITIH4 peptide, clusterin peptide, complement C4-alpha peptide, fibrinopeptideA peptide, bradykinin peptide, APO A-I peptide, APOA-IV peptide, APO E peptide, kininogen peptide, factor XIII peptide, transthyretin peptide and fibrinogenA peptide and instructions for use and/or a packaging means thereof

BRIEF DESCRIPTION OF THE FIGURES

FIG. 5A lists the groups ('ladders') of overlapping sequences of the peptides identified by MALDI-TOF/TOF MS/MS. Taken together, 61 peptide-ions on the list have clear peptide-ion marker potential (adjusted $p<0.0002$; see FIG. 5B, below) for at least one type of cancer and are color-coded in blue (prostate cancer), green (bladder cancer) or red (breast cancer). The resulting 'barcodes' for the three cancer types consist of 26 (prostate), 50 (bladder) and 25 (breast) peptide-ions. Color-coded peptides have either higher (no dot) or lower (black dot) differential ion intensities in a particular cohort of cancer samples as compared to controls. Of the 8 non-markers listed here, full-length C3f (m/z=2021.05) and one member of the fibrinogen-alpha cluster (m/z=2553.01) gave comparable ion signals in all patient group and control sera (see FIG. 5B; FIG. 3, '2021'), and, therefore, represent virtual internal standards (yellow-coded). Six peptides (pink-coded) in the clusters were randomly observed in samples of the cancer and control groups and have neither discriminant nor internal control value. Note that the measured m/z values, as listed, are mono-isotopic and, therefore, smaller than the corresponding average isotopic values in FIG. 13a. Amino acids in brackets were not experimentally observed but are shown to either indicate putative full-length sequences of the founders, each resulting from specific proteolyis of precursor proteins, and/or of the positions of the putative 'trypsin-like' cleavage sites (Arg/Lys-Xaa). FIG. 5A discloses SEQ ID NOS 116, 1-6, 117-123, 60, 124-127, 8-10, 26, 11, 128, 27, 28, 12, 29, 76-77, 30-31, 78-81, 34-35, 82, 37, 13-14, 38, 15, 83, 16, 39, 84-88, 43, 89-91, 47-48, 92-94, 18-20 and 95-99, respectively, in order of appearance.

FIG. 5B depicts a table listing additional details of the identified peptides as m/z values, MS-ion intensities, and 'barcodes' (blue, green or red—as described above). The actual barcodes (blue, green or red) are composed of entries that showed clear peptide-ion marker potential (adjusted $p<0.0002$) for at least one type of cancer. Adjusted p-value is the overriding criterion, leading to final barcodes of 26 (prostate), 50 (bladder) and 25 (breast) peptide-ions. The second column lists median intensities of each m/z-peak in the control samples. Peak intensity ratios (columns 3-5) were calculated by dividing the median values of each m/z-peak in each cancer group by the median value of the corresponding peak in the control samples. Ratios (r) for the peptides that are part of one or more barcodes are shaded; dark grey when the median signal was of higher intensity in a particular cancer ($r \geq 1.6$), lighter grey when it was lower ($r \leq 0.66$). The significance levels (p values) of three different one-way ANOVA Mann-Whitney tests (columns 6-8) and of a multi-class Kluskal-Wallis test (column 9) are given. C3f (coded yellow) has virtually no discriminant value.

FIG. 6 discloses SEQ ID NOS 116, 1-6, 24-25, 127, 8-10, 26, 11, 27-28, 12, 21-22, 30-31, 59, 100, 33, 36-37, 13-14, 38, 15-16 and 39, respectively, in order of appearance.

FIG. 8A schematically depicts the independent prostate cancer serum sample groups identified for the validation of the established biomarkers.

FIGS. 8B and 8C show the results of Hierarchical Cluster (HCA) and Principal Component (PCA) Analyses of all spectra from the Prostate #1 (blue), Prostate #2 (cyan) and control groups (yellow). Two limited sets of peptide-ions were used for the analyses: the 68 combined peptides that had statistically significant differences in intensity for the three binary comparisons (FIG. 2B; FIG. 17) (left), and the 26 sequenced peptides that constitute the prostate cancer barcode (color-coded blue in FIG. 5) (right). The rest of the ~650 peptide-ions were ignored for the cluster analysis. Dendrogram colors follow the color-coding scheme of panel A. The heat map scale of normalized ion-intensities is from 0 (green) to 2,000 (red), with the midpoint at 1,000 (yellow). For the PCA, the first three principal components, accounting for most of the variance in the original data set, are shown.

FIG. 8D shows a table listing the results of class prediction analysis of the prostate cancer validation set (Prostate #2) using Support Vector Machine (SVM) and either all 651 m/z-values or the 68-, 26-feature sets described above. Analyses were done using linear kernel. The proportions of correct predictions are listed. The binomial confidence intervals (at 95%) were 87.1-99.9% for 40 correct predictions out of 41, and 91.4-100% for 41/41. The training sets were either Prostate #1 versus control ('binary') or the 3 cancer groups (Prostate #1, bladder and breast cancer) plus controls ('multi-class').

FIG. 13A shows a table listing averages plus (±) standard deviations and medians (in brackets) of the intensities of each m/z-peak (i.e., serum peptide) within a particular data set derived from each of the three cancer patient groups and of the healthy controls. Intensities refer to normalized units that were calculated for each peak by dividing its raw intensity by the total of all of the intensities in that spectrum (TIC—Total Ion Count). The resultant values were then multiplied by fixed scaling factor ($1\times10^7$) to convert the data to a 'user-friendly' scale (i.e. most values $\geq 1$).

FIG. 13B shows a table listing ratios calculated by dividing the median normalized intensity of each m/z-peak in each cancer group by the median of the same m/z-peak in the control group. To avoid having to divide by zero, any median value of less than was converted to 1. This was applied to all groups. Data for a second, independent validation set of prostate cancer samples is also listed.

FIG. 13C shows a table listing the false discovery rate adjusted p-values calculated for each m/z-peak using the Mann-Whitney rank sum test (for binary comparisons) or the Kruskal-Wallis test (for multi-class comparisons). The group of 68 m/z-peaks listed were derived from the original peak list, containing normalized ion intensities (and medians within a group, case/control ratios and adjusted p-values) for each of the 651 m/z-peaks for each of the 106 samples, by applying p-value and median intensity cut-off filters (p<0.00001; median intensity $\geq$500 'units'). Entries which passed both filters in one or more cancer groups are color-coded: prostate cancer (14; blue), breast cancer (14; red) and bladder cancer (58; green).

FIG. 14 shows a table listing the total serum peptide sequences, organized per overlapping cluster; with clusters organized per precursor protein (NCBI ID nos. are given). Positions in the precursor proteins are indicated. Residues between brackets were not observed but are listed in the present table to indicate the putative primary cleavage sites by endoproteases. Additional information is given, as for instance the relative position of adjacently located peptides or peptide clusters, identity of previously known serum petides (e.g., FPA, C3f), position of propeptides, and location of C-termini (C-t). Key: $Met_{ox}$ or $M_{ox}$, oxidized methionine; $Pro_{hydroxyl}$, hydroxylated proline. FIG. 14 discloses SEQ ID NOS 25, 24, 6, 5, 4, 3, 2, 1, 116, 71, 123, 122, 121, 120, 101, 60, 102, 126, 125, 12, 28, 27, 128, 11, 26, 10, 9, 8, 127, 29, 31, 30, 77, 76, 103, 80, 79, 78, 104, 39, 16, 83, 15, 38, 14, 13, 37, 82, 35, 34, 84-85, 89, 88, 43, 87, 86, 90, 48, 105, 91, 47, 106, 107, 93, 92, 18 and 94, respectively, in order of appearance.

FIG. 15 shows a table listing the locations of sequenced serum peptides in the precursor proteins. NCBI ID nos. are given, as well as the positions of known, processed serum proteins, peptides and propeptides. The peptide sequences obtained herein are shown in bold and are underlined. FIG. 15 discloses SEQ ID NOS 108-115, respectively, in order of appearance.

FIG. 16A shows, in table form, the data set of 651 unique m/z-peaks derived from MALDI-TOF MS serum peptide profiling of three groups of cancer patients and healthy controls. Presented are the averages plus (±) standard deviations and the median values (in brackets) of the intensities of each m/z-peak (i.e., serum peptide) within a particular data set derived from each of the three cancer patient groups and of the healthy controls; a second, independent validation set of prostate cancer samples is also listed. Intensities refer to normalized units that were calculated for each peak by dividing its raw intensity by the total of all the intensities in that spectrum (TIC—Total Ion Count). The resultant values were then multiplied by fixed scaling factor ($1 \times 10^7$) to convert the data to a 'user-friendly' scale (i.e. most values $\geq 1$).

FIG. 16B shows, in table form, the data set of 651 unique m/z-peaks derived from MALDI-TOF MS serum peptide profiling of three groups of cancer patients and healthy controls.

FIG. 16C shows, in table form, the data set of 651 unique m/z-peaks derived from MALDI-TOF MS serum peptide profiling of three groups of cancer patients and healthy controls.

FIGS. 17A, 17B, and 17C show, in table form, the data set of 68 putative biomarker m/z-peaks, derived from MALDI-TOF MS serum peptide profiling of three groups of cancer patients and healthy controls. The figures contain (i) means plus (±) standard deviations, and medians (in brackets); (ii) discriminant analysis false positive rates (p-values); and (iii) ratios of the median intensities in a group for all 68 m/z-peaks retained after applying p-value and median intensity cutoff filters (p<0.00001; median intensity $\geq 500$ units). All values were extracted from FIGS. 16A-C, above. Entries which passed both filters in one or more cancer groups are color-coded: prostate cancer (14; blue), breast cancer (14; red) and bladder cancer (58; green).

FIG. 18 shows SEQ ID NO:63, GENBANK Accession No. AAH00664, C3F protein (Homo sapiens), amino acid residues 1-436.

FIG. 19 shows SEQ ID NO:64, GENBANK Accession No. Q14624, Inter-alpha-trypsin inhibitor heavy chain H4 precursor (ITI heavy chain H4) (Homo sapiens), amino acid residues 1 to 930, wherein 29-661="70 kDa inter-alpha-trypsin inhibitor heavy chain H4" and 689-930="35 kDa inter-alpha-trypsin inhibitor heavy chain H4."

FIG. 20 shows SEQ ID NO:65, GENBANK Accession No. AAP88927, clusterin (complement lysis inhibitor (Homo sapiens), amino acid residues 1 to 447.

FIG. 21 shows SEQ ID NO:66, GENBANK Accession No. AAR89159, C4A (Homo sapiens), amino acid residues 1 to 534.

FIG. 22 shows SEQ ID NO:67, GENBANK Accession No. NP_068657, fibrinogen, alpha chain isoform alpha preproprotein (Homo sapiens), amino acid residues 1 to 644, wherein 20-35 product="fibrinopeptide A."

FIG. 23 shows SEQ ID NO:68, GENBANK Accession No. P01042, kininogen precursor (Alpha-2-thiol proteinase inhibitor) (Homo sapiens), amino acid residues 1 to 644, wherein 381-389="Bradykinin."

FIG. 24 shows SEQ ID NO:69, GENBANK Accession No. NM_021871, Homo sapiens fibrinogen alpha chain (FGA), transcript variant alpha, mRNA.

FIG. 25 shows SEQ ID NO:70, GENBANK Accession No. NM_000039, Homo sapiens apolipoprotein A-I (APOA1), mRNA.

FIG. 26 shows SEQ ID NO:71, GENBANK Accession No. NM_000482, Homo sapiens apolipoprotein A-IV (APOA4), mRNA.

FIG. 27 shows SEQ ID NO:72, GENBANK Accession No. NM_000041, Homo sapiens apolipoprotein E (APOE), mRNA.

FIG. 28 shows SEQ ID NO:73, GENBANK Accession No. NM_000893, Homo sapiens kininogen (KNG1).

FIG. 29 shows SEQ ID NO:74, GENBANK Accession No. NM_000129, Homo sapiens coagulation factor XIII, A1 polypeptide (F13A1), mRNA.

FIG. 30 shows SEQ ID NO:75, GENBANK Accession No. NM_000371, Homo sapiens transthyretin (prealbumin, amyloidosis type I)(TTR), mRNA.

FIG. 31 shows, in table form, 66 reference peptides. All amino acids are ID-stereo-isomers, except for the isotope-containing (L-isomer). Isotope-labeled amino acids: L, $^{13}C(6)$-Leu; F, $^{13}C$(6-ring)-Phe; V, $^{13}C(5)/^{15}N(1)$-Val. (Note: isotope labels result in a molecular mass increase by 6 Da for each peptide). Surrogate marker code: P, prostate cancer; B, breast cancer; BL, bladder cancer; T, thyroid cancer; +, median ion intensity of this particular peptide in MALDI-TOF MS is higher in cancer samples than in controls; −, median ion intensity lower in cancer than controls. FIG. 31 discloses SEQ ID NOS 24-25, 6, 5, 4, 3, 2, 1, 116, 61, 58, 57, 56, 55, 60, 62, 12, 28, 27, 75, 11, 26, 10, 9, 8, 129, 130, 31, 30, 22, 77, 33, 23, 32, 39, 131-132, 16, 83, 15, 38, 14, 13, 133, 35, 34, 40-41, 44, 42-43, 45, 48, 46-47, 50, 49, 18, 17, 134, 20, 19, 52, 51 and 53-54, respectively, in order of appearance.

FIG. 33 shows, in table form, founder peptides. Total 15 syntheses, including 2 (#7 and 11) or more multi-samplings; 18 cleavages, purifications, QC and quantitation. Isotope-labeled amino acids: L, $^{13}C(6)$-Leu; F, $^{13}C$(6-ring)-Phe; V, $^{13}C(5)/^{15}N(1)$-Val; A, $^{13}C(3)/^{15}N(1)$-Ala; resulting in molecular mass increase of 12 Da per peptide. FIG. 33 discloses SEQ ID NOS 116, 55, 135, 127, 77, 136, 137-141, 35, 142-143, 43, 47, 17, 134 and 144-145, respectively, in order of appearance.

FIG. 34 discloses SEQ ID NOS 127, 8-10, 26, 11, 27-28, 12 and 146-148, respectively, in order of appearance.

FIG. 35 discloses SEQ ID NOS127, 8-10, 26, 11, 128, 27-28, 12, 127, 8, 28 and 12, respectively, in order of appearance.

DETAILED DESCRIPTION OF THE INVENTION

I. Definitions

Figure 1A:
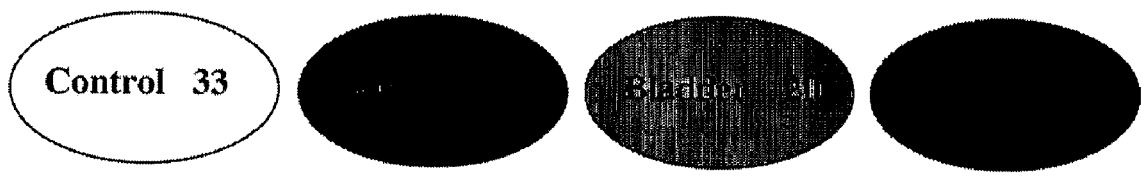
FIG. 1A shows the color-coding scheme followed in the representation of data collected for the blood samples from healthy volunteers (n=33) and from patients with advanced prostate (n=32), bladder (n=20) and breast (n=21) cancer.

Unless defined otherwise, all technical and scientific terms used herein have the meaning commonly understood by a person skilled in the art to which this invention belongs. As used herein, the following terms have the meanings ascribed to them unless specified otherwise.

A "subject" is a vertebrate, preferably a mammal, more preferably a primate and still more preferably a human. Mammals include, but are not limited to, primates, humans, farm animals, sport animals, and pets.

As used herein, "serum" refers to the fluid portion of the blood obtained after removal of the fibrin clot and blood cells, distinguished from the plasma in circulating blood. As used herein, "plasma" refers to the fluid, noncellular portion of the blood, distinguished from the serum obtained after coagulation.

As used herein, "sample" or "biological sample" refers to anything, which may contain an analyte (e.g., peptide) for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind including, for example, connective, epithelium, muscle and nerve tissues. Examples of biological tissues also include organs, tumors, lymph nodes, arteries and individual cell(s).

The term "isolated" refers to one or more compositions obtained from and/or contained in a sample apart from the body.

The term "identified" as in an "identified peptide" or "peptide profile" refers to one or more compositions or information relating thereto (e.g., a peptide and its amino acid sequence information) obtained under conditions of selection. Such information may optionally be stored by electronic means.

As used herein, the terms "gene" and "recombinant gene" refer to nucleic acid molecules comprising an open reading frame encoding a marker protein.

"Gas phase ion spectrometer" refers to an apparatus that detects gas phase ions. Gas phase ion spectrometers include an ion source that supplies gas phase ions. Gas phase ion spectrometers include, for example, mass spectrometers, ion mobility spectrometers, and total ion current measuring devices. "Gas phase ion spectrometry" refers to the use of a gas phase ion spectrometer to detect gas phase ions.

"Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions.

"Laser desorption mass spectrometer" refers to a mass spectrometer that uses laser energy as a means to desorb, volatilize, and ionize an analyte.

"Tandem mass spectrometer" refers to any mass spectrometer that is capable of performing two successive stages of m/z-based discrimination or measurement of ions, including ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that is capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF-TOF mass spectrometers, Fourier transform ion cyclotron resonance mass spectrometers, electrostatic sector—magnetic sector mass spectrometers, and combinations thereof.

"Mass analyzer" refers to a sub-assembly of a mass spectrometer that comprises means for measuring a parameter that can be translated into mass-to-charge ratios of gas phase ions. In a time-of-flight mass spectrometer the mass analyzer comprises an ion optic assembly, a flight tube and an ion detector.

The term "MALDI" is used herein to refer to Matrix-Assisted Laser Desorption/Ionization, a process wherein analyte is embedded in a solid or crystalline "matrix" of light-absorbing molecules (e.g., nicotinic, sinapinic, or 3-hydroxypicolinic acid), then desorbed by laser irradiation and ionized from the solid phase into the gaseous or vapor phase, and accelerated as intact molecular ions towards a detector. The "matrix" is typically a small organic acid mixed in solution with the analyte in a 10,000:1 molar ratio of matrix/analyte. The matrix solution can be adjusted to neutral pH before use.

The term "MALDI-TOF MS" is used herein to refer to Matrix-Assisted Laser Desorption/Ionization Time-of-Flight mass spectrometry.

The term "MALDI ionization surface" is used herein to refer to a surface for presentation of matrix-embedded analyte into a mass spectrometer for MALDI. In general, the terms "probe" or "probe element" are used interchangeably to refer to a device for presenting analyte into a mass spectrometer for irradiation and desorption. Metals such as gold, copper and stainless steel are typically used to form MALDI ionization surfaces. However, other commercially-available inert materials (e.g., glass, silica, nylon and other synthetic polymers, agarose and other carbohydrate polymers, and plastics) can be used where it is desired to use the surface to actively capture an analyte or as a reaction zone for chemical modification of the analyte.

"Solid support" refers to a solid material, which can be derivatized with, or otherwise attached to, a capture reagent. Exemplary solid supports include probes, microtiter plates and chromatographic resins.

"Eluant" or "wash solution" refers to an agent, typically a solution, which is used to affect or modify adsorption of an analyte to an adsorbent surface and/or remove unbound materials from the surface. The elution characteristics of an eluant can depend on, for example, pH, ionic strength, hydrophobicity, degree of chaotropism, detergent strength and temperature.

"Monitoring" refers to recording changes in a continuously varying parameter (e.g. monitoring progression of a cancer).

"Biochip" refers to a solid substrate having a generally planar surface to which an adsorbent is attached. Frequently, the surface of the biochip comprises a plurality of addressable locations, each of which location has the adsorbent bound there. Biochips can be adapted to engage a probe interface, and therefore, function as probes.

"Protein biochip" refers to a biochip adapted for the capture of polypeptides.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

An "exogenous peptide" is a peptide obtained from a biological source that is external to the subject's body or by synthetic means.

The terms "peptide", "peptide marker", "marker" and "biomarker" are used interchangeably in the context of the present invention and refer to a polypeptide which is differentially present in a sample taken from subjects having human cancer as compared to a comparable sample taken from control subjects (e.g., a person with a negative diagnosis or undetectable cancer, normal or healthy subject). The markers are identified by molecular mass in Daltons, and include the masses centered around the identified molecular masses for each marker.

The term "detecting" means methods which include identifying the presence or absence of marker(s) in the sample, quantifying the amount of marker(s) in the sample, and/or qualifying the type of biomarker. Detecting includes identifying the presence, absence or amount of the object to be detected (e.g. a serum peptide marker).

"Diagnostic" means identifying the presence or nature of a pathologic condition, i.e., cancer. While a particular diagnostic method may not provide a definitive diagnosis of a condition, it suffices if the method provides a positive indication that aids in diagnosis.

As used herein, the term "sensitivity" is the percentage of marker-detected subjects with a particular disease.

As used herein, the term "specificity" is the percentage of subjects correctly identified as having a particular disease i.e., normal or healthy subjects. For example, the specificity is calculated as the number of subjects with a particular disease as compared to non-cancer subjects (e.g., normal healthy subjects).

The phrase "differentially present" refers to differences in the quantity and/or the frequency of a marker present in a sample taken from subjects having human cancer as compared to a control subject. For example, serum peptide markers described herein are present at an elevated level in samples of subjects compared to samples from control subjects. In contrast, other markers described herein are present at a decreased level in samples of cancer subjects compared to samples from control subjects. Furthermore, a marker can be a polypeptide, which is detected at a higher frequency or at a lower frequency in samples of human cancer subjects compared to samples of control subjects. A marker can be differentially present in terms of quantity, frequency or both. A polypeptide is differentially present between two samples if the amount of the polypeptide in one sample is statistically significantly different from the amount of the polypeptide in the other sample. Alternatively or additionally, a polypeptide is differentially present between two sets of samples if the frequency of detecting the polypeptide in the cancer subjects' samples is statistically significantly higher or lower than in the control samples.

"Optional" or "optionally" means that the subsequently described feature or structure may or may not be present in the analysis system or that the subsequently described event or circumstance may or may not occur, and that the description includes instances where said feature or structure is present and instances where the feature or structure is absent, or instances where the event or circumstance occurs and instances where it does not.

The term "obtaining" as in "obtaining the exogenous peptide" is intended to include purchasing, synthesizing or otherwise acquiring the exogenous (or indicated substance or material).

The terms "comprises", "comprising", and the like are intended to have the broad meaning ascribed to them in U.S. Patent Law and can mean "includes", "including" and the like.

It is to be understood that this invention is not limited to the particular component parts of a device described or process steps of the methods described, as such devices and methods may vary. It is also to be understood that the terminology used herein is for purposes of describing particular embodiments only, and is not intended to be limiting. As used in the specification and the appended claims, the singular forms "a", "an", and "the" include plural referents unless the context clearly indicates otherwise. Thus, for example, reference to "an analyte" includes mixtures of analytes, reference to "a MALDI ionization surface" includes two or more such ionization surfaces, reference to "a microchannel" includes more than one such component, and the like. Furthermore, reference to "cancer" may signify cancer in general (i.e., cancer of any type) or cancer of a specific type. Accordingly, the description herein of a subject as having no detectable cancer may signify a subject in which a specific type of cancer (for example, bladder) is not detectable. However, such a description may not necessarily signify that the subject has no type of cancer whatsoever.

Other definitions appear in context throughout the specification.

II. Methods and Peptide Profiles of the Invention

The present invention provides peptide markers generated from comparisons of protein profiles from subjects diagnosed with cancer and from subjects without known neoplastic diseases. In particular, the invention provides that these markers, used individually or in combination with other markers, provide a method of diagnosing and monitoring cancer in a subject having cancer of the prostate, of the bladder, or of the breast.

Markers that are differentially present in samples of cancer subjects and control subjects find application in methods and kits for determining cancer status. Accordingly, methods are provided for identifying cancer of the prostate, bladder, or breast in a subject comprising detecting a differential presence of a biomarker in subjects with cancer of the prostate, bladder, or breast vs. without cancer of the prostate, bladder, or breast in a biological sample obtained from the subject. The amount of one or more biomarkers found in a test sample compared to a control, or the presence or absence of one or more markers in the test sample provides useful information regarding the cancer status of the patient.

A. Types of Samples

The markers can be measured in different types of biological samples. The sample is preferably a biological fluid sample. Examples of a biological fluid sample useful in this invention include blood, blood serum, plasma, vaginal secretions, urine, tears, saliva, urine, tissue, cells, organs, seminal fluids, bone marrow, cerebrospinal fluid, nipple aspirate, etc. Blood serum is a preferred sample source for embodiments of the invention.

If desired, the sample can be prepared to enhance detectability of the markers. For example, to increase the detectability of markers, a blood serum sample from the subject can be preferably fractionated by, e.g., Cibacron blue agarose chromatography and single stranded DNA affinity chromatography, anion exchange chromatography, affinity chromatography (e.g., with antibodies) and the like. The method of fractionation depends on the type of detection method used. Any method that enriches for the protein of interest can be used. Typically, preparation involves fractionation of the sample and collection of fractions determined to contain the biomarkers. Methods of pre-fractionation include, for example, size exclusion chromatography, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis.

B. Detection of Serum Peptide Markers

Serum Peptide Marker Modification

A marker can be modified before analysis to improve its resolution or to determine its identity. For example, the markers may be subject to proteolytic digestion before analysis. Any protease can be used. Proteases, such as trypsin, that are likely to cleave the markers into a discrete number of fragments are particularly useful. The fragments that result from digestion function as a fingerprint for the markers, thereby enabling their detection indirectly. This is particularly useful where there are markers with similar molecular masses that might be confused for the marker in question. Also, proteolytic fragmentation is useful for high molecular weight markers because smaller markers are more easily resolved by mass spectrometry. In specific embodiments, the proteases occur or naturally exist in the biological sample.

To improve detection resolution of the markers, neuraminidase can, for instance, be used to remove terminal sialic acid residues from glycoproteins to improve binding to an anionic adsorbent (e.g., cationic exchange ProteinChip® arrays) and to improve detection resolution. In another example, the markers can be modified by the attachment of a tag of particular molecular weight that specifically bind to molecular markers, further distinguishing them. Optionally, after detecting such modified markers, the identity of the markers can be further determined by matching the physical and chemical characteristics of the modified markers in a protein database (e.g., SwissProt).

It has been found that proteins frequently exist in a sample in a plurality of different forms characterized by a detectably different mass. These forms can result from either, or both, of pre- and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. Modified forms of any marker of this invention also may be used, themselves, as biomarkers. In certain cases the modified forms may exhibit better discriminatory power in diagnosis than the specific forms set forth herein.

Serum Peptide Marker Purification

For some of the method embodiments of the invention, it may be helpful to purify the marker detected by the methods disclosed herein prior to subsequent analysis. Nearly any means known to the art for the purification and separation of small molecular weight substances, e.g., anion or cation exchange chromatography, gas chromatography, liquid chromatography or high pressure liquid chromatography may be used. Methods of selecting suitable separation and purification techniques and means of carrying them out are known in the art (see, e.g., Labadarious et. al., *J. Chromatography* (1984) 310:223-231, and references cited therein; and Shahrokhin and Gehrke, *J. Chromatography* (1968) 36:31-41, and Niessen J. *Chromatography* (1998) 794:407-435).

In another embodiment of the method of the invention, purification of the marker comprises fractioning a sample comprising one or more protein markers by size-exclusion chromatography and collecting a fraction that includes the one or more marker; and/or fractioning a sample comprising the one or more markers by anion exchange chromatography and collecting a fraction that includes the one or more markers. Fractionation is monitored for purity on normal phase and immobilized nickel arrays. Generating data on immobilized marker fractions on an array is accomplished by subjecting the array to laser ionization and detecting intensity of signal for mass/charge ratio; and transforming the data into computer readable form. Preferably, fractions are subjected to gel electrophoresis and correlated with data generated by mass spectrometry. In one aspect, gel bands representative of potential markers are excised and subjected to enzymatic treatment and are applied to biochip arrays for peptide mapping.

Methods of Detection

Any suitable method can be used to detect one or more of the markers described herein. Successful practice of the invention can be achieved with one or a combination of methods that can detect and, preferably, quantify the markers. These methods include, without limitation, hybridization-based methods including those employed in biochip arrays, mass spectrometry (e.g., laser desorption/ionization mass spectrometry), fluorescence (e.g. sandwich immunoassay), surface plasmon resonance, ellipsometry and atomic force microscopy. Methods may further include, by one or more of electrospray ionization mass spectrometry (ESI-MS), ESI-MS/MS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photo-ionization mass spectrometry (APPI-MS), APPI-MS/MS, and APPI-(MS)$_n$, quadrupole mass spectrometry, fourier transform mass spectrometry (FTMS), and ion trap mass spectrometry, where n is an integer greater than zero.

Biochip-Based Methods

Detection methods may include use of a biochip array. Biochip arrays useful in the invention include protein and nucleic acid arrays. One or more markers are captured on the biochip array and subjected to laser ionization to detect the molecular weight of the markers. Analysis of the markers is, for example, by molecular weight of the one or more markers against a threshold intensity that is normalized against total ion current.

The biochip surfaces may, for example, be ionic, anionic, hydrophobic; comprised of immobilized nickel or copper ions, comprised of a mixture of positive and negative ions; and/or comprised of one or more antibodies, single or double stranded nucleic acids, proteins, peptides or fragments thereof, amino acid probes, or phage display libraries. Many protein biochips are described in the art. These include, for example, protein biochips produced by Ciphergen Biosystems (Fremont, Calif.), Packard BioScience Company (Meriden, Conn.), Zyomyx (Hayward, Calif.) and Phylos (Lexington, Mass.). Examples of such protein biochips are described in the following patents or patent applications: U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); U.S. Pat, No.

6,329,209 (Wagner et al., "Arrays of protein-capture agents and methods of use thereof," Dec. 11, 2001) and International publication WO 00/56934 (Englert et al., "Continuous porous matrix arrays," Sep. 28, 2000).

Markers may be captured with capture reagents immobilized to a solid support, such as a biochip, a multiwell microtiter plate, a resin, or nitrocellulose membranes that are subsequently probed for the presence of proteins. Capture can be on a chromatographic surface or a biospecific surface. For example, a sample containing the markers, such as serum, may be placed on the active surface of a biochip for a sufficient time to allow binding. Then, unbound molecules are washed from the surface using a suitable eluant, such as phosphate buffered saline. In general, the more stringent the eluant, the more tightly the proteins must be bound to be retained after the wash.

Upon capture on a biochip, analytes can be detected by a variety of detection methods selected from, for example, a gas phase ion spectrometry method, an optical method, an electrochemical method, atomic force microscopy and a radio frequency method. Gas phase ion spectrometry methods are described herein. Of particular interest is the use of mass spectrometry, and in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Mass Spectrometry-Based Methods

Mass spectrometry (MS) is a well-known tool for analyzing chemical compounds. Thus, in one embodiment, the methods of the present invention comprise performing quantitative MS to measure the serum peptide marker. The method may be performed in an automated (Villanueva, et al., *Nature Protocols* (2006) 1(2):880-891) or semi-automated format. This can be accomplished, for example with MS operably linked to a liquid chromatography device (LC-MS/MS or LC-MS) or gas chromatography device (GC-MS or GC-MS/MS). Methods for performing MS are known in the field and have been disclosed, for example, in US Patent Application Publication Nos: 20050023454; 20050035286; U.S. Pat. No. 5,800,979 and references disclosed therein.

The protein fragments, whether they are peptides derived from the main chain of the protein or are residues of a side-chain, are collected on the collection layer. They may then be analyzed by a spectroscopic method based on matrix-assisted laser desorption/ionization (MALDI) or electrospray ionization (ESI). The preferred procedure is MALDI with time of flight (TOF) analysis, known as MALDI-TOF MS. This involves forming a matrix on the membrane, e.g. as described in the literature, with an agent which absorbs the incident light strongly at the particular wavelength employed. The sample is excited by UV, or IR laser light into the vapour phase in the MALDI mass spectrometer. Ions are generated by the vaporization and form an ion plume. The ions are accelerated in an electric field and separated according to their time of travel along a given distance, giving a mass/charge (m/z) reading which is very accurate and sensitive. MALDI spectrometers are commercially available from Perseptive Biosystems, Inc. (Frazingham, Mass., USA) and are described in the literature, e.g. M. Kussmann and P. Roepstorff, cited above.

Magnetic-based serum processing can be combined with traditional MALDI-TOF. Through this approach, improved peptide capture is achieved prior to matrix mixture and deposition of the sample on MALDI target plates. Accordingly, methods of peptide capture are enhanced through the use of derivatized magnetic bead based sample processing.

MALDI-TOF MS allows scanning of the fragments of many proteins at once. Thus, many proteins can be run simultaneously on a polyacrylamide gel, subjected to a method of the invention to produce an array of spots on the collecting membrane, and the array may be analyzed. Subsequently, automated output of the results is provided by using the ExPASy server, as at present used for MIDI-TOF MS and to generate the data in a form suitable for computers.

Other techniques for improving the mass accuracy and sensitivity of the MALDI-TOF MS can be used to analyze the fragments of protein obtained on the collection membrane. These include the use of delayed ion extraction, energy reflectors and ion-trap modules. In addition, post source decay and MS—MS analysis are useful to provide further structural analysis. With ESI, the sample is in the liquid phase and the analysis can be by ion-trap, TOF, single quadrupole or multi-quadrupole mass spectrometers. The use of such devices (other than a single quadrupole) allows MS—MS or MS$^n$ analysis to be performed. Tandem mass spectrometry allows multiple reactions to be monitored at the same time.

Capillary infusion may be employed to introduce the marker to a desired MS implementation, for instance, because it can efficiently introduce small quantities of a sample into a mass spectrometer without destroying the vacuum. Capillary columns are routinely used to interface the ionization source of a MS with other separation techniques including gas chromatography (GC) and liquid chromatography (LC). GC and LC can serve to separate a solution into its different components prior to mass analysis. Such techniques are readily combined with MS, for instance. One variation of the technique is that high performance liquid chromatography (HPLC) can now be directly coupled to mass spectrometer for integrated sample separation/and mass spectrometer analysis.

Quadrupole mass analyzers may also be employed as needed to practice the invention. Fourier-transform ion cyclotron resonance (FTMS) can also be used for some invention embodiments. It offers high resolution and the ability of tandem MS experiments. FTMS is based on the principle of a charged particle orbiting in the presence of a magnetic field. Coupled to ESI and MALDI, FTMS offers high accuracy with errors as low as 0.001%.

In one embodiment, the marker qualification methods of the invention may further comprise identifying significant peaks from combined spectra. The methods may also further comprise searching for outlier spectra. In another embodiment, the method of the invention further comprises determining distant dependent K-nearest neighbors.

In another embodiment of the method of the invention, an ion mobility spectrometer can be used to detect and characterize serum peptide markers. The principle of ion mobility spectrometry is based on different mobility of ions. Specifically, ions of a sample produced by ionization move at different rates, due to their difference in, e.g., mass, charge, or shape, through a tube under the influence of an electric field. The ions (typically in the form of a current) are registered at the detector which can then be used to identify a marker or other substances in a sample. One advantage of ion mobility spectrometry is that it can operate at atmospheric pressure.

For the mass values of the markers disclosed herein, the mass accuracy of the spectral instrument is considered to be about within +/−0.15 percent of the disclosed molecular weight value. Additionally, to such recognized accuracy variations of the instrument, the spectral mass determination can vary within resolution limits of from about 400 to 1000 m/dm, where m is mass and dm is the mass spectral peak width at 0.5 peak height. Mass accuracy and resolution variances and thus meaning of the term "about" with respect to the mass of each of the markers described herein is inclusive of variants of the markers as may exist due to sex, genotype and/or ethnicity of the subject and the particular cancer or origin or stage thereof.

In an additional embodiment of the methods of the present invention, multiple markers are measured. The use of multiple markers increases the predictive value of the test and provides greater utility in diagnosis, toxicology, patient stratification and patient monitoring. The process called "Pattern recognition" detects the patterns formed by multiple markers greatly improves the sensitivity and specificity of clinical proteomics for predictive medicine. Subtle variations in data from clinical samples indicate that certain patterns of protein expression can predict phenotypes such as the presence or absence of a certain disease, a particular stage of cancer-progression, or a positive or adverse response to drug treatments.

C. Data Analysis

Data generated by desorption and detection of markers can be analyzed using any suitable means. In one embodiment, data is analyzed and/or stored by electronic means, such as with the use of a programmable digital computer. The computer program generally contains a readable medium that stores codes. Certain code can be devoted to memory that includes the location of each feature on a probe, the identity of the adsorbent at that feature and the elution conditions used to wash the adsorbent. The computer also contains code that receives as input, data on the strength of the signal at various molecular masses received from a particular addressable location on the probe. This data can indicate the number of markers detected, including the strength of the signal generated by each marker.

Data analysis can include the steps of determining signal strength (e.g., height of peaks) of a marker detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each marker or other biomolecules can be displayed in the form of relative intensities in the scale desired (e.g., 100). Alternatively, a standard (e.g., a serum protein) may be admitted with the sample so that a peak from the standard can be used as a reference to calculate relative intensities of the signals observed for each marker or other markers detected.

The computer can transform the resulting data into various formats for displaying, such as "spectrum view or retentate map," "peak map," "gel view," "3-D overlays," "difference map view," and Spotfire Scatter Plot. For each sample, markers that are detected and the amount of markers present in the sample can be saved in a computer readable medium. This data can then be compared to a control (e.g., a profile or quantity of markers detected in control, e.g., subjects in whom human cancer is undetectable).

When the sample is measured and data is generated, e.g., by mass spectrometry, the data is then analyzed by a computer software program. Generally, the software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" and human cancer and determines the closeness of fit between the two signals. The software also can include code indicating which the test sample is closest to, thereby providing a probable diagnosis.

TOF-to-M/Z transformation involves the application of an algorithm that transforms times-of-flight into mass-to-charge ratio (M/Z). In this step, the signals are converted from the time domain to the mass domain. That is, each time-of-flight is converted into mass-to-charge ratio, or M/Z. Calibration can be done internally or externally. In internal calibration, the sample analyzed contains one or more analytes of known M/Z. Signal peaks at times-of-flight representing these massed analytes are assigned the known M/Z. Based on these assigned M/Z ratios, parameters are calculated for a mathematical function that converts times-of-flight to M/Z. In external calibration, a function that converts times-of-flight to M/Z, such as one created by prior internal calibration, is applied to a time-of-flight spectrum without the use of internal calibrants.

Baseline subtraction improves data quantification by eliminating artificial, reproducible instrument offsets that perturb the spectrum. It involves calculating a spectrum baseline using an algorithm that incorporates parameters such as peak width, and then subtracting the baseline from the mass spectrum.

High frequency noise signals are eliminated by the application of a smoothing function. A typical smoothing function applies a moving average function to each time-dependent bin. In an improved version, the moving average filter is a variable width digital filter in which the bandwidth of the filter varies as a function of, e.g., peak bandwidth, generally becoming broader with increased time-of-flight. See, e.g., WO 00/70648, Nov. 23, 2000 (Gavin et al., "Variable Width Digital Filter for Time-of-flight Mass Spectrometry").

As mentioned briefly above, analysis generally involves the identification of peaks in the spectrum that represent signal from an analyte. Peak data from one or more spectra can be subject to further analysis by, for example, creating a spreadsheet in which each row represents a particular mass spectrum, each column represents a peak in the spectra defined by mass, and each cell includes the intensity of the peak in that particular spectrum. Various statistical or pattern recognition approaches can applied to the data.

The spectra that are generated in embodiments of the invention can be classified using a pattern recognition process that uses a classification model. In some embodiments, data derived from the spectra (e.g., mass spectra or time-of-flight spectra) that are generated using samples such as "known samples" can then be used to "train" a classification model. A "known sample" is a sample that is pre-classified (e.g., cancer or not cancer). The data that are derived from the spectra and are used to form the classification model can be referred to as a "training data set". Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased vs. non diseased).

The classification models can be formed on and used on any suitable digital computer. The digital computer that is used may be physically separate from the mass spectrometer that is used to create the spectra of interest, or it may be coupled to the mass spectrometer.

MALDI-TOF MS-Based Quantitative Profiling

Relative quantitation of serum peptides of interest can be done by comparing the MS-ion intensities to those of added, exogenous, isotopically labeled, reference peptides, having the exact same sequence and otherwise same chemical properties as the endogenous ones (i.e. distinguishable by molecular mass only). As such, all peptide pairs will display the exact same MALDI-ionization characteristics. Comparing ion intensities will therefore provide a means of normalizing the values for each peptide. For instance, when the ion intensity of peptide A is two-fold higher than the spiked reference in sample X but two-fold lower in sample Y, then the difference would be about 4-fold between the same peptide in the two samples. When done on a systematic, larger scale, this approach can be referred to as relative "quantitative" profiling. Of note, the reference peptides will be added to the raw serum (i.e., before peptide extraction and MALDI sample prep), so that putative losses during processing are accounted for.

66 reference peptides (listed in FIG. 31) can be synthesized, 44 of which have been determined to be surrogate markers for either prostate or breast cancer, 18 additional ones for bladder or thyroid cancer, and 4 non-marker control peptides. These reference peptides should not degrade in serum, and are, thus, synthesized using D-amino acids (i.e., D-stereo-isomers). One amino acid (Leu, Val, or Phe) of each reference peptide is labeled by incorporation of 6 (L, F) or 5 (V) $^{13}C$ isotopes, and one additional $^{15}N$ isotope (V only). $^{13}C$-labeled, FMOC-amino acids (for solid phase-peptide synthesis) are only commercially available in the L-form, which should not compromise stability as peptide bonds between a D- and L-amino acids are not protease sensitive.

MALDI-TOF MS-Based Protease Assays

A large part of the human serum 'peptidome', as detected by MALDI-TOF MS, is generated ex vivo (i.e., after blood collection) by protease degradation of blood proteins. Endoproteases produce 'founder peptides' which are then pared down by exoproteases into ladder-like clusters. Panels of proteolytic activity in the blood contribute important cancer type-specific information, and that the resulting metabolic patterns have utility as surrogate markers for detection and classification of cancer. Degradation occurs during clotting. The use of exogenous synthetic peptides, identical to previously observed founder peptides, can be used to monitor cancer-specific proteolytic degradation in plasma or serum that contains proteases. Conditions in terms of time, temperature and added amounts of substrates can hereby be readily controlled. Coupled to a MALDI-based read-out, such analyses are blood "protease assays" to monitor the tumor-dependent activities inferred from prior studies. Simultaneous addition of non-degradable, exogenous reference peptides also enables relative quantitation of all rungs in the ladders.

Exogenous peptide degradation assays can be done, for example, in plasma, where there are no endogenous peptides that clutter the spectra, therefore simplifying interpretation. Thus, in addition to serving as (i) an alternative to endogenous serum peptide profiling, and as (ii) a highly reproducible, functional proteomics approach, the external peptide degradation assay (iii) permit analysis of plasma by the NY consortium, which is important as plasma is preferred by many for proteomic studies.

15 founder peptides (listed in FIG. 33) can be synthesized, all 'double-isotopically' labeled to be 12 Da heavier in molecular mass than their endogenous counterparts and 6 Da heavier than the non-degradable reference peptides. Selection is based on a sequence comparison of all previously observed peptide ladders in serum, most of which contain some known surrogate marker peptides. Synthesis, QC, quantitation and storage of the peptides will be done as described previously.

The degradation conditions and times are studied and optimized for each of the 15 synthetic founder peptides in each of the plasmas from the different groups of cancer patients and controls. The permissible inter-mixability of the different founders, and, particularly, of their resulting degradation ladders is determined in order to avoid disturbing the peak patterns (by ion suppression effects) and to avoid overlapping isotopic envelopes (when the peaks are too close).

As aminopeptidases come in varieties that remove one two or three amino acids, shorter endogenous peptides may have conceivably been derived from another precursor by leap-frogging over the stalled position. For non-degradable "founder" peptides, limited N-terminal ladders can be synthesized (by sequential sampling of resin during a pilot scale synthesis of unlabeled peptides), for instance, as shown in FIG. 33 (founder #7; five alternative 'test' founder peptides), and degradability can be tested in pooled cancer patient plasma in a time course (15 min to 4 hours) experiment. Similar tests are performed for founder peptides 8, 9, 10 and 12A in FIG. 33. Each time, synthesis is carried out of the "full-length" founder, but resin sampled at 5, 4, 3, 2 and 1 amino acid away from the N-terminus, or as appropriate. The longest peptide is cleaved from the resin, purified, and tested. If no degradation in plasma is observed, the shorter versions are also cleaved, purified and tested. An isotope-labeled version of the peptide with the best founder properties (i.e., generating the best ladder in plasma) is then produced.

The assay may be divided into 'founder pools' if two or more time points are too far apart or in the case of peptide inter-mixability problems. Once the ideal conditions and founder pools have been selected, and the resulting degradation products are identified, a relative quantitation aspect can be added to the blood protease assay by using the same non-degradable reference peptides as shown in FIG. 31.

D. Diagnosis

As indicated above, the invention provides methods for aiding a human cancer diagnosis using one or more markers, as specified herein. These markers can be used alone, in combination with other markers in any set, or with entirely different markers in aiding human cancer diagnosis. The markers are differentially present in samples of a human cancer patient and a normal subject in whom human cancer is undetectable. For example, some of the markers are expressed at an elevated level and/or are present at a higher frequency in human prostate cancer subjects than in normal subjects, while some of the markers are expressed at a decreased level and/or are present at a lower frequency in human prostate cancer subjects than in normal subjects. Therefore, detection of one or more of these markers in a person would provide useful information regarding the probability that the person may have prostate cancer.

The detection of the peptide marker is then correlated with a probable diagnosis of cancer. In some embodiments, the detection of the mere presence or absence of a marker, without quantifying the amount thereof, is useful and can be correlated with a probable diagnosis of cancer. The measurement of markers may also involve quantifying the markers to correlate the detection of markers with a probable diagnosis of cancer. Thus, if the amount of the markers detected in a subject being tested is different compared to a control amount (i.e., higher or lower than the control, depending on the marker), then the subject being tested has a higher probability of having cancer.

The correlation may take into account the amount of the marker or markers in the sample compared to a control amount of the marker or markers (up or down regulation of the marker or markers) (e.g., in normal subjects or in non-cancer subjects such as where cancer is undetectable). A control can be, e.g., the average or median amount of marker present in comparable samples of normal subjects in normal subjects or in non-cancer subjects such as where cancer is undetectable. The control amount is measured under the same or substantially similar experimental conditions as in measuring the test amount. As a result, the control can be employed as a reference standard, where the normal (non-cancer) phenotype is known, and each result can be compared to that standard, rather than re-running a control.

Accordingly, a marker profile may be obtained from a subject sample and compared to a reference marker profile obtained from a reference population, so that it is possible to classify the subject as belonging to or not belonging to the reference population. The correlation may take into account the presence or absence of the markers in a test sample and the frequency of detection of the same markers in a control. The correlation may take into account both of such factors to facilitate determination of cancer status.

In certain embodiments of the methods of qualifying cancer status, the methods further comprise managing subject treatment based on the status. The invention also provides for such methods where the markers (or specific combination of markers) are measured again after subject management. In these cases, the methods are used to monitor the status of the cancer, e.g., response to cancer treatment, remission of the disease or progression of the disease.

The markers of the present invention have a number of other uses. For example, they can be used to monitor responses to certain treatments of human cancer. In yet another example, the markers can be used in heredity studies. For instance, certain markers may be genetically linked. This can be determined by, e.g., analyzing samples from a population of human cancer subjects whose families have a history of cancer. The results can then be compared with data obtained from, e.g., cancer subjects whose families do not have a history of cancer. The markers that are genetically linked may be used as a tool to determine if a subject whose family has a history of cancer is pre-disposed to having cancer.

Any marker, individually, is useful in aiding in the determination of cancer status. First, the selected marker is detected in a subject sample using the methods described herein (e.g. mass spectrometry). Then, the result is compared with a control that distinguishes cancer status from non-cancer status. As is well understood in the art, the techniques can be adjusted to increase sensitivity or specificity of the diagnostic assay depending on the preference of the diagnostician.

While individual markers are useful diagnostic markers, in some instances, a combination of markers provides greater predictive value than single markers alone. The detection of a plurality of markers (or absence thereof, as the case may be) in a sample can increase the percentage of true positive and true negative diagnoses and decrease the percentage of false positive or false negative diagnoses. Thus, preferred methods of the present invention comprise the measurement of more than one marker.

E. Kits

In one aspect, the invention provides kits for monitoring and diagnosing cancer, wherein the kits can be used to detect the markers described herein. For example, the kits can be used to detect any one or more of the markers potentially differentially present in samples of cancer subjects vs. normal subjects. The kits of the invention have many applications. For example, the kits can be used to differentiate if a subject has cancer or has a negative diagnosis, thus aiding a cancer diagnosis. In another embodiment, the invention provides kits for aiding the diagnosis of cancer or the diagnosis of a specific type of cancer such as, for example, cancer of the prostate, of the bladder, or of the breast. The kits can also be used to identify compounds that modulate expression of one or more of the herein-described markers in in vitro or in vivo animal models for cancer.

In specific embodiments, kits of the invention contain an exogenous reference peptide, which is optionally isotopically labeled, for use in conducting the diagnostic assays of the invention.

The kits of the invention may include instructions for the assay, reagents, testing equipment (test tubes, reaction vessels, needles, syringes, etc.), standards for calibrating the assay, and/or equipment provided or used to conduct the assay. Reagents may include acids, bases, oxidizing agents, marker species. The instructions provided in a kit according to the invention may be directed to suitable operational parameters in the form of a label or a separate insert.

The kits may also include an adsorbent, wherein the adsorbent retains one or more markers selected from one or more of the markers described herein, and written instructions for use of the kit for detection of cancer. Such a kit could, for example, comprise: (a) a substrate comprising an adsorbent thereon, wherein the adsorbent is suitable for binding a marker, and (b) instructions to detect the marker or markers by contacting a sample with the adsorbent and detecting the marker or markers retained by the adsorbent. Accordingly, the kit could comprise (a) a DNA probe that specifically binds to a marker; and (b) a detection reagent. Such a kit could further comprise an eluant (as an alternative or in combination with instructions) or instructions for making an eluant, wherein the combination of the adsorbent and the eluant allows detection of the markers using gas phase ion spectrometry.

Optionally, the kit may further comprise a standard or control information so that the test sample can be compared with the control information standard to determine if the test amount of a marker detected in a sample is a diagnostic amount consistent with a diagnosis of cancer.

This invention is further illustrated by the following examples, which should not be construed as limiting. A skilled artisan should readily understand that other similar instruments with equivalent function/specification, either commercially available or user modified, are suitable for practicing the instant invention. Rather, the invention should be construed to include any and all applications provided herein and all equivalent variations within the skill of the ordinary artisan.

EXAMPLES

Example 1

Unsupervised Hierarchical Clustering and PCA of Mass Spectrometry-Based Serum Peptide Profiling Data In order to determine if selected patterns of serum peptides with known sequences can (i) separate cancer from non-cancer, (ii) distinguish between different types of solid tumors, and (iii) allow class prediction with an independent validation set, the serum peptide profiles were analyzed from patients with advanced prostate, breast, or bladder cancer, as well as control sera from healthy volunteers, all collected using a standardized protocol (Villanueva, J., et al., 2005. *J Proteome Res:* 4:1060-1072).

A. Methods

Serum Samples

Blood samples from n=33 healthy volunteers (mixed gender; ages 23 to 49) with no known malignancies and from patients diagnosed with advanced prostate cancer (n=32), bladder cancer (n=20), or breast cancer (n=21) were collected following a standard clinical protocol (Villanueva, J., et al., 2005. *J Proteome Res:* 4:1060-1072) and approved by the MSKCC Institutional Review and Privacy Board. Blood samples were obtained in 8.5-mL, BD Vacutainer, glass 'red-top' tubes (Becton Dickinson # 366430, Franklin Lakes, N.J.), allowed to clot at room temperature for 1 hour, and centrifuged at 1400-2000 RCF for 10 min, at RT.

Sera (upper phase) were transferred to four 4-mL cryovials (Fisher # 0566966), ~1 mL serum in each, and stored frozen at −80° C. until further use (Villanueva, J., et al. 2005. *J Proteome Res:* 4:1060-1072). A similar procedure was followed for preparation of plasma in heparin-containing 'green-top' tubes (BD #366480), except that centrifugation was done immediately after blood collection. Upon delivery at the mass spectrometry (MS) laboratory, the cryovials (source vials) were barcoded. One cryovial of each sample was thawed on ice and used to generate nine smaller aliquots (50 μL each) in barcoded micro-eppendorf tubes and stored at −80° C. in barcoded freezer boxes. In the present study, every serum sample underwent two freeze/thaw cycles, the second thawing step occurring immediately prior to peptide extraction and MS analysis.

All 106 serum samples were processed automatically as a single batch with a robot liquid handler followed within one hour by automated MALDI-TOF mass spectrometric analysis. The four clinical groups were randomized before automated solid-phase peptide extraction and MALDI-TOF mass spectrometry.

Automated, Solid-Phase Peptide Extraction

Serum peptide profiling was accomplished using a technology platform developed for simultaneous measurement of large numbers of serum polypeptides (Villanueva, J., et al. 2004. *Anal Chem* 76:1560-1570). It uses magnetic bead-based, solid-phase extraction of predominantly small peptides followed by a MALDI-TOF MS read-out. The system is intrinsically more sensitive than any surface capture on chips, as spherical particles have larger combined surface areas than small-diameter spots. When combined with high-resolution MS, hundreds of peptides are detected in a single droplet of serum.

For the present analysis, peptides were captured and concentrated using SiMAG-C8/K superparamagnetic, silica-based particles ($\leq$1 micron diameter; 80% iron oxide; non-porous), bearing C8 reversed-phase (RP) ligands (Chemicell, Berlin, Germany). All analyses were performed in a 96-well format, using the same batch of C8 magnetic particles, in 0.2-mL polypropylene tubes (8×12-tube 'Temp Plate II'; USA Scientific, Ocala, Fla.).

The protocol is based on a detailed investigation of serum handling, RP ligand and eluant selection (Villanueva, J., et al. 2004. *Anal Chem* 76:1560-1570), and is automated using a 'Genesis Freedom 100' (Tecan; Research Triangle Park, N.C.) liquid handling workstation for throughput and reproducibility. The system was programmed either directly via its standard software or, when individual wells needed to be accessed independently, indirectly through its work-lister capability. This system automates all of the liquid-handling steps, including magnetic separation via a robotic manipulating arm, mixing of eluates with MALDI matrix and deposition onto the Bruker 384-spot MALDI target plates. A computer randomization program was used to position case and control samples for both solid-phase extraction and mass spectrometry.

Mass Spectrometry

Peptide profiles were analyzed with an Autoflex MALDI-TOF mass spectrometer (Bruker; Bremen, Germany) equipped with a 337 nm nitrogen laser, a gridless ion source, delayed-extraction (DE) electronics, a high-resolution timed ion selector (TIS), and a 2 GHz digitizer. Separate spectra were obtained for two restricted mass-to-charge (m/z) ranges, corresponding to polypeptides with molecular mass of 0.7-4 kDa ("$\leq$4kD") and 4-15 kDa ("$\geq$4kD") (assuming z=1), under specifically optimized instrument settings. Each spectrum was the result of 400 laser shots, per m/z segment per sample, delivered in four sets of 100 shots (at 50-Hz frequency) to each of four different locations on the surface of the matrix spot.

The peak list (normalized intensities of 651 m/z-peaks, i.e., peptide-ions, in all 106 samples) generated was subjected to a Mann-Whitney U test, for each of the cancer groups individually versus the control. In a first selection, 196 peaks with adjusted p-values <0.00001 (arbitrarily chosen) for at least one cancer type were retained. This number was reduced to 68 by applying an arbitrary threshold (500 'units') to the median intensities of each individual peptide peak within a group. An m/z-peak was selected if it passed the threshold in at least one of the cancer groups or the control (FIG. 13).

A weekly performance test was carried out with commercial human reference serum (# S-7023, lot 034K8937; Sigma, St Louis, Mo.), and the effective laser energy delivered to the target was adjusted when necessary. The entire irradiation program was automated using the instrument's 'AutoXecute' function. Spectra were acquired in linear mode geometry under 20 kV (18.6 kV during DE) of ion accelerating and −1.3 kV multiplier potentials, and with gating of mass ions $\leq$400 m/z ($\leq$4kD segment) or $\leq$3,000 m/z ($\geq$4kD segment). DE was maintained for 80 ($\leq$4kD) or 50 nanoseconds ($\geq$4kD) to give appropriate time-lag focusing after each laser shot.

Peptide samples were consistently mixed with two volumes of pre-made a-cyano-4-hydroxycinnamic acid (ACCA) matrix solution (Agilent; Palo Alto, Calif.), deposited onto the stainless steel target surface, in every other column of the 384-spot layout, and allowed to dry at room temperature. Thirty fmoles (per peptide) and 500 fmoles (per protein) of commercially available calibration standards (Bruker Daltonics # 206195 (<4kD) and # 206355 (>4kD)) were also mixed with ACCA matrix and separately deposited onto the target plates, adjacent to each spotted serum sample (one sample/one standard), in the alternating columns. All spectra were acquired within less than 1-2 hours after completion of robotic sample processing, as an adverse effect had previously been observed upon increasing times between crystallization and mass spectral acquisition.

The AutoFlex MALDI-TOF has a probe at the output of the laser, before the attenuator. The accuracy of this monitoring device was verified prior to the calibration of the settings of the attenuator (displayed on the computer screen as an arbitrary scale of 100-0%) by measuring transmitted energy at varying %. This allowed the generation of a calibration curve to convert before-to-after attenuation laser energy. The optimal laser setting that had been empirically determined was then measured to yield 16-μJ energy per pulse, post-attenuation. Laser output energy was measured and documented on a weekly basis, and adjustments were made accordingly to compensate for fading laser energy over time.

Samples from patients with different cancers and from controls were randomly distributed during processing and analysis.

Signal Processing

Once acquired, all data were stored with a naming convention that allows each sample to be associated with its calibrant. The spectra were first converted from binary format to ASCII files containing two columns of data (x: m/z, y: intensity) by a custom written macro in FlexAnalysis (Bruker). For the lower mass range (700-4,000 Da), about 48,000 x,y-points were generated, while for the upper mass range (4-15 kDa), there were about 77,000 points.

Further data processing was carried out in MATLAB with a custom script called 'Qcealign' using only the ASCII versions of the raw spectra. 'Qcealign' used the 'Qpeaks' program (Spectrum Square Associates, Ithaca, N.Y.) for smoothing, baseline subtraction and peak labeling. The singletwidth parameter required by 'Qpeaks' was set to −400 for the lower mass range and −200 for the upper mass range, thereby specifying the resolution, $(m/z)\Delta(m/z)$, for processing. This peak information was used automatically by 'Qpeaks' in setting the parameters for smoothing, baseline-subtraction, and binning. The noise statistics were assumed 'Normal'.

Following parameter selection, a setup file was created. 'Qcealign' then queries the setup file to obtain a list of all the directories for processing. During a single processing run, all data files in all listed directories are aligned with each other. For each directory, singletwidth information is provided in the setup file, along with parameters controlling calibration, peak labeling sensitivity, alignment, etc. The files containing the polypeptide standards are calibrated first. The centroid positions of peaks in these calibration files are obtained from the peak table created by 'Qpeaks', compared to the known polypeptide peak positions, and a quadratic calibration equation for correcting the measured masses in each calibration file is created. The calibration equations are saved to disk for use in calibrating the mass axes of the sample files.

'Qcealign' subsequently creates a reference file to which all sample spectra will later be aligned. The first data file is loaded and calibrated by applying the curve calculated from its associated calibrant spectrum. This file's x-axis (m/z) becomes the x-axis (and thus the calibration) used in the reference file. 'Qcealign' then loads all other sample files, calibrates them, and adds their intensities to the reference file's intensity. After all samples have been added, the reference spectrum becomes the average of all the sample files. The reference is processed with 'Qpeaks' to find a baseline, which is subtracted, and is then normalized to unit size by dividing each intensity value by the Total Ion Count (TIC). Once normalized, a scaling factor is added by multiplying each intensity value by a user-selected number (e.g., $10^7$). This scaling factor is constant within a data set and is used to convert the normalized spectrum to a "user friendly" scale, where most peak heights are greater than one. Next, 'Qcealign' processes each sample file with 'Qpeaks' to create a peak table, smoothed curve and a baseline. This spectrum is then taken for alignment.

Alignment

Processed spectra were aligned using the custom 'Entropycal' program described herein above. A custom alignment algorithm, 'Entropycal', aligns sample data files to a reference file using a minimum entropy algorithm by taking unsmoothed ('raw'), baseline-corrected data. Taking raw spectra for alignment facilitates the use of all statistical information in the data; processed data contains less information. The alignment is performed in two steps: 'Entropycal' and binning. 'Entropycal' slides each data file by 'n' data points to the right or left along the x-axis of the reference file. At each relative position n, the Shannon entropy of the sum of the two files is computed. The optimal alignment occurs at the shift that produces the minimum Shannon entropy. Second, the aligned peak lists are binned by using the resolution of the peaks: all peaks in rows within $\Delta(m/z)$ of the strongest peak at a given value of m/z are binned together, and a spreadsheet is created for further statistical analysis.

Three software modules, developed in MATLAB, were used for visualization and signal processing of the spectra. (I) Signal Processing & Preview (SPP), a graphical viewer for spectra in ASCII format, allows to plot raw and processed spectra side-by-side to review the outcome of signal processing. Furthermore, parameters of 'Qpeaks' (the signal processing software) can be adjusted. (II) Mass Spectra Viewer (MSV), a visual interface for processed spectral data, plots spectra as X-Y curves (mass vs. magnitude) for examining the signatures of several groups of samples. MSV supports regular browsing functions such as scroll, zoom, highlighting, etc. (III) HeatMap (HM) displays spectra as a 2D heat map images, in which the magnitude of the peaks are color-coded on a continuous scale. In addition to browsing functions such as zoom and scroll, the rank of X- and Y-position coordinates can be reorganized without the constraints of statistical correlation that are enforced by most HeatMap commercial software packages.

Ratios were calculated by dividing the median normalized intensity of each m/z-peak in each cancer group by the median of the same m/z-peak in the control group. To avoid having to divide by zero, any median value of less than was converted to 1; this was applied to all groups. For hierarchical clustering, the 651 m/z-values were subjected to average-linkage hierarchical clustering analysis using the available algorithm in 'GeneSpring'. The peaks were organized by creating mock-phylogenetic trees (dendrograms) termed 'gene trees' and 'experiment tree' in the software. The trees were displayed with the samples along the X-axis and the masses along the Y-axis. The clustering method for both trees also measured similarity by Standard Correlation (also known as 'Pearson correlation around zero') as the distance matrix.

A spreadsheet ('peak list'), containing the normalized intensities of all 651 peaks for each of the samples was taken for unsupervised, average-linkage hierarchical clustering using standard correlation. This resulted in a high degree of separation between each of the cancer types and the controls in either binary or multi-class comparisons (FIGS. 1B and 1C). Recognizing that correlations between patient samples involving 651 features would be difficult at different times and locations, statistical feature selection was performed to identify the most discriminant peaks.

The binned spreadsheet, containing data from spectra obtained for all samples of cancer patients or healthy subjects (106 samples total; 651 m/z values, with normalized intensities for each sample; >70,000 data points), as well as the test set for prostate ('Prostate #2'; 41 samples; ~27,000 data points), were imported into the 'GeneSpring' program (Agilent; Palo Alto, Calif.) and analyzed using various statistical algorithms, such as one-way ANOVA, PCA, hierarchical clustering, K-NN and SVM.

Different "experiments" were created in 'GeneSpring' to represent the masses. No normalizations were applied to the experiment, since the masses were normalized by the database that binned them. In the parameter section of the experiments, a parameter called 'cancertype' was created to label samples as prostate cancer, breast cancer, bladder cancer, or control. In the Experiment's Interpretation section, the Analysis mode was set to "Ratio (signal/control)", and all measurements were used. No Cross-Gene Error model was used.

For ANOVA, once the experiments were created, the m/z-values ('peaks') were filtered by using non-parametric tests: Mann-Whitney test (for binary comparisons) and Kluskal-Wallis test (for multi-class comparisons) with Benjamini and Hochberg False Discovery Rate at $p<1e-5$. These tests are meant to find peaks that show statistically significant differences between the clinical groups studied.

For class prediction, K-nearest-neighbor (K-NN) analysis and Support Vector Machine (SVM) were carried out by using the Class Prediction Tool in 'GeneSpring'. The training groups constituted either a binary comparison (prostate #1 and Control) or a multi-class comparison (prostate #1, breast, bladder and control). The test set was 'prostate #2'. The Parameter to Predict was set to Cancertype. The Gene selection was set to use different groups of masses previously selected (e.g., 651, 68, 14, 13). In K-NN, the number of neighbors was set to five with a p-value decision cutoff of 1. The SVM was done with the same training sets and parameters and set to predict the Prostate #2 test set. The kernel used was polynomial dot product (Order 1) with a diagonal scaling of 0.

B. Results

1. Distribution of serum peptides, detected by MALDI-TOF MS, as a function of mass-to-charge (m/z) range and normalized intensity.

Figure 11A:
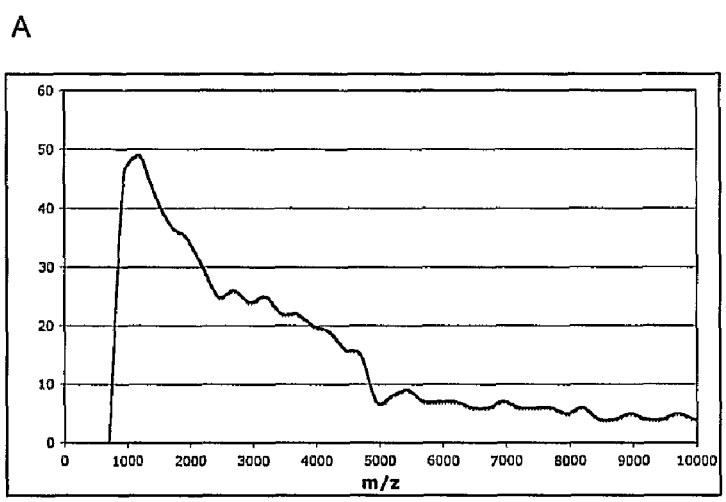
FIG. 11A graphically depicts the distribution of serum peptides. Number of m/z-peaks are plotted as a function of m/z range. The first bin, from m/z=0 to 700, is empty, as no data was collected in that region. No bins are shown in the range >10 kDa.

Peptides were extracted from 106 different serum samples (50 μL), drawn from one of three groups of cancer patients or healthy controls, analyzed by MALDI-TOF MS and the m/z-peaks were exported from the aligned spectra, as described earlier. In FIG. 11A, a total of 651 unique m/z-peaks, i.e., peptide-ions, derived from the combined spectra, are grouped in successive bins of 250 amu, starting at m/z=700.

Figure 11B:
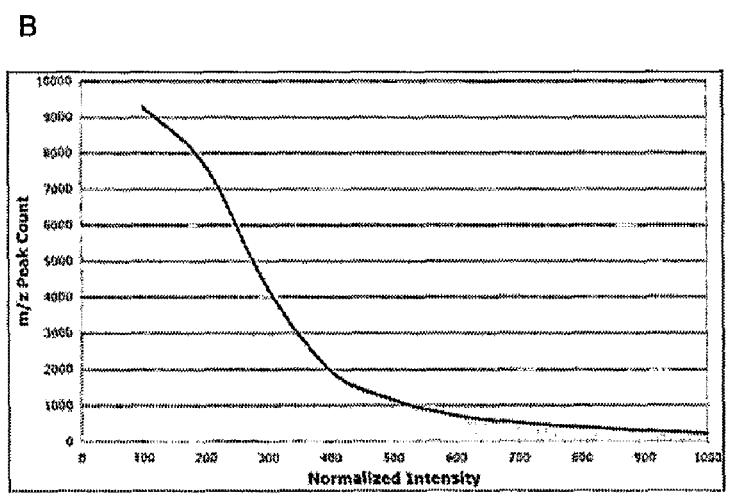
FIG. 11B likewise graphically depicts the distribution of serum peptides. Here, however, number of m/z-peaks are plotted as a function of normalized intensity. No bins are shown in the region over 1,000 arbitrary units. The highlighted area indicates the range above the median peak-intensity threshold, used for selecting potential biomarkers (FIG. 17).

In FIG. 11B, all peak intensities of all samples (i.e., 651× 106 peaks) are grouped in successive bins of 100 arbitrary units, starting at zero. The intensities refer to normalized units that were calculated for each peak by dividing its raw intensity by the total of all the intensities in that spectrum (TIC—Total Ion Count). The resultant values were then multiplied by fixed scaling factor ($1\times10^7$) to convert the data to a 'user-friendly' scale (i.e. most values $\geq 1$) Serum peptide profiling resulted in a total of 651 distinct mass/charge (m/z) values resolved in the 800-15,000 Dalton range (FIG. 16A).

2. Serum peptides, determined by MALDI-OF MS, before and after two successive feature selection steps for candidate markers.

One-way ANOVA Mann-Whitney test, for each individual cancer versus control, selected 196 peaks (red bars, FIG. 12) with a false positive rate of $p<0.00001$ (arbitrarily chosen) for at least one cancer type. This number was further reduced to 68 (yellow bars, FIG. 12) by applying an arbitrary threshold of 500 'units' to the median intensities of each individual peptide peak within a group. The threshold was set high enough to select only robust peaks in the spectra, with intensities that would permit MALDI MS/MS-based tandem mass spectrometric sequencing and to exclude closely positioned neighboring peaks or 'shoulders'.

An m/z-peak was selected if this criterion was met in at least one of the cancer groups or the control (FIG. 13). When feature selection was repeated using a multi-class Kluskal-Wallis test (adjusted $p<1e-5$) and the same median intensity threshold as above, 214 and 67 peaks were selected (data not shown). The majority of selected peaks corresponded to peptides with molecular mass <2,000 Da; most peptides with a mass >4,000 Da were removed (FIG. 2A; FIG. 13). Thus, significance levels (p-values) were calculated for each m/z-peak using the Mann-Whitney rank sum test (for binary comparisons) or the Kruskal-Wallis test (for multi-class comparisons) (FIG. 16B).

Example 2

Feature Selection and Comparative Analysis of Serum Peptide Profiling Data

Feature Selection

Figure 12:
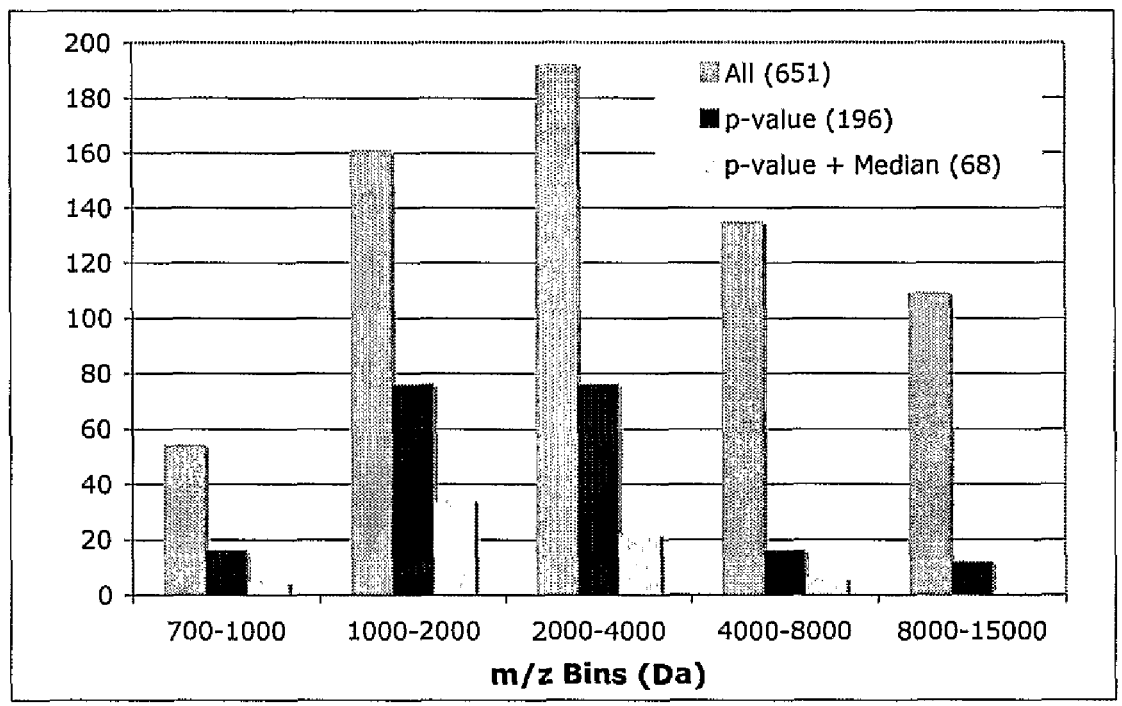
FIG. 12 depicts a histogram that shows, starting with a total of 651 unique m/z-peaks (blue bars) derived from three groups of cancer patients and healthy controls, the number of peptides in each mass range that passed two filters applied during feature selection.

The peak list (normalized intensities of 651 m/z-peaks in all 106 samples), generated as described in Example 1, above, was subjected to one-way ANOVA Mann-Whitney test for each of the three previously identified cancer groups individually vs. the control. For each of the three cancer groups versus the control, 196 peaks with a p-value <1e-5 were arbitrarily selected and retained (FIG. 12). This number was subsequently reduced to 68 by applying an arbitrary threshold (500 'units') to the median intensities of each individual peptide peak within a group. The threshold was set high enough to only select robust peaks in the spectra, with intensities that would permit MALDI TOF/TOF-based tandem mass spectrometric sequencing and to exclude closely positioned neighboring peaks or 'shoulders'. An m/z peak was selected if it passed the threshold in at least one of the cancer groups or the control.

Figure 2A:
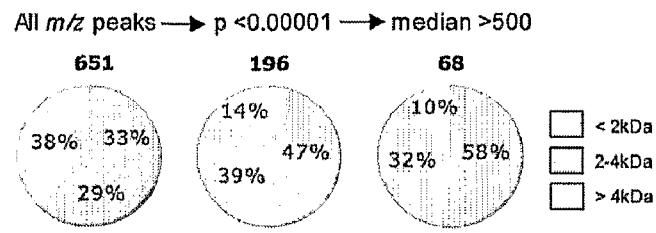
FIG. 2A shows pie charts depicting the peak number reduction in three m/z ranges, which illustrates the impact of each filter on peptides of different molecular mass.

The pie-charts depicted in FIG. 2A illustrate the effect of using a significance level ($p<0.00001$) cutoff by itself, or in combination with a cutoff for the median of normalized intensities ($\geq 500$) within any one group, on the m/z distribution of the candidate biomarker peptides. After the first filter, the 196 remaining peptides were redistributed in groups of 92, 76 and 28 for the increasing mass ranges. Sixty eight peptides passed the second filter; 39, 22 and merely 7 in the low-, medium- and high-mass ranges, respectively (right panel, FIG. 2A).

Figure 2B:
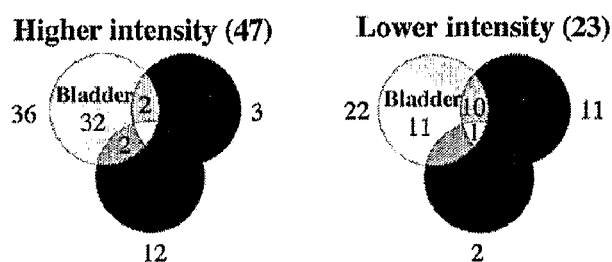
FIG. 2B depicts the Venn-diagrams showing the number of peptides that passed two selection steps. m/z-peaks with higher intensities in one (or more) of the cancer groups as compared to controls are shown in the left panel, while those with lower intensities are shown in the right panel. The numbers shown outside the diagrams indicate the total number of peptides of a specific cancer group that were either up or down.
Figure 2C:
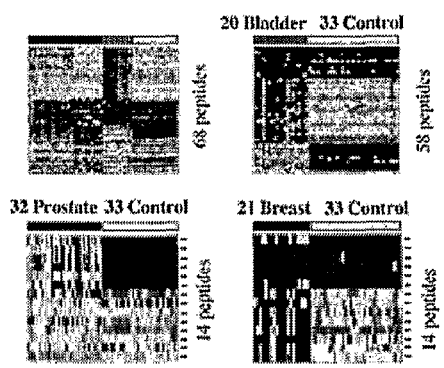
FIG. 2C shows heat maps comparing the selected features of the three cancer groups with controls in multi-class and binary formats. Columns represent samples (as indicated per group); rows are peptide m/z-peaks (not in numerical order). The number of peptides used in each binary comparison (i.e., 58, 14, and 14) is the sum of those that were specifically higher and lower in each cancer group; the multi-class heat map contains the total, non-redundant number of peptides (i.e., 68). The 'multi-class', 'bladder' and 'breast' heat map scales of normalized intensities are from 0 (green) to 500 (red), with the midpoint at 250 (yellow); those of the 'prostate' heat map are, respectively, 0, 2,000 and 1,000.
Figure 2D:
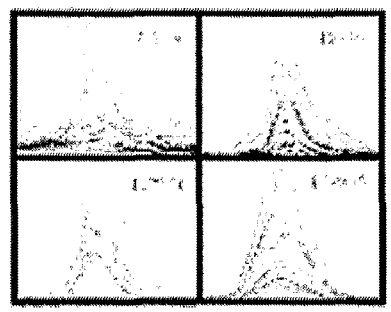
FIG. 2D depicts overlays of mass spectra obtained from the three binary comparisons (cancer vs. control). Mono-isotopic masses are listed for each peak. Two statistically significant differences in peptide intensities (one higher; one lower) between prostate cancer (blue) and controls (yellow) are shown, as well as one higher-intensity peptide for bladder cancer (green) and one for breast cancer (red).

Examples are shown in FIGS. 2D and 3. The majority of the selected peaks corresponded to peptides with molecular mass <2,000 Da; most peptides with a mass >4,000 Da were eliminated (FIGS. 12 and 2A). Color-coded spectra from all samples were subsequently overlaid to visually inspect the 68 peaks for correct assignment, degree of separation, and overall difference between cancer and control. Of the peptides that passed the above-delineated two selection steps, 47 m/z peaks had higher intensities in one or more of the cancer groups, as compared to the controls, and 23 had lower intensities, as compared with the control. Of those, two were higher in breast cancer but lower in bladder cancer.

The total numbers of peptides of a specific cancer group that were observed to be up or down (have specific biomarker potential) were as follows: 3 peptides were up and 11 down (14 total—1 unique, 3 shared) in serum samples from prostate cancer patients, 12 up/2 down (14 total—11 unique) in breast cancer, and 36 up/22 down (58 total—43 unique) in bladder cancer (FIG. 2B).

Comparative analysis via heat map display and mass spectral overlay: Comparison of the selected features (Tables 17A-C) of the three cancer groups with controls in multi-class and binary formats was accomplished with heat maps. Heat map displays were generated using a MATLAB custom software tool.

Three software modules, developed in MATLAB, were used for visualization and signal processing of the spectra. (I)

Signal Processing & Preview (SPP), a graphical viewer for spectra in ASCII format, allows the plotting of raw and processed spectra side-by-side to review the outcome of signal processing. Furthermore, parameters of 'Qpeaks' (the signal processing software) can be adjusted. (II) Mass Spectra Viewer (MSV), a visual interface for processed spectral data, plots spectra as X-Y curves (mass vs. magnitude) for examining the signatures of several groups of samples. MSV supports regular browsing functions such as scroll, zoom, highlighting, etc. (III) HeatMap (HM) displays spectra as 2D heat map images, in which the magnitude of the peaks are color-coded on a continuous scale. In addition to browsing functions such as zoom and scroll, the rank of X- and Y-position coordinates can be reorganized without the constraints of statistical correlation that are enforced by most HeatMap commercial software packages.

The results, when represented in the form of heat maps in FIG. 2C, indicated that data reduction (by ~90%) did not adversely affect the separation of the clinical groups.

Subsequently, mass spectra for the three binary comparisons (cancer vs. control) were processed as described earlier and displayed using Mass Spectra Viewer (MSV) (FIG. 2C).

Example 3

Serum Peptide Barcodes for Advanced Prostate, Bladder, and Breast Cancer

A. Methods

Assigning Peptide Sequences

A set of peptides previously selected on the basis of statistical differences in intensity between cancers and control groups was analyzed by MALDI-TOF/TOF tandem mass spectrometry, using an UltraFlex TOF/TOF instrument (Bruker; Bremen, Germany) operated in 'LIFT' mode. The mono-isotopic masses were first assigned by one-dimensional reflectron-TOF MS, in the presence of three peptide calibrants (6 fmoles each; calculated monoisotopic masses of 2,108.155 Da, 1,307.762 Da and 969.575 Da in the protonated form), as previously described (Winkler, G. S., et al; 2002, *Methods* 26:260-269).

Spectra were obtained by averaging multiple signals; laser irradiance and number of acquisitions (typically 100-150) were operator-adjusted to yield maximal peak deflections derived from the digitizer in real time. Mono-isotopic masses were assigned for all selected and other prominent peaks after visual inspection, and the low- and high-end internal standards were used for recalibration. The pass/fail criterion for recalibration is a correct assignment of an m/z value for the 'middle' calibrant with a mass accuracy equal or better than 12 ppm.

Alternatively, a QSTAR XL Hybrid quadrupole (Q) time-of-flight mass spectrometer (Applied Biosystems/MDS Sciex; Concord, Canada), equipped with an o-MALDI ion source, was used for both duplicate and additional tandem-MS analyses. By selecting precursor ions of interest in 'Q1' (operated in the mass-filter mode), mass measurements of fragment ions could be obtained in the TOF detector following collision-induced dissociation (CID) in 'Q2'. Typically, a mass window of 3 Da was selected in order to transmit the entire isotopic envelope of the precursor ion species. Collision energy was operator adjusted to yield maximum number and intensities of the fragment ions.

Fragment ion spectra resulting from TOF/TOF analyses (300-1,000 acquisitions averaged per spectrum) were taken to search a "non-redundant" human database ('NCBInr'; release data: 09-20-2004; 106,486 entries; National Center for Biotechnology Information, Bethesda, Md.) using the MASCOT MS/MS ion search program, version 2.0.04 for Windows (Matrix Science Ltd., London, UK) with the following search parameters: mono-isotopic precursor mass tolerance of 35 ppm, fragment mass tolerance of 0.5 Da, and without a specified protease cleavage site.

Mascot 'mowse' scores greater than 35 were considered significant. Any identification thus obtained was verified independently by two different people, by comparing the computer-generated fragment ion series of the predicted peptide with the experimental MS/MS data. Some sequence assignments had below-threshold scores but could, nonetheless, be unequivocally assigned, as the precursor ion mass and selected fragment ion masses (b" or y") matched a particular peptide, representing a rung in one of the serum peptide sequence ladders.

B. Results

Peptide sequence assignment: 46 of the 68 previously selected peptides (FIGS. 2B and 17) were positively identified by MALDI-TOF/TOF MS/MS and MALDI-Q/TOF MS/MS analysis and database searches (FIG. 5A, additionally showing others (including m/z=1786.86, 2021.05, 2305.20, 2627.48)). Note that the m/z values listed in FIG. 5A are mono-isotopic and therefore smaller than the corresponding average isotopic values listed in FIGS. 16 and 17. Of note, all but a few of the peptide sequences clustered into the sets of overlapping fragments, lined up within each group at either the C- or N-terminal end, and with ladder-like truncations at the opposite ends. Some sequence assignments had below-threshold scores but could, nonetheless, be unequivocally assigned, as the precursor ion mass and selected fragment ion masses (b" or y") matched a particular rung in one of the ladders, taking into account whether the limited CID patterns were in agreement with established rules (Kapp, E. A. et al., 2003. *Anal Chem* 75:6251-6264) of preferential peptide bond cleavage (e.g., Xaa-Pro or Asp/Glu-Xaa) and the putative sequence.

Furthermore, 23 additional peptides, outside the original group of 68, could also be matched to certain sequence clusters by hypothesis-driven, targeted MS/MS analysis. Fifteen of those had significant discriminant analysis adjusted p-values (<0.0002) for at least on cancer type but typically lower ion intensities (FIG. 5B). Two others ('2553' and '2021'; yellow-coded in FIGS. 5A and 5B) displayed very high but similar MS ion intensities across all cancer groups and the control, with adjusted p-values >0.04, and can therefore be regarded as quasi-internal controls. Six more peptides (pink-coded in FIGS. 5A and 5B) that fit into the clusters were randomly observed in samples of the cancer and control groups and have neither discriminant nor internal control value. It should be noted that we used an unbiased approach to identify 'marker peptides', in which the peptides were selected first on the basis of discriminant analysis and then sequenced. This approach, commonly referred to as 'ion mapping', can be taken using any type of mass spectrometric platform (Gao, J. et al., 2003. *J Proteome Res* 2:643-649; Fach, E. M. et al. 2004. *Mol Cell Proteomics* 3:1200-1210).

Three clusters derived from naturally occurring serum peptides, fibrinopeptide A (FPA), complement C3f and bradykinin, that are themselves generated from various plasma proteins through endoproteolytic cleavage, either before (bradykinin, cleaved from H-kininogen by a kallekrein) or during (FPA, N-terminally cleaved from fibrinogen by thrombin to form fibrin; C3f, released by Factors I and H after prior conversion of C3 to C3b) serum preparation (Jandl, J. H.

1996. *Blood: Textbook of hematology*. New York, N.Y.: Little, Brown and Co.; Sahu, A., and Lambris, J. D. 2001. *Immunol Rev* 180:35-48).

The full-length 'founder' peptides end with Arg, preceded by a hydrophobic amino acid (Val, Leu or Phe). Arg is partially removed from C3f and bradykinin (to form desArg-bradykinin). Similar 'trypsin-like' cleavages (Arg/Lys—Xaa) underlie formation of all other peptide clusters as well (see below). The C-terminal basic amino acid is preceded by a hydrophobic amino acid (F, L, V, I, W, A) in 21 and by S, Q or N in 15 out of the 39 observed cleavage sites (FIG. 15). Arg/Lys is typically removed (fully or in part) by a carboxypeptidase, except when preceded by Pro (3 out of 3 cases) or sometimes when preceded by Val (2 out 4). Further exoprotease degradation then proceeds at the N-terminal or C-terminal ends, either to completion or until it stalls; many or all of the 'intermediates' are typically represented (FIGS. 5A and 14). Of note, full-length C3f (m/z=2021.05) was found to be present at equally high concentrations in all patient and control sera (see B), and therefore represents a virtual internal standard.

Diagnostic MALDI-TOF spectral patterns consisting of N-terminal FPA and C3f truncations have previously been found in sera of myocardial infarction patients (Marshall, J. et al., 2003. *J Proteome Res* 2:361-372). In contrast, nearly all of these peptides (19 total) were detected in control sera (FIG. 3B), and their presence was shown to be either consistently lower (all FPA fragments in all cancers; three C3f fragments in breast cancer) and/or higher (several Cf3 fragments in bladder and prostate cancer; one FPA fragment in breast cancer) in patient sera (FIG. 5A). Full-length C3f was present in all samples at equally high concentrations. Full-length FPA was virtually absent in sera from bladder cancer patients; no fibrinopeptide B or fragments thereof were found in any of the samples.

Decreased levels of FPA (fragments) in prostate, bladder and breast cancer patients, as shown here, also contrast with earlier findings indicating elevated levels of phospho-FPA in sera of ovarian cancer patients (measured by ESI-MS (Bergen, H. R., 3rd, et al., 2003. *Dis Markers* 19:239-249) and of FPA in gastrointestinal and breast cancers (measured immunochemically (Abbasciano, V. et al., 1987. *Med Oncol Tumor Pharmacother* 4:75-79; Auger, M. J. et al., 1987. *Haemostasis* 17:336-339).

Bradykinin and desArg-bradykinin levels were higher in sera of breast cancer patients and lower in bladder cancer patients. Of note, the pro-hydroxylated forms of each peptide also followed that trend (data not shown). The bradykinin and FPA parent proteins, fibrinogen alpha and HMW-kininogen, each contributed one additional sequence cluster, located in a different section of the precursor sequence, to the cancer serum peptide barcodes (FIGS. 5A and 6; FIGS. 14 and 15). Interestingly, the bradykinin and 'other' kininogen-derived peptides have very different marker properties. For example, whereas bradykinin and desArg-bradykinin were generally of lower ion intensity in bladder cancer than in control sera, the other two peptides ('1944' and '2209') actually showed higher relative intensities in bladder cancer (FIGS. 5A and 16).

One of the peptides ('2724', FIG. 5A) in a cluster of sequences is derived from the inter-alpha-trypsin inhibitor heavy chain H4 (ITIH4) precursor (Salier, J. P. et al., 1996. *Biochem J* 315 (Pt 1): 1-9) and covers amino acids 662-687 (FIG. 17) and is bracketed by two kallikrein cleavage sites (Phe-Arg—Xaa). Residues 662-688 likely represent a 'propeptide' of unknown function (Nishimura, H. et al., 1995. *FEBS Lett* 357:207-211). Like bradykinin, it ends with Pro-Phe-Arg. Several longer ITIH4 precursor fragments actually span the first kallikrein cleavage site, including '3272' at 658-687, that has been reported as a biomarker for early stage ovarian cancer (Zhang, Z. et al., 2004. *Cancer Res* 64:5882-5890). Variations in N-terminal truncation by just a few amino acids in the ITIH4 cluster were found to produce relatively selective 'markers' for each of the three different cancers. Median ion intensities of peptides '3971' and '3273', for instance, were clearly highest in bladder cancer samples, peptides '2358' and '2184' were highest in breast cancer, and '2271' was highest in prostate cancer. Also of note, peptide '2115' matches the sequence of an ITIH4 splice variant (PRO1851; FIG. 15) and appears to have strong marker capacity for each cancer type, particularly for bladder and breast (FIG. 16).

A seventh cluster of 8 sequences, 4 on either site of a single Ile-Arg—Xaa cleavage site, is derived from the complement C4a precursor (Belt, K. T. et al., 1984. *Cell* 36:907-914) (FIGS. 5A, 14, and 15). This C4a-cluster has the highest incidence of ion markers for breast cancer; more than any in other cluster and also more than C4a-derived bladder cancer markers (FIG. 16). Only a single ion ('1763') of this cluster is an ion marker for prostate cancer, and is shared in that capacity with the other two cancer types. On the other hand, all but one ion marker derived from apolipoproteins (APO) A-I, A-IV and E are bladder cancer specific, all with appreciably higher ion intensities; the exception (APO A-IV, peptide '1971 ') is actually highly selective and statistically the most significant (p=5.5e-13) ion marker for breast cancer (FIGS. 5A and 16).

Up-regulation of clusterin, i.e., 'APO J', has been correlated, by immuno-histochemistry, with progression of both prostate and bladder cancer (July, L. V. et al., 2002. *Prostate* 50:179-188; Scaltriti, M. et al., 2004. *Int J Cancer* 108:23-30; Miyake, H. et al., 2002. Urology 59:150-154). The 10-amino acid clusterin fragment detected at elevated concentrations in sera of bladder and prostate cancer patients is located at the C-terminus of the beta-chain. A single cut is, therefore, sufficient to release this peptide, following separation of the clusterin beta (N-t) and alpha (C-t) chains by cleavage of a Val-Arg—Xaa bond. A 6-amino acid sub-fragment has statistically relevant marker potential for bladder cancer (FIGS. 5A and 16), which is in keeping with the trend for most other peptides from APO A-I, A-IV, and E. Two ions ('2602'; '2451'), each with significantly higher median intensities in breast cancer samples than in controls, corresponded to peptides derived from, respectively, Factor XIIIa and thransthyretin (FIGS. 5A and 5B). In contrast to the aforementioned clusters, each peptide was the only fragment from the respective precursors that we observed. Peptide '2602' actually represents the C-terminal 25 amino acids of the Factor XIIIa propeptide (37-residues long) (FIGS. 14 and 15). Interestingly, Factor XIII itself has been found significantly down-regulated in breast tumors compared to normal mammary tissues (Jiang, W. G. et al., 2003. *Oncol Rep* 10:2039-2044).

Example 4

Figure 3A:
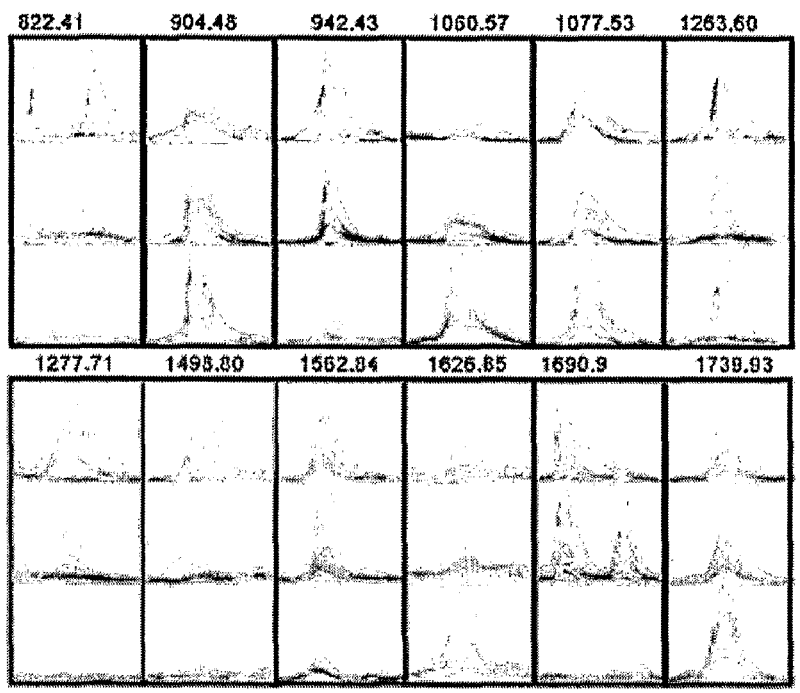
FIGS. 3A and 3B show MALDI-TOF mass spectral overlays of selected peaks derived from serum peptide profiling of three groups of cancer patients and healthy controls. Each overlay shows a binary comparison for all spectra from either the bladder cancer (n=20; green), or prostate cancer (n=32; blue) or breast cancer patient group (n=21; red) versus the control group (n=33; yellow). They are arrayed in a way that the same mass range window is shown for each of the three binary comparisons, in which spectral intensities were normalized and scaled to the same size, except for '2021.05', which is included herein as an example of the vast majority of peptide-ions with intensities not statistically different between any two groups. (A) Overlays of mass spectra of selected peptides of known sequence (see FIG. 3) that showed statistically significant differences between peak intensities in one or more of the three binary comparisons. The mono-isotopic mass (m/z) of the peak is shown for each peptide. (B) Overlays of mass spectra of some as yet unidentified peptides that also showed statistically significant differences between peak intensities in one or more of the three binary comparisons. The bin 'name' (a number that is close to the average isotopic mass) is shown for each peptide.
Figure 3B:
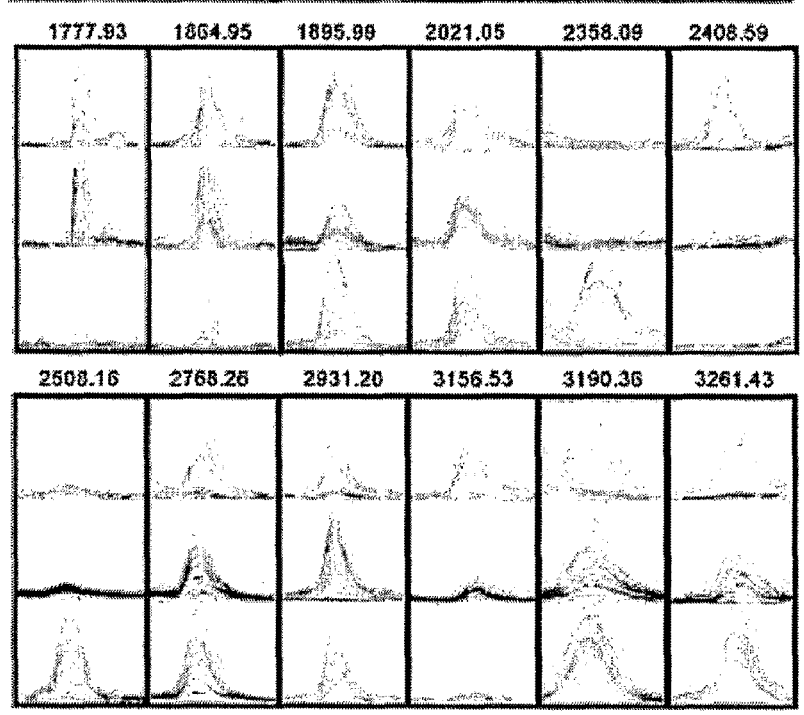

MALDI-TOF Mass Spectral Overlays of Selected Peaks Derived from Serum Peptide Profiling of Three Groups of Cancer Patients and Healthy Controls All spectra were obtained and aligned as described above, and subsequently displayed using the Mass Spectra Viewer (MSV) (FIGS. 3A and 3B). Overlays of mass spectra of selected peptides of known sequence (FIG. 5) that showed statistically significant differences between peak intensities in one or more of the three binary comparisons are shown in FIG. 3A. Peptide '2021.05' (i.e., C3f) is shown as an example of a peptide that is present in about equal concentrations in all serum samples analyzed in this study. Overlays of mass spectra of some as yet unidentified peptides that also showed statistically significant differences between peak intensities in one or more of the three binary comparisons are shown in FIG. 3B.

Peptides from a serum sample obtained from a breast cancer patient were extracted and analyzed by MS, and the ion of choice selected for MS/MS analysis. The fragment ion spectrum shown herein was taken for a MASCOT MS/MS Ion Search of the human segment of NR database, and retrieved a peptide sequence, GLEEELQFSLGSKINVKVGGNS (SEQ ID NO: 23) ($[MH]^+$=2305.19; $\Delta$=4 ppm) with a Mascot score of 38.

Taken together, a total of 69 serum peptides are listed in FIG. 5A (with matching information provided in FIG. 5B; all 79 sequenced peptides listed in FIG. 14). Of those, 61 have clear MALDI-TOF MS-ion marker potential (adjusted $p<0.0002$; and, in most cases, much lower) for at least one type of cancer and are color-coded in blue (prostate cancer), green (bladder cancer) or red (breast cancer). The resulting 'barcodes' for the three cancer types consist of 26 (prostate), 50 (bladder) and 25 (breast) 'bars', i.e., peptides, several in common between any two or all three. Compared to healthy control samples, median intensities of ion markers could be up or down (represented by black dots in the colored barcodes in FIG. 5A) in any particular cancer group; 16 higher and 10 lower (16+/10−) in prostate cancer, 31+/−19 in bladder cancer, and 19+/6− in breast cancer. Only three peptides in each of the up- or down-categories were shared by all cancer groups.

One peptide from the C4a- and two from the ITIH4-cluster had consistently higher ion intensities in all cancers than in healthy controls; three FPA fragments were lower in all cancers. The rest of the ion markers were either in common between 2 groups or, more often, unique to a single patient cohort (FIG. 5A). Twenty six (17+/9−) of those were unique for bladder cancer and 16 (13+/3−) for breast cancer. To be noted are the nine APO[A-I, A-IV, E, J]-peptides and three C3f-peptides exclusively of higher ion intensities in bladder cancer, and the four C4a-two bradykinin- and one transthyretin-peptides in breast cancer. All three serum peptide ions that were uniquely of lower intensity in the breast cancer cohort each derived from C3f. Interestingly, a number of 'shared' marker ions had, in fact, higher median intensities than the controls in one type cancer and lower in another (FIGS. 5A and 5B). For instance, one ITIH4-peptide ('842') and one C3f-peptide ('1865') had higher median ion intensities in sera from prostate cancer patients than in, respectively, bladder and breast cancer. Five peptide ions (including those corresponding to bradykinin and desArg-bradykinin) that had higher median intensities in breast cancer samples were lower in bladder cancer and had no appreciable marker value for prostate cancer.

Figure 6:
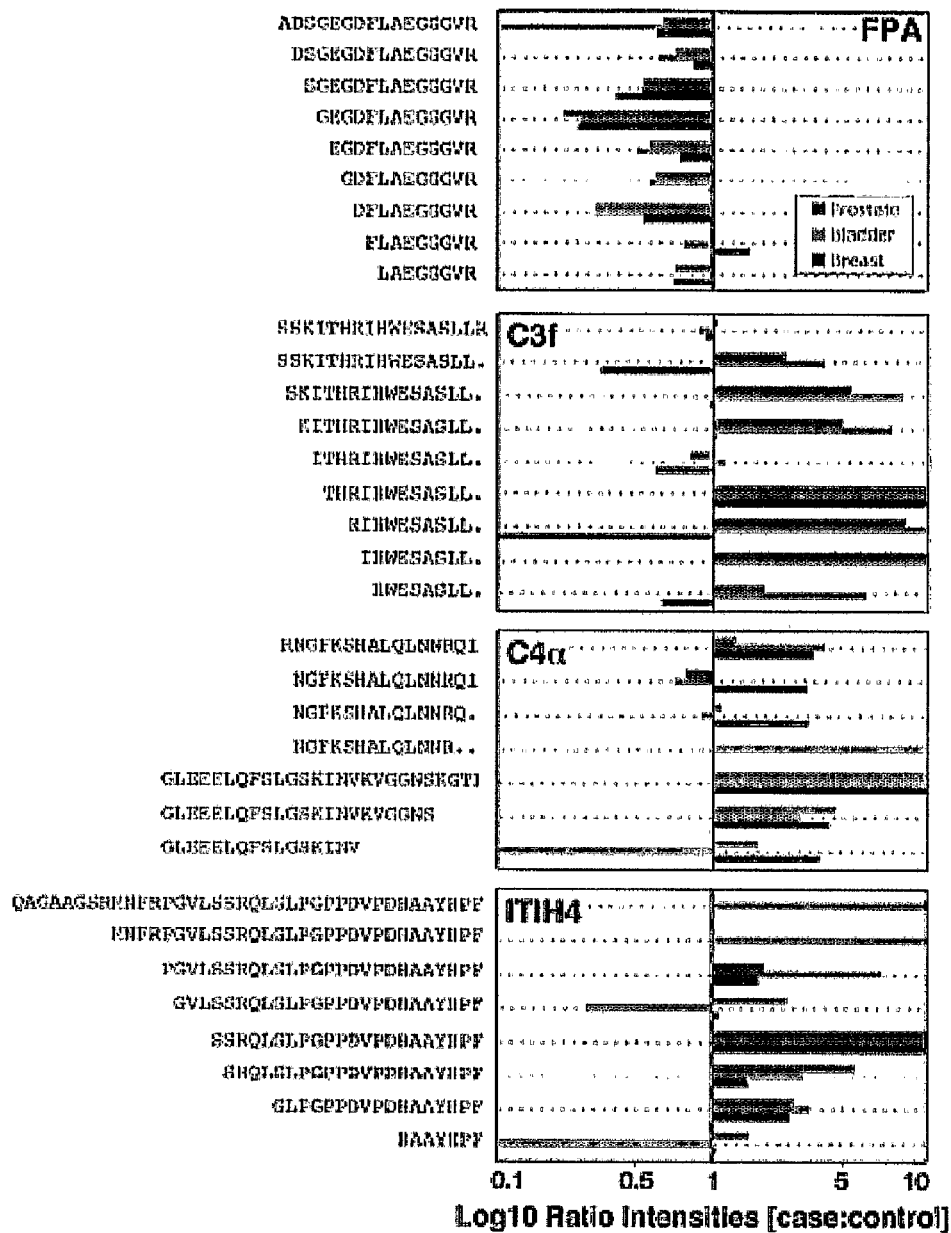
FIG. 6 shows, in bar graph form, the median intensity for each serum peptide in each of the three cancer groups (color-coding as indicated) plotted as the ratio versus the median intensity of the counterpart in the control group (r=case/control). Ratios are plotted on a log scale ranging from 0.1 to 10. Bars pointing to the left (r<1) or right (r>1) indicate, respectively, lower or higher median intensities in a cancer group as in the control group. Peptides that didn't show much difference in median ion intensity between case and control groups map closely to or onto the centerline (r=1).

In an attempt to find trends in what clusters might have ion marker value for a type of cancer, or to at least better visualize any global differences that might exist, we plotted the ratios of the median ion intensities were plotted, for each of the peptides in the four major clusters, between each cancer group and the healthy controls (i.e., r=case/control). The center line in the panels of FIG. 6 represents no difference (r=1); bars pointing to the left (r<1) or right (r>1) indicate, respectively, lower or higher median. Even in case of the FPA ladder where nearly all peptides in cancer sera produced ion signals of lower intensities than in controls, the actual ratios vary for each 'rung' and for each cancer type. Of particular note is the seemingly total absence (r=0) of full-length FPA in sera of bladder cancer patients. The three other clusters exhibit an even more pronounced 'internal' variability, with median intensity ratios that were mostly over, but also equal to or under 1.

Visual inspection of the 4 color-coded graphs (33×3 total data points) in FIG. 6 readily distinguishes the three cancer types. There is a trend for peptides in bladder cancer sera to exhibit relatively high ion intensities in the C3f cluster and rather variable intensities in the C4a and ITIH4 clusters, and for some peptides in the C3f-cluster to be of lower intensity and others in the C4a-cluster to be of higher intensity in breast cancer sera. Ion intensities of peptides in prostate cancer sera don't seem to follow those trends, but are selectively more pronounced in some of the smaller peptides of the ITIH4-cluster. Interestingly, there is one rung in each of the C3f-, C4a- and ITIH4-ladders (respectively the $6^{th}$, $5^{th}$ and $5^{th}$ rung in the corresponding panels in FIG. 6) for which median ion intensities in the control samples were virtually zero, yet much higher in all three cancer types, resulting in very high ratios for each.

Figure 4:
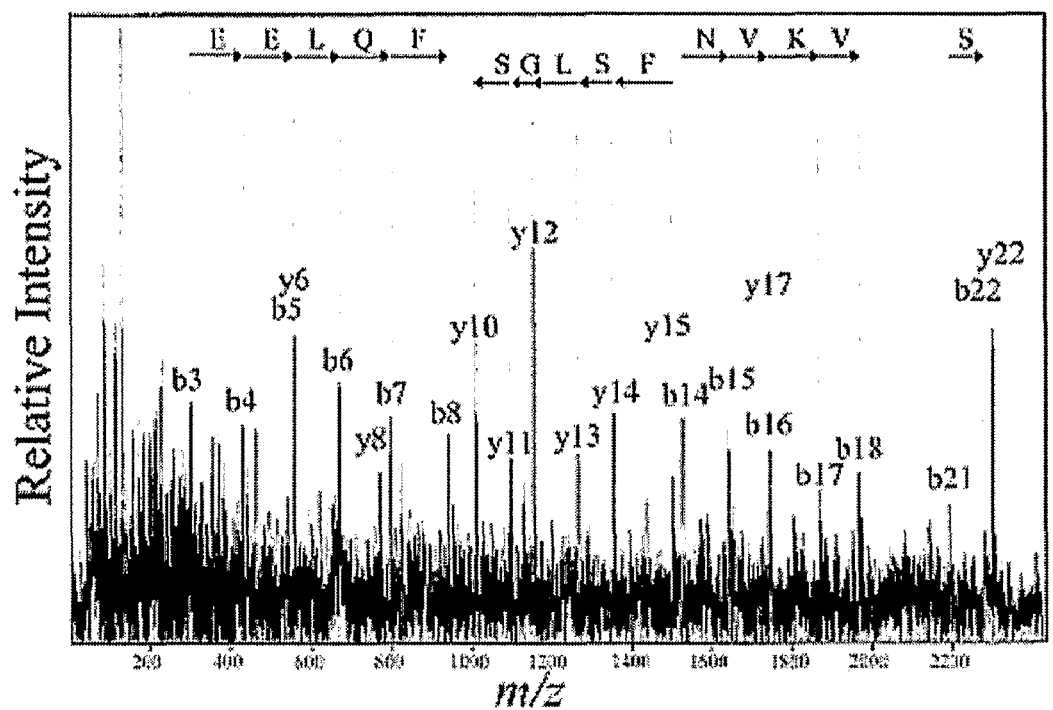
FIG. 4 shows a fragment ion spectrum for MALDI-TOF/TOF MS/MS identification of serum peptide (SEQ ID NO: 7) 2305.20 as a fragment of complement 4a. b''- and y''-fragment ion series are indicated, together with the limited sequences (above arrows). Note that y''-ions originate at the C-terminus and that the sequence therefore reads backwards (see direction of the arrows).

Taken together, the data in FIG. 6, based in parts on statistical analysis (FIG. 5B), visual inspection of spectra overlays (FIG. 3), peptide sequencing (FIGS. 4 and 5A) and relative ion intensity analysis, now strongly indicate that the human serum peptidome holds information, in the form of barcodes consisting of a few dozen peptides each, that can distinguish three different cancers from controls as well as from each other.

Example 5

Independent Set of Prostate Cancer Serum Samples for Validation of Established 'Peptide-Signature' Biomarkers It was next tested whether the identified markers would correctly predict the class of an external validation set.

Sample Groups

Figure 1B:
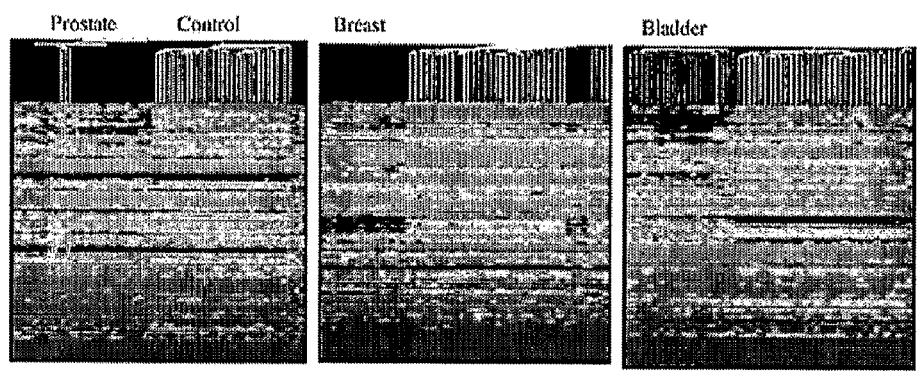
FIG. 1B shows the results of unsupervised, average-linkage hierarchical clustering performed using standard correlation as a distance metrics ('GeneSpring' program), between each cancer group and the control, in binary format. The entire peak list (651×106) was used. Columns represent samples; rows are m/z-peaks (i.e., peptides). Dendrogram colors follow the color-coding scheme of panel A. The heat map scale of normalized intensities is from 0 (green) to 200 (red), with the midpoint at 100 (yellow).
Figures 1C, 1D:
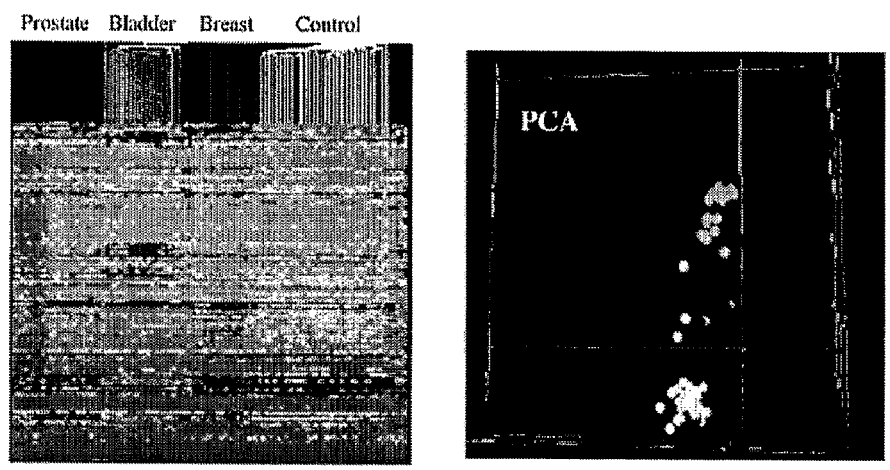
FIG. 1C shows the results of hierarchical clustering performed for the three cancer groups plus control (as in 1B, above).
FIG. 1D shows the results of Principal Component Analysis (PCA) of the three cancer groups plus controls based on the full peak list. Color-coding is as in panel A. The first three principal components, accounting for most of the variance in the original data set are shown.

An initial set of 32 serum samples from patients with advanced prostate cancer (Prostate #1) were analyzed together with 33 samples from healthy controls and two additional groups of cancer patient samples (FIG. 1A). One month later, an entirely different group of 41 advanced prostate cancer patients (Prostate #2), none previously studied, was analyzed using identical methodology (FIG. 8A), and a new spreadsheet with all data from the original 106 subjects and the new validation set, was generated. The assignment of the prostate cancer samples into the training set (Prostate 1—'PR1') or the test set (Prostate 2—'PR2') was random, but preserving the same demographic/pathological parameters (e.g., age, PSA levels, Gleason score, survival time).

Figure 7:
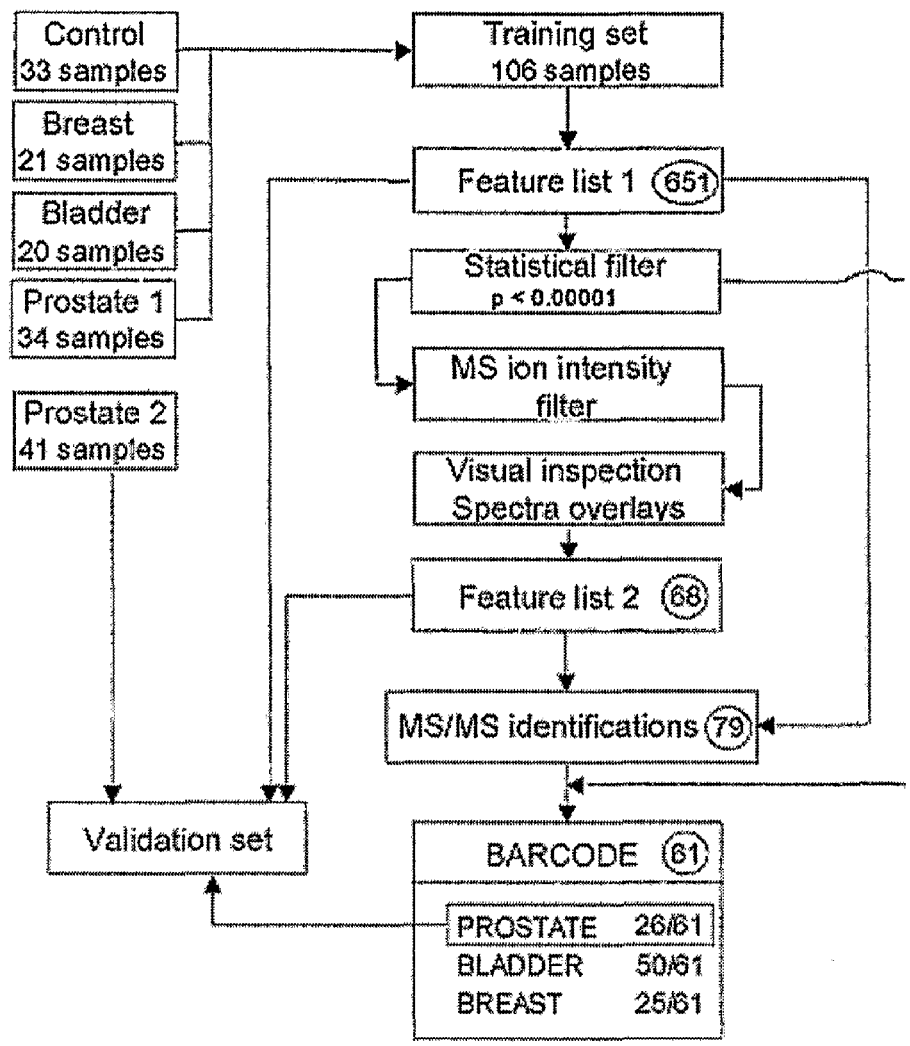
FIG. 7 shows a flow chart-type diagram delineating the approach used for development and validation of (i) the 68-peptide-ion signature and (ii) the prostate cancer barcode consisting of 26 serum peptides with known sequence (blue-coded in FIG. 5). Numbers that are encircled indicate total number of selected peptides at that stage of the study.

Peptide ions from 'feature list #2' (68 peptides; see FIGS. 2A and 7) and from the 'prostate cancer barcode' (26 sequenced peptides; blue 'barcode' in FIGS. 5A and 5B) were then selectively used for comparison of the control, PR1 and PR2 groups by hierarchical clustering and principal component analysis. While not a perfect fit, samples from prostate cancer sets #1 and #2 were mixed to some extent but for the most part separated from the controls. Individual comparisons of each of these 26 peptide ions between the three sample groups indicated that the intensities of 26 out of 26 were statistically different (adjusted $p<0.0002$; i.e. the p-value to create the barcode—FIG. 5B) between PR1 and control, 23 out of 26 between PR2 and control, and only 1 out of 26 between PR1 and PR2.

Class Prediction Analysis of the Prostate Cancer Validation

Support vector machine (SVM)-based class predictions, in either binary or multi-class formats, were carried out using all 651, or the 68 or 14 previously selected peptides. Analyses were carried out using linear kernel (as described earlier). Similar sensitivities were obtained in all three instances, namely 100% (41/41) and 97.5% (40/41) accuracy for, respectively, binary and multi-group class predictions.

Example 6

Aminoprotease Activities in Plasma

Figure 9:
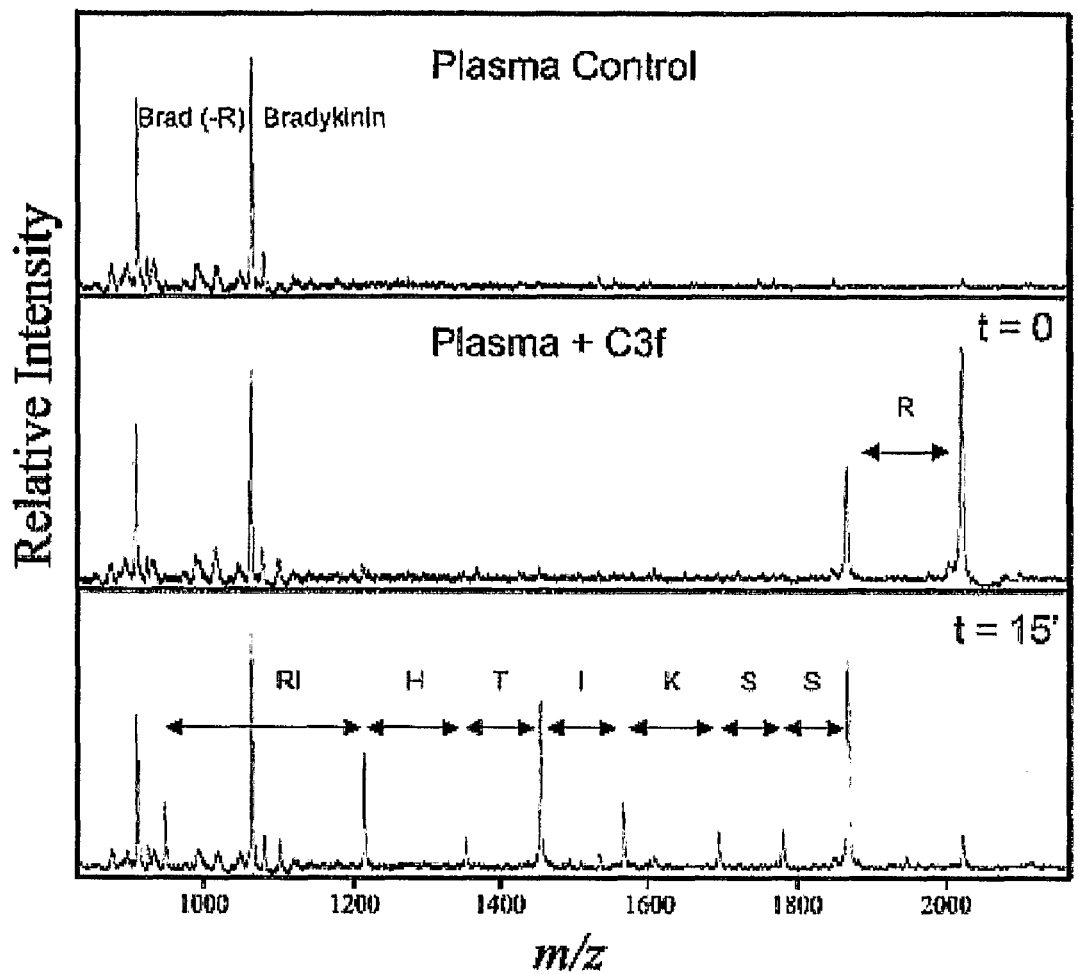
FIG. 9 shows MALDI-TOF MS read-outs of fresh plasma (top panel), indicating very low levels of small peptides, except for bradykinin and desArg-bradykinin, of an aliquot withdrawn immediately (i.e., after 15-20 s) after addition of synthetic C3f (1 pmole/µL plasma) (middle panel, indicating removal of the C-terminal Arg, by a carboxypeptidase, in a matter of seconds), and of an aliquot withdrawn after another 15 minutes at room temperature (lower panel, indicating that C3f is then further degraded by the activity of aminopeptidases to result in a type of sequence ladder as endogenously present in serum).
Figure 10:
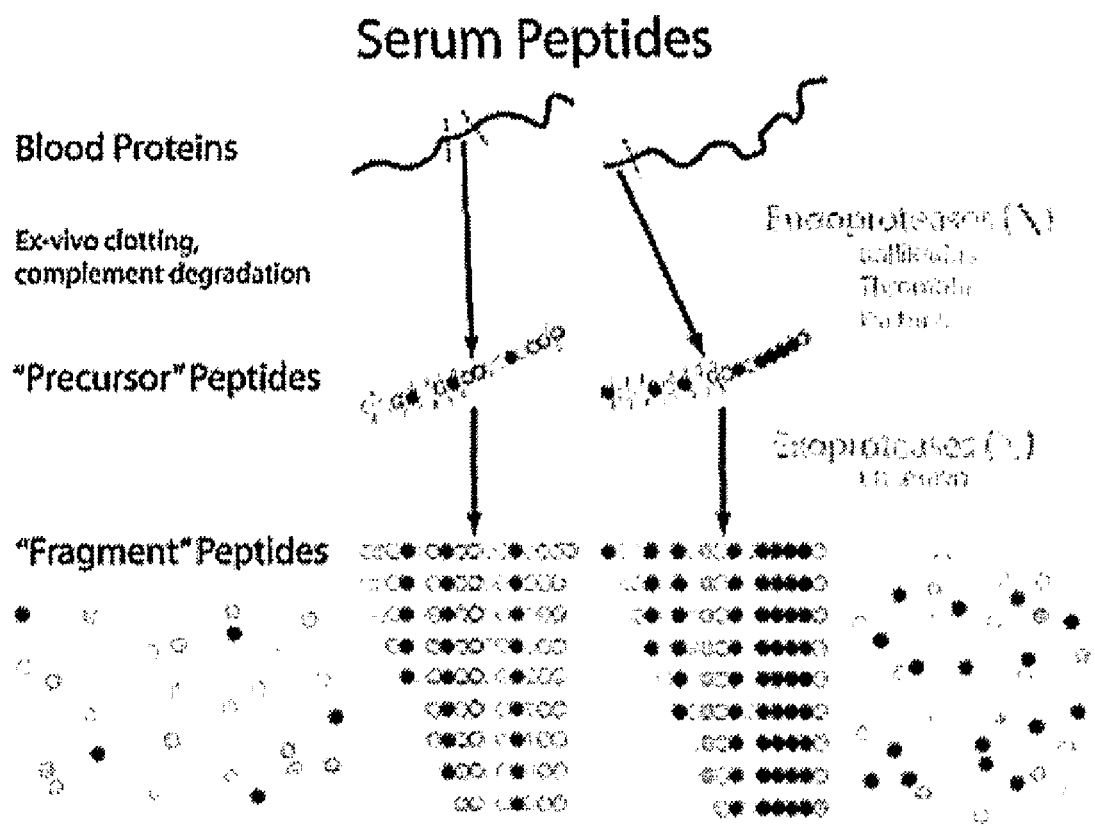
FIG. 10 schematically depicts the activity of serum proteases. Amino acids are color-coded to represent sequence clusters of C3f (left) or FPA (right), which are just two examples of all the observed clusters.

The serum peptidome is likely largely the product of resident substrates, more specifically their proteolytic breakdown products (Koomen, J. M. et al., 2005. *J Proteome Res* 4:972-981); findings herein), and, therefore, represents a read-out of the repertoire of proteases that exist in plasma and/or become activated during clotting. With the exception of bradykinin, much higher peptide concentrations were consistently observed in serum than in plasma (FIG. 9; and data not shown). The data presented herein indicate that cancer cells contribute unique proteases, perhaps exoproteases, which result in subtle but signature alterations of the complex equation of hundreds of peptides that can be resolved from human serum.

In an effort to begin to understand the presence and roles of exoproteases, synthetic C3f was added to fresh plasma at a concentration close to that observed in serum. As shown in FIG. 9, degradation is very fast. C-terminal Arg was removed within seconds, and the N-terminal truncations occurred in 10-15 min. The resulting pattern was similar to the endogenous one observed in serum and also illustrated the disparate ion intensities for different rungs in the ladder. However, most of the C3f ladder, except its smallest rung, disappeared upon prolonged incubation (data not shown). Exoproteolytic degradation of synthetic FPA in plasma followed a similar time course, but FPB was completely degraded in just a few minutes (data not shown). The results suggest that the operative exoprotease concentrations and activities are roughly equivalent in plasma and serum, and therefore not the consequence of coagulation.

As per Example 6, above, it is indicated that a sizable part of the human serum 'peptidome', as detected by MALDI-TOF MS, is generated by degradation of endogenous substrates by endogenous proteases. Peptide profiling is, therefore, a form of activity-based proteomics, by using a 'metabolomic' read-out that is subject to variations in enzyme panels, cofactors and inhibitors. Here, proteolytic activities of the ex-vivo coagulation and complement-degradation pathways, in combination with exoproteases, have been shown to contribute to generation of not only cancer-specific, but also 'cancer type'-specific serum peptides. The specificity derives largely from aminopeptidase panels in serum, which is consistent with previous observations (van Hensbergen, Y., et al., 2002, *Clin Cancer Res* 8:3747-3754; Matrisian, L. M., et al., 2003, *Cancer Res* 63:6105-6109; Moffatt, S., et al., 2005, *Hum Gene Ther* 16:57-67; Kehlen, A., et al., 2003, *Cancer Res* 63:8500-8506; Rocken, C., et al., 2004, *Int J Oncol* 24:487-495; Carl-McGrath, S, et al., 2004, *Int J Oncol* 25:1223-1232; Kojima, K., et al., 1987, *Biochem Med Metab Biol* 37:35-41; Essler, M., et al., 2002, *Proc Natl Acad Sci USA* 99:2252-2257; Carrera, M. P., et al., 2005, *Anticancer Res* 25:193-196; Pulido-Cejudo, G., et al., 2004, *Biotechnol Lett* 26:1335-1339; Suganuma, T., et al., 2004, *Lab Invest* 84:639-648; Selvakumar, P., et al., 2004, *Clin Cancer Res* 10:2771-2775; Ni, R. Z., et al., 2003, *World J Gastroenterol* 9:710-713; Sheppard, G. S., et al., 2004, *Bioorg Med Chem Lett* 14:865-868; Griffith, E. C., et al., 1998, *Proc Natl Acad Sci USA* 95:15183-15188; Pasqualini, R., et al., 2000, *Cancer Res* 60:722-727; Petrovic, N., et al., 2003, *J Biol Chem* 278: 49358-49368; O'Malley, P. G., et al., 2005, *Biochem J; Fair, W. R., et al.*, 1997, *Prostate* 32:140-148).

In the discovery phase of the present studies, hundreds of features were sorted through to identify several that are most predictive of outcome. Reduction in the number of key peptides to only a few that are easily recognized between samples has been shown not to adversely affect class predictions. Focused mass spectrometric quantitation of key peptides should facilitate introduction of this technology into general clinical practice.

Example 7

MALDI-TOF MS-Based Quantitative Profiling

Figure 32A:
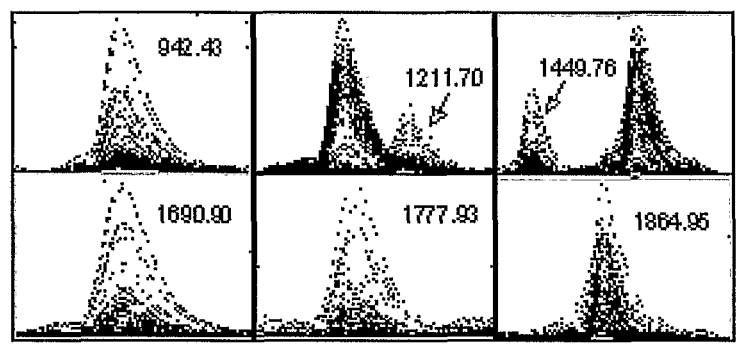
FIG. 32 shows the MALDI-based, relative quantitation of serum peptides: A, normalized ion intensities as spectral overlays and B, as a heat plot. C shows the relative quantitation of normalized ion intensities in bar graph form.
FIG. 32B discloses SEQ ID NOS 27, 11, 10, 9, 8 and 12, respectively, in order of appearance.
Figure 32B:
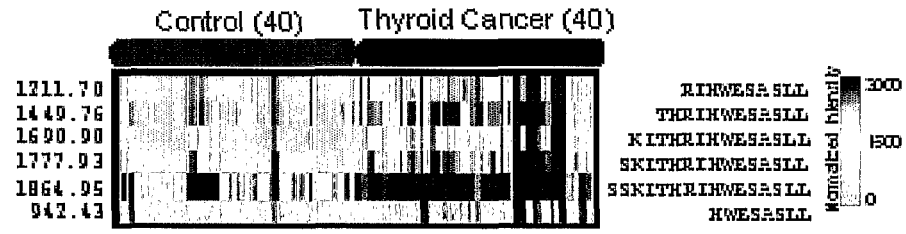
Figure 32C:
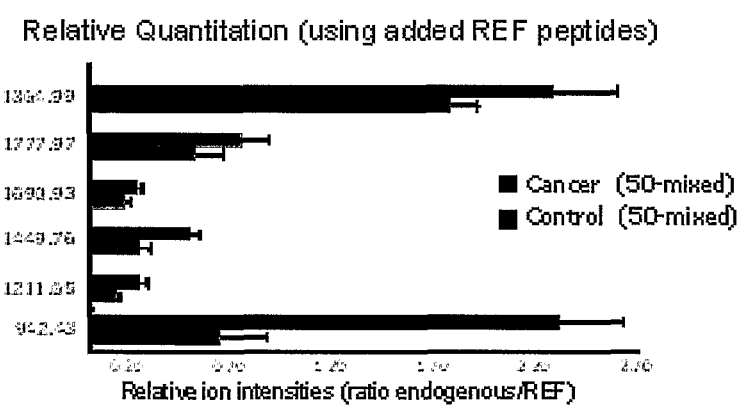

Relative quantitation of the rungs of a C3f ladder in a pool of 50 serum samples from thyroid carcinoma patients and a pool of 50 healthy controls was carried out. Ten reference peptides (FIG. 31) were added to the raw sera (2 picomoles/50 µL), peptides extracted on magnetic beads, MALDI spectra taken and ion intensity ratios calculated for each pair, for each pool. The relative ion intensities (ratio: endogenous/REF) were consistently higher for the peptides in the 'cancer sera' compared to the controls (~20% to 100% higher) (FIG. 32, panel C). These results are in agreement with the normalized ion intensity comparisons of 40 individual cancer and 40 individual control samples; presented as spectral overlays and a heat plot in FIG. 32, panels A and B.

Example 8

MALDI-TOF MS-Based Protease Assays

Figure 34A:
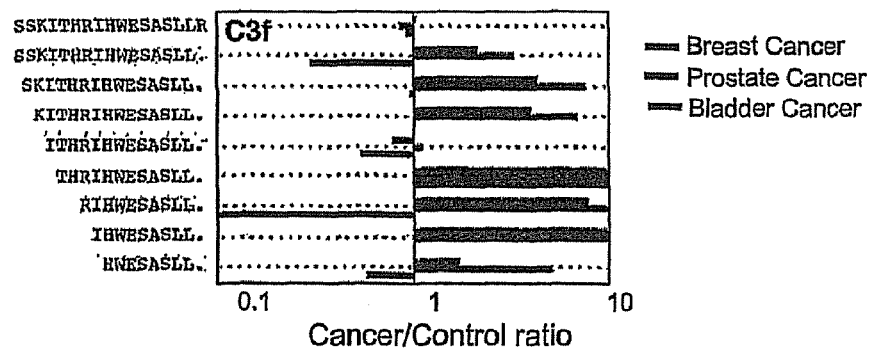
FIG. 34A shows median ion intensities in MALDI spectra taken of breast cancer sera vs. control sera.
Figure 34B:
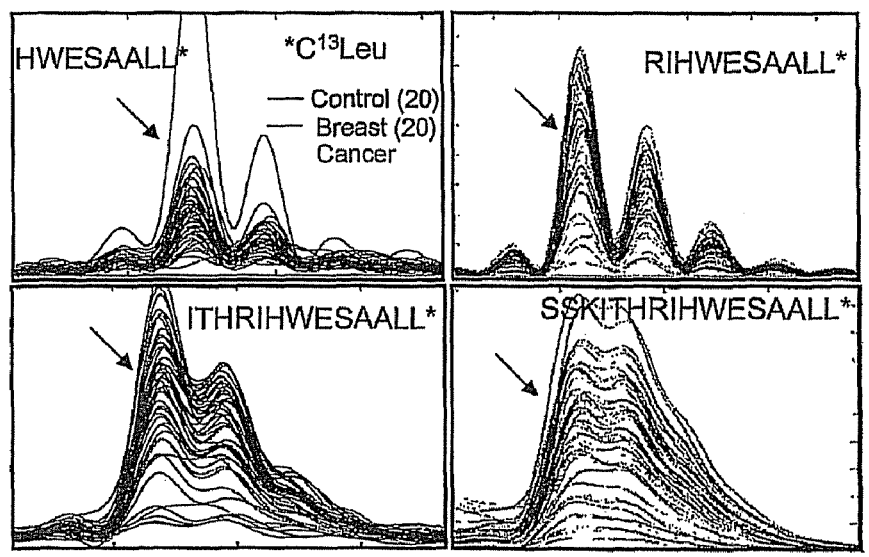
FIG. 34B shows selected views of isotopically resolved or partially resolved peptide-ion peaks; red, breast cancer; black, controls.

The degradation conditions and times were studied for C3f and FPA in serum and plasma as described above. Synthetic C3f and FPA readily degraded in control serum and plasma; C3f rapidly (within 15-30 min), FPA rather slowly (up to 4 hours). 2 picomoles [$^{13}$C-Leu]-labeled C3f was incubated for 30 min at RT with 50-µL aliquots of serum from 20 different breast cancer patients and 20 control samples. Four rungs (m/z=942, 1212, 1563, 1865) of the endogenous C3f degradation ladder were previously found to have a lower median ion intensity in MALDI spectra taken of breast cancer sera than control sera ((12); FIG. 34A). Upon overlay of the 40 color-coded spectra (FIG. 34B), the equivalent four rungs in the ladder resulting from degradation of exogenous [$^{13}$C Lou] C3f had aslo generally lower ion intensities in the spectra of cancer patient sera compared to the controls, thus closely matching the endogenous patterns.

A synthetic version of the longest ITIH4-derived founder peptide (FIG. 33; #7, with N-t Pro) did not degrade in serum or plasma (data not shown), indicating that it probably is not a founder but rather a stalled degradation product of a bigger peptide.

Figure 35:
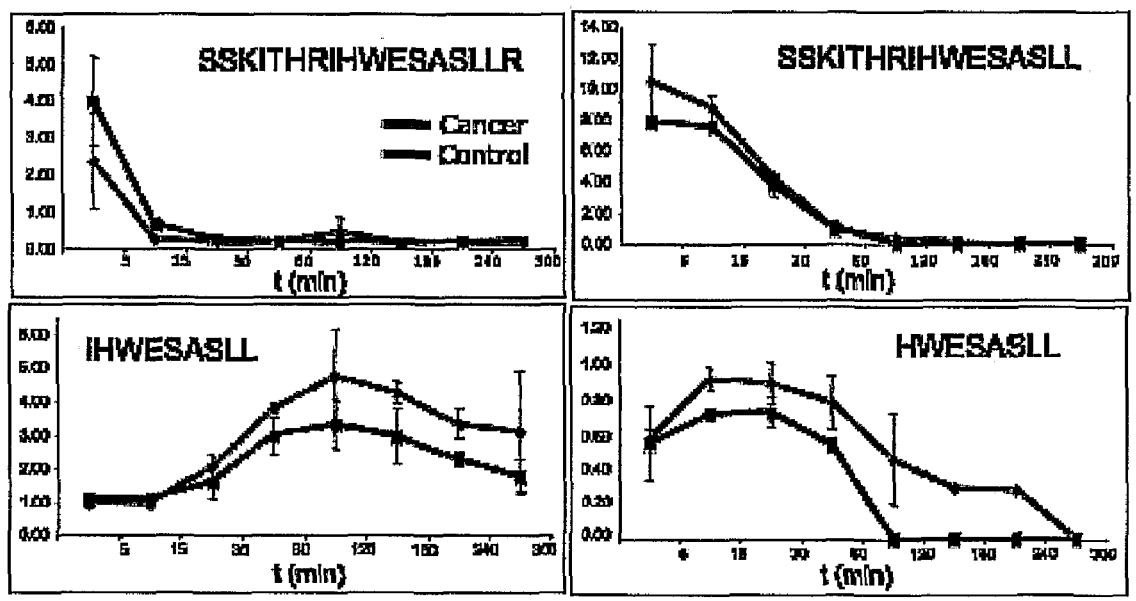
FIG. 35 shows ten peptide-triplets and plots of the ratios between exogenously derived peptides and reference peptide calculated. Inset is a small section of the MALDI spectrum showing the position of the monoisotopic envelopes for each of the three iso-peptides.

Labeled C3f was added to two pools of serum, one from 50 samples obtained from thyroid carcinoma patients, and one from age- and gender-matched healthy controls. Aliquots were retrieved at various time points, ranging from 5 min to 5 hours, and analyzed by magnetic bead processing and a MALDI read-out; in triplicate. The 10 peptide-triplets (one for each rung in the C3f ladder) were then selected for each time point and each of the triplicates, the ratios between exogenously derived peptide and reference peptide calculated and plotted (FIG. 35).

The exogenous peptide was singly labeled ($^{13}$C-Leu), and the reference peptide doubly labeled with $^{13}$C/$^{15}$N-Leu, hence the 14 Da mass difference from the endogenous peptide. The time course results indicate that during the first 5 or so minutes, peptide degradation (removal of the C-t Arg) kinetics are faster in the cancer sera than in the controls. Furthermore, after 1-2 hours of incubation, clear differences in relative ion intensity were observed for the two smallest peptides in the ladder between the two samples; both higher in the cancer sample, indicating that the founder peptide was either more rapidly degraded in the cancer serum or that, alternatively, it was completely degraded to single amino acids in the control serum.

The invention claimed is:

1. A method of generating a peptide profile of a subject having cancer of the prostate, comprising the steps of:
   i) combining an exogenous peptide selected from the group consisting of a complement C3f, ITIH4, clusterin, complement C4-alpha, fibrinopeptide A, kininogen, factor XIII, fibrinogenA peptide and combinations thereof with a biological sample from the subject; and
   ii) proteolytically digesting a peptide of step i), wherein combining the biological sample and said peptide proteolytically digests said peptide, and wherein the biological sample is serum or plasma,
   thereby generating a peptide profile of the subject.

2. The method of claim 1, wherein the exogenous peptide is labeled with an isotope.

3. The method of claim 1, wherein the peptide profile indicates that the subject has cancer of the prostate.

4. A method of generating a peptide profile of a subject having cancer of the bladder, comprising the steps of:
   i) combining an exogenous peptide selected from the group consisting of a complement C3f, ITIH4, clusterin, complement C4-alpha, fibrinopeptide A, bradykinin, APO A-I, APO A-IV, APO E, kininogen, fibrinogenA peptide and combinations thereof with a biological sample from the subject; and
   ii) proteolytically digesting a peptide of step i), wherein combining the biological sample and said peptide proteolytically digests said peptide, and wherein the biological sample is serum or plasma,
   thereby generating a peptide profile of the subject.

5. The method of claim 4, wherein the exogenous peptide is labeled with an isotope.

6. The method of claim 4, wherein the peptide profile indicates that the subject has cancer of the bladder.

7. A method of generating a peptide profile of a subject having cancer of the breast, comprising the steps of:
   i) combining an exogenous peptide selected from the group consisting of a ITIH4, bradykinin, complement C4-alpha, fibrinopeptide A, complement C3f, APO A-IV, factor XIII, transthyretin, fibrinogenA peptide and combinations thereof with a biological sample from the subject; and
   ii) proteolytically digesting a peptide of step i), wherein combining the biological sample and said peptide proteolytically digests said peptide, and wherein the biological sample is serum or plasma,
   thereby generating a peptide profile of the subject.

8. The method of claim 7, wherein the exogenous peptide is labeled with an isotope.

9. The method of claim 7, wherein the peptide profile indicates that the subject has cancer of the breast.

10. A method of generating a peptide profile of a subject having cancer of the thyroid, comprising the steps of:
    i) combining an exogenous peptide selected from the group consisting of a fibrinopeptide A, fibrinogenA peptide, complement C3f and combinations thereof with a biological sample from the subject; and
    ii) proteolytically digesting a peptide of step i), wherein combining the biological sample and said peptide proteolytically digests said peptide, and wherein the biological sample is serum or plasma,
    thereby generating a peptide profile of the subject.

11. The method of claim 10, wherein the exogenous peptide is labeled with an isotope.

12. The method of claim 10, wherein the peptide profile indicates that the subject has cancer of the thyroid.

* * * * *